(12) United States Patent
Vogel et al.

(10) Patent No.: US 10,370,693 B2
(45) Date of Patent: Aug. 6, 2019

(54) TRANSAMINASES

(71) Applicant: C-LEcta GmbH, Leipzig (DE)

(72) Inventors: Andreas Vogel, Leipzig (DE); Daniel Schwarze, Jena (DE); Rico Czaja, Leipzig (DE); Sally Bayer, Leipzig (DE); Sebastian Bartsch, Leipzig (DE)

(73) Assignee: C-LEcta GmbH, Leipzig (DE)

( * ) Notice: Subject to any disclaimer, the term of this patent is extended or adjusted under 35 U.S.C. 154(b) by 36 days.

(21) Appl. No.: 15/735,165

(22) PCT Filed: Jun. 10, 2016

(86) PCT No.: PCT/EP2016/063387
§ 371 (c)(1),
(2) Date: Dec. 9, 2017

(87) PCT Pub. No.: WO2016/198660
PCT Pub. Date: Dec. 15, 2016

(65) Prior Publication Data
US 2018/0298354 A1    Oct. 18, 2018

(30) Foreign Application Priority Data

Jun. 12, 2015 (EP) .................................. 15171924

(51) Int. Cl.
| | | |
|---|---|---|
| *C12N 9/10* | (2006.01) | |
| *C12P 13/00* | (2006.01) | |
| *C12P 7/26* | (2006.01) | |
| *C12P 41/00* | (2006.01) | |

(52) U.S. Cl.
CPC .......... *C12P 41/006* (2013.01); *C12N 9/1096* (2013.01); *C12P 7/26* (2013.01); *C12P 13/001* (2013.01); *C12Y 206/01* (2013.01)

(58) Field of Classification Search
None
See application file for complete search history.

(56) References Cited

FOREIGN PATENT DOCUMENTS

| EP | 2022852 B1 | 7/2017 |
|---|---|---|
| JP | 2007185133 A | 7/2007 |
| WO | 2004085624 A2 | 10/2004 |
| WO | 2006063336 A2 | 6/2006 |
| WO | 2010081053 A2 | 7/2010 |
| WO | 2011159910 A3 | 3/2014 |

OTHER PUBLICATIONS

EBI accession No. GSP: ADS78319, Aminotransferase/mutase/deaminase enzyme #40, Dec. 30, 2004.
EBI accession No. GSP: AGH64081, Pseudomonas corrugata (S)-amine transaminase, SEQ ID 6, Jan. 10, 2008.
Neto, L.A., et al., Process Considerations for the Asymmetric Synthesis if ChiralAmines using—Transaminase, http://orbit.dtu.dk/flies/69085333/PhD_Thesis_Watson_Neto_final_print_version_thesis.pdf , Aug. 1, 2013, pp. 42-61.
Seo, et al., Exploring sequence space: Profile analysis and protein-ligand docing to screen [omega]-aminotransferases with expanded substrate specificity, Biotechnology Journal, Apr. 8, 2008, vol. 3, No. 5, pp. 676-686.

*Primary Examiner* — Suzanne M Noakes
*Assistant Examiner* — Jae W Lee
(74) *Attorney, Agent, or Firm* — Agris & Von Natzmer, LLP; Joyce Von Natzmer

(57) ABSTRACT

The invention relates to transaminases that are particularly useful for catalyzing the conversion of amine substrates to ketone products and/or vice versa.

21 Claims, No Drawings
Specification includes a Sequence Listing.

TRANSAMINASES

CROSS-REFERENCE TO RELATED APPLICATIONS

This is the U.S. national stage of International application PCT/EP2016/063387, filed Jun. 10, 2016 designating the United States and claiming priority to EP 15171924.2, filed Jun. 12, 2015.

INCORPORATION OF SEQUENCE LISTING

The sequence listing was filed as a text file as part of International application PCT/EP2016/063387, filed Jun. 10, 2016 is hereby incorporated by reference. An extra copy of this text file named "eolf-seql.txt", which is 537 kilobytes (measured in MS-WINDOWS), dated Nov. 21, 2017 was downloaded from WIPO and is submitted herewith via the USPTO EFS system.

The application claims priority of EP15171924, filed on Jun. 12, 2015.

The invention relates to transaminases, also called aminotransferases, or more specifically to amine transaminases, in the following also abbreviated and referred to as "ATA". The ATAs according to the invention are particularly useful for catalyzing the conversion of amines to ketones and/or vice versa.

Transaminases are ubiquitous enzymes found in all kingdoms of life. Transaminases catalyze the transfer of an amino group from an amine donor molecule to an amine acceptor ketone molecule and vice versa. Transaminases are divided into six classes based on common structural features and sequence similarity (Steffen-Munsberg et al. 2015). So called "omega transaminases (ω transaminase) transfer amino groups that are more distant from a carboxylic group (e.g. in β, γ or δ position) and are often part of aminotransferase class-III family (mainly (S)-selective amine transaminases) or class-IV (mainly (R)-selective amine transaminases). For determining a protein's family membership, the InterPro web tool can be used (www.ebi.ac.uk/interpro; Hunter et al., 2012).

The term "Amine transaminases" (ATA) describes transaminases, including omega transaminases, that allow for the conversion of amines independently from the presence or absence of carboxylic groups in the substrate, and predominantly are a subgroup of class III transaminases. Accordingly, the terminology of omega transaminase is misleading but often used in publications. ATAs are all enzymes which belong to the EC sub-subclass EC 2.6.1, as defined by the International Union of Biochemistry and Molecular Biology. As of the date of this invention, no specific EC serial number for transaminases primarily converting non-carboxyl substrates has been appointed, and ATAs often are referred to as EC 2.6.1.X whereas X stands for any enzyme classified in the sub-subclass EC 2.6.1, and as of the date of this invention for any figure from 1 to 107 (i.e. EC 2.6.1.1, EC 2.6.1.2, EC 2.6.1.3, . . . until EC 2.6.1.107). Other examples of members of the class III transaminases with different primary functions are acetylornithine aminotransferase (EC 2.6.1.11), ornithine aminotransferase (EC 2.6.1.13), omega-amino acid-pyruvate aminotransferase (EC 2.6.1.18), 4-aminobutyrate aminotransferase (EC 2.6.1.19), DAPA aminotransferase (EC 2.6.1.62), 2, 2-dialkylglycine decarboxylase (EC 4.1.1.64), or glutamate-1-semialdehyde aminotransferase (EC 5.4.3.8).

The reaction of ATAs converts ketone substrates (A) into amine products (C) while simultaneously converting amino donor cosubstrates (B) into the corresponding ketone coproduct (D):

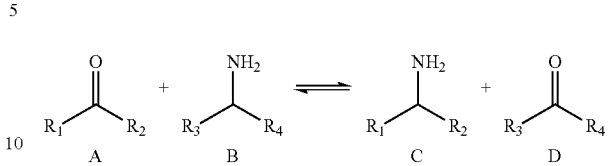

According to their stereoselectivity, two classes of ATAs have been distinguished: (S)-ATAs that preferentially catalyze formation of an (S)-amine from a keto group, and (R)-ATAs that preferentially catalyze formation of an (R)-amine from a keto group. However, this distinction in (S)-ATAs and (R)-ATAs can be misleading, as it depends on the nature of the substrate, namely the substituents of the keto group and their priority according to the rules of the CIP nomenclature (Cahn-Ingold-Prelog). Thus, a given ATA may be regarded as an (S)-ATA with respect to the conversion of one keto group, whereas the same ATA may be regarded as an (R)-ATA with respect to the conversion of another keto group.

The stereoselective synthesis of amine compounds, in particular of chiral amine compounds, is of outstanding interest for synthetic chemistry in particular in the pharmaceutical industry (Shaheer Malik et al, 2012), but also plays an important role in polymer chemistry (polyamides). Furthermore, ATAs can be applied for kinetic resolution of racemic amines.

The reaction that is catalyzed by ATAs is reversible (equilibrium reaction) and may undergo substrate or product inhibition, depending on the specific reaction equilibrium. In order to obtain industrially relevant amounts of a desired product, ATAs are required that catalyze the conversion of substrates with high specific activity. It may be required to bias the equilibrium reaction toward production of the desired amine compound by choosing optimal reaction conditions, resulting in high product yields over process time. Also other kinetic factors, such as substrate selectivity, $K_M$ and stereoselectivity may play an important role. Other relevant aspects may include but are not limited to diastereoselectivity, regioselectivity, inhibition by other factors (e.g. crude extract components, substrate contaminants or side products), and recombinant soluble expressability in suitable hosts.

Another important criterion in the industrial use of ATAs is a long process stability, which often correlates with a high stability at elevated temperatures, and good stability in solvents and/or at high concentrations of substrate and product, respectively. In industrial applications, process stability also may encompass chemical and physical stability, enzymatic activity in differing solvents (aqueous, non-aqueous environments, biphasic systems), and/or at a broad pH-range, e.g. from about pH 4 to about pH 11, and/or applicability with any solid supports or other processing technique.

For an efficient and economic use of ATAs in industrial applications it is desirable to employ ATAs with a high specific activity, high stereoselectivity, and high thermostability and high conversion.

Many of the currently known ATAs, however, do not possess sufficient thermostability, high conversion, or high stereoselective, and do not provide the desired (chiral) amine in sufficient yield.

Improvement of enzymes can be achieved by enzyme engineering. This technique involves the development of variants of a starting enzyme with improved properties (for review: S. Lutz, U. T. Bornscheuer, Protein Engineering Handbook, Wiley VCH, Weinheim, 2009).

The engineering of ATAs for improving stereoselectivity, thermostability or conversion has been described in the literature.

W Lima Afonso Neto et al., Technical University of Denmark, Phd Thesis, relates to process considerations for the asymmetric synthesis of chiral amines using ω transaminase.

JP 2007 185133 (GSP:AGH64081) relates to an aminotransaminase maintaining its enzyme activity under a high temperature condition. This aminotransaminase is encoded by a polynucleotide derived from *Pseudomonas corrugata* and having a specific base sequence. It is possible to produce the aminotransaminase by preparing transformed cells by using a vector containing the polynucleotide. Thereby, it is also possible to produce an optically active amino compound such as an optically active 1-benzyl-3-aminopyrrolidine, etc.

EP 2 022 852 relates to a method for producing an optically-active amine compound. The method is characterized by using a transaminase (A), an alpha-keto acid reductase (B), and an enzyme (C), each having specific properties, in an identical reaction system to convert a ketone compound into a corresponding optically-active amine compound in which a carbon atom with an amino group bonded thereto serves as an asymmetric center.

WO 2004/085624 (GSP:ADS78319) relates to methods of enzymatic detoxification of aminated toxins, e.g., mycotoxins, such as fumonisin. The reference provides methods to enzymatically detoxify plants, foods or feeds or any contaminated product or surface, including detoxification of mycotoxins, such as fumonisin, e.g., fumonisin B1 and fumonisin B2. The reference provides methods to prevent the contamination of plants, foods or feeds or any contaminated product or surface by application or a polypeptide having a deaminase activity. In one aspect, the reference relates to polypeptides having an aminotransferase, an aminomutase and/or a deaminase activity, polynucleotides encoding these enzymes, methods of making and using these polynucleotides and polypeptides.

WO 2006/063336 discloses thermostable omega-transaminases, particularly thermostable omega-transaminases which are said to have a high reaction rate and which are said to be tolerant to high concentrations of donor amine.

WO 2010/081053 provides engineered transaminase enzymes having improved properties as compared to a naturally occurring wild-type transaminase enzyme. Also provided are polynucleotides encoding the engineered transaminase enzymes, host cells capable of expressing the engineered transaminase enzymes, and methods of using the engineered transaminase enzymes to synthesize a variety of chiral compounds.

WO 2011/159910 relates to engineered transaminase polypeptides which are said to have improved properties as compared to naturally occurring transaminases including the ability of converting the substrate, 3'-hydroxyacetophenone to (S)-3-(1-aminoethyl)-phenol in enantiomeric excess and high percentage conversion.

The ATAs of the prior art, however, are not satisfactory in every respect and there is a demand for improved ATAs having advantages compared to conventional ATAs, in particular with respect to high process stabilities at high temperatures for the industrial production of chiral amine products with good yields in high enantiomeric excess.

It is an object of the invention to provide ATAs that have advantages to the ATAs of the prior art. This problem has been solved by the subject-matter of the patent claims.

The invention provides new ATAs, particularly engineered ATAs exhibiting improved properties as compared to the wildtype enzyme, preferably the wildtype ATA of SEQ ID NO:3.

A first aspect of the invention relates to an ATA comprising an amino acid sequence with a homology of at least 75%, preferably of at least 80%, more preferably of at least 85%, still more preferably of at least 90%, to the amino acid sequence of SEQ ID NO:3.

Preferably, the transaminase comprises an amino acid sequence with at least 80% homology to SEQ ID NO:3, wherein the transaminase is engineered compared to SEQ ID NO:3 at least in position N161. Preferably, the transaminase is additionally engineered compared to SEQ ID NO:3 in position Y164 and/or position G51. In a particularly preferred embodiment of the invention, the transaminase comprises at least two substitutions selected from the group consisting of N161A, N161F, N161M, N161Y, N161Q, N161I, Y164L, Y164M, Y164A, Y164F, Y164I, and G51S.

Preferably, the ATA according to the invention comprises an amino acid sequence with a homology to SEQ ID NO:3 of at least 76%, or at least 77%, or at least 78%, or at least 79%, or at least 80%, more preferably at least 81%, or at least 82%, or at least 83%, or at least 84%, or at least 85%, still more preferably at least 86%, or at least 87%, or at least 88%, or at least 89%, or at least 90%, yet more preferably at least 91%, or at least 92%, or at least 93%, or at least 94%, or at least 95%, and most preferably at least 96%, or at least 97%, or at least 98%, or at least 99%. Preferably, the ATA comprises an amino acid sequence with a homology to the amino acid sequence of SEQ ID NO:3 of at least 98.6 or at least 98.7%, more preferably at least 98.8 or at least 99.0%, still more preferably at least 99.1% or at least 99.2%, yet more preferably at least 99.3 or at least 99.4%, even more preferably at least 99.5% or at least 99.6%, most preferably at least 99.7 or at least 99.8% and in particular at least 99.9% or about 100%.

Preferably, the ATA according to the invention comprises an amino acid sequence which is engineered compared to SEQ ID NO:3 at least in position N161, preferably at least in positions N161 and Y164, or at least in positions N161 and G51, with a homology to SEQ ID NO:3 of at least 80%, more preferably at least 81%, or at least 82%, or at least 83%, or at least 84%, or at least 85%, still more preferably at least 86%, or at least 87%, or at least 88%, or at least 89%, or at least 90%, yet more preferably at least 91%, or at least 92%, or at least 93%, or at least 94%, or at least 95%, and most preferably at least 96%, or at least 97%, or at least 98%, or at least 99%. Preferably, the ATA comprises an amino acid sequence with a homology to the amino acid sequence of SEQ ID NO:3 of at least 98.6% or at least 98.7%, more preferably at least 98.8 or at least 99.0%, still more preferably at least 99.1% or at least 99.2%, yet more preferably at least 99.3 or at least 99.4%, even more preferably at least 99.5% or at least 99.6%, most preferably at least 99.7 or at least 99.8% and in particular at least 99.9% or about 100%.

The ATA according to the invention comprises such an amino acid sequence with a defined homology to the amino acid sequence of SEQ ID NO:3. This means that the ATA according to the invention may comprise said amino acid sequence as a subsequence of its overall amino acid sequence, or that the ATA according to the invention may essentially consist of said amino acid sequence. When the ATA according to the invention comprises said amino acid sequence as a subsequence of its overall amino acid sequence, said overall amino acid sequence may be extended, i.e. may comprise additional amino acid residues, at the N-terminus and/or at the C-terminus of said subsequence. Such extension may be advantageous, for example, when the ATA is to be immobilized on a solid support, e.g. for purification purposes.

In the meaning of this invention, the homology is preferably calculated as identity using BLASTP (Stephen F. Altschul, Thomas L. Madden, Alejandro A. Schäffer, Jinghui Zhang, Zheng Zhang, Webb Miller, and David J. Lipman (1997) "Gapped BLAST and PSI-BLAST: a new generation of protein database search programs", Nucleic Acids Res. 25:3389-3402; Stephen F. Altschul, John C. Wootton, E. Michael Gertz, Richa Agarwala, Aleksandr Morgulis, Alejandro A. Schäffer, and Yi-Kuo Yu (2005) "Protein database searches using compositionally adjusted substitution matrices." FEBS J. 272:5101-5109), preferably using version BLASTP 2.2.29+(blast.ncbi.nlm.nih.gov/Blast.cgi), preferably using the following settings:

Field "Enter Query Sequence": Query subrange: none
Field "Choose Search Set": Database: non-redundant protein sequences (nr); optional parameters: none
Field "Program Selection": Algorithm: blastp (protein-protein BLAST)
Algorithm parameters: Field "General parameters": Max target sequences: 100; Short queries: Automatically adjust parameters for short input sequences; Expect threshold: 10; Word size: 3; Max matches in a query range: 0
Algorithm parameters: Field "Scoring parameters": Matrix: BLOSUM62; Gap Costs: Existence: 11 Extension: 1; Compositional adjustments: Conditional compositional score matrix adjustment
Algorithm parameters: Field "Filters and Masking": Filter: none; Mask: none.

Preferably, the ATA according to the invention is capable of catalyzing the conversion of a ketone substrate (A) to an amine (C). Concomitantly, the ATA according to the invention is capable to catalyzing the conversion of an amine donor molecule (B) to a ketone product (D). Also preferably, the ATA according to the invention is capable of catalyzing the conversion of an amine (C) to a ketone product (A), thereby concomitantly catalyzing the conversion of an amine acceptor (D) into an amine molecule (B):

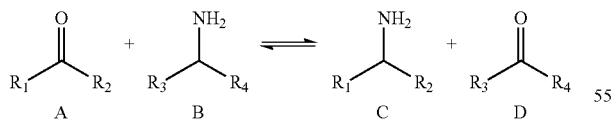

In a preferred embodiment, the ATA according to the invention is capable of catalyzing the stereoselective conversion of a ketone substrate (A) to a chiral (S)-amine (C), and/or vice versa of a chiral (S)-amine (C) to a ketone product (A).

In another preferred embodiment, the ATA according to the invention is capable of catalyzing the stereoselective conversion of a ketone substrate (A) to a chiral (R)-amine (C), and/or vice versa of a chiral (R)-amine (C) to a ketone product (A).

The ATA according to the invention is preferably capable of catalyzing the conversion of
(i) a ketone substrate according to general formula (I)

to an amine product according to general formula (II)

and/or the preferably concomitant conversion of
(ii) an amine cosubstrate according to general formula (III)

to a ketone coproduct according to general formula (IV)

or vice versa;
wherein the amine product according to general formula (II) preferably has (S)-configuration or (R)-configuration at the central carbon atom as shown in general formula (II); and
wherein X and Y as well as A and B, in either case, independently of one another, are selected from saturated or unsaturated, unsubstituted or mono- or polysubstituted aliphatic or alicyclic $C_{1-12}$-hydrocarbon residues; unsubstituted or mono- or polysubstituted $C_{6-10}$-aromatic hydrocarbon residues, optionally being bridged through a saturated or unsaturated, unsubstituted or mono- or polysubstituted aliphatic $C_{1-12}$-hydrocarbon residue; unsubstituted or mono- or polysubstituted heteroaromatic hydrocarbon residues, optionally being bridged through a saturated or unsaturated, unsubstituted or mono- or polysubstituted aliphatic $C_{1-12}$-hydrocarbon residue; and sugar residues or desoxysugar residues in each case comprising mono-, di- or oligosaccharides;
wherein one of residues X or Y, as well as one of residues A or B, in either case, independently of one another, may be hydrogen;
wherein mono- or polysubstituted means independently substituted with one or more functional groups selected from -halo, —OH, =O, —O$C_{1-12}$-alkyl, —O$C_{6-10}$-aryl, —O-heteroaryl, —OCO$C_{1-12}$-alkyl, —OCO$C_{6-10}$-aryl, —OCO-heteroaryl, —SH, —S$C_{1-12}$-alkyl, —S$C_{6-10}$-aryl, —S-heteroaryl, —S(=O)$_{1-2}$OH, —NO, —NO$_2$, —N$_3$, —NH$_2$, —NH ($C_{1-12}$-alkyl), —N($C_{1-12}$-alkyl)$_2$, —NH($C_{6-10}$-aryl), —N($C_{6-10}$-aryl)$_2$, —NH(heteroaryl), —N(heteroaryl)$_2$, —CN, —CHO, —CO$_2$H, CO—$C_{1-2}$-alkyl, —CO—$C_{6-10}$-aryl and —CO-heteroaryl.

A skilled person recognizes that when X≠Y≠hydrogen, the central carbon atom as shown in general formula (II) is chiral and may have either (S)-configuration or (R)-configuration. The same applies to A, B and general formula (IV).

Preferably, the ATA according to the invention is preferably capable of catalyzing the stereoselective conversion of
(i) a ketone substrate according to general formula (I)

(I)

to a chiral amine product according to general formula (II)

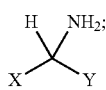
(II)

and/or the preferably concomitant conversion of
(ii) a chiral or non-chiral amine cosubstrate according to general formula (III)

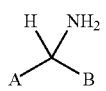
(III)

to a ketone coproduct according to general formula (IV)

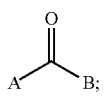
(IV)

or vice versa;
wherein the chiral amine product according to general formula (II) preferably has (S)-configuration or (R)-configuration; and
wherein X and Y as well as A and B, in either case, independently of one another, are selected from saturated or unsaturated, unsubstituted or mono- or polysubstituted aliphatic or alicyclic $C_{1-12}$-hydrocarbon residues; unsubstituted or mono- or polysubstituted $C_{6-10}$-aromatic hydrocarbon residues, optionally being bridged through a saturated or unsaturated, unsubstituted or mono- or polysubstituted aliphatic $C_{1-12}$-hydrocarbon residue; unsubstituted or mono- or polysubstituted heteroaromatic hydrocarbon residues, optionally being bridged through a saturated or unsaturated, unsubstituted or mono- or polysubstituted aliphatic $C_{1-12}$-hydrocarbon residue; and sugar residues or desoxysugar residues in each case comprising mono-, di- or oligosaccharides;
wherein one of residues X or Y, as well as one of residues A or B, in either case, independently of one another, may be hydrogen;
wherein mono- or polysubstituted means independently substituted with one or more functional groups selected from -halo, —OH, =O, —O$C_{1-12}$-alkyl, —O$C_{6-10}$-aryl, —O-heteroaryl, —OCO$C_{1-12}$-alkyl, —OCO$C_{6-10}$-aryl, —OCO-heteroaryl, —SH, —S$C_{1-12}$-alkyl, —S$C_{6-10}$-aryl, —S-heteroaryl, —S(=O)$_{1-2}$OH, —NO, —NO$_2$, —N$_3$, —NH$_2$, —NH($C_{1-12}$-alkyl), —N($C_{1-12}$-alkyl)$_2$, —NH($C_{6-10}$-aryl), —N($C_{6-10}$-aryl)$_2$, —NH(heteroaryl), —N(heteroaryl)$_2$, —CN, —CHO, —CO$_2$H, CO—$C_{1-2}$-alkyl, —CO—$C_{6-10}$-aryl and —CO-heteroaryl.

X and Y as well as A and B, in either case, independently of one another, can be alkyl, cycloalkyl, alkylcycloalkyl, aryl, alkylaryl, heteroaryl or alkylheteroaryl, which in each case can be unsubstituted or substituted with one or more chemical groups that do not interfere with enzyme catalysis, and where X or Y as well as A and B may be hydrogen. Further, X and Y may not be identical in structure and chirality, and may already contain a center of chirality. X and Y may also form a ring, which may be substituted or unsubstituted or fused to other rings. A and B of the cosubstrate may be identical or not identical in structure or chirality, and like X and Y, may form a ring, which may be substituted or unsubstituted or fused to other rings.

Preferably, X and Y as well as A and B, in either case, independently of one another, are each independently selected from unsubstituted or mono- or polysubstituted $C_{1-12}$-alkyl; unsubstituted or mono- or polysubstituted $C_{6-10}$-aryl, optionally being bridged through a unsubstituted or mono- or polysubstituted $C_{1-12}$-alkylene residue; unsubstituted or mono- or polysubstituted heteroaryl, optionally being bridged through a unsubstituted or mono- or polysubstituted aliphatic $C_{1-12}$-alkylene residue; and sugar residues or desoxysugar residues in each case comprising mono-, di- or oligosaccharides;
wherein mono- or polysubstituted means independently substituted with one or more functional groups selected from -halo, —OH, =O, —O$C_{1-12}$-alkyl, —O$C_{6-10}$-aryl, —O-heteroaryl, —OCO$C_{1-12}$-alkyl, —OCO$C_{6-10}$-aryl, —OCO-heteroaryl, —SH, —S$C_{1-12}$-alkyl, —S$C_{6-10}$-aryl, —S-heteroaryl, —S(=O)$_{1-2}$OH, —NO, —NO$_2$, —N$_3$, —NH$_2$, —NH($C_{1-12}$-alkyl), —N($C_{1-12}$-alkyl)$_2$, —NH($C_{6-10}$-aryl), —N($C_{6-10}$-aryl)$_2$, —NH(heteroaryl), —N(heteroaryl)$_2$, —CN, —CHO, —CO$_2$H, CO—$C_{1-2}$-alkyl, —CO—$C_{6-10}$-aryl and —CO-heteroaryl.

For the purpose of the description, saturated or unsaturated aliphatic $C_{1-12}$-hydrocarbon residues include but are not limited to alkyl, alkenyl and alkynyl residues, such as —CH$_3$, —CH$_2$CH$_3$, —CH$_2$CH$_2$CH$_3$, —CH(CH$_3$)$_2$, —CH$_2$CH$_2$CH$_2$CH$_3$, —CH(CH$_3$)CH$_2$CH$_3$, —CH$_2$CH(CH$_3$)$_2$, —C(CH$_3$)$_3$, —CH=CH$_2$, —CH=CHCH=CH$_2$, —C≡CH, and —CH=CHC≡CH.

For the purpose of the description, saturated or unsaturated alicyclic $C_{1-12}$-hydrocarbon residues include but are not limited to $C_{3-12}$-cycloalkyl, wherein 1 or 2 carbon ring atoms may optionally be replaced by heteroatoms selected from N, O and S ($C_{1-12}$-heterocycloalkyl).

For the purpose of the description, $C_{6-10}$-aromatic hydrocarbon residues (=$C_{6-10}$-aryl) include but are not limited to phenyl and naphthyl.

For the purpose of the description, heteroaromatic hydrocarbon residues (=heteroaryl) include but are not limited to monocyclic ring systems, bicyclic ring systems and tricyclic ring systems. Examples of monocyclic heteroaryls include but are not limited to azetidinyl, azepanyl, aziridinyl, diazepinyl, 1, 3-dioxolanyl, dioxanyl, dithianyl, furyl, imidazolyl, imidazolinyl, imidazolidinyl, isothiazolyl, isothiazolinyl, isothiazolidinyl, isoxazolyl, isoxazolinyl, isoxazolidinyl, morpholinyl, oxadiazolyl, oxadiazolinyl, oxadiazolidinyl, oxazolyl, oxazolinyl, oxazolidinyl, piperazinyl, piperidinyl, pyranyl, pyrazinyl, pyrazolyl, pyrazolinyl, pyrazolidinyl, pyridinyl, pyrimidinyl, pyridazinyl, pyrrolyl, pyrrolinyl, pyrrolidinyl, tetrahydrofuranyl, tetrahydrothienyl, tetrazinyl, tetrazolyl, thiadiazolyl, thiadiazolinyl, thiadiazolidinyl, thiazolyl, thiazolinyl, thiazolidinyl, thienyl, thiomorpholinyl, 1, 1-dioxidothiomorpholinyl (thiomorpholine sulfone), thiopyranyl, triazinyl, triazolyl, and trithianyl. Examples of bicyclic heteroaryls include but are not limited to benzimidazolyl, benzodioxinyl, benzothiazolyl, benzothienyl, benzotriazolyl, benzoxazolyl, benzofuranyl, benzopyranyl, benzothiopyranyl, cinnolinyl, indazolyl, indolyl, 2, 3-dihydroindolyl, indolizinyl, naphthyridinyl, isobenzofuranyl, isobenzothienyl, isoindolyl, isoquinolinyl, phthalazinyl, 4H-pyrido(1,2-a)pyrimidin-4-one, pyranopyridinyl, quinolinyl, quinolizinyl, quinoxalinyl, quinazolinyl, tetrahydroisoquinolinyl, tetrahydroquinolinyl, and thiopyranopyridinyl. Examples of tricyclic heteroaryls include but are not limited to acridinyl, carbazolyl, carbolinyl, dibenzo(b, d)furanyl, dibenzo(b,d) thienyl, naphtho(2,3-b)furan, naphtho(2, 3-b)thienyl, phenazinyl, phenothiazinyl, phenoxazinyl, thianthrenyl, thioxanthenyl and xanthenyl.

For the purpose of the description, mono- or polysubstituted with regard to alkyl (e.g. —$C_{1-12}$-alkyl), cycloalkyl (e.g. —$C_{3-5}$-cycloalkyl), aryl (e.g. —$C_{6-10}$-aryl) and heteroaryl, respectively, preferably independently means replacement of a hydrogen from the core by one or more functional groups selected from -halo (preferably —F, —Cl, —Br, —I), —OH, =O, —$OC_{1-12}$-alkyl, —$OC_{6-10}$-aryl, —O-heteroaryl, —$OCOC_{1-12}$-alkyl, —$OCOC_{6-10}$-aryl, —OCO-heteroaryl, —SH, —$SC_{1-12}$-alkyl, —$SC_{6-10}$-aryl, —S-heteroaryl, —$S(=O)_{1-2}$OH, —NO, —$NO_2$, —$N_3$, —$NH_2$, —$NH(C_{1-12}$-alkyl), —$N(C_{1-12}$-alkyl)$_2$, j—$NH(C_{6-10}$-aryl), —$N(C_{6-10}$-aryl)$_2$, —NH(heteroaryl), —N(heteroaryl)$_2$, —CN, —CHO, —$CO_2$H, CO—$C_{1-2}$-alkyl, —CO—$C_{6-10}$-aryl and —CO-heteroaryl.

For the purpose of the description, sugar residues or desoxysugar residues in each case comprising mono-, di- or oligosaccharides means that the ketone substrate of general formula (I) or the amine cosubstrate of general formula (III) may be a polyhydroxycarbonyl compound, optionally linked to other polyhydroxycarbonyl compounds through acetal and/or ketal bonds. For example, when X is $C_1$ alkyl monosubstituted with —OH and Y is $C_2$ alkyl polysubstituted with —OH, wherein every carbon atom bears a single —OH substituent, the ketone substrate of general formula (I) is a ketotetrose encompassing both enantiomers, D-erythrulose as well as L-erythrulose. Analogously, the ketone substrate of general formula (I) may be a ketopentose or a ketohexose which in turn may be linked to other sugar residues thus forming disaccharides or oligosaccharides.

Preferably, the ATA according to the invention is capable converting a ketone substrate to an amine with a broad specific activity for amine donor substrates chosen. Suitable amine donors may be selected according their specific activity in a given reaction. Examples for amine donors that can be used used with the invention include, without limitation, isopropylamine (hereinafter also referred to as "IPA", also known as 2-aminopropane or propan-2-amine), phenylethylamine (also known as 1-phenylethylamine, and often also incorrectly referred to as methyl-benzylamine, hereinafter also referred to as "MBA"), 1-methyl-3-phenylpropylamine (also known as 2-amino-4-phenylbutane), glycine, glutamic acid, glutamate, monosodium glutamate, D-alanine, L-alanin, aspartic acid, lysine, ornithine, 3-alanine, taurine, n-octylamine, cyclohexylamine, 1,4-butanediamine, 1,6-hexanediamine, 6-aminohexanoic acid, 4-ammobutyric acid, tyramine, and benzyl amine, 2-aminobutane, 2-amino-1-butanol, 1-amino-1-phenylethane, 1-amino-1-(2-methoxy-5-fluorophenyl)ethane, 1-amino-1-phenylpropane, 1-amino-1-(4-hydroxyphenyl)propane, 1-amino-1-(4-bromophenyl)propane, 1-amino-1-(4-nitrophenyl)propane, 1-phenyl-2-aminopropane, 1-(3-trifluoromethyl-phenyl)-2-aminopropane (also known as norfenfluramine), 2-aminopropanol, 1-amino-1-phenylbutane, 1-phenyl-2-aminobutane, 1-(2,5-dimethoxy-4-methylphenyl)-2-aminobutane, 1-phenyl-3-aminobutane, 1-(4-hydroxyphenyl)-3-aminobutane, 1-amino-2-methylcyclopentane, 1-amino-3-methylcyclopentane, 1-amino-2-methylcyclohexane, 1-amino-1-(2-naphthyl)ethane, 3-methylcyclopentylamine, 2-methylcyclopentylamine, 2-ethylcyclopentylamine, 2-methylcyclohexylamine, 3-methylcyclohexylamine, 1-aminotetralin, 2-aminotetralin, 2-amino-5-methoxytetralin, and 1-aminoindan, each example also including its structure enantionmers and isomers, as the case may be and where possible, and including all possible salts thereof.

Preferably, the ATA according to the invention is capable converting an amine to a ketone substrate with a broad specific activity for amine acceptor substrates chosen. Suitable amine acceptors may be selected according their specific activity in a given reaction. Examples for amine acceptors that can be used used with the invention include, without limitation, 1-phenylethanone (also known as acetophenone, hereinafter referred to as "AP"), 4-phenyl-2-butanone (also known as benzylacetone, hereinafter referred to as "BA"), 2-oxo-acetic acid, 2-oxo-pentanedioic acid (also known as alpha-ketoglutaric acid), 5-amino-2-oxo-pentanoic acid, pyruvate, 2-ketosuccinic acid, 6-amino-2-oxo-hexanoic acid, 6-oxo-norleucine, 5-amino-2-oxo pentanoic acid, 5-oxo-norvaline, 3-oxo-propanoic acid, 2-oxo-ethanesulfonic acid, octanal, cyclohexanone, 4-aminobutanal, butanedial, 6-amino-hexanal, hexanedial, 6-oxo-hexanoic acid, 4-oxo-butyric acid, 4-hydroxy-benzeneacetaldehyde, benz-aldehyde, 2-butanone, 1-hydroxy-2-butanone, 1-phenylethanone, 1-(5-fluoro-2-methoxyphenyl)-ethanone, 1-phenyl-1-propanone, 1-(4-hydroxyphenyl)-1-propanone, 1-phenyl-1-propanone, 1-(4-bromophenyl)-1-propanone, 1-phenyl-1-propanone, 1-(4-nitrophenyl)-1-propanonelphenyl-2-propanone, 1-(3-trifluoromethylphenyl)-2-propanone, 1-Hydroxy-2-propanone, 1-phenyl-1-butanone, 1-phenyl-2-butanone, 1-(2.5-dimethoxy-4-methylphenyl)-2-butanone, 1-phenyl-3-butanone, 1-(4-hydroxyphenyl)-3-butanone, 2-methyl-cyclopentanone, 3-methylcyclopentanone, 2-methylcyclohexanone, 1-(2-naphthalenyl) ethanone, 1-methyl-3-cyclopentanone, 2-methylcyclopentanone, 2-ethylcyclopentanone, 2-methylcyclohexanone, 3-methylcyclohexanone, 1,2,3,4-tetrahydro-1-oxonaphthalene, 1,2,3,4-tetrahydro-2-naphthalenone, 2-oxo-5-methoxy-1,2,3,4-tetrahydronaphthalene and 1-indone, each example including its structure enantionmers and isomers, as the case may be and where possible, and including all possible salts thereof.

Preferably, the ATA according to the invention converting a ketone substrate to an amine, or vice versa an amine to a ketone product has a
   a high thermostability,
   has a high specific activity
   allows for a high conversion activity under different reaction conditions involving high amine concentrations.

It was surprisingly found, that the ATA of SEQ ID NO:3 according to the invention shows superior thermostability, specific activity, and conversion under certain amine concentrations in comparison to other ATAs currently described.

In particular, it has surprisingly been found, that the ATA according to the invention converting a ketone substrate to an amine, or vice versa an amine to a ketone product already has a high stability at mesophilic or high temperatures, measured as a high Tm(80%) value as described in Example 5 below. Preferably, the ATA according to the invention has a $T_m(80\%)$ value of at least 55° C., preferably of at least 56° C., preferably of at least 57° C., preferably of at least 58° C., preferably of at least 59° C., and most preferably of at least 60° C.

In particular, it furthermore has been surprisingly found, that the ATA according to the invention converting a ketone substrate to an amine product, or vice versa an amine substrate to a ketone product already has a high specific activity under Transaminase Standard Conditions as described in Example 2 below. In particular, the ATA according to the invention has a high specific activity for the conversion of racemic 1-phenylethan-1-amine (MBA) and pyruvate to 1-phenylethanone (acetophenone) and L-alanine as described below. Preferably, the specific activity of the ATA according to the invention in converting a ketone substrate to an amine, or vice versa an amine to a ketone product under Transaminase Standard Conditions is at least 0.5 U/mg, preferably at least 0.6 U/mg, preferably at least 0.7 U/mg, preferably at least 0.8 U/mg, preferably at least 0.9 U/mg, preferably at least 1 U/mg, most preferably at least 1.1 U/mg.

In particular, it furthermore has been surprisingly found, that the ATA according to the invention converting a ketone substrate to an amine product, or vice versa an amine substrate to a ketone product shows high conversion of a substrate at certain concentrations of different amine donor co-substrates of industrial relevance. In particular, the ATA according to the invention shows high conversion properties at reaction conditions of relevant for preparative synthesis applications with the different amine donors, isopropylamine (IPA), racemic 1-phenylethan-1-amine (MBA) or racemic alanine, respectively with the substrate 4-phenyl-2-butanone (BA) as described in Example 3. In particular the ATA according to the invention is very efficient in conversion upon at the Condition A (50 mM BA, 100 mM IPA), the Condition B (50 mM BA, 200 mM rac. MBA), the Condition C (50 mM BA, 500 mM IPA), the Condition D (50 mM BA, 1000 mM rac. MBA), or the Condition E (50 mM BA, 200 mM racemic alanine).

Preferably, the ATA according to the invention in converting a ketone substrate to an amine product, or vice versa an amine substrate to a ketone product under Transaminase Conversion Assay conditions shows a conversion of at Condition A a conversion of at least 5%, preferably of at least 6%, preferably of at least 7%, preferably of at least 8%, preferably of at least 9%, preferably of at least 10%, preferably of at least 11%, and most preferably of at least 11.9%; and/or at Condition B a conversion of at least 10%, preferably of at least 20%, preferably of at least 30%, preferably of at least 40%, preferably of at least 50%, preferably of at least 60%, preferably of at least 70%, and most preferably of at least 71%; and/or at Condition C a conversion of at least 10%, preferably of at least 20%, preferably of at least 25%, and most preferably of at least 25.8%; and/or at Condition D a conversion of at least 1%, preferably of at least 2%, preferably of at least 3%, preferably of at least 3.5%, and most preferably of at least 3.7%; and/or at Condition E a conversion of at least 2%, preferably of at least 2.5%, preferably of at least 3%, and most preferably of at least 3.2%.

In preferred embodiments, the ATA according to the invention is a derivative of SEQ ID NO:3 obtainable by protein engineering, i.e. the ATA according to the invention can preferably be regarded as an engineered ATA with respect to the wildtype of SEQ ID NO:3.

It has been surprisingly found that upon selective engineering, the characteristics of an ATA variant with respect to industrial use can be even further enhanced, and that ATA variants can be obtained that exhibit in comparison to the wildtype sequence of SEQ ID NO:3
an improved stereoselectivity, and/or
an increased thermostability, and/or
an increased conversion.

Therefore, in some embodiments the ATA according to the invention exhibits improved properties, e.g. conversion, thermostability, and/or stereoselectivity upon engineering of SEQ ID NO:3.

Preferably, with respect to SEQ ID NO:3 the ATA according to the invention is engineered in at least one or more positions such that (A) the stereoselectivity of the engineered ATA is higher than that of the wildtype ATA of SEQ ID NO:3, in particular such that the stereoselectivity measured as an enantiomeric excess (% ee) is at least 50% ee, preferably alt least 60% ee, more preferably at least 65% ee, more preferably at least 70% ee, still more preferably at least 75% ee, still more preferably at least 80% ee, still more preferably at least 85% ee, still more preferably at least 90% ee, yet more preferably at least 91% ee, yet more preferably at least 92% ee, yet more preferably at least 93% ee, yet more preferably at least 94% ee, yet more preferably at least 95% ee, yet more preferably at least 96% ee, even more preferably at least 97% ee, most preferably at least 98% ee, and in particular at least 99% ee, and in particular at least 99.9% ee; and/or (B) the thermostability of the engineered ATA is higher than that of the wildtype ATA of SEQ ID NO:3, in particular such that the ATA is stable at at least 65° C., more preferably at at least 70° C., still more preferably at at least 75° C., still more preferably at least 76° C., still more preferably at at least 77° C., still more preferably at at least 78° C., still more preferably at at least 79° C., still more preferably at at least 80° C., still more preferably at at least 81° C., still more preferably at at least 82° C., still more preferably at at least 83° C., still more preferably at at least 84° C. and most preferably at at least 85° C.; and/or (C) the conversion of the engineered ATA is higher than that of the wildtype ATA of SEQ ID NO:3, in particular such that the conversion rate
at Condition G is at least 5.0%, preferably at least 5.1%, at least 5.2%, at least 5.3%, at least 5.4%, at least 5.5%, at least 5.6%, at least 5.7%, at least 5.8%, at least 5.9%, at least 6%, at least 7%, at least 8%, at least 9%, at least 10%, at least 11%, at least 12%, or at least 13%, more preferably at least 14%, and most preferably at least 15%; and/or
at Condition H is at least 34%, preferably at least 35%, preferably at least 36%, preferably at least 37%, preferably at least 38%, preferably at least 39%, preferably at least 40%, preferably at least 41%, preferably at least 42%, preferably at least 43%, preferably at least 44%, preferably at least 45%, preferably at least 46%, preferably at least 47%, preferably at least 48%, preferably at least 49%, preferably at least 50%, preferably at least 51%, preferably at least 52%, preferably at least 53%, preferably at least 54%, preferably at least 55%, preferably at least 66%, preferably at least 67%, preferably at least 58%, preferably at least 59%, preferably at least 60%, preferably at least 61%, preferably at least 62%, preferably at least 63%, preferably at least 64%, preferably at least 65%, preferably at least 66%, preferably at least 67%, preferably at least 68%, preferably at least 69%, more preferably at least 70%, more preferably at least 80%, more preferably at least 90%, more preferably at least 95%, more preferably at least 98%, more preferably at least 99%; and most preferably at least 99.9%; and/or.

at Condition I is at least 30%, preferably at least 35%, preferably at least 40%, preferably at least 45%, preferably at least 46%, preferably at least 47%, preferably at least 48%, preferably at least 49%, preferably at least 50%, preferably at least 51%, preferably at least 52%, preferably at least 53%, preferably at least 54%, preferably at least 55%, preferably at least 56%, preferably at least 57%, preferably at least 58%, preferably at least 59%, preferably at least 60%, preferably at least 61%, preferably at least 62%, preferably at least 63%, preferably at least 64%, preferably at least 65%, preferably at least 66%, preferably at least 67%, preferably at least 68%, preferably at least 69%, preferably at least 70%, preferably at least 71%, preferably at least 72%, preferably at least 73%, preferably at least 74%, preferably at least 75%, preferably at least 76%, preferably at least 77%, preferably at least 78%, preferably at least 79%, preferably at least 80% preferably at least 81%, preferably at least 82%, preferably at least 83%, preferably at least 84%, preferably at least 85%, preferably at least 86%, preferably at least 87%, preferably at least 88%, preferably at least 89%, preferably at least 90% preferably at least 91%, preferably at least 92%, preferably at least 93%, preferably at least 94%, preferably at least 95%, preferably at least 96%, preferably at least 97%, preferably at least 98%, preferably at least 99%, and most preferably at least 99.9%; and/or at Condition J is at least 30%, preferably at least 35%, preferably at least 40%, preferably at least 45%, preferably at least 50%, preferably at least 55%, preferably at least 60%, preferably at least 65%, preferably at least 70%, preferably at least 75%, preferably at least 76%, preferably at least 77%, preferably at least 78%, preferably at least 79%, preferably at least 80% preferably at least 81%, preferably at least 82%, preferably at least 83%, preferably at least 84%, preferably at least 85%, preferably at least 86%, preferably at least 87%, preferably at least 88%, preferably at least 89%, preferably at least 90% preferably at least 91%, preferably at least 92%, preferably at least 93%, preferably at least 94%, preferably at least 95%, preferably at least 96%, preferably at least 97%, preferably at least 98%, preferably at least 99%, and most preferably at least 99.9%.

For the purpose of the specification, stereoselectivity is the property of a chemical reaction in which a single reactant forms an unequal mixture of stereoisomers during the non-stereospecific creation of a new stereocenter or during the non-stereospecific transformation of a pre-existing one. The selectivity typically arises from differences in steric effects and electronic effects in the mechanistic pathways leading to the different products. The enantiomeric excess (ee) of one chiral product over the other product obtained from an enzymatic reaction is a measure for the stereoselectivity of the enzyme, in particular of the ATA according to the invention:

$$\% \ ee = \frac{[\text{product(chirality1)}] - [\text{product(chirality2)}]}{[\text{product(chirality1)}] + [\text{product(chirality2)}]}.$$

The enantiomeric excess (expressed in percent) is calculated as the difference between the quantity of two products with differing chirality (product(chirality 1), product(chirality2)) expressed as absolute value divided by the sum of the concentration of both products, multiplied by 100. Preferably, the conversion of a substrate into a chiral product under catalysis of the ATA according to the invention provides the desired chiral product with an enantiomeric excess of at least 50% ee, more preferably at least 60% ee, more preferably at least 65% ee, more preferably at least 70% ee, more preferably at least 75% ee, still more preferably at least 80% ee, still more preferably at least 85% ee, still more preferably at least 90% ee, yet more preferably at least 91% ee, yet more preferably at least 92% ee, yet more preferably at least 93% ee, yet more preferably at least 94% ee, yet more preferably at least 95% ee, yet more preferably at least 96% ee, even more preferably at least 97% ee, most preferably at least 98% ee, and in particular at least 99% ee, and in particular at least 99.9% ee.

An improved stereoselectivity according to the invention relates to an enantiomeric excess of the product provided by means of an engineered ATA which is higher than the enantiomeric excess of the product provided by means of the non-engineered ATA of SEQ ID NO:3. Preferably, the enantiomeric excess provided by an engineered ATA is increased by at least 0.1% ee, at least 0.5% ee, at least 1% ee, at least 3% ee, at least 5% ee, at least 7% ee, at least 9% ee, at least 11% ee, at least 13% ee, at least 15% ee, at least 17% ee, at least 19% ee, at least 21% ee, at least 23% ee, at least 25% ee, at least 27% ee, at least 29% ee, at least 31% ee, at least 32% ee, at least 33% ee, at least 34% ee, at least 35% ee, at least 36% ee, at least at least 37% ee, at least 38% ee, at least 39% ee, at least 40% ee, at least 41% ee, at least 42% ee, at least 43% ee, at least 44% ee, at least 45% ee, at least 46% ee, at least 47% ee, at least 48% ee, at least 49% ee, at least 50% ee, at least 55% ee, or at least 60% ee, at least 65% ee, at least 70% ee, at least 75% ee, at least 80% ee, at least 85% ee, at least 90% ee, at least 95% ee, at least 97% ee, at least 98% ee, at least 99% ee, or at least 99.5% ee and in particular at least 99.9% ee compared to the non-engineered ATA of SEQ ID NO:3 for a given substrate. The improved stereoselectivity may also mean that the engineered ATA does have a certain stereoselectivity towards the desired chiral product, whereas the non-engineered ATA has no significant stereoselectivity towards said chiral product. The improved stereoselectivity may also mean that the engineered ATA has a certain stereoselectivity towards one desired chiral product, whereas the non-engineered ATA has a stereoselectivity towards the reverse chiral product, e.g. the engineered ATA has a stereoselectivity for building an (R)-amine while the non-engineered ATA has a stereoselectivity for the (S)-amine and vice versa.

For the purpose of the specification, thermostability is the property of an enzyme to retain enzymatic activity upon incubation at high temperatures for a given time. The enzyme activity thereby can be determined at any assay conditions. For the purpose of this invention, the thermostability is expressed as Tm(80%) value, indicating the temperature at which an enzyme retains 80% of its in initial enzyme activity upon incubation in a given buffer system for 15 minutes at said temperature.

The thermostability of an ATA according to the invention, preferably the thermostability of the wild type ATA of SEQ ID NO:3 or an engineered ATA according to this invention, is preferably determined by incubation of the ATA containing crude extract for 15 minutes at several given temperatures in a PCR cycler. One sample of each ATA crude extract is incubated for 15 minutes in ice as a reference. Afterwards all crude extracts are incubated on ice for 30 minutes. Insoluble proteins are separated by centrifugation and the supernatant is analyzed regarding its remaining ATA activity in the Transaminase Standard Assay as described in Example 2 monitoring the conversion of 1-phenylethan-1-amine (MBA) and pyruvate to 1-phenylethanone (Acetophenone) and L-alanine.

An improved thermostability according to the invention relates to a higher Tm(80%) value of an engineered ATA in comparison to the non-engineered ATA of SEQ ID NO:3. Preferably, the Tm(80%) value is increased by at least 1° C., at least 2° C., at least 3° C., at least 4° C., at least 5° C., at least 6° C., at least 7° C., at least 8° C., at least 9° C., at least 10° C., at least 11° C., at least 12° C., at least 13° C., at least 14° C., at least 15° C., at least 16° C., at least 17° C., at least 18° C., at least 19° C., at least 20° C., at least 21° C., at least 22° C., at least 23° C., at least 24° C., at least 25° C., and most preferably at least 30° C. compared to the non-engineered ATA of SEQ ID NO:3.

For the purpose of the specification, the conversion of an enzyme according this invention is the yield of a given product after a given time in a reaction involving the enzyme. For the purpose of this invention, the conversion rate is expressed as X % conversion after a given time using 4-phenyl-2-butanone as substrate together with isopropylamine (IPA) or (S)-1-phenylethan-1-amine (S-MBA) as amine donor to the corresponding product 1-methyl-3-phenylpropylamine and acetone or 1-phenylethanone (acetophenone) under a respective condition. While the conversion of a given ATA according this invention may deviate depending on different substrates used, the improved conversion of an engineered ATA according to this invention can be determined in either of the Transaminase Conversion Assay conditions Condition G (150 mM BA, 300 mM IPA), Condition H (150 mM BA, 300 mM (S)-MBA), Condition I (150 mM BA, 1000 mM IPA) and/or Condition J (50 mM BA, 1000 mM IPA) as described in Example 6 below.

An improved conversion according to the invention relates to a conversion of an engineered ATA which is higher than the conversion of the non-engineered ATA of SEQ ID NO:3 under a respective Condition. Preferably, the conversion is either
under Condition G: at least 0.1%, preferably at least 0.2%, at 0.3%, at least 0.4%, at least 0.5%, at least 1%, at least 1.5%, at least 2%, at least 2.5%, at least 3%, more preferably at least 3.5%, more preferably at least 4%, more preferably at least 4.5%, more preferably at least 5%, more preferably at least 6%, more preferably at least 7%, more preferably at least 8%, more preferably at least 9%, more preferably at least 10%, and most preferably at least 20% higher than the conversion of the non-engineered ATA of SEQ ID NO:3; and/or
under Condition H: at least 0.1%, preferably at least 0.2%, at 0.3%, at least 0.4%, at least 0.5%, at least 1%, at least 1.5%, at least 2.5%, at least 5%, at least 7.5%, more preferably at least 10%, more preferably at least 12.5%, more preferably at least 15%, more preferably at least 17.5%, more preferably at least 20%, more preferably at least 22.5%, more preferably at least 25%, more preferably at least 27.5%, more preferably at least 30%, and most preferably at least 40% higher than the conversion of the non-engineered ATA of SEQ ID NO:3; and/or
under Condition I: is at least 30%, preferably at least 35%, preferably at least 40%, preferably at least 45%, preferably at least 46%, preferably at least 47%, preferably at least 48%, preferably at least 49%, preferably at least 50%, preferably at least 51%, preferably at least 52%, preferably at least 53%, preferably at least 54%, preferably at least 55%, preferably at least 56%, preferably at least 57%, preferably at least 58%, preferably at least 59%, preferably at least 60%, preferably at least 61%, preferably at least 62%, preferably at least 63%, preferably at least 64%, preferably at least 65%, preferably at least 66%, preferably at least 67%, preferably at least 68%, preferably at least 69%, preferably at least 70%, preferably at least 71%, preferably at least 72%, preferably at least 73%, preferably at least 74%, preferably at least 75%, preferably at least 76%, preferably at least 77%, preferably at least 78%, preferably at least 79%, preferably at least 80% preferably at least 81%, preferably at least 82%, preferably at least 83%, preferably at least 84%, preferably at least 85%, preferably at least 86%, preferably at least 87%, preferably at least 88%, preferably at least 89%, preferably at least 90% preferably at least 91%, preferably at least 92%, preferably at least 93%, preferably at least 94%, preferably at least 95%, preferably at least 96%, preferably at least 97%, preferably at least 98%, most preferably at least 99%, higher than the conversion of the non-engineered ATA of SEQ ID NO:3; and/or
under Condition J: is at least 30%, preferably at least 35%, preferably at least 40%, preferably at least 45%, preferably at least 50%, preferably at least 55%, preferably at least 60%, preferably at least 65%, preferably at least 70%, preferably at least 75%, preferably at least 76%, preferably at least 77%, preferably at least 78%, preferably at least 79%, preferably at least 80% preferably at least 81%, preferably at least 82%, preferably at least 83%, preferably at least 84%, preferably at least 85%, preferably at least 86%, preferably at least 87%, preferably at least 88%, preferably at least 89%, preferably at least 90% preferably at least 91%, preferably at least 92%, preferably at least 93%, preferably at least 94%, preferably at least 95%, preferably at least 96%, preferably at least 97%, preferably at least 98%, most preferably at least 99% higher than the conversion of the non-engineered ATA of SEQ ID NO:3.

For the purpose of the specification, "engineered ATA" refers to an ATA differing from the specified wildtype sequence, e.g. the non-engineered ATA of SEQ ID NO:3. Engineering can mean substitution of an amino acid residue of the specified wildtype sequence by another amino acid residue. In addition, engineering can also mean deletion of an amino acid residue of the specified wildtype sequence, or insertion of an amino acid residue into the specified wildtype sequence, or substitution of an amino acid residue of the specified wildtype sequence by more than a single other amino acid residues.

In a preferred embodiment, the engineered ATA according to the invention differs from the wildtype ATA of SEQ ID NO:3 by 1 to 70 amino acids, typically by 1 to 50 amino acids, more typically by 1 to 30 amino acids, even more typically by 1 to 25 amino acids, even more typically by 1 to 20 amino acids, even more typically by 1 to 15 amino acids, even more typically by 1 to 10 amino acids, even more typically by 1 to 5 amino acids, and most typically by 1 to 4 amino acids.

In this regard, engineering means that one or more amino acids in a given position are substituted with any other proteinogenic amino acid selected from the group consisting of Ala, Arg, Asn, Asp, Cys, Gln, Glu, Gly, His, Ile, Leu, Lys, Met, Phe, Pro, Ser, Thr, Trp Tyr, and Val. In a preferred embodiment, the substitution does not alter the sequence length, i.e. a single amino acid residue is replaced by another single amino acid residue. However, it is also possible to delete one or more amino acid residues without replacement and/or to insert one or more amino acid residues.

In one specific embodiment, the engineered ATA according to the invention is a fragment of at least 380 amino acid residues, more preferably at least 400 amino acid residues, more preferably at least 420 amino acid residues, more preferably at least 425 amino acid residues, more preferably at least 430 amino acid residues, more preferably at least 435 amino acid residues, more preferably at least 440 amino acid residues, more preferably at least 445 amino acid residues, and most preferably at least 446 amino acids residues of the polypeptide of SEQ ID NO:3. In this regard, "fragment" refers to a consecutive subsequence of the respective SEQ ID NO:3, but that is shortened at the N-terminus and/or the C-terminus.

In principle, a substitution in any position of an enzyme may be a conservative substitution where such amino acid is substituted with an amino acid of comparable characteristics (e.g. substitution of a hydrophobic amino acid with another hydrophobic amino acid). In addition, a substitution in any position of an enzyme may be a non-conservative substitution where such amino acid is substituted with an amino acid of other characteristics (e.g. substitution of a hydrophobic amino acid with a hydrophilic amino acid).

The technique of enzyme engineering is reviewed in: S. Lutz, U. T. Bornscheuer, Protein Engineering Handbook, Wiley VCH, Weinheim, 2009.

Any substitution according to this invention excludes amino acid substitutions in positions of the ATA according to the invention, which are indispensable for the catalytic activity of the ATA, preferably position K284 of SEQ ID NO:3. It is furthermore known in the state of the art, that sequence positions participating in predictable protein structure elements, e.g. alpha helices, or beta sheets, or ionic interactions, are sensitive to mutagenesis and may require no substitution or only concomitant substitution with a counter-position.

In a preferred embodiment, the engineered ATA according to the invention differs from the wildtype ATA of SEQ ID NO:3 by 1 to 70 amino acids, typically by 1 to 50 amino acids, more typically by 1 to 30 amino acids, even more typically by 1 to 25 amino acids, even more typically by 1 to 20 amino acids, even more typically by 1 to 15 amino acids, even more typically by 1 to 10 amino acids, even more typically by 1 to 5 amino acids, and most typically by 1 to 4 amino acids and in addition is a fusion protein of the amino acid sequence with any other amino acid, oligo- or polypeptide, which is fused to the N-terminus and/or the C-terminus.

In a preferred embodiment, the engineered ATA according to the invention is a fusion protein that comprises the wildtype ATA of SEQ ID NO:3 which differs by 1 to 70 amino acids, typically by 1 to 50 amino acids, more typically by 1 to 30 amino acids, even more typically by 1 to 25 amino acids, even more typically by 1 to 20 amino acids, even more typically by 1 to 15 amino acids, even more typically by 1 to 10 amino acids, even more typically by 1 to 5 amino acids, and most typically by 1 to 4 amino acids, and additionally, at least 1 amino acid residues, at least 2 amino acid residues, at least 4 amino acid residues, at least 6 amino acid residues, at least 10 amino acid residues, more preferably at least 20 amino acid residues, even more preferably at least 30 amino acid residues, and most preferably at least 40 amino acid residues, independently selected from the group consisting of Ala, Arg, Asn, Asp, Cys, Gln, Glu, Gly, His, Ile, Leu, Lys, Met, Phe, Pro, Ser, Thr, Trp Tyr, and Val.

Preferably, the transaminase according to the invention comprises at least two substitutions selected from the group consisting of N161A, N161F, N161M, N161Y, N161Q, N161I, Y164L, Y164M, Y164A, Y164F, Y164I, and G51S.

Preferably, the transaminase according to the invention comprises a substitution selected from the group consisting of N161A, N161C, N161D, N161E, N161G, N161I, N161K, N161L, N161M, N161P, N161Q, N161R, N161S, N161T, N161V, N161W, and N161Y; more preferably selected from the group consisting of N161A, N161F, N161M, N161Y, N161Q, and N161I.

Preferably, the transaminase according to the invention comprises a substitution selected from the group consisting of Y164A, Y164C, Y164D, Y164E, Y164F, Y164G, Y164H, Y164I, Y164K, Y164L, Y164M, Y164N, Y164P, Y164Q, Y164R, Y164S, Y164T, Y164V, and Y164W; more preferably selected from the group consisting of Y164L, Y164M, Y164A, Y164F, and Y164I.

Preferably, the transaminase according to the invention comprises a substitution selected from the group consisting of G51A, G51C, G51D, G51E, G51F, G51H, G51I, G51K, G51L, G51M, G51N, G51P, G51Q, G51R, G51S, 51T, G51V, G51W, and G51Y; more preferably G51S.

The invention also relates to engineered ATA that differ from the amino acid sequence of the wildtype ATA of SEQ ID NO:3 by 1 to 70 residue changes, preferably by 1 to 50 residue changes, more preferably by 1 to 30 residue changes, even more preferably by 1 to 25 residue changes, even more preferably by 1 to 20 residue changes, even more preferably by 1 to 15 residue changes, even more preferably by 1 to 10 residue changes, even more preferably by 1 to 5 residue changes and most preferably by 1 to 4 residue changes, preferably including changes at one or more of the following positions of SEQ ID NO:3: N7, E9, M16, V29, G33, Q44, R45, G51, L53, W54, A67, A68, A71, L73, F82, H87, V109, G114, R140, N146, G147, Y148, Y151, N161, Y164, H165, E222, A227, G228, V230, V257, V258, A288, Q300, A349, A353, Q354, Y366, M378, Q391, R415, I417, K420, I422, T430, and E433.

Preferably, the engineered ATA according to the invention differs from the amino acid sequence of the wildtype ATA of SEQ ID NO:3 by 1 to 70, more preferably by 1 to 50, still more preferably by 1 to 30, even more preferably by 1 to 25, even more preferably by 1 to 20, even more preferably by 1 to 15, even more preferably by 1 to 10 residue changes, even more preferably by 1 to 5 residue changes and most preferably by 1 to 4 residue changes, preferably including one or more of the following residue changes: N7L, E9R, M16F, M16C, M16V, M16L, M16A, M16W, V29L, V29I, G33Y, Q44R, Q44N, Q44H, R45K, G51S, L53F, L53W, L53V, L53A, L53S, L53G, W54A, W54I, W54L, W54Y, W54S, W54C, W54F, W54V, A67N, A68P, A71G, L73M, F82V, F82A, F82G, F82L, F82Y, H87T H87N, V109I, G114S, R140K, N146Y, N146D, N146S, G147S, Y148F, Y148S, Y148G, V151A, V151W, V151I, V151F, V151Y, V151S, N161A, N161F, N161M, N161Y, N161Q, N161I, Y164L, Y164M, Y164A, Y164F, Y164I, H165R, E222S, E222A, E222D, A227Y, A227V, A227I, A227G, A227F, A227M, G228A, G228I, V230A, V230G, V230I, V230L, V257A, V258I, V258A, A288G, Q300E, A349G, A353R, Q354F, Y366H, Y366F, M378L, M378V, M378I, M378F, M378Y, M378T, M378A, M378C, Q391K, Q391E, R415A, R415V, R415L, R415G, R415Y, R415T, R415C, I417T, I417C, I417F, I417V, I417Y, I417A, K420H, K420S, K420N, I422V, I422S, I422A, I422L, T430N, and E433D.

Preferably, the ATA according to the invention is engineered compared to SEQ ID NO:3 in at least one or more positions selected from the group consisting of the positions N7, E9, M16, V29, G33, Q44, R45, G51, L53, W54, A67, A68, A71, L73, F82, H87, V109, G114, R140, N146, G147, Y148, Y151, N161, Y164, H165, E222, A227, G228, V230, V257, V258, A288, Q300, A349, A353, Q354, Y366, M378, Q391, R415, I417, K420, I422, T430, and E433.

More preferably, the ATA according to the invention is engineered compared to SEQ ID NO:3 in at least one or more positions selected from the group consisting of the positions N7, E9, M16, G33, R45, G51, L53, W54, A67, A68, A71, L73, F82, H87, V109, G114, R140, N146, G147, Y148, Y151, N161, Y164, H165, E222, A227, G228, V230, V257, V258, A288, Q300, A349, A353, Q354, Y366, M378, Q391, R415, I417, K420, I422, T430, and E433.

Still more preferably, the ATA according to the invention is engineered compared to SEQ ID NO:3 in at least one or more positions selected from the group consisting of the positions N7, E9, M16, G33, R45, G51, L53, W54, A67, A68, A71, L73, F82, H87, V109, G114, R140, N146, G147, Y148, Y151, N161, Y164, H165, E222, A227, G228, V230, V257, V258, A288, Q300, A353, Q354, Y366, M378, Q391, R415, I417, K420, T430, and E433.

In particularly preferred embodiments, the ATA according to the invention is engineered compared to SEQ ID NO:3 in at least one or more positions such that it comprises at least one or more substitutions selected from the group consisting of
  at position N7 substitution to N7L; and/or
  at position E9 substitution to E9R; and/or
  at position M16 substitution to M16F, M16C, M16V, M16L, M16A, or M16W; preferably M16C, M16W, or M16F; and/or
  at position V29 substitution to V29L or V29I; preferably V29L; and/or
  at position G33 substitution to G33Y; and/or
  at position Q44 substitution to Q44R, Q44N, or Q44H; preferably Q44R or Q44N; and/or
  at position R45 substitution to R45K; and/or
  at position G51 substitution to G51 S; and/or
  at position L53 substitution to L53F, L53W, L53V, L53A, L53S, or L53G; and/or
  at position W54 substitution to W54A, W54I, W54L, W54Y, W54S, W54C, W54F, or W54V; preferably W54I, W54L, W54Y, or W54A; and/or
  at position A67 substitution to A67N; and/or
  at position A68 substitution to A68P; and/or
  at position A71 substitution to A71G; and/or
  at position L73 substitution to L73M; and/or
  at position F82 substitution to F82V, F82A, F82G, F82L, or F82Y; and/or
  at position H87 substitution to H87T or H87N; and/or
  at position V109 substitution to V109I; and/or
  at position G114 substitution to G114S; and/or
  at position R140 substitution to R140K; and/or
  at position N146 substitution to N146Y, N146D, or N146S; preferably, N146Y and/or
  at position G147 substitution to G147S; and/or
  at position Y148 substitution to Y148F, Y148S, or Y148G; and/or
  at position V151 substitution to V151A, V151W, V151I, V151F, V151Y, or V151S; and/or
  at position N161 substitution to N161A, N161F, N161M, N161Y, N161Q, or N161I; preferably N161M, N161Q, N161I, N161A, or N161F; and/or
  at position Y164 substitution to Y164L, Y164M, Y164A, Y164F, or Y164I; preferably Y164L, Y164F, Y164M or Y164I; and/or
  at position H165 substitution to H165R; and/or
  at position E222 substitution to E222S, E222A, or E222D; and/or
  at position A227 substitution to A227Y, A227V, A227I, A227G, A227F, or A227M; preferably A227Y; and/or
  at position G228 substitution to G228A, or G228I; preferably G228A; and/or
  at position V230 substitution to V230A, V230G, V230I, or V230L; preferably V230A; and/or
  at position V257 substitution to V257A; and/or
  at position V258 substitution to V258A or V258I; preferably V258I; and/or
  at position A288 substitution to A288G; and/or
  at position Q300 substitution to Q300E; and/or
  at position A349 substitution to A349G; and/or
  at position A353 substitution to A353R; and/or
  at position Q354 substitution to Q354F; and/or
  at position Y366 substitution to Y366H or Y366F; and/or
  at position M378 substitution to M378L, M378V, M378I, M378F, M378Y, M378T, M378A, or M378C; and/or
  at position Q391 substitution to Q391K or Q391E; and/or
  at position R415 substitution to R415A, R415V, R415L, R415G, R415Y, R415T, or R415C; preferably R415A, R415V, or R415L; and/or
  at position I417 substitution to I417T, I417C, I417F, I417V, I417Y, or I417A; preferably I417V, I417T, I417C, I417A, or I417F; and/or
  at position K420 substitution to K420H, K420S, or K420N; and/or
  at position I422 substitution to I422V, I422S, I422A, I422L or I422C; preferably I422S, I422C, or I422V; more preferably I422S or I422C;
  at position T430 substitution to T430N; and/or
  at position E433 substitution to E433D.

Preferably, the ATA according to the invention is engineered compared to SEQ ID NO:3 in
(I) at least one position selected from the group consisting of N7, E9, M16, V29, G33, Q44, R45, G51, L53, W54, A67, A68, A71, L73, F82, H87, V109, G114, R140, N146, G147, Y148, Y151, N161, Y164, H165, E222, A227, G228, V230, V257, V258, A288, Q300, A349, A353, Q354, Y366, M378, Q391, R415, I417, K420, I422, T430, and E433; and
(II) in addition in at least one other position selected from the group consisting of N7, E9, M16, V29, G33, Q44, R45, G51, L53, W54, A67, A68, A71, L73, F82, H87, V109, G114, R140, N146, G147, Y148, Y151, N161, Y164, H165, E222, A227, G228, V230, V257, V258, A288, Q300, A349, A353, Q354, Y366, M378, Q391, R415, I417, K420, I422, T430, and E433.

Preferably, the ATA according to the invention is engineered compared to SEQ ID NO:3 in
(I) at least one position selected from the group consisting of M16, L53, W54, F82, N146, Y148, Y151, N161, Y164, E222, A227, G228, V230, V257, V258, M378, R415, I417, and I422; and (II) in addition in at least one other position selected from the group consisting of N7, E9, M16, V29, G33, Q44, R45, G51, L53, W54, A67, A68, A71, L73, F82, H87, V109, G114, R140, N146, G147, Y148, Y151, N161, Y164, H165, E222, A227, G228, V230, V257, V258, A288, Q300, A349, A353, Q354, Y366, M378, Q391, R415, I417, K420, I422, T430, and E433.

Preferably, the ATA according to the invention is engineered compared to SEQ ID NO:3 in (I) at least one position selected from the group consisting of M16, W54, N146, N161, Y164, A227, G228, V230, V258, R415, I417, and I422; and (II) in addition in at least one other position selected from the group consisting of N7, E9, M16, V29, G33, Q44, R45, G51, L53, W54, A67, A68, A71, L73, F82, H87, V109, G114, R140, N146, G147, Y148, Y151, N161, Y164, H165, E222, A227, G228, V230, V257, V258, A288, Q300, A349, A353, Q354, Y366, M378, Q391, R415, I417, K420, I422, T430, and E433.

More preferably, the ATA according to the invention is engineered compared to SEQ ID NO:3 in (I) at least one position selected from the group consisting of M16, W54, N146, N161, Y164, A227, G228, V230, V258, R415, I417, and I422; and (II) in addition in at least one other position selected from the group consisting of N7, E9, M16, G33, R45, G51, L53, W54, A67, A68, A71, L73, F82, H87, V109, G114, R140, N146, G147, Y148, Y151, N161, Y164, H165, E222, A227, G228, V230, V257, V258, A288, Q300, A349, A353, Q354, Y366, M378, Q391, R415, I417, K420, I422, T430, and E433.

Still more preferably, the ATA according to the invention is engineered compared to SEQ ID NO:3 in (I) at least one position selected from the group consisting of M16, W54, N146, N161, Y164, A227, G228, V230, V258, R415, and I417; and (II) in addition in at least one other position selected from the group consisting of N7, E9, M16, G33, R45, G51, L53, W54, A67, A68, A71, L73, F82, H87, V109, G114, R140, N146, G147, Y148, Y151, N161, Y164, H165, E222, A227, G228, V230, V257, V258, A288, Q300, A353, Q354, Y366, M378, Q391, R415, I417, K420, T430, and E433.

Preferably, the ATA according to the invention is engineered compared to SEQ ID NO:3 in at least two positions selected from the group consisting of N161 as well as Y164;
I417 as well as I422; and
N146 as well as N161.

Preferably, the ATA according to the invention is engineered compared to SEQ ID NO:3 in at least two positions such that it comprises (i) at position N161 a substitution selected from the group consisting of N161A, N161F, N161M, N161Y, N161I, or N161Q; preferably N161A, N161F, N161M, N161Q, or N161I; more preferably N161M, N161Q, or N161I; as well as at position Y164 a substitution selected from the group consisting of Y164L, Y164M, Y164A, Y164F, or Y164I; preferably Y164L, Y164M, Y164F or Y164I; and/or (ii) at position I417 a substitution selected from the group consisting of I417T, I417C, I417F, I417V, I417Y, or I417A; preferably I417T, I417C, I417F, I417V, or I417A; more preferably I417V, I417F, or I417A; as well as at position I422 a substitution selected from the group consisting of I422V, I422S, I422A, I422L, or I422C; preferably I422S, I422C, or I422V; more preferably I422S or I422C; and/or (iii) at position N146 a substitution selected from the group consisting of N146Y, N146D, or N146S; preferably N146Y; as well as at position N161 a substitution selected from the group consisting of N161A, N161F, N161M, N161Y, N161I, or N161Q; preferably N161A, N161F, N161M, N161Q, or N161I; more preferably N161M, N161Q, or N161I; and most preferably N161Q.

Preferably, the ATA according to the invention is engineered compared to SEQ ID NO:3 in at least two positions such that it comprises at least two substitutions selected from the group consisting of the substitutions N161M as well as Y164L; N161I as well as Y164L; N161Q as well as Y164L; N161I as well as Y164M; N161M as well as Y164M; N161Q as well as Y164M; N161I as well as Y164F; N161M as well as Y164I; I417V as well as I422S; I417V as well as I422C; I417A as well as I422S; I417F as well as I422V; I417A as well as I422C; and N146Y as well as N161Q.

More preferably, the ATA according to the invention is engineered compared to SEQ ID NO:3 in at least two positions such that it comprises at least two substitutions selected from the group consisting of the substitutions N161I as well as Y164L; N161M as well as Y164I; N161Q as well as Y164L; I417V as well as I422S; I417V as well as I422C; I417A as well as I422S; and I417A as well as I422C.

Still more preferably, the ATA according to the invention is engineered compared to SEQ ID NO:3 in at least two positions such that it comprises at least the two substitutions N161I as well as Y164L.

Preferably, the ATA according to the invention is engineered compared to SEQ ID NO:3 in (i) at least two positions selected from the group consisting of N161 as well as Y164; or I417 as well as I422; or N146 as well as N161; and (ii) in addition in at least one other position selected from the group consisting of N7, E9, M16, V29, G33, Q44, R45, G51, L53, W54, A67, A68, A71, L73, F82, H87, V109, G114, R140, N146, G147, Y148, Y151, N161, Y164, H165, E222, A227, G228, V230, V257, V258, A288, Q300, A349, A353, Q354, Y366, M378, Q391, R415, I417, K420, I422, T430, and E433.

More preferably, the ATA according to the invention is engineered compared to SEQ ID NO:3 in (i) at least two positions selected from the group consisting of N161 as well as Y164; or I417 as well as I422; or N146 as well as N161; and (ii) in addition in at least one other position selected from the group consisting of N7, E9, M16, G33, R45, G51, L53, W54, A67, A68, A71, L73, F82, H87, V109, G114, R140, N146, G147, Y148, Y151, N161, Y164, H165, E222, A227, G228, V230, V257, V258, A288, Q300, A349, A353, Q354, Y366, M378, Q391, R415, I417, K420, I422, T430, and E433.

Still more preferably, the ATA according to the invention is engineered compared to SEQ ID NO:3 in (i) at least two positions selected from the group consisting of N161 as well as Y164; or I417 as well as I422; or N146 as well as N161; and (ii) in addition in at least one other position selected from the group consisting of N7, E9, M16, G33, R45, G51, L53, W54, A67, A68, A71, L73, F82, H87, V109, G114, R140, N146, G147, Y148, Y151, N161, Y164, H165, E222, A227, G228, V230, V257, V258, A288, Q300, A353, Q354, Y366, M378, Q391, R415, I417, K420, T430, and E433.

Preferably, the ATA according to the invention is engineered compared to SEQ ID NO:3 in (i) at least two positions such that is comprises at least two substitutions selected from the group consisting of N146Y as well as N161Q; N161M as well as Y164L; N161I as well as Y164L; N161Q as well as Y164L; N161I as well as Y164M; N161M as well as Y164M; N161Q as well as Y164M; N161I as well as Y164F; N161M as well as Y164I; I417V as well as I422S; I417V as well as I422C; I417A as well as I422S; I417F as well as I422V; and I417A as well as I422C; preferably N146Y as well as N161Q; N161I as well as Y164L; N161M as well as Y164I; and N161Q as well as Y164L; I417V as well as I422S; I417V as well as I422C; I417A as well as I422S; I417A as well as I422C; and (ii) in addition in at least one other position such that is comprises at least one other substitution selected from the group consisting of N7L;
E9R;
M16F, M16C, M16V, M16L, M16A, or M16W; preferably M16C, M16W, or M16F
V29L, or V29I; preferably V29L;
G33Y;
Q44R, Q44N, or Q44H; preferably Q44R or Q44N;
R45K;
G51S;
L53F, L53W, L53V, L53A, L53S, or L53G;
W54A, W54I, W54L, W54Y, W54S, W54C, W54F, or W54V; preferably W54I, W54L, W54Y, or W54A;
A67N;
A68P;
A71G;
L73M;
F82V, F82A, F82G, F82L, or F82Y;
H87T or H87N;
V109I;
G114S;
R140K;
N146Y, N146D, or N146S;
G147S;
Y148F, Y148S, or Y148G;
V151A, V151W, V151I, V151F, V151Y, or V151S;
N161A, N161F, N161M, N161Y, N161Q, or N161I; preferably N161M, N161Q, N161I, N161A, or N161F, more preferably N161I, N161M, or N161Q;
Y164L, Y164M, Y164A, Y164F, or Y164I; preferably Y164L, Y164F, Y164M or Y164I;
H165R;
E222S, E222A, or E222D;
A227V, A227I, A227G, A227F, A227Y, or A227M; preferably A227Y
G228A or G228I; preferably G228A;
V230G, V230A, V230I, or V230L; preferably V230A;
V257A;
V258A or V258I; preferably V258I;
A288G;
Q300E;
A349G;
A353R;
Q354F;
Y366H or Y366F;
M378L, M378V, M378I, M378F, M378Y, M378T, M378A, or M378C;
Q391K or Q391E;
R415A, R415V, R415L, R415G, R415Y, R415T, or R415C; preferably R415A, R415V, or R415L;
I417T, I417C, I417F, I417V, I417Y, or I417A; preferably I417V, I417T, I417C, I417A, or I417F;
K420H, K420S, or K420N;
I422V, I422S, I422A, I422L or I422C; preferably I422S, I422C, or I422V; more preferably I422S or I422C;
T430N; and/or
E433D.

Preferably, the ATA according to the invention is engineered compared to SEQ ID NO:3 in at least in three positions such that it comprises at least three substitutions, wherein (i) the first substitution of said at least three substitutions is selected from the group consisting of N161I, N161M, and N161Q; preferably N161I; and (ii) the second substitution of said at least three substitutions is selected from the group consisting of Y164L, and Y164I; and (iii) the third substitution of said at least three substitutions is selected from the group consisting of N7L, E9R, M16F, M16W, V29L, V29I, G33Y, Q44R, Q44N, Q44H, R45K, G51S, W54A, A67N, A68P, A71G, L73M, H87T, H87N, V109I, G114S, R140K, G147S, H165R, V230A, A288G, Q300E, A349G, A353R, Q354F, Y366H, Y366F, Q391K, Q391E, K420H, K420S, K420N, T430N, and E433D.

Preferably, the ATA according to the invention is engineered compared to SEQ ID NO:3 in at least in four positions such that it comprises at least four substitutions, wherein (i) the first substitution of said at least four substitutions is selected from the group consisting of N161I, N161M, and N161Q; and (ii) the second substitution of said at least four substitutions is selected from the group consisting of Y164L, and Y164I; and (iii) the third substitution of said at least four substitutions is selected from the group consisting of M16F, M16C, M16V, M16L, M16A, or M16W; preferably M16W or M16F; and (iv) the fourth substitution of said at least four substitutions is selected from the group consisting of V230G, V230A, V230I, or V230L; preferably V230A.

Preferably, the ATA according to the invention is engineered compared to SEQ ID NO:3 in at least one, two, three or four positions and is selected from the group of the following engineered sequences:

| SEQ ID NO | Number Mutations | Mutation 1 | Mutation 2 | Mutation 3 | Mutation 4 |
|---|---|---|---|---|---|
| 3 | — | | | | |
| 4 | 1 | M16F | | | |
| 5 | 1 | M16C | | | |
| 6 | 1 | M16V | | | |
| 7 | 1 | M16L | | | |
| 8 | 1 | M16A | | | |
| 9 | 1 | M16W | | | |
| 10 | 1 | L53F | | | |
| 11 | 1 | L53W | | | |
| 12 | 1 | L53V | | | |
| 13 | 1 | L53A | | | |
| 14 | 1 | L53S | | | |
| 15 | 1 | L53G | | | |
| 16 | 1 | W54A | | | |
| 17 | 1 | W54I | | | |
| 18 | 1 | W54L | | | |
| 19 | 1 | W54Y | | | |

| SEQ ID NO | Number Mutations | Mutation 1 | Mutation 2 | Mutation 3 | Mutation 4 |
|---|---|---|---|---|---|
| 20 | 1 | W54S | | | |
| 21 | 1 | W54C | | | |
| 22 | 1 | W54F | | | |
| 23 | 1 | W54V | | | |
| 24 | 1 | F82V | | | |
| 25 | 1 | F82A | | | |
| 26 | 1 | F82G | | | |
| 27 | 1 | F82L | | | |
| 28 | 1 | F82Y | | | |
| 29 | 1 | N146Y | | | |
| 30 | 1 | N146D | | | |
| 31 | 1 | N146S | | | |
| 32 | 1 | Y148F | | | |
| 33 | 1 | Y148S | | | |
| 34 | 1 | Y148G | | | |
| 35 | 1 | V151A | | | |
| 36 | 1 | V151W | | | |
| 37 | 1 | V151I | | | |
| 38 | 1 | V151F | | | |
| 39 | 1 | V151Y | | | |
| 40 | 1 | V151S | | | |
| 41 | 1 | N161A | | | |
| 42 | 1 | N161F | | | |
| 43 | 1 | N161M | | | |
| 44 | 1 | N161Y | | | |
| 45 | 1 | N161Q | | | |
| 46 | 1 | N161I | | | |
| 47 | 1 | Y164L | | | |
| 48 | 1 | Y164M | | | |
| 49 | 1 | Y164A | | | |
| 50 | 1 | Y164F | | | |
| 51 | 1 | Y164I | | | |
| 52 | 1 | E222S | | | |
| 53 | 1 | E222A | | | |
| 54 | 1 | E222D | | | |
| 55 | 1 | A227Y | | | |
| 56 | 1 | A227V | | | |
| 57 | 1 | A227I | | | |
| 58 | 1 | A227G | | | |
| 59 | 1 | A227F | | | |
| 60 | 1 | A227M | | | |
| 61 | 1 | G228A | | | |
| 62 | 1 | G228I | | | |
| 63 | 1 | V230A | | | |
| 64 | 1 | V230G | | | |
| 65 | 1 | V230I | | | |
| 66 | 1 | V230L | | | |
| 67 | 1 | V257A | | | |
| 68 | 1 | V258I | | | |
| 69 | 1 | V258A | | | |
| 70 | 1 | M378L | | | |
| 71 | 1 | M378V | | | |
| 72 | 1 | M378I | | | |
| 73 | 1 | M378F | | | |
| 74 | 1 | M378Y | | | |
| 75 | 1 | M378T | | | |
| 76 | 1 | M378A | | | |
| 77 | 1 | M378C | | | |
| 78 | 1 | R415A | | | |
| 79 | 1 | R415V | | | |
| 80 | 1 | R415L | | | |
| 81 | 1 | R415G | | | |
| 82 | 1 | R415Y | | | |
| 83 | 1 | R415T | | | |
| 84 | 1 | R415C | | | |
| 85 | 1 | I417T | | | |
| 86 | 1 | I417C | | | |
| 87 | 1 | I417F | | | |
| 88 | 1 | I417V | | | |
| 89 | 1 | I417Y | | | |
| 90 | 1 | I417A | | | |
| 91 | 1 | I422V | | | |
| 92 | 1 | I422S | | | |
| 93 | 1 | I422A | | | |
| 94 | 1 | I422L | | | |
| 95 | 1 | I422C | | | |
| 96 | 2 | I417V | I422S | | |
| 97 | 2 | I417V | I422C | | |
| 98 | 2 | I417A | I422S | | |
| 99 | 2 | I417F | I422V | | |
| 100 | 2 | I417A | I422C | | |
| 101 | 2 | N161M | Y164L | | |
| 102 | 2 | N161I | Y164L | | |
| 103 | 2 | N161Q | Y164L | | |
| 104 | 2 | N161I | Y164M | | |
| 105 | 2 | N161M | Y164M | | |
| 106 | 2 | N161Q | Y164M | | |
| 107 | 2 | N161I | Y164F | | |
| 108 | 2 | N146Y | N161Q | | |
| 109 | 3 | G51S | N161I | Y164L | |
| 110 | 3 | N161I | Y164L | A288G | |
| 111 | 3 | A67N | N161I | Y164L | |
| 112 | 3 | Q44R | N161I | Y164L | |
| 113 | 3 | A68P | N161I | Y164L | |
| 114 | 3 | N161I | Y164L | A349G | |
| 115 | 3 | N161I | Y164L | T430N | |
| 116 | 3 | N161I | Y164L | K420H | |
| 117 | 3 | N161I | Y164L | Q300E | |
| 118 | 3 | L73M | N161I | Y164L | |
| 119 | 3 | G33Y | N161I | Y164L | |
| 120 | 3 | N161I | Y164L | K420S | |
| 121 | 3 | Q44N | N161I | Y164L | |
| 122 | 3 | N161I | Y164L | K420N | |
| 123 | 3 | R45K | N161I | Y164L | |
| 124 | 3 | N161I | Y164L | Q391K | |
| 125 | 3 | N161I | Y164L | Y366H | |
| 126 | 3 | N161I | Y164L | Q354F | |
| 127 | 3 | N161I | Y164L | E433D | |
| 128 | 3 | N161I | Y164L | A353R | |
| 129 | 3 | N161I | Y164L | Y366F | |
| 130 | 3 | Q44H | N161I | Y164L | |
| 131 | 3 | V29L | N161I | Y164L | |
| 132 | 3 | H87T | N161I | Y164L | |
| 133 | 3 | E9R | N161I | Y164L | |
| 134 | 3 | G147S | N161I | Y164L | |
| 135 | 3 | N7L | N161I | Y164L | |
| 136 | 3 | R140K | N161I | Y164L | |
| 137 | 3 | N161I | Y164L | H165R | |
| 138 | 3 | H87N | N161I | Y164L | |
| 139 | 3 | V29I | N161I | Y164L | |
| 140 | 3 | A71G | N161I | Y164L | |
| 141 | 3 | G114S | N161I | Y164L | |
| 142 | 3 | V109I | N161I | Y164L | |
| 143 | 3 | N161I | Y164L | Q391E | |
| 144 | 4 | M16W | N161I | Y164L | V230A |
| 145 | 4 | M16F | N161M | Y164I | V230A |
| 146 | 4 | M16W | W54A | N161Q | Y164L |

Preferably, the ATA according to to the invention comprises an amino acid sequence of at least 85% homology, preferably at least 86% or at least 87%, more preferably at least 88% or at least 89%, still more preferably at least 90% or at least 91%, yet more preferably at least 92% or at least 93%, even more preferably at least 94% or at least 95%, most preferably at least 96% or at least 97%, and in particular at least 98% or at least 99% to the SEQ ID NO:4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57.58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, or 150.

In a preferred embodiment, the ATA according to the invention is a variant of the polypeptide of SEQ ID NO: 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57.58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, or 150 comprising a substitution, deletion and/or insertion of 3 by 1 to 70 amino acids, typically by 1 to 50 amino acids, more typically by 1 to 30 amino acids, even more typically by 1 to 25 amino acids, even more typically by 1 to 20 amino acids, even more typically by 1 to 15 amino acids, even more typically by 1 to 10 amino acids, even more typically by 1 to 5 amino acids, and most typically by 1 to 4 amino acids.

In one specific embodiment, the engineered ATA according to the invention is a fragment of at least 380 amino acid residues, more preferably at least 400 amino acid residues, more preferably at least 420 amino acid residues, more preferably at least 425 amino acid residues, more preferably at least 430 amino acid residues, more preferably at least 435 amino acid residues, more preferably at least 440 amino acid residues, more preferably at least 445 amino acid residues, and most preferably at least 446 amino acids residues of the polypeptide of SEQ ID NO: 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57.58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, or 150. In this regard, "fragment" refers to a consecutive subsequence of the respective SEQ ID NO but that is shortened at the N-terminus and/or the C-terminus.

In a preferred embodiment, the ATA according to the invention is a fusion protein of the amino acid sequence of SEQ ID NO:3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57.58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, or 150 with any other amino acid, oligo- or polypeptide, which is fused to the N-terminus and/or the C-terminus.

In a preferred embodiment, the ATA according to the invention is a fusion protein that comprises the amino acid sequence of SEQ ID NO: 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57.58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, or 150 and additionally at least 1 amino acid residues, at least 2 amino acid residues, at least 4 amino acid residues, at least 6 amino acid residues, at least 10 amino acid residues, more preferably at least 20 amino acid residues, even more preferably at least 30 amino acid residues, and most preferably at least 40 amino acid residues, independently selected from the group consisting of Ala, Arg, Asn, Asp, Cys, Gln, Glu, Gly, His, Ile, Leu, Lys, Met, Phe, Pro, Ser, Thr, Trp Tyr, and Val.

In another preferred embodiment the ATA of the invention is engineered compared to SEQ ID NO:3 in at least one or more positions selected from the group consisting of the positions N7, E9, M16, V29, G33, Q44, R45, G51, L53, W54, A67, A68, A71, L73, F82, H87, V109, G114, R140, N146, G147, Y148, Y151, N161, Y164, H165, E222, A227, G228, V230, V257, V258, A288, Q300, A349, A353, Q354, Y366, M378, Q391, R415, I417, K420, I422, T430, and E433, and exhibits a stereoselectivity that is higher than that of the wildtype ATA of SEQ ID NO:3 as described above.

Preferably, the ATA of the invention is engineered compared to SEQ ID NO:3 in at least one or more positions selected from the group consisting of the positions N7, E9, M16, V29, G33, Q44, R45, G51, L53, W54, A67, A68, A71, L73, F82, H87, V109, G114, R140, N146, G147, Y148, Y151, N161, Y164, H165, E222, A227, G228, V230, V257, V258, A288, Q300, A349, A353, Q354, Y366, M378, Q391, R415, I417, K420, I422, T430, and E433, and exhibits a stereoselectivity that is higher than that of the wildtype ATA of SEQ ID NO:3 as described above, and is selected from the group of engineered ATA comprising SEQ ID NO: SEQ ID NO: 4, 5, 17, 18, 19, 47, 48, 55, 61, 68, 78, 79, 80, 85, 86, 87, 88, 96, 97, 98, 99, 100, 101, 102, 103, 104, 105, 106, 107, 108, 109, 110, 111, 112, 113, 114, 115, 116, 117, 118, 119, 120, 121, 122, 144, 145, or 146.

In another preferred embodiment the ATA of the invention is engineered compared to SEQ ID NO:3 in at least one or more positions selected from the group consisting of the positions N7, E9, M16, V29, G33, Q44, R45, G51, L53, W54, A67, A68, A71, L73, F82, H87, V109, G114, R140, N146, G147, Y148, Y151, N161, Y164, H165, E222, A227, G228, V230, V257, V258, A288, Q300, A349, A353, Q354, Y366, M378, Q391, R415, I417, K420, I422, T430, and E433, and exhibits a thermostability that is higher than that of the wildtype ATA of SEQ ID NO:3 as described above.

Preferably, the ATA of the invention is engineered compared to SEQ ID NO:3 in at least one or more positions selected from the group consisting of the positions N7, E9, M16, V29, G33, Q44, R45, G51, L53, W54, A67, A68, A71, L73, F82, H87, V109, G114, R140, N146, G147, Y148, Y151, N161, Y164, H165, E222, A227, G228, V230, V257, V258, A288, Q300, A349, A353, Q354, Y366, M378, Q391, R415, I417, K420, I422, T430, and E433, and exhibits a thermostability that is higher than that of the wildtype ATA of SEQ ID NO:3 as described above, and is selected from the group of engineered ATA comprising SEQ ID NO: 4, 16, 47, 48, 87, 101, 102, 103, 104, 105, 106, 107, 108, 109, 110, 123, 124, 125, 126, 127, or 146.

In another preferred embodiment the ATA of the invention is engineered compared to SEQ ID NO:3 in at least one or more positions selected from the group consisting of the positions N7, E9, M16, V29, G33, Q44, R45, G51, L53, W54, A67, A68, A71, L73, F82, H87, V109, G114, R140, N146, G147, Y148, Y151, N161, Y164, H165, E222, A227, G228, V230, V257, V258, A288, Q300, A349, A353, Q354, Y366, M378, Q391, R415, I417, K420, I422, T430, and E433, and exhibits a conversion that is higher than that of the wildtype ATA of SEQ ID NO:3. as described above.

In another preferred embodiment the ATA of the invention is engineered compared to SEQ ID NO:3 in at least one or more positions selected from the group consisting of the positions N7, E9, M16, V29, G33, Q44, R45, G51, L53, W54, A67, A68, A71, L73, F82, H87, V109, G114, R140, N146, G147, Y148, Y151, N161, Y164, H165, E222, A227, G228, V230, V257, V258, A288, Q300, A349, A353, Q354, Y366, M378, Q391, R415, I417, K420, I422, T430, and E433, and exhibits a conversion that is higher than that of the wildtype ATA of SEQ ID NO:3. as described above, and is selected from the group of engineered ATA comprising SEQ ID NO: 47, 48, 101, 102, 103, 104, 105, 106, 107, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, or 146.

Another aspect of the invention relates to ATAs which are obtained from the ATA of SEQ ID NO:148, by engineering, but which are not identical to SEQ ID NO:148.

Preferably, the engineered ATAs obtained from the ATA of SEQ ID NO:148 according to the invention are capable of catalyzing the conversion of a ketone substrate according to general formula (I) as defined above to an amine product according to general formula (II) as defined above; and/or the preferably concomitant conversion of (ii) an amine cosubstrate according to general formula (III) as defined above to a ketone coproduct according to general formula (IV) as defined above, or vice versa.

It has been surprisingly found that upon selective engineering of SEQ ID NO:148, the characteristics of the respective ATA can be further enhanced, and that ATA variants can be obtained that exhibit in comparison to the wildtype sequence of SEQ ID NO: 148
a further improved stereoselectivity, and/or
a further increased thermostability, and/or
a further increased conversion; and/or
a shift in activity and/or conversion of substrate specificity.

Preferably, the ATA of SEQ ID NO:148 of this embodiment of the invention is engineered in at least one or more positions preferably by 1 to 20 residue changes, even more preferably by 1 to 15 residue changes, even more preferably by 1 to 11 residue changes, even more preferably by 1 to 7 residue changes and most preferably by 1 to 4 residue changes, preferably including changes at one or more of the following positions of SEQ ID NO:148: V13, E15, M22, F25, P35, T39, D48, T50, R51, N57, L59, Y60, A73, A74, E77, L79, T88, V93, V115, T120, L140, H146, D147, Y148, W151, L161, Y164, P195, E237, A242, G243, S244, A245, N268, V271, L272, S302, K314, V328, K358, E362, Y363, H375, L387, T409, H410, K424, G434, V436, M437, T440, R442, and S450.

Preferably, the ATA of SEQ ID NO: 148 of this embodiment of the invention is engineered in at least one or more positions preferably by 1 to 20 residue changes, even more preferably by 1 to 15 residue changes, even more preferably by 1 to 11 residue changes, even more preferably by 1 to 7 residue changes and most preferably by 1 to 4 residue changes, preferably including changes at one or more of the following positions of SEQ ID NO:148: V13, E15, M22, F25, P35, T39, D48, T50, R51, N57, L59, Y60, A73, A74, E77, L79, T88, V93, V115, T120, L140, H146, D147, Y148, W151, L161, Y164, P195, E237, A242, G243, S244, A245, N268, V271, L272, S302, K314, V328, K358, E362, Y363, H375, L387, T409, H410, K424, G434, V436, M437, T440, R442, and S450 with substitution of any of the amino acids of these positions with any other proteinogenic amino acid selected from the group consisting of Ala, Arg, Asn, Asp, Cys, Gln, Glu, Gly, His, Ile, Leu, Lys, Met, Phe, Pro, Ser, Thr, Trp Tyr, and Val.

More preferably, the ATA of SEQ ID NO:148 of this embodiment of the invention is engineered such that it comprises at least one or more substitutions selected from the group consisting of
in position V13 substitution to V13L; and/or
in position E15 substitution to E15R; and/or
in position M22 substitution to M22F, M22C, M22V, M22L, M22A, or M22W; and/or
in position F25 substitution to F25L; and/or
in position P35 substitution to P35L or P35I; and/or
in position T39 substitution to T39Y; and/or
in position D48 substitution to D48G; and/or
in position T50 substitution to T50R, T50N, or T50H; and/or
in position R51 substitution to R51K; and/or
in position N57 substitution to N57S; and/or
in position L59 substitution to L59F, L59W, L59V, L59A, L59S, or L59G; and/or
in position Y60 substitution to Y60A, Y60I, Y60L, Y60F, or Y60V; and/or
in position A73 substitution to A73N; and/or
in position A74 substitution to A74P; and/or
in position E77 substitution to E77G; and/or
in position L79 substitution to L79M; and/or
in position T88 substitution to T88V, T88A, T88G, T88L, or T88Y; and/or
in position Y93 substitution to Y93T or Y93N; and/or
in position V115 substitution to V115I; and/or
in position T120 substitution to T120S; and/or
in position L140 substitution to L140K; and/or
in position H146 substitution to H146Y, H146D, or H146S; and/or
in position D147 substitution to D147S; and/or
in position Y148 substitution to Y148F, Y148S, or Y148G; and/or
in position W151 substitution to W151A, W151I, W151F, W151Y, or W151S; and/or
in position L161 substitution to L161A, L161F, L161M, L161Y, L161I, or L161Q; and/or
in position Y164 substitution to Y164F or Y164M; and/or
in position P195 substitution to P195S; and/or
in position E237 substitution to E237S, E237A, or E237D; and/or
in position A242 substitution to A242V, A242Y, or A242G; and/or
in position G243 substitution to G243A or G243; and/or
in position S244 substitution to S244A, S244G, S244I, or S244L; and/or
in position A245 substitution to S245T; and/or
in position F255 substitution to F255L; and/or
in position N268 substitution to N268A; and/or
in position V271 substitution to V271A; and/or
in position L272 substitution to L272I or L272A; and/or
in position S302 substitution to S302G; and/or
in position K314 substitution to K314E; and/or
in position V328 substitution to V328G; and/or
in position K358 substitution to K358E; and/or
in position E362 substitution to E362R; and/or
in position Y363 substitution to Y363F; and/or
in position H375 substitution to H375F; and/or
in position L387 substitution to L387V, L387I, L387F, L387Y, L387T, L387A, or L387C; and/or
in position T409 substitution to T409R; and/or
in position H410 substitution to H410K or H410E; and/or in position K424 substitution to K424E; and/or
in position G434 substitution to G434A, G434V, G434L, G434Y, G434T, or G434C; and/or
in position V436 substitution to V436A; and/or
in position M437 substitution to M437T, M437C, M437F, M437V, M437Y, or M437A; and/or
in position T440 substitution to T440H, T440S, or T440N; and/or
in position R442 substitution to R442V, R442S, R442A, R442L, or R442C; and/or
in position S450 substitution to S450N.

More preferably, the ATA of SEQ ID NO:148 of this embodiment of the invention is engineered in at least one or more positions of SEQ ID NO: 148 selected from the group comprising positions M22, F25, T39, D48, T50, Y60, A73, V93, H146, L161, Y164, P195, A242, G243, S244, A245, F255, N268, V328, T409, K424, G434, V436, M437, T440, and R442.

Even more preferably, the ATA of SEQ ID NO:148 of this embodiment of the invention is engineered in at least one or more positions of SEQ ID NO:148 selected from the group comprising positions F25, D48, Y164, P195, A242, A245, F255, N268, V328, T409, K424, and V436.

Most preferably, the ATA of SEQ ID NO:148 of this embodiment of the invention is engineered in the positions D48, Y164, P195, A242, A245, F255, N268, T409, K424, and/or V436; preferably D48G, Y164F, P195S, A242V, A245T, F255L, N268A, T409R, K424E, and/or V436A; and/or
F255, and V328, preferably F255L and/or V328G; and/or
F25, Y164, and/or F255; preferably F25L, Y164M, and/or F255L.

Preferably, the engineered ATA of SEQ ID NO:148 according to the invention comprises an amino acid sequence of at least 50% homology, preferably at least 55%. more preferably at least 60%, even more preferably at least 70%, still more preferably at least 80%, yet more preferably at least 90% homology, yet more preferably at least 91% homology, yet more preferably at least 92% homology, yet more preferably at least 93% homology, yet more preferably at least 94% homology, yet more preferably at least 95% homology, yet more preferably at least 96% homology, yet more preferably at least 97% homology, yet more preferably at least 98% homology, yet more preferably at least 99% homology, yet more preferably at least 99.1% homology, yet more preferably at least 99.2% homology, yet more preferably at least 99.3% homology, yet more preferably at least 99.4% homology, yet more preferably at least 99.5% homology, yet more preferably at least 99.6% homology, yet more preferably at least 99.7% homology, yet more preferably at least 99.8% homology, or at least 99.9%, homology to SEQ ID NO:147, SEQ ID NO:148, SEQ ID NO:149, and/or SEQ ID NO:150. As far as SEQ ID NO:148 is concerned, however, the homology must not be 100%.

More preferably, the ATA of SEQ ID NO:148 of this embodiment of the invention is engineered in at least one or more positions of SEQ ID NO: 148 selected from the group comprising positions M22, F25, T39, D48, T50, Y60, A73, V93, H146, L161, Y164, P195, A242, G243, S244, A245, F255, N268, V328, T409, K424, G434, V436, M437, T440, and R442; and comprises an amino acid sequence of at least 50% homology, preferably at least 55%. more preferably at least 60%, even more preferably at least 70%, still more preferably at least 80%, yet more preferably at least 90% homology, yet more preferably at least 91% homology, yet more preferably at least 92% homology, yet more preferably at least 93% homology, yet more preferably at least 94% homology, yet more preferably at least 95% homology, yet more preferably at least 96% homology, yet more preferably at least 97% homology, yet more preferably at least 98% homology, yet more preferably at least 99% homology, yet more preferably at least 99.1% homology, yet more preferably at least 99.2% homology, yet more preferably at least 99.3% homology, yet more preferably at least 99.4% homology, yet more preferably at least 99.5% homology, yet more preferably at least 99.6% homology, yet more preferably at least 99.7% homology, yet more preferably at least 99.8% homology, or at least 99.9%, homology to SEQ ID NO: 147, SEQ ID NO: 148, SEQ ID NO:149, and/or SEQ ID NO:150. As far as SEQ ID NO:148 is concerned, however, the homology must not be 100%.

Even more preferably, the ATA of SEQ ID NO:148 of this embodiment of the invention is engineered in at least one or more positions of SEQ ID NO:148 selected from the group comprising positions F25, D48, Y164, P195, A242, A245, F255, N268, V328, T409, K424, and V436; and comprises an amino acid sequence of at least 50% homology, preferably at least 55%. more preferably at least 60%, even more preferably at least 70%, still more preferably at least 80%, yet more preferably at least 90% homology, yet more preferably at least 91% homology, yet more preferably at least 92% homology, yet more preferably at least 93% homology, yet more preferably at least 94% homology, yet more preferably at least 95% homology, yet more preferably at least 96% homology, yet more preferably at least 97% homology, yet more preferably at least 98% homology, yet more preferably at least 99% homology, yet more preferably at least 99.1% homology, yet more preferably at least 99.2% homology, yet more preferably at least 99.3% homology, yet more preferably at least 99.4% homology, yet more preferably at least 99.5% homology, yet more preferably at least 99.6% homology, yet more preferably at least 99.7% homology, yet more preferably at least 99.8% homology, or at least 99.9%, homology to SEQ ID NO:147, SEQ ID NO:148, SEQ ID NO:149, and/or SEQ ID NO:150. As far as SEQ ID NO:148 is concerned, however, the homology must not be 100%.

In a specific embodiment of this invention, any engineered ATA of SEQ ID NO:148 of this embodiment in comparison to the non-engineered ATA of SEQ ID NO: 148
provides an improved stereoselectivity of at least 35%, preferably at least 40%, preferably at least 45%, preferably at least 50%, preferably at least 55%, preferably at least 60%, preferably at least 65%, preferably at least 70%, preferably at least 75%, preferably at least 80%, preferably at least 85%, preferably at least 90%, preferably at least 95%, preferably at least 98%, preferably at least 99%, preferably at least 99.5%, and most preferably at least 99.9%; and/or
provides a thermostability of at least 65° C., more preferably at at least 70° C., still more preferably at at least 75° C., still more preferably at least 80° C., and most preferably at at least 85° C.; and/or
provides a further increased conversion of referably at least 35%, preferably at least 40%, preferably at least 45%, preferably at least 50%, preferably at least 55%, preferably at least 60%, preferably at least 65%, preferably at least 70%, preferably at least 75%, preferably at least 802%, preferably at least 85%, preferably at least 90%, preferably at least 55%, preferably at least 95%, and most preferably of at least 99%; and/or
provides an improved conversion and an increased substrate specificity for of substrate specificity and/or activity for (R)-phenylacetylcarbinol, 1-phenyl-1-butanone, 2-methyl-1-phenyl-1-propanone, 1-phenyl-1-pentanone, methyl-3-oxo-3-phenylpropanoate, and/or methyl 3-oxo-3-phenyl-butyrate.

Another aspect of the invention relates to a method for for the conversion of
(i) a ketone substrate according to general formula (I) as described above to an amine product according to general formula (II) as described above;
and/or the preferably concomittant conversion of
(ii) an amine cosubstrate according to general formula (III) as described above to a ketone coproduct according to general formula (IV) as described above,
or vice versa;
wherein the amine product according to general formula (II) preferably has (S)-configuration or (R)-configuration; and
wherein the method comprises the step of reacting a ketone substrate according to general formula (I) and/or an amine product according to general formula (II) and/or an amine cosubstrate according to general formula (III) and/or a ketone coproduct according to general formula (IV) in the presence of an ATA according to the invention.

Preferably, the invention relates to a method for for the stereoselective conversion of
(i) a ketone substrate according to general formula (I) as described above to a chiral amine product according to general formula (II) as described above;
and/or the preferably concomittant conversion of
(ii) a chiral or non-chiral amine cosubstrate according to general formula (III) as described above to a ketone coproduct according to general formula (IV) as described above,
or vice versa;
wherein the chiral amine product according to general formula (II) preferably has (S)-configuration or (R)-configuration; and
wherein the method comprises the step of reacting a ketone substrate according to general formula (I) and/or a chiral amine product according to general formula (II) and/or a chiral or non-chiral amine cosubstrate according to general formula (III) and/or a ketone coproduct according to general formula (IV) in the presence of an ATA according to the invention.

Another aspect of the invention relates to the use of an ATA according to the invention as described above for the amidation of a keto group in any possible direction, preferably in the method according to the invention as described above.

Preferably, the invention relates to the use of an ATA according to the invention as described above for the conversion of
(i) a ketone substrate according to general formula (I) as described above to an amine product according to general formula (II) as described above;
and/or the preferably concomittant conversion of
(ii) an amine cosubstrate according to general formula (III) as described above to a ketone coproduct according to general formula (IV) as described above,
or vice versa;
wherein the amine product according to general formula (II) preferably has (S)-configuration or (R)-configuration.

Preferably, the invention relates to the use of an ATA according to the invention as described above for the stereoselective conversion of
(i) a ketone substrate according to general formula (I) as described above to a chiral amine product according to general formula (II) as described above;
and/or the preferably concomittant conversion of
(ii) a chiral or non-chiral amine cosubstrate according to general formula (III) as described above to a ketone coproduct according to general formula (IV) as described above,
or vice versa;
wherein the chiral amine product according to general formula (II) has (S)-configuration or (R)-configuration.

Particularly preferred embodiments Emb-1 to 15 of the invention are summarized hereinafter: Emb-1: A transaminase comprising an amino acid sequence with at least 75% homology to SEQ ID NO:3. Emb-2: The transaminase according to Emb-1, which is capable of catalyzing the conversion of (i) a ketone substrate according to general formula (I)

to an amine product according to general formula (II)

and/or the preferably concomittant conversion of (ii) an amine cosubstrate according to general formula (III)

to a ketone coproduct according to general formula (IV)

or vice versa; wherein X and Y as well as A and B, in either case, independently of one another, are selected from saturated or unsaturated, unsubstituted or mono- or polysubstituted aliphatic or alicyclic $C_{1-12}$-hydrocarbon residues; unsubstituted or mono- or polysubstituted $C_{6-10}$-aromatic hydrocarbon residues, optionally being bridged through a saturated or unsaturated, unsubstituted or mono- or polysubstituted aliphatic $C_{1-12}$-hydrocarbon residue; unsubstituted or mono- or polysubstituted heteroaromatic hydrocarbon residues, optionally being bridged through a saturated or unsaturated, unsubstituted or mono- or polysubstituted aliphatic $C_{1-12}$-hydrocarbon residue; and sugar residues or desoxysugar residues in each case comprising mono-, di- or oligosaccharides; wherein one of residues X or Y, as well as one of residues A or B, in either case, independently of one another, may be hydrogen; wherein mono- or polysubstituted means independently substituted with one or more functional groups selected from -halo, —OH, =O, —O$C_{1-12}$-alkyl, —O$C_{6-10}$-aryl, —O-heteroaryl, —OCOC$_{1-12}$-alkyl, —OCOC$_{6-10}$-aryl, —OCO-heteroaryl, —SH, —SC$_{1-12}$-alkyl, —SC$_{6-10}$-aryl, —S-heteroaryl, —S(═O)$_{1-2}$OH, —NO, —NO$_2$, —N$_3$, —NH$_2$, —NH(C$_{1-12}$-alkyl), —N(C$_{1-12}$-alkyl)$_2$, —NH(C$_{6-10}$-aryl), —N(C$_{6-10}$-aryl)$_2$, —NH(heteroaryl), —N(heteroaryl)$_2$, —CN, —CHO, —CO$_2$H, CO—C$_{1-2}$-alkyl, —CO—C$_{6-10}$-aryl and —CO-heteroaryl. Emb-3: The transaminase according to Emb-1 or 2, which is characterized by either (A) a temperature stability of at least 50° C., preferably 55° C., and most preferably of 60° C., and/or (B) a specific activity of at least 0.5 U/mg, preferably, 075 U/mg, more preferably of 1 U/mg, and most preferably at 1, 1 U/mg in Transaminase Standard Assays; and/or (C) a high conversion activity under different reaction conditions involving high amine concentrations. Emb-4: The transaminase according to any of the preceding Embs, which is engineered compared to SEQ ID NO:3 in at least one or more positions such that (A) the stereoselectivity of the engineered transaminase is higher than that of the wildtype transaminase of SEQ ID NO:3; and/or (B) the thermostability of the engineered transaminase is higher than that of the wildtype transaminase of SEQ ID NO:3; and/or (C) the conversion of the engineered transaminase is higher than that of the wildtype transaminase of SEQ ID NO:3. Emb-5: The transaminase according to any of the preceding Embs, which is engineered compared to SEQ ID NO:3 in at least one or more positions selected from the group consisting of the positions N7, E9, M16, V29, G33, Q44, R45, G51, L53, W54, A67, A68, A71, L73, F82, H87, V109, G114, R140, N146, G147, Y148, Y151, N161, Y164, H165, E222, A227, G228, V230, V257, V258, A288, Q300, A349, A353, Q354, Y366, M378, Q391, R415, I417, K420, I422, T430, and E433. Emb-6: The transaminase according to any of the preceding Embs, which is engineered compared to SEQ ID NO:3 in at least one or more positions such that it comprises at least one or more substitutions selected from the group consisting of N7L, E9R, M16F, M16C, M16V, M16L, M16A, M16W, V29L, V29I, G33Y, Q44R, Q44N, Q44H, R45K, G51S, L53F, L53W, L53V, L53A, L53S, L53G, W54A, W54I, W54L, W54Y, W54S, W54C, W54F, W54V, A67N, A68P, A71G, L73M, F82V, F82A, F82G, F82L, F82Y, H87T, H87N, V109I, G114S, R140K, N146Y, N146D, N146S, G147S, Y148F, Y148S, Y148G, V151A, V151W, V151I, V151F, V151Y, V151S, N161A, N161F, N161M, N161Y, N161Q, N161I, Y164L, Y164M, Y164A, Y164F, Y164I, H165R, E222S, E222A, E222D, A227Y, A227V, A227I, A227G, A227F, A227M, G228A, G228I, V230A, V230G, V230I, V230L, V257A, V258A, V258I, A288G, Q300E, A349G, A353R, Q354F, Y366H, Y366F, M378L, M378V, M378I, M378F, M378Y, M378T, M378A, M378C, Q391K, Q391E, R415A, R415V, R415L, R415G, R415Y, R415T, I417T, I417C, I417F, I417V, I417Y, I417A, K420H, K420S, K420N, I422V, I422S, I422A, I422L, I422C, T430N, and E433D. Emb-7: The transaminase according to any of the preceding Embs, which is engineered compared to SEQ ID NO:3 in (I) at least one position selected from the group consisting of M16, W54, N146, N161, Y164, A227, G228, V230, V258, R415, I417, and I422; and (II) in addition in at least one other position selected from the group consisting of N7, E9, M16, V29, G33, Q44, R45, G51, L53, W54, A67, A68, A71, L73, F82, H87, V109, G114, R140, N146, G147, Y148, Y151, N161, Y164, H165, E222, A227, G228, V230, V257, V258, A288, Q300, A349, A353, Q354, Y366, M378, Q391, R415, I417, K420, I422, T430, and E433. Emb-8: The transaminase according to any of the preceding Embs, which is engineered compared to SEQ ID NO:3 in at least two positions selected from the group consisting of N161 as well as Y164; I417 as well as I422; and N146 as well as N161. Emb-9: The transaminase according to any of the preceding Embs, which is engineered compared to SEQ ID NO:3 in at least two positions such that it comprises (i) at position N161 a substitution selected from the group consisting of N161A, N161F, N161M, N161Y, N161I, or N161Q; as well as at position Y164 a substitution selected from the group consisting of Y164L, Y164M, Y164A, Y164F, or Y164I; and/or (ii) at position I417 a substitution selected from the group consisting of I417T, I417C, I417F, I417V, I417Y, or I417A; as well as at position I422 a substitution selected from the group consisting of I422V, I422S, I422A, I422L, or I422C; and/or (iii) at position N146 a substitution selected from the group consisting of N146Y, N146D, or N146S; as well as at position N161 a substitution selected from the group consisting of N161A, N161F, N161M, N161Y, N161I, or N161Q. Emb-10: The transaminase according to any of the preceding Embs, which is engineered compared to SEQ ID NO:3 in at least two positions such that it comprises at least two substitutions selected from the group consisting of the substitutions N161M as well as Y164L; N161I as well as Y164L; N161Q as well as Y164L; N161I as well as Y164M; N161M as well as Y164M; N161Q as well as Y164M; N161I as well as Y164F; N161M as well as Y164I; I417V as well as I422S; I417V as well as I422C; I417A as well as I422S; I417F as well as I422V; I417A as well as I422C; and N146Y as well as N161Q. Emb-11: The transaminase according to any of the preceding Embs, which is engineered compared to SEQ ID NO:3 in (i) at least two positions selected from the group consisting of N161 as well as Y164; or I417 as well as I422; or N146 as well as N161; and (ii) in addition in at least one other position selected from the group consisting of N7, E9, M16, V29, G33, Q44, R45, G51, L53, W54, A67, A68, A71, L73, F82, H87, V109, G114, R140, N146, G147, Y148, Y151, N161, Y164, H165, E222, A227, G228, V230, V257, V258, A288, Q300, A349, A353, Q354, Y366, M378, Q391, R415, I417, K420, I422, T430, and E433. Emb-12: The transaminase according to any of the preceding Embs, which is engineered compared to SEQ ID NO:3 in (i) at least two positions such that is comprises at least two substitutions selected from the group consisting of N146Y as well as N161Q; N161M as well as Y164L; N161I as well as Y164L; N161Q as well as Y164L; N161I as well as Y164M; N161Q as well as Y164M; N161I as well as Y164F; N161M as well as Y164I; I417V as well as I422S; I417V as well as I422C; I417A as well as I422S; I417F as well as I422V; and I417A as well as I422C; and (ii) in addition in at least one other position that is comprises at least one other substitution selected from the group consisting of N7L, E9R, M16F, M16C, M16V, M16L, M16A, M16W, V29L, V29I, G33Y, Q44R, Q44N, Q44H, R45K, G51S, L53F, L53W, L53V, L53A, L53S, L53G, W54A, W54I, W54L, W54Y, W54S, W54C, W54F, W54V, A67N, A68P, A71G, L73M, F82V, F82A, F82G, F82L, F82Y, H87T, H87N, V109I, G114S, R140K, N146Y, N146D, N146S, G147S, Y148F, Y148S, Y148G, V151A, V151W, V151I, V151F, V151Y, V151S, N161A, N161F, N161M, N161Y, N161Q, N161I, Y164L, Y164M, Y164A, Y164F, Y164I, H165R, E222S, E222A, E222D, A227V, A227I, A227G, A227F, A227Y, A227M, G228A, G228I, V230G, V230A, V230I, V230L, V257A, V258A, V258I, A288G, Q300E, A349G, A353R, Q354F, Y366H, Y366F, M378L, M378I, M378F, M378Y, M378T, M378A, M378C, Q391K, Q391E, R415A, R415V, R415L, R415G, R415Y, R415T, R415C, I417T, I417C, I417F, I417V, I417Y, I417A, K420H, K420S, K420N, I422V, I422S, I422A, I422L, I422C, T430N, and E433D. Emb-13: The transaminase according to any of the preceding Embs, which is engineered compared to SEQ ID NO:3 in at least in three positions such that it comprises at least three substitutions, wherein (i) the first substitution of said at least three substitutions is selected from the group consisting of N161I, N161M, and N161Q; and (ii) the second substitution of said at least three substitutions is selected from the group consisting of Y164L, and Y164I; and (iii) the third substitution of said at least three substitutions is selected from the group consisting of N7L, E9R, M16F, M16W, V29L, V29I, G33Y, Q44R, Q44N, Q44H, R45K, G51S, W54A, A67N, A68P, A71G, L73M, H87T, H87N, V109I, G114S, R140K, G147S, H165R, V230A, A288G, Q300E, A349G, A353R, Q354F, Y366H, Y366F, Q391K, Q391E, K420H, K420S, K420N, T430N, and E433D. Emb-14: The transaminase according to any of the preceding Embs, which comprises an amino acid sequence of at least 85% homology to the SEQ ID NO: 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57.58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, or 150. Emb-15: A method for the conversion of (i) a ketone substrate according to general formula (I)

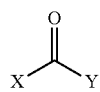
(I)

to an amine product according to general formula (II)

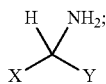
(II)

and/or the preferably concomitant conversion of (ii) a cosubstrate according to general formula (III)

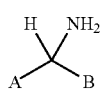
(III)

to a ketone coproduct according to general formula (IV)

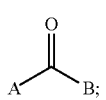
(IV)

or vice versa; wherein X and Y as well as A and B, in either case, independently of one another, are selected from saturated or unsaturated, unsubstituted or mono- or polysubstituted aliphatic or alicyclic $C_{1-12}$-hydrocarbon residues; unsubstituted or mono- or polysubstituted $C_{6-10}$-aromatic hydrocarbon residues, optionally being bridged through a saturated or unsaturated, unsubstituted or mono- or polysubstituted aliphatic $C_{1-12}$-hydrocarbon residue; unsubstituted or mono- or polysubstituted heteroaromatic hydrocarbon residues, optionally being bridged through a saturated or unsaturated, unsubstituted or mono- or polysubstituted aliphatic $C_{1-12}$-hydrocarbon residue; and sugar residues or desoxysugar residues in each case comprising mono-, di- or oligosaccharides; wherein one of residues X or Y, as well as one of residues A or B, in either case, independently of one another, may be hydrogen; wherein mono- or polysubstituted means independently substituted with one or more functional groups selected from -halo, —OH, =O, —$OC_{1-12}$-alkyl, —$OC_{6-10}$-aryl, —O-heteroaryl, —$OCOC_{1-12}$-alkyl, —$OCOC_{6-10}$-aryl, —OCO-heteroaryl, —SH, —$SC_{1-12}$-alkyl, —$SC_{6-10}$-aryl, —S-heteroaryl, —$S(=O)_{1-2}OH$, —NO, —$NO_2$, —$N_3$, —$NH_2$, —NH($C_{1-12}$-alkyl), —N($C_{1-12}$-alkyl)$_2$, —NH($C_{6-10}$-aryl), —N($C_{6-10}$-aryl)$_2$, —NH(heteroaryl), —N(heteroaryl)$_2$, —CN, —CHO, —$CO_2H$, CO—$C_{1-2}$-alkyl, —CO—$C_{6-10}$-aryl and —CO-heteroaryl; wherein the method comprises the step of reacting a ketone substrate according to general formula (I) and/or an amine product according to general formula (II) and/or a amine cosubstrate according to general formula (III) and/or a ketone coproduct according to general formula (IV) in the presence of a transaminase according to any of Embs-1 to 14.

The following examples further illustrate the invention but are not to be construed as limiting its scope.

EXAMPLE 1: IDENTIFICATION OF A NEW ATA GENE CORRESPONDING TO SEQ ID NO:1

The gene of the new aminotransferase was detected during a screening for new aminotransferases by selective enrichment of wild type strains expressing aminotransferases. Soil samples from different habitats were randomly collected and five grams of each sample were suspended in 20 ml of 0.9% NaCl. A non-selective rich medium TSB (15 g/L peptone from casein, 5 g/L peptone from soymeal, 5 g/L NaCl) was inoculated by these suspensions and incubated at 30° C. for several hours for obtaining a first pre-culture. This first pre-culture has been used to inoculate a second pre-culture in defined minimal medium MA (50 mM potassium phosphate pH 7, 100 mM glycerol, 0.2 mM $CaCl_2$, 4 mM $MgSO_4$, 1 g/L $NH_4Cl$, 10 ml/L 100× trace element stock solution [10 mg/L $ZnCl_2$, 10 mg/ml $MnSO_4×4 H_2O$, 2 mg/L $H_3BO_3$, 10 mg/L $CuSO_4×5 H_2O$, 5 mg/L $CoCl_2$, 10 mg/L $NiSO_4×6 H_2O$, 200 mg/L $Na_2MoO_4$, 400 mg/L $FeSO_4×7 H_2O$]). After overnight cultivation this second pre-culture was washed with 0.9% NaCl for remove of residual sources of nitrogen. The washed cells were used to inoculate a selective enrichment medium consisting of the defined minimal medium MA where the original nitrogen-source has been replaced by a collection of different amines (e.g. R/S-α-Methylbenzylamine or R/S-1-Methyl-3-phenylpropylamine). The amines have been added at concentrations of 50 mM. Enrichment has been ensured by repetitive dilution of grown culture into new enrichment medium. After third dilution of enriched cultures, the enriched cells were plated on agar plates containing enrichment medium MA with the respective nitrogen source in order to select single clones. Single clones have been further verified by liquid cultivation in enrichment medium as well as by direct detection of transaminase activity.

Transaminase activity was detected by culturing selected strains in 400 µl half concentrated LB medium for two days at 30° C. Cells were harvested by centrifugation and resuspended in 200 µl substrate solution consisting of 5 mM 4-phenyl-2-butanone, 100 mM 1-phenylethan-1-amine (MBA), 50 mM potassium phosphate pH 7.4, and 1 mM pyridoxalphosphate. The reaction went overnight at 30° C., was stopped by adding 200 µl methanol, and analyzed by HPLC as described in Example 3.

Identification of the corresponding transaminase genes, genomic libraries have been built from active strains. The DNA of selected microorganisms grown in a 96-well format was isolated, mechanically fragmented to the desired size range, and cloned into pF2F4 (WO2010/075956 A1). The resulting plasmids were transformed to E. coli BL21(DE3) placI(+) cells. Screening of the library was done with cluster screening (WO2005/040376 A2) with cluster sizes of about 300,000 to 350,000 clones per plate also by selective enrichment.

For expression of the genomic library cells were cultivated in defined minimal medium supplemented with kanamycin (50 mg/l) and chloramphenicol (34 mg/l)). Expression of the genes of the genomic library was induced at logarithmic phase either by IPTG (0.5 mM) or arabinose (0.1 (v/v)). Cultivations were carried out at 30° C. for 16 hours after which cells were washed with 0.9% NaCl remove the residual sources of nitrogen. Washed cells were cultivated in defined minimal medium with the original nitrogen-source being replaced by the respective amine for enrichment. Enrichment was accomplished in three repetitive dilutions. After third dilution plasmids have been purified from grown enriched cultures and the transaminase gene sequences have been determined.

EXAMPLE 2: EXPRESSION OF A NEW ATA GENE CORRESPONDING TO SEQ ID NO:1 AND 2

The newly found ATA gene sequences corresponding to SEQ ID NO:1 was codon optimized for E. coli expression while simultaneously decreasing the GC-content, corresponding to SEQ ID NO:2. Both genes according to SEQ ID NO:1 and SEQ ID NO:2 were cloned into the expression vector pLE1A17 (derivative of pRSF-1b, Novagen). The resulting plasmids were used for transformation of E. coli BL21(DE3) cells.

For expression of the new ATA corresponding to SEQ ID NO:1 and SEQ. ID NO:2 cells were cultivated in ZYM505 medium (F. William Studier, Protein Expression and Purification 41 (2005) 207-234) supplemented with kanamycin (50 mg/l) at 37° C. Expression of the gene was induced at logarithmic phase by IPTG (0.1 mM) and carried out at 30° C. for 16-18 hours.

Cells were harvested by centrifugation (3220×g, 20 min, 4° C.) and disrupted by resuspending corresponding to an optical density, measured at 600 nm ($OD_{600}$) of 100 with cell lysis buffer (50 mM Tris-HCl pH 7.0; 2 mM MgCl2, 1× CelLytic B (Sigma); DNA nuclease 0.02 U, lysozyme 0.5 mg/ml). The crude extracts were separated from cell debris by centrifugation (3220×g 30 min, 4° C.), resulting in enzymatic active preparations of the ATA of SEQ ID NO:3. For detection of the enzymatic activity of an ATA of the invention, a lyophilisate of the active preparation of the ATA may be obtained. The crude extract lyophilisate was investigated regarding the ATA activity using the Transaminase Standard Assay.

The Transaminase Standard Assay monitors the conversion of racemic 1-phenylethan-1-amine (MBA) and pyruvate to 1-phenylethanone (Acetophenone) and L-alanine. The reaction is performed at 30° C. in 50 mM phosphate buffer (pH 7, 4) and 0.1 mM pyridoxalphosphate (PLP) using 10 mM racemic 1-phenylethan-1-amine and 10 mM sodium-pyruvate as substrates. The production of 1-phenylehanone is followed photometrically at 300 nm. One unit (U) liberates 1 µmol 1-phenylethanone (Acetophenone) per minute. Specific activity refers to units per milligram crude extract lyophilisate (U/mg)

EXAMPLE 3: CHARACTERIZATION OF ENZYMATIC PROPERTIES OF NEW ATA OF SEQ ID NO:3

An enzymatic active preparation of ATA of SEQ ID NO:3 was prepared as described in Example 2. For comparison of its enzymatic properties, enzymatic active preparations of several other omega-transaminases were prepared in a similar way. These include omega-transaminase well known in the literature (J. S. Shin et al., Appl. Microbiol. Biotechnol. 2003, 61 463-471. WO 2010/081053. J. H. Seo, et al. Biotechnol. J 3 (5):676-686, 2008. S. Schatzle, et al. Anal. Chem. 81 (19):8244-8248, 2009.).

The enzymatic activity of these enzymes was analyzed with the Transaminase Standard Assay as described in Example 2. Furthermore, the thermostability of each enzyme was analyzed as described in Example 5.

| Entry | transaminase origin | No. of mutations | Tm (80%) [° C.] | Activity (Transaminase standard assay Example 2) [U/mg] | seq reference |
|---|---|---|---|---|---|
| 1 | Example 1 | none, wildtype | 60 | 1.1 | SEQ ID NO: 3 |
| 2 | Vibrio fluvialis | none, wildtype | 61 | 0.1 | WP_040602310 |
| 3 | Agrobacterium tumefaciens | none, wildtype | 57 | 0.04 | WP_010972924 |
| 4 | Rhodobacter spheroides | none, wildtype | 53 | 0.05 | WP_002720543 |
| 5 | Bradyrhizobium | none, wildtype | 57 | 0.1 | WP_011086907 |
| 6 | Arthrobacter citreus | One | 57 | 0.2 | SEQ ID NO: 148 |
| 7 | SEQ ID NO: 147 | 10 | 59 | 0.1 | SEQ ID NO: 147 |

Additionally the conversion properties of these enzymes were investigated in Transaminase Conversion Assays.

Transaminase Conversion Assays monitors enzyme properties at different reaction conditions that are relevant for a preparative synthesis application at high concentration of different amine donors, isopropylamine (IPA), racemic 1-phenylethan-1-amine (MBA) or (S)-1-phenylethan-1-amine (S-MBA) or racemic alanine, respectively. The ketone acceptor was 4-phenyl-2-butanone (BA). The reaction was performed at 30° C. in 50 mM phosphate buffer (pH 7, 4) and 0.1 mM pyridoxalphosphate (PLP).

Conversion from BA to 1-methyl-3-phenylpropylamine was analyzed by HPLC after a given time of reaction, typically 6 h or 20 h. Analytical conditions are:

Column: Gemini 5µ C18, 150×4.6 mm (Phenomenex);
Eluents: A) dH2O, 0.1% trifluoroacetic acid (TFA); B) Acetonitrile, 0.1% TFA;
Flow: 1 ml/min; gradient: 20% B to 80% B in 6 min, hold for 1 min, to 20% B in 1 min, hold for 3 min;
Oven temperature: 35° C.;
Detection: 210 nm.
The retention times of the analytes are 6.52 min for BA and 3.65 min for 1-methyl-3-phenylpropylamine.

Overall, Transaminase Conversion Assays may be done at conditions differing in the type of amine donor (IPA, MBA, and alanine) and the respective concentration of the reactants.

Condition A: 50 mM BA, 100 mM IPA; after 6 h
Condition B: 50 mM BA, 200 mM rac. MBA; after 6 h
Condition C: 50 mM BA, 500 mM IPA; after 6 h
Condition D: 50 mM BA, 1000 mM rac. MBA; after 6 h
Condition E: 50 mM BA, 200 mM rac. alanine; after 6 h
Condition F: 10 mM BA, 50 mM IPA; after 6 h
Condition G: 150 mM BA, 300 mM IPA; after 20 h
Condition H: 150 mM BA, 300 mM (S)-MBA; after 20 h
Condition I: 150 mM BA, 1000 mM IPA; after 20 h
Condition J: 50 mM BA, 1000 mM IPA; after 20 h The transaminases under this example were analyzed at the Conditions A, B, C, D, and E.

| Entry | transaminase origin | % conversion cond. A | % conversion cond. B | % conversion cond. C | % conversion cond. D | % conversion cond. E |
|---|---|---|---|---|---|---|
| 1 | see Example 1 | 11.9 | 71.0 | 25.8 | 3.7 | 3.2 |
| 2 | Vibrio fluvialis | 5.2 | 1.7 | 3.3 | 0.0 | 1.6 |
| 3 | Agrobacterium tumefaciens | 0.3 | 0.0 | 0.0 | 0.0 | 0.7 |
| 4 | Rhodobacter spheroides | 2.8 | 0.6 | 2.0 | 0.0 | 2.0 |
| 5 | Bradyrhizobium | 5.0 | 2.1 | 1.0 | 0.0 | 1.8 |
| 6 | Arthrobacter citreus | 15.9 | 8.2 | 27.0 | 0.0 | 1.6 |
| 7 | SEQ ID NO: 147 | 33.7 | 88.8 | 70.7 | 54.8 | 1.6 |

Among the wild type enzymes analyzed, the new transaminase enzyme SEQ ID NO:3 shows the highest transaminase standard activity and the best properties with respect to substrate conversion at the different process relevant conditions.

EXAMPLE 4: ANALYSIS OF STEREOSELECTIVITY OF ENGINEERED ATAS

Several ATA variants that had been engineered in comparison to SEQ ID NO:3 were analyzed regarding their stereoselectivity in the formation of (S)-1-methyl-3-phenyl-propylamine. For analysis of stereoselectivity, Transaminase Conversion Assays with each ATA were performed as described in Example 3 under Condition F.

The products were analyzed by chiral HPLC analysis. Analytical conditions are:

Column: chiralpak IB (Daicel);
Eluent: 98% n-hexane, 2% isopropanol, 0.1% ethylenediamine;
Flow 1 ml/min;
Oven temperature: 35° C.;
Detection: 267 nm.
The retention times of the analytes are 5.6 min for (R)-1-methyl-3-phenylpropylamine and 5.9 min for (S)-1-methyl-3-phenylpropylamine.

Calculation of the enantiomeric excess (% ee) of the (S) enantiomer is done by integrating the peak areas of the enantiomers using the formula:

$$\% \text{ ee} = [(S)\text{enantiomer} - (R)\text{enantiomer}] / [(S)\text{enantiomer} + (R)\text{enantiomer}]$$

It was found, that the engineered ATAs showed an improved stereoselectivity in comparison to the wild type ATA SEQ ID No:3: The stereoselectivities of mutants are listed in the table below.

| SEQ ID NO | % ee | Mutation 1 | Mutation 2 | Mutation 3 | Mutation 4 |
|---|---|---|---|---|---|
| 3 | 59 | | | | |
| 96 | 99.1 | I417V | I422S | | |
| 97 | 97.8 | I417V | I422C | | |
| 98 | 95.3 | I417A | I422S | | |
| 99 | 88.8 | I417F | I422V | | |
| 100 | 78.0 | I417A | I422C | | |
| 101 | 97.1 | N161M | Y164L | | |
| 102 | 96.6 | N161I | Y164L | | |
| 103 | 94.2 | N161Q | Y164L | | |
| 104 | 92.6 | N161I | Y164M | | |
| 105 | 90.3 | N161M | Y164M | | |
| 106 | 89.4 | N161Q | Y164M | | |
| 107 | 87.7 | N161I | Y164F | | |

-continued

| SEQ ID NO | % ee | Mutation 1 | Mutation 2 | Mutation 3 | Mutation 4 |
|---|---|---|---|---|---|
| 108 | 67.2 | N146Y | N161Q | | |
| 109 | 93.1 | G51S | N161I | Y164L | |
| 110 | 96.2 | N161I | Y164L | A288G | |
| 111 | 93.5 | A67N | N161I | Y164L | |
| 112 | 93.5 | Q44R | N161I | Y164L | |
| 113 | 95.6 | A68P | N161I | Y164L | |
| 114 | 94.4 | N161I | Y164L | A349G | |
| 115 | 93.6 | N161I | Y164L | T430N | |
| 116 | 93.3 | N161I | Y164L | K420H | |
| 117 | 93.2 | N161I | Y164L | Q300E | |

| SEQ ID NO | % ee | Mutation 1 | Mutation 2 | Mutation 3 | Mutation 4 |
|---|---|---|---|---|---|
| 118 | 92.6 | L73M | N161I | Y164L | |
| 119 | 92.4 | G33Y | N161I | Y164L | |
| 120 | 91.8 | N161I | Y164L | K420S | |
| 121 | 91.2 | Q44N | N161I | Y164L | |
| 122 | 90.5 | N161I | Y164L | K420N | |
| 144 | 75.3 | M16W | N161I | Y164L | V230A |
| 145 | 70.3 | M16F | N161M | Y164I | V230A |
| 146 | 95.8 | M16W | W54A | N161Q | Y164L |

EXAMPLE 5: DETECTION OF THERMOSTABILITY OF ENGINEERED ATAS

Several ATA variants that had been engineered in comparison to SEQ ID NO:3 were analyzed regarding their thermostability. Crude extracts of a respective ATA were obtained as described in Example 2. Melting profiles of these active enzymatic active preparations of a respective ATA were recorded by incubation the crude extract for 15 minutes at different temperatures in a PCR cycler. Afterwards the crude extracts were incubated on ice for 30 minutes. Insoluble proteins were separated by centrifugation and the supernatants were analyzed regarding their remaining ATA activity in a Transaminase Standard Assay as described in Example 2.

Thermostability was expressed as the temperature at which 80% of the initial activity of the ATA variant remains after 15 min of incubation [Tm(80%)]. The initial activity is the activity of the respective ATA variant without any high temperature treatment, i.e. with 15 min incubation on ice instead of incubation at different temperatures in a PCR cycler.

It was found, that the engineered ATAs showed an improved thermostability in comparison to the wild type ATA SEQ ID No:3: The melting temperatures of mutants are listed in the table below.

| SEQ ID NO | Thermostability $T_m$ (80%) [° C.] | Mutation 1 | Mutation 2 | Mutation 3 | Mutation 4 |
|---|---|---|---|---|---|
| 3 | 61 | | | | |
| 4 | 62 | M16F | | | |
| 16 | 67 | W54A | | | |
| 47 | 65 | Y164L | | | |
| 48 | 62 | Y164M | | | |
| 87 | 62 | I417F | | | |
| 101 | 77 | N161M | Y164L | | |
| 102 | 78 | N161I | Y164L | | |
| 103 | 67 | N161Q | Y164L | | |
| 104 | 73 | N161I | Y164M | | |
| 105 | 71 | N161M | Y164M | | |
| 106 | 62 | N161Q | Y164M | | |
| 107 | 73 | N161I | Y164F | | |
| 108 | 67 | N146Y | N161Q | | |
| 109 | 81 | G51S | N161I | Y164L | |
| 110 | 76 | N161I | Y164L | A288G | |
| 123 | 79 | R45K | N161I | Y164L | |
| 124 | 79 | N161I | Y164L | Q391K | |
| 125 | 79 | N161I | Y164L | Y366H | |
| 126 | 79 | N161I | Y164L | Q354F | |
| 127 | 75 | N161I | Y164L | E433D | |
| 146 | 72 | M16W | W54A | N161Q | Y164L |

EXAMPLE 6: EVALUATION FOR IMPROVED CONVERSION UNDER RELEVANT PROCESS CONDITIONS

Several ATA variants that had been engineered in comparison to SEQ ID NO:3 were analyzed in Transaminase Conversion Assays for properties relevant for a preparative synthesis application at high concentration of amine donors, isopropylamine (IPA) and racemic 1-phenylethan-1-amine (MBA), respectively. Reactions were performed and analysed for conversion as described in Example 3, with analysis of conversion after a reaction time of 20 h. For the reaction 20% of the total reaction volume was crude extract of the respective ATA, obtained as described in Example 2. Different Conditions were used varying the concentrations of reactants and type of amino donor as indicated for each table.

| SEQ ID NO | Number Mutations | Mutation 1 | Mutation 2 | Mutation 3 | Mutation 4 | Conversion Condition G [%] | Conversion Condition H [%] |
|---|---|---|---|---|---|---|---|
| 3 | — | | | | | 5 | 34 |
| 101 | 2 | N161M | Y164L | | | 8 | 52 |
| 102 | 2 | N161I | Y164L | | | 8 | 57 |
| 103 | 2 | N161Q | Y164L | | | 9 | 53 |
| 104 | 2 | N161I | Y164M | | | 6 | 44 |
| 105 | 2 | N161M | Y164M | | | 8 | 51 |
| 106 | 2 | N161Q | Y164M | | | 7 | 47 |
| 107 | 2 | N161I | Y164F | | | 5 | 41 |
| 146 | 4 | M16W | W54A | N161Q | Y164L | 6 | 37 |

| SEQ ID NO | Mutation 1 | Mutation 2 | Mutation 3 | Conversion Condition I [%] | Conversion Condition J [%] |
|---|---|---|---|---|---|
| 3 | | | | 0 | 0 |
| 102 | N161I | Y164L | | 49 | 89 |
| 109 | G51S | N161I | Y164L | 66 | 88 |
| 110 | N161I | Y164L | A288G | 68 | 78 |
| 111 | A67N | N161I | Y164L | 65 | 91 |
| 112 | Q44R | N161I | Y164L | 63 | 90 |
| 113 | A68P | N161I | Y164L | 47 | 86 |
| 114 | N161I | Y164L | A349G | 51 | 87 |
| 115 | N161I | Y164L | T430N | 51 | 88 |
| 116 | N161I | Y164L | K420H | 52 | 86 |
| 117 | N161I | Y164L | Q300E | 56 | 88 |
| 118 | L73M | N161I | Y164L | 58 | 90 |
| 119 | G33Y | N161I | Y164L | 56 | 89 |
| 120 | N161I | Y164L | K420S | 46 | 86 |

| | | | | | |
|---|---|---|---|---|---|
| 121 | Q44N | N161I | Y164L | 54 | 90 |
| 122 | N161I | Y164L | K420N | 45 | 86 |
| 123 | R45K | N161I | Y164L | 55 | 88 |
| 124 | N161I | Y164L | Q391K | 50 | 88 |
| 125 | N161I | Y164L | Y366H | 49 | 84 |
| 126 | N161I | Y164L | Q354F | 44 | 85 |
| 127 | N161I | Y164L | E433D | 57 | 92 |
| 128 | N161I | Y164L | A353R | 61 | 87 |
| 129 | N161I | Y164L | Y366F | 61 | 88 |
| 130 | Q44H | N161I | Y164L | 61 | 89 |
| 131 | V29L | N161I | Y164L | 59 | 87 |
| 132 | H87T | N161I | Y164L | 58 | 90 |
| 133 | E9R | N161I | Y164L | 57 | 88 |
| 134 | G147S | N161I | Y164L | 56 | 87 |
| 135 | N7L | N161I | Y164L | 55 | 88 |
| 136 | R140K | N161I | Y164L | 55 | 87 |
| 137 | N161I | Y164L | H165R | 54 | 88 |
| 138 | H87N | N161I | Y164L | 53 | 89 |
| 139 | V29I | N161I | Y164L | 53 | 92 |
| 140 | A71G | N161I | Y164L | 52 | 92 |
| 141 | G114S | N161I | Y164L | 51 | 88 |
| 142 | V109I | N161I | Y164L | 51 | 86 |
| 143 | N161I | Y164L | Q391E | 47 | 83 |

EXAMPLE 7 CHARACTERIZATION OF ENZYMATIC PROPERTIES OF ENGINEERED ATA OF SEQ ID NO:148

An enzymatic active preparation of ATA of SEQ ID NO:148 and SEQ ID NO147 were prepared as described in Example 2. Analysis of their properties in the Transaminase Standard Assay has been shown in Example 3

Active enzyme preparations of SEQ ID NO:147 and SEQ ID NO:148 have been further subjected to Transaminase Conversion Assays as described in Example 3, but at conditions:

Condition K (100 mM BA; 500 mM rac. MBA), or
Condition L (200 mM BA; 500 mM rac. MBA), or
Condition M (10 g/L BA, 900 mM IPA)

| Entry | transaminase origin | % conversion cond. K | % conversion cond. L | % conversion cond. M | $T_m$ (80%) [° C.] | ee % |
|---|---|---|---|---|---|---|
| 1 | SEQ ID NO: 148 | 0.0 | 0.0 | 0.0 | 51 | |
| 2 | SEQ ID NO: 147 | 74 | 53 | 80 | 58 | >99 |

The invention claimed is:

1. A transaminase comprising an amino acid sequence with at least 80% identity to SEQ ID NO:3, wherein the transaminase is substituted compared to SEQ ID NO:3 at least in position N161 and/or in position Y164, and has a transaminase activity.

2. The transaminase according to claim 1, which is substituted compared to SEQ ID NO:3 in position Y164.

3. The transaminase according to claim 1, which is additionally substituted compared to SEQ ID NO:3 in position G51.

4. The transaminase according to claim 1, which comprises at least two substitutions selected from the group consisting of N161A, N161F, N161M, N161Y, N161Q, N161I, Y164L, Y164M, Y164A, Y164F, Y164I, and G51S.

5. The transaminase according to claim 1, which comprises a substitution selected from the group consisting of N161A, N161C, N161 D, N161E, N161G, N161I, N161K, N161L, N161M, N161P, N161Q, N161R, N161S, N161T, N161V, N161W, and N161Y.

6. The transaminase according claim 5, which comprises a substitution selected from the group consisting of N161A, N161F, N161M, N161Y, N161Q, and N161I.

7. The transaminase according to claim 1, which comprises a substitution selected from the group consisting of Y164A, Y164C, Y164D, Y164E, Y164F, Y164G, Y164H, Y164I, Y164K, Y164L, Y164M, Y164N, Y164P, Y164Q, Y164R, Y164S, Y164T, Y164V, and Y164W and/or which comprises a substitution selected from the group consisting of G51A, G51C, G51 D, G51E, G51F, G51H, G51I, G51K, G51L, G51M, G51N, G51P, G51Q, G51R, G51S, G51T, G51V, G51W, and G51Y.

8. The transaminase according to claim 7, which comprises a substitution selected from the group consisting of Y164L, Y164M, Y164A, Y164F, and Y164I or which comprises the substitution G51S.

9. The transaminase according to claim 1, wherein the identity to SEQ ID NO:3 is at least 90%.

10. The transaminase according to claim 1, which is additionally substituted compared to SEQ ID NO:3 in at least one or more positions selected from the group consisting of the positions N7, E9, M16, V29, G33, Q44, R45, L53, W54, A67, A68, A71, L73, F82, H87, V109, G114, R140, N146, G147, Y148, Y151, H165, E222, A227, G228, V230, V257, V258, A288, Q300, A349, A353, Q354, Y366, M378, Q391, R415, I417, K420, I422, T430, and E433.

11. The transaminase according claim 1, which has
(A) a temperature stability of at least 50° C., and/or
(B) a specific activity of at least 0.5 U/mg in Transaminase Standard Assays; and/or
(C) a high conversion activity under different reaction conditions involving high amine concentrations.

12. The transaminase according to claim 1, comprising at least one or more additional substitutions selected from the group consisting of N7L, E9R, M16F, M16C, M16V, M16L, M16A, M16W, V29L, V29I, G33Y, Q44R, Q44N, Q44H, R45K, L53F, L53W, L53V, L53A, L53S, L53G, W54A, W54I, W54L, W54Y, W54S, W54C, W54F, W54V, A67N, A68P, A71G, L73M, F82V, F82A, F82G, F82L, F82Y, H87T, H87N, V109I, G114S, R140K, N146Y, N146D, N146S, G147S, Y148F, Y148S, Y148G, V151A, V151W, V151I, V151F, V151Y, V151S, H165R, E222S, E222A, E222D, A227Y, A227V, A227I, A227G, A227F, A227M, G228A, G228I, V230A, V230G, V230I, V230L, V257A, V258A, V258I, A288G, Q300E, A349G, A353R, Q354F, Y366H, Y366F, M378L, M378V, M378I, M378F, M378Y, M378T, M378A, M378C, Q391K, Q391E, R415A, R415V, R415L, R415G, R415Y, R415T, R415C, I417T, I417C, I417F, I417V, I417Y, I417A, K420H, K420S, K420N, I422V, I422S, I422A, I422L, I422C, T430N, and E433D or
being substituted in at least one other position selected from the group consisting of N7, E9, M16, V29, G33, Q44, R45, L53, W54, A67, A68, A71, L73, F82, H87, V109, G114, R140, N146, G147, Y148, Y151, H165, E222, A227, G228, V230, V257, V258, A288, Q300, A349, A353, Q354, Y366, M378, Q391, R415, I417, K420, I422, T430, and E433.

13. The transaminase according to claim 1, which is substituted compared to SEQ ID NO:3 in at least two positions selected from the group consisting of N161 as well as Y164; and N146 as well as N161.

14. The transaminase according to claim 1, which is substituted compared to SEQ ID NO:3 in at least two positions such that it comprises
(i) at position N161 a substitution selected from the group consisting of N161A, N161F, N161M, N161Y, N161I, or N161Q; as well as
at position Y164 a substitution selected from the group consisting of Y164L, Y164M, Y164A, Y164F, or Y164I; and/or
(ii) at position N146 a substitution selected from the group consisting of N146Y, N146D, or N146S; as well as
at position N161 a substitution selected from the group consisting of N161A, N161F, N161M, N161Y, N161I, or N161Q.

15. The transaminase according to claim 1, which is substituted compared to SEQ ID NO:3 in at least two positions such that it comprises at least two substitutions selected from the group consisting of the substitutions N161M as well as Y164L; N161I as well as Y164L; N161Q as well as Y164L; N161I as well as Y164M; N161M as well as Y164M; N161Q as well as Y164M; N161I as well as Y164F; N161M as well as Y164I; and N146Y as well as N161Q.

16. The transaminase according to claim 1, which is substituted compared to SEQ ID NO:3 in
(i) at least two positions selected from the group consisting of N161 as well as Y164; or N146 as well as N161; and
(ii) in addition in at least one other position selected from the group consisting of N7, E9, M16, V29, G33, Q44, R45, G51, L53, W54, A67, A68, A71, L73, F82, H87, V109, G114, R140, N146, G147, Y148, Y151, Y164, H165, E222, A227, G228, V230, V257, V258, A288, Q300, A349, A353, Q354, Y366, M378, Q391, R415, I417, K420, I422, T430, and E433.

17. The transaminase according to claim 1, which is substituted compared to SEQ ID NO:3 in (i) at least two positions wherein the transaminase comprises at least two substitutions selected from the group consisting of N161M as well as Y164L; N161I as well as Y164L; N161Q as well as Y164L; N161I as well as Y164M; N161M as well as Y164M; N161Q as well as Y164M; N161I as well as Y164F; N161M as well as Y164I and N146Y as well as N161Q; and (ii) in addition in at least one other position the transaminase comprises at least one other substitution selected from the group consisting of N7L, E9R, M16F, M16C, M16V, M16L, M16A, M16W, V29L, V29I, G33Y, Q44R, Q44N, Q44H, R45K, G51S, L53F, L53W, L53V, L53A, L53S, L53G, W54A, W54I, W54L, W54Y, W54S, W54C, W54F, W54V, A67N, A68P, A71G, L73M, F82V, F82A, F82G, F82L, F82Y, H87T, H87N, V109I, G114S, R140K, N146Y, N146D, N146S, G147S, Y148F, Y148S, Y148G, V151A, V151W, V151I, V151F, V151Y, V151S, H165R, E222S, E222A, E222D, A227V, A227I, A227G, A227F, A227Y, A227M, G228A, G228I, V230G, V230A, V230I, V230L, V257A, V258A, V258I, A288G, Q300E, A349G, A353R, Q354F, Y366H, Y366F, M378L, M378V, M378I, M378F, M378Y, M378T, M378A, M378C, Q391K, Q391E, R415A, R415V, R415L, R415G, R415Y, R415T, R415C, I417T, I417C, I417F, I417V, I417Y, I417A, K420H, K420S, K420N, I422V, I422S, I422A, I422L, I422C, T430N, and E433D.

18. The transaminase according to claim 1, which is substituted compared to SEQ ID NO:3 in at least in three positions such that it comprises at least three substitutions, wherein
(i) the first substitution of said at least three substitutions is selected from the group consisting of N161I, N161M, and N161Q; and
(ii) the second substitution of said at least three substitutions is selected from the group consisting of Y164L, and Y164I; and
(iii) the third substitution of said at least three substitutions is selected from the group consisting of N7L, E9R, M16F, M16W, V29L, V29I, G33Y, Q44R, Q44N, Q44H, R45K, G51S, W54A, A67N, A68P, A71G, L73M, H87T, H87N, V109I, G114S, R140K, G147S, H165R, V230A, A288G, Q300E, A349G, A353R, Q354F, Y366H, Y366F, Q391K, Q391E, K420H, K420S, K420N, T430N, and E433D.

19. The transaminase according to claim 1, which comprises an amino acid sequence of at least 85% identity to the SEQ ID NO: 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57.58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, or 150.

20. A method for the conversion of
(i) a ketone substrate according to general formula (I)

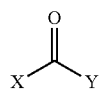

(I)

to an amine product according to general formula (II)

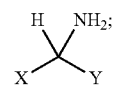

(II)

and/or the preferably concomittant conversion of
(ii) a cosubstrate according to general formula (III)

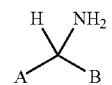

(III)

to a ketone coproduct according to general formula (IV)

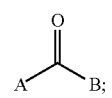

(IV)

or vice versa;
wherein X and Y as well as A and B, in either case, independently of one another, are selected from saturated or unsaturated, unsubstituted or mono- or polysubstituted aliphatic or alicyclic $C_{1-12}$-hydrocarbon residues; unsubstituted or mono- or polysubstituted $C_{6-10}$-aromatic hydrocarbon residues, optionally being bridged through a saturated or unsaturated, unsubstituted or mono- or polysubstituted aliphatic $C_{1-12}$-hydrocarbon residue; unsubstituted or mono- or polysubstituted heteroaromatic hydrocarbon residues, optionally being bridged through a saturated or unsaturated, unsubstituted or mono- or polysubstituted aliphatic $C_{1-12}$-hydrocarbon residue; and sugar residues or desoxysugar residues in each case comprising mono-, di- or oligosaccharides;
wherein one of residues X or Y, as well as one of residues A or B, in either case, independently of one another, may be hydrogen;
wherein mono- or polysubstituted means independently substituted with one or more functional groups selected from -halo, —OH, =O, —O$C_{1-12}$-alkyl, —O$C_{6-10}$-aryl, —O-heteroaryl, —OCO$C_{1-12}$-alkyl, —OCO$C_{6-10}$-aryl, —OCO-heteroaryl, —SH, —S$C_{1-12}$-alkyl, —S$C_{6-10}$-aryl, —S-heteroaryl, —S(=O)$_{1-2}$OH, —NO, —NO$_2$, —N$_3$, —NH$_2$, —NH($C_{1-12}$-alkyl), —N($C_{1-12}$-alkyl)$_2$, —NH($C_{6-10}$-aryl), —N($C_{6-10}$-aryl)$_2$, —NH(heteroaryl), —N(heteroaryl)$_2$, —CN, —CHO, —CO$_2$H, CO—$C_{1-2}$-alkyl, —CO—$C_{6-10}$-aryl and —CO-heteroaryl;
wherein the method comprises the step of reacting a ketone substrate according to general formula (I) and/or an amine product according to general formula (II) and/or a amine cosubstrate according to general formula (III) and/or a ketone coproduct according to general formula (IV) in the presence of the transaminase of claim 1.

21. The transaminase according to claim 1, which is substituted compared to SEQ ID NO:3 in position N161.

\* \* \* \* \*

SEQUENCE LISTING

<160> NUMBER OF SEQ ID NOS: 150

<210> SEQ ID NO 1
<211> LENGTH: 1350
<212> TYPE: DNA
<213> ORGANISM: unknown
<220> FEATURE:
<223> OTHER INFORMATION: isolated from library

<400> SEQUENCE: 1

```
atgtacgaga aatacaagaa cgccgaaaaa aaattctggc accccatggg ctccagcgcc      60
gcgccgcacc gtgacaaaac cctggtcatc gcccggggcg acggcaacta catcaccgac     120
atcgacggcc agcgcatgct cgatggcgtg ggcgggctgt ggaacgtcaa catcgggcac     180
aaccgcgcca gcgtgaaggc ggcgattgcc gcacagttgg atgagctggc gtattaccag     240
accttcgacg gcattgccca ccctcgggtg tttgacctgg ccgaacggct gaccggcatg     300
ttcgcccagg agcgcatggc gcgggtgttg ttcagttctg gtggttcgga tgcggtcgag     360
accgcgctga aaatggcccg gcaatactgg atcgccagcg gcgagcccgg cgtacgcgc     420 ttcctgtccc tgcgcaacgg ctatcacggc gtgcacatgg cggcacctc ggtgggcggc     480 aatggggtgt accactacaa ccacggccaa ctcctcgccg gttgccactt gctcgacacg     540
ccctggctgt atcgcaaccc ctgggattgc cgcgatcccc aagcgctgac cgcgcactgc     600
```

```
atccgccagt tggaagagca gatcgcgttg ctcggcgccc agaccatcgc ggccttgatc      660
gctgagcccg tgcaaggggc gggcggggtg atcgtgcctc cggccgacta ttggccgcgt      720
ttgcgcgagg tgtgcgaccg ccacggcatt ctgttgattg ccgacgaagt ggtcactggc      780
ttcgggcgtt cgggctgcat gctcggcagt cgcggctggg gcgtggcacc ggacatcctg      840
tgcctggcca agggcatcac cgccggttac atcccgctgg gtgccacgct gttcaaccag      900
cgcatcgccg atgccatcga aaacggccag ggtttcagcc acatgatcat gcacggctac      960
acctacagcg ggcacccgac cgcgtgtgcg gcggcgctgg cggtgctgga tatcgtcgaa     1020
gccgaagacc tgccgggtaa cgccgccaag gtgggtgcgc aactgctgga caactccag     1080 ccactggttg aacgctacgc ggtggtgggt gaggtgcgcg gcaagggcct gatgattgcc     1140
ctggacctgg tcagcgacaa gcgtacccgc cagcccctcg acccggccgc gggccaaccg     1200
tcacgcatcg ccgacgaggc gcgccgtgcc ggagtgctgg tacggccgat cggcaacaag     1260
atcatcctct cgccgccatt gaccctcacc cgcgacgagg cgggcttgat ggtgtcggcg     1320
ctggaagcgg cattcgcccg ctgcggctag                                     1350
```

<210> SEQ ID NO 2
<211> LENGTH: 1350
<212> TYPE: DNA
<213> ORGANISM: unknown
<220> FEATURE:
<223> OTHER INFORMATION: codon optimized artificial sequence

<400> SEQUENCE: 2

```
atgtacgaga atacaaaaa cgccgagaaa aaattctggc atccgatggg tagcagcgca       60
gcaccgcatc gtgataaaac cctggttatt gcacgtggtg atggtaacta tattaccgat      120
attgatggtc agcgtatgct ggatggtgtt ggtggtctgt ggaatgttaa tattggtcat      180
aatcgtgcaa gcgtgaaagc agcaattgca gcacagctgg atgaactggc atattatcag      240 accttgatg gtattgcaca tccgcgtgtt tttgatctgg cagaacgtct gaccggtatg      300
tttgcacaag aacgtatggc acgtgttctg tttagcagcg tggtagtga tgcagttgaa      360 accgcactga aaatggcacg tcagtattgg attgcaagcg tgaaccggg tcgtacccgt      420 tttctgagcc tgcgtaatgg ttatcatggt gttcatatgg gtggcaccag cgttggtggt      480
aatggtgttt atcattataa tcatggtcag ctgctggcag gttgtcatct gctggatacc      540
ccgtggctgt atcgtaatcc gtgggattgt cgtgatccgc aggcactgac cgcacattgt      600
attcgtcagc tggaagaaca aattgcactg ctgggtgcac agaccattgc agccctgatt      660
gcagaaccgg tgcagggtgc cggtggtgtt attgttccgc ctgcagatta ttggcctcgt      720
ctgcgtgaag tttgtgatcg tcatggtatt ctgctgattg ccgatgaagt tgttaccggt      780
tttggtcgta gcggttgtat gctgggtagc cgtggttggg gtgttgcacc ggatattctg      840
tgtctggcaa aaggtattac cgcaggttat attccgctgg gtgcgaccct gtttaatcag      900
cgtattgcag atgcaattga aaacggtcag ggctttagcc atatgattat gcatggttat      960
acctatagcg gtcatccgac cgcatgtgca gcagcactgg cagttctgga tattgttgaa     1020
gccgaagatc tgcctggtaa tgcagcaaaa gttggtgcac aactgctgga cagctgcag     1080 ccgctggttg aacgttatgc agttgttggt gaagttcgtg gtaaaggcct gatgattgca     1140
ctggatctgg ttagcgataa acgtacccgt cagcctctgg atccggcagc aggtcagccg     1200
agccgtattg cggatgaagc acgtcgtgcc ggtgttctgg ttcgtccgat tggcaataaa     1260
```

```
atcattctga gccctccgct gaccctgacc cgtgatgaag caggtctgat ggttagcgca   1320
ctggaagcag catttgcccg ttgtggttaa                                   1350
```

<210> SEQ ID NO 3
<211> LENGTH: 449
<212> TYPE: PRT
<213> ORGANISM: unknown
<220> FEATURE:
<223> OTHER INFORMATION: isolated from library

<400> SEQUENCE: 3

```
Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
        35                  40                  45

Gly Val Gly Gly Leu Trp Asn Val Asn Ile Gly His Asn Arg Ala Ser
    50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
    130                 135                 140

Arg Asn Gly Tyr His Gly Val His Met Gly Thr Ser Val Gly Gly
145                 150                 155                 160

Asn Gly Val Tyr His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
    210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala
        275                 280                 285

Gly Tyr Ile Pro Leu Gly Ala Thr Leu Phe Asn Gln Arg Ile Ala Asp
    290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Ala Leu Ala Val Leu
                325                 330                 335

Asp Ile Val Glu Ala Glu Asp Leu Pro Gly Asn Ala Ala Lys Val Gly
            340                 345                 350
```

Ala Gln Leu Leu Glu Gln Leu Gln Pro Leu Val Glu Arg Tyr Ala Val
            355                 360                 365

Val Gly Glu Val Arg Gly Lys Gly Leu Met Ile Ala Leu Asp Leu Val
    370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Ala Gly Val Leu Val Arg Pro
                405                 410                 415

Ile Gly Asn Lys Ile Ile Leu Ser Pro Pro Leu Thr Leu Thr Arg Asp
            420                 425                 430

Glu Ala Gly Leu Met Val Ser Ala Leu Glu Ala Ala Phe Ala Arg Cys
            435                 440                 445

Gly

<210> SEQ ID NO 4
<211> LENGTH: 449
<212> TYPE: PRT
<213> ORGANISM: unknown
<220> FEATURE:
<223> OTHER INFORMATION: isolated from library

<400> SEQUENCE: 4

Met Tyr Glu Lys Tyr Lys Asn Ala Glu Lys Lys Phe Trp His Pro Phe
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
        35                  40                  45

Gly Val Gly Gly Leu Trp Asn Val Asn Ile Gly His Asn Arg Ala Ser
    50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
    130                 135                 140

Arg Asn Gly Tyr His Gly Val His Met Gly Thr Ser Val Gly Gly
145                 150                 155                 160

Asn Gly Val Tyr His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
    210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

-continued

```
Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala
        275                 280                 285

Gly Tyr Ile Pro Leu Gly Ala Thr Leu Phe Asn Gln Arg Ile Ala Asp
    290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Leu Ala Val Leu
                325                 330                 335

Asp Ile Val Glu Ala Glu Asp Leu Pro Gly Asn Ala Ala Lys Val Gly
            340                 345                 350

Ala Gln Leu Leu Glu Gln Leu Gln Pro Leu Val Glu Arg Tyr Ala Val
        355                 360                 365

Val Gly Glu Val Arg Gly Lys Gly Leu Met Ile Ala Leu Asp Leu Val
    370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Ala Gly Val Leu Val Arg Pro
                405                 410                 415

Ile Gly Asn Lys Ile Ile Leu Ser Pro Pro Leu Thr Leu Thr Arg Asp
            420                 425                 430

Glu Ala Gly Leu Met Val Ser Ala Leu Glu Ala Ala Phe Ala Arg Cys
        435                 440                 445

Gly

<210> SEQ ID NO 5
<211> LENGTH: 449
<212> TYPE: PRT
<213> ORGANISM: unknown
<220> FEATURE:
<223> OTHER INFORMATION: isolated from library

<400> SEQUENCE: 5

Met Tyr Glu Lys Tyr Lys Asn Ala Glu Lys Lys Phe Trp His Pro Cys
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
        35                  40                  45

Gly Val Gly Gly Leu Trp Asn Val Asn Ile Gly His Asn Arg Ala Ser
    50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
    130                 135                 140

Arg Asn Gly Tyr His Gly Val His Met Gly Gly Thr Ser Val Gly Gly
145                 150                 155                 160

Asn Gly Val Tyr His Tyr Asn His Gly Gln Leu Leu Ala Gly Cys His
```

```
                 165                 170                 175
Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
    210                 215                 220

Gln Gly Ala Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala
        275                 280                 285

Gly Tyr Ile Pro Leu Gly Ala Thr Leu Phe Asn Gln Arg Ile Ala Asp
    290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Ala Leu Ala Val Leu
                325                 330                 335

Asp Ile Val Glu Ala Glu Asp Leu Pro Gly Asn Ala Ala Lys Val Gly
            340                 345                 350

Ala Gln Leu Leu Glu Gln Leu Gln Pro Leu Val Glu Arg Tyr Ala Val
        355                 360                 365

Val Gly Glu Val Arg Gly Lys Gly Leu Met Ile Ala Leu Asp Leu Val
    370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Arg Pro
                405                 410                 415

Ile Gly Asn Lys Ile Ile Leu Ser Pro Pro Leu Thr Leu Thr Arg Asp
            420                 425                 430

Glu Ala Gly Leu Met Val Ser Ala Leu Glu Ala Ala Phe Ala Arg Cys
        435                 440                 445

Gly

<210> SEQ ID NO 6
<211> LENGTH: 449
<212> TYPE: PRT
<213> ORGANISM: unknown
<220> FEATURE:
<223> OTHER INFORMATION: isolated from library

<400> SEQUENCE: 6

Met Tyr Glu Lys Tyr Lys Asn Ala Glu Lys Lys Phe Trp His Pro Val
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
        35                  40                  45

Gly Val Gly Gly Leu Trp Asn Val Asn Ile Gly His Asn Arg Ala Ser
    50                  55                  60

Val Lys Ala Ala Ile Ala Ala Gln Leu Asp Glu Leu Ala Tyr Tyr Gln
65                  70                  75                  80
```

-continued

```
Thr Phe Asp Gly Ile Ala His Pro Arg Val Phe Asp Leu Ala Glu Arg
             85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
    130                 135                 140

Arg Asn Gly Tyr His Gly Val His Met Gly Gly Thr Ser Val Gly Gly
145                 150                 155                 160

Asn Gly Val Tyr His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
    210                 215                 220

Gln Gly Ala Gly Gly Val Ile Val Pro Ala Asp Tyr Trp Pro Arg
225                 230                 235                 240

Leu Arg Glu Val Cys Asp Arg His Gly Ile Leu Ile Ala Asp Glu
                245                 250                 255

Val Val Thr Gly Phe Gly Arg Ser Gly Cys Met Leu Gly Ser Arg Gly
                260                 265                 270

Trp Gly Val Ala Pro Asp Ile Leu Cys Leu Ala Lys Gly Ile Thr Ala
            275                 280                 285

Gly Tyr Ile Pro Leu Gly Ala Thr Leu Phe Asn Gln Arg Ile Ala Asp
    290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Ala Leu Ala Val Leu
                325                 330                 335

Asp Ile Val Glu Ala Asp Leu Pro Gly Asn Ala Ala Lys Val Gly
                340                 345                 350

Ala Gln Leu Leu Glu Gln Leu Gln Pro Leu Val Glu Arg Tyr Ala Val
    355                 360                 365

Val Gly Glu Val Arg Gly Lys Gly Leu Met Ile Ala Leu Asp Leu Val
370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Arg Pro
                405                 410                 415

Ile Gly Asn Lys Ile Ile Leu Ser Pro Pro Leu Thr Leu Thr Arg Asp
            420                 425                 430

Glu Ala Gly Leu Met Val Ser Ala Leu Glu Ala Ala Phe Ala Arg Cys
                435                 440                 445

Gly
```

<210> SEQ ID NO 7
<211> LENGTH: 449
<212> TYPE: PRT
<213> ORGANISM: unknown
<220> FEATURE:
<223> OTHER INFORMATION: isolated from library

```
<400> SEQUENCE: 7

Met Tyr Glu Lys Tyr Lys Asn Ala Glu Lys Lys Phe Trp His Pro Leu
1               5                   10                  15

Gly Ser Ser Ala Ala Pro His Arg Asp Lys Thr Leu Val Ile Ala Arg
                20                  25                  30

Gly Asp Gly Asn Tyr Ile Thr Asp Ile Asp Gly Gln Arg Met Leu Asp
            35                  40                  45

Gly Val Gly Gly Leu Trp Asn Val Asn Ile Gly His Asn Arg Ala Ser
        50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
130                 135                 140

Arg Asn Gly Tyr His Gly Val His Met Gly Gly Thr Ser Val Gly Gly
145                 150                 155                 160

Asn Gly Val Tyr His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala
        275                 280                 285

Gly Tyr Ile Pro Leu Gly Ala Thr Leu Phe Asn Gln Arg Ile Ala Asp
290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Ala Leu Ala Val Leu
                325                 330                 335

Asp Ile Val Glu Ala Glu Asp Leu Pro Gly Asn Ala Ala Lys Val Gly
            340                 345                 350

Ala Gln Leu Leu Glu Gln Leu Gln Pro Leu Val Glu Arg Tyr Ala Val
        355                 360                 365

Val Gly Glu Val Arg Gly Lys Gly Leu Met Ile Ala Leu Asp Leu Val
370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Arg Pro
```

```
              405                 410                 415
Ile Gly Asn Lys Ile Ile Leu Ser Pro Pro Leu Thr Leu Thr Arg Asp
            420                 425                 430

Glu Ala Gly Leu Met Val Ser Ala Leu Glu Ala Ala Phe Ala Arg Cys
        435                 440                 445

Gly

<210> SEQ ID NO 8
<211> LENGTH: 449
<212> TYPE: PRT
<213> ORGANISM: unknown
<220> FEATURE:
<223> OTHER INFORMATION: isolated from library

<400> SEQUENCE: 8

Met Tyr Glu Lys Tyr Lys Asn Ala Glu Lys Lys Phe Trp His Pro Ala
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
        35                  40                  45

Gly Val Gly Gly Leu Trp Asn Val Asn Ile Gly His Asn Arg Ala Ser
    50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
    130                 135                 140

Arg Asn Gly Tyr His Gly Val His Met Gly Gly Thr Ser Val Gly Gly
145                 150                 155                 160

Asn Gly Val Tyr His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
    210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala
        275                 280                 285

Gly Tyr Ile Pro Leu Gly Ala Thr Leu Phe Asn Gln Arg Ile Ala Asp
    290                 295                 300

Ala Ile Glu Asn Gly Gln Gly Phe Ser His Met Ile Met His Gly Tyr
305                 310                 315                 320
```

Thr Tyr Ser Gly His Pro Thr Ala Cys Ala Ala Leu Ala Val Leu
                325                 330                 335

Asp Ile Val Glu Ala Glu Asp Leu Pro Gly Asn Ala Ala Lys Val Gly
            340                 345                 350

Ala Gln Leu Leu Glu Gln Leu Gln Pro Leu Val Glu Arg Tyr Ala Val
        355                 360                 365

Val Gly Glu Val Arg Gly Lys Gly Leu Met Ile Ala Leu Asp Leu Val
370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Arg Pro
                405                 410                 415

Ile Gly Asn Lys Ile Ile Leu Ser Pro Pro Leu Thr Leu Thr Arg Asp
            420                 425                 430

Glu Ala Gly Leu Met Val Ser Ala Leu Glu Ala Ala Phe Ala Arg Cys
        435                 440                 445

Gly

<210> SEQ ID NO 9
<211> LENGTH: 449
<212> TYPE: PRT
<213> ORGANISM: unknown
<220> FEATURE:
<223> OTHER INFORMATION: isolated from library

<400> SEQUENCE: 9

Met Tyr Glu Lys Tyr Lys Asn Ala Glu Lys Lys Phe Trp His Pro Trp
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
        35                  40                  45

Gly Val Gly Gly Leu Trp Asn Val Asn Ile Gly His Asn Arg Ala Ser
50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
130                 135                 140

Arg Asn Gly Tyr His Gly Val His Met Gly Gly Thr Ser Val Gly Gly
145                 150                 155                 160

Asn Gly Val Tyr His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
            245                 250                 255

Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala
        275                 280                 285

Gly Tyr Ile Pro Leu Gly Ala Thr Leu Phe Asn Gln Arg Ile Ala Asp
        290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Ala Leu Ala Val Leu
            325                 330                 335

Asp Ile Val Glu Ala Glu Asp Leu Pro Gly Asn Ala Ala Lys Val Gly
            340                 345                 350

Ala Gln Leu Leu Glu Gln Leu Gln Pro Leu Val Glu Arg Tyr Ala Val
        355                 360                 365

Val Gly Glu Val Arg Gly Lys Gly Leu Met Ile Ala Leu Asp Leu Val
370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Arg Pro
            405                 410                 415

Ile Gly Asn Lys Ile Ile Leu Ser Pro Pro Leu Thr Leu Thr Arg Asp
        420                 425                 430

Glu Ala Gly Leu Met Val Ser Ala Leu Glu Ala Ala Phe Ala Arg Cys
        435                 440                 445

Gly

<210> SEQ ID NO 10
<211> LENGTH: 449
<212> TYPE: PRT
<213> ORGANISM: unknown
<220> FEATURE:
<223> OTHER INFORMATION: isolated from library

<400> SEQUENCE: 10

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
        35                  40                  45

Gly Val Gly Gly Phe Trp Asn Val Asn Ile Gly His Asn Arg Ala Ser
    50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
            85                  90                  95

Leu Thr Gly Met Phe Ala Gln Glu Arg Met Ala Arg Val Leu Phe Ser
        100                 105                 110

Ser Gly Gly Ser Asp Ala Val Glu Thr Ala Leu Lys Met Ala Arg Gln
    115                 120                 125

Tyr Trp Ile Ala Ser Gly Glu Pro Gly Arg Thr Arg Phe Leu Ser Leu

```
            130                 135                 140
Arg Asn Gly Tyr His Gly Val His Met Gly Gly Thr Ser Val Gly Gly
145                 150                 155                 160

Asn Gly Val Tyr His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala
        275                 280                 285

Gly Tyr Ile Pro Leu Gly Ala Thr Leu Phe Asn Gln Arg Ile Ala Asp
290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Ala Leu Ala Val Leu
                325                 330                 335

Asp Ile Val Glu Ala Glu Asp Leu Pro Gly Asn Ala Ala Lys Val Gly
            340                 345                 350

Ala Gln Leu Leu Glu Gln Leu Gln Pro Leu Val Glu Arg Tyr Ala Val
        355                 360                 365

Val Gly Glu Val Arg Gly Lys Gly Leu Met Ile Ala Leu Asp Leu Val
370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Arg Pro
                405                 410                 415

Ile Gly Asn Lys Ile Ile Leu Ser Pro Pro Leu Thr Leu Thr Arg Asp
            420                 425                 430

Glu Ala Gly Leu Met Val Ser Ala Leu Glu Ala Ala Phe Ala Arg Cys
        435                 440                 445

Gly

<210> SEQ ID NO 11
<211> LENGTH: 449
<212> TYPE: PRT
<213> ORGANISM: unknown
<220> FEATURE:
<223> OTHER INFORMATION: isolated from library

<400> SEQUENCE: 11

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
        35                  40                  45
```

```
Gly Val Gly Gly Trp Trp Asn Val Asn Ile Gly His Asn Arg Ala Ser
    50              55                  60

Val Lys Ala Ala Ile Ala Gln Leu Asp Glu Leu Ala Tyr Tyr Gln
65              70              75              80

Thr Phe Asp Gly Ile Ala His Pro Arg Val Phe Asp Leu Ala Glu Arg
                85              90              95

Leu Thr Gly Met Phe Ala Gln Glu Arg Met Ala Arg Val Leu Phe Ser
            100             105             110

Ser Gly Gly Ser Asp Ala Val Glu Thr Ala Leu Lys Met Ala Arg Gln
        115             120             125

Tyr Trp Ile Ala Ser Gly Glu Pro Gly Arg Thr Arg Phe Leu Ser Leu
    130             135             140

Arg Asn Gly Tyr His Gly Val His Met Gly Gly Thr Ser Val Gly Gly
145             150             155             160

Asn Gly Val Tyr His Tyr Asn His Gly Gln Leu Leu Ala Gly Cys His
                165             170             175

Leu Leu Asp Thr Pro Trp Leu Tyr Arg Asn Pro Trp Asp Cys Arg Asp
            180             185             190

Pro Gln Ala Leu Thr Ala His Cys Ile Arg Gln Leu Glu Glu Gln Ile
        195             200             205

Ala Leu Leu Gly Ala Gln Thr Ile Ala Ala Leu Ile Ala Glu Pro Val
210             215             220

Gln Gly Ala Gly Gly Val Ile Val Pro Pro Ala Asp Tyr Trp Pro Arg
225             230             235             240

Leu Arg Glu Val Cys Asp Arg His Gly Ile Leu Leu Ile Ala Asp Glu
                245             250             255

Val Val Thr Gly Phe Gly Arg Ser Gly Cys Met Leu Gly Ser Arg Gly
            260             265             270

Trp Gly Val Ala Pro Asp Ile Leu Cys Leu Ala Lys Gly Ile Thr Ala
        275             280             285

Gly Tyr Ile Pro Leu Gly Ala Thr Leu Phe Asn Gln Arg Ile Ala Asp
    290             295             300

Ala Ile Glu Asn Gly Gln Gly Phe Ser His Met Ile Met His Gly Tyr
305             310             315             320

Thr Tyr Ser Gly His Pro Thr Ala Cys Ala Ala Ala Leu Ala Val Leu
                325             330             335

Asp Ile Val Glu Ala Glu Asp Leu Pro Gly Asn Ala Ala Lys Val Gly
            340             345             350

Ala Gln Leu Leu Glu Gln Leu Gln Pro Leu Val Glu Arg Tyr Ala Val
        355             360             365

Val Gly Glu Val Arg Gly Lys Gly Leu Met Ile Ala Leu Asp Leu Val
    370             375             380

Ser Asp Lys Arg Thr Arg Gln Pro Leu Asp Pro Ala Ala Gly Gln Pro
385             390             395             400

Ser Arg Ile Ala Asp Glu Ala Arg Arg Ala Gly Val Leu Val Arg Pro
                405             410             415

Ile Gly Asn Lys Ile Ile Leu Ser Pro Pro Leu Thr Leu Thr Arg Asp
            420             425             430

Glu Ala Gly Leu Met Val Ser Ala Leu Glu Ala Ala Phe Ala Arg Cys
        435             440             445

Gly
```

-continued

```
<210> SEQ ID NO 12
<211> LENGTH: 449
<212> TYPE: PRT
<213> ORGANISM: unknown
<220> FEATURE:
<223> OTHER INFORMATION: isolated from library

<400> SEQUENCE: 12
```

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
        35                  40                  45

Gly Val Gly Gly Val Trp Asn Val Asn Ile Gly His Asn Arg Ala Ser
    50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
    130                 135                 140

Arg Asn Gly Tyr His Gly Val His Met Gly Gly Thr Ser Val Gly Gly
145                 150                 155                 160

Asn Gly Val Tyr His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
    210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala
        275                 280                 285

Gly Tyr Ile Pro Leu Gly Ala Thr Leu Phe Asn Gln Arg Ile Ala Asp
    290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Ala Leu Ala Val Leu
                325                 330                 335

Asp Ile Val Glu Ala Glu Asp Leu Pro Gly Asn Ala Ala Lys Val Gly
            340                 345                 350

Ala Gln Leu Leu Glu Gln Leu Gln Pro Leu Val Glu Arg Tyr Ala Val
        355                 360                 365

Val Gly Glu Val Arg Gly Lys Gly Leu Met Ile Ala Leu Asp Leu Val

```
                370                 375                 380
Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Arg Pro
                405                 410                 415

Ile Gly Asn Lys Ile Ile Leu Ser Pro Pro Leu Thr Leu Thr Arg Asp
            420                 425                 430

Glu Ala Gly Leu Met Val Ser Ala Leu Glu Ala Ala Phe Ala Arg Cys
        435                 440                 445

Gly

<210> SEQ ID NO 13
<211> LENGTH: 449
<212> TYPE: PRT
<213> ORGANISM: unknown
<220> FEATURE:
<223> OTHER INFORMATION: isolated from library

<400> SEQUENCE: 13

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
        35                  40                  45

Gly Val Gly Gly Ala Trp Asn Val Asn Ile Gly His Asn Arg Ala Ser
    50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
    130                 135                 140

Arg Asn Gly Tyr His Gly Val His Met Gly Gly Thr Ser Val Gly Gly
145                 150                 155                 160

Asn Gly Val Tyr His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
    210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala
        275                 280                 285
```

```
Gly Tyr Ile Pro Leu Gly Ala Thr Leu Phe Asn Gln Arg Ile Ala Asp
            290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Leu Ala Val Leu
                325                 330                 335

Asp Ile Val Glu Ala Glu Asp Leu Pro Gly Asn Ala Ala Lys Val Gly
            340                 345                 350

Ala Gln Leu Leu Glu Gln Leu Gln Pro Leu Val Glu Arg Tyr Ala Val
            355                 360                 365

Val Gly Glu Val Arg Gly Lys Gly Leu Met Ile Ala Leu Asp Leu Val
    370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Arg Pro
                405                 410                 415

Ile Gly Asn Lys Ile Ile Leu Ser Pro Pro Leu Thr Leu Thr Arg Asp
                420                 425                 430

Glu Ala Gly Leu Met Val Ser Ala Leu Glu Ala Ala Phe Ala Arg Cys
            435                 440                 445

Gly

<210> SEQ ID NO 14
<211> LENGTH: 449
<212> TYPE: PRT
<213> ORGANISM: unknown
<220> FEATURE:
<223> OTHER INFORMATION: isolated from library

<400> SEQUENCE: 14

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
        35                  40                  45

Gly Val Gly Gly Ser Trp Asn Val Asn Ile Gly His Asn Arg Ala Ser
    50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
    130                 135                 140

Arg Asn Gly Tyr His Gly Val His Met Gly Gly Thr Ser Val Gly Gly
145                 150                 155                 160

Asn Gly Val Tyr His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190
```

Pro Gln Ala Leu Thr Ala His Cys Ile Arg Gln Leu Glu Gln Ile
            195                 200                 205

Ala Leu Leu Gly Ala Gln Thr Ile Ala Ala Leu Ile Ala Glu Pro Val
        210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Ile Ala Asp Glu
                245                 250                 255

Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala
        275                 280                 285

Gly Tyr Ile Pro Leu Gly Ala Thr Leu Phe Asn Gln Arg Ile Ala Asp
    290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Ala Leu Ala Val Leu
                325                 330                 335

Asp Ile Val Glu Ala Glu Asp Leu Pro Gly Asn Ala Ala Lys Val Gly
            340                 345                 350

Ala Gln Leu Leu Glu Gln Leu Gln Pro Leu Val Glu Arg Tyr Ala Val
        355                 360                 365

Val Gly Glu Val Arg Gly Lys Gly Leu Met Ile Ala Leu Asp Leu Val
    370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Arg Pro
                405                 410                 415

Ile Gly Asn Lys Ile Ile Leu Ser Pro Pro Leu Thr Leu Thr Arg Asp
            420                 425                 430

Glu Ala Gly Leu Met Val Ser Ala Leu Glu Ala Ala Phe Ala Arg Cys
        435                 440                 445

Gly

<210> SEQ ID NO 15
<211> LENGTH: 449
<212> TYPE: PRT
<213> ORGANISM: unknown
<220> FEATURE:
<223> OTHER INFORMATION: isolated from library

<400> SEQUENCE: 15

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
        35                  40                  45

Gly Val Gly Gly Gly Trp Asn Val Asn Ile Gly His Asn Arg Ala Ser
    50                  55                  60

Val Lys Ala Ala Ile Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser

```
            100                 105                 110
Ser Gly Gly Ser Asp Ala Val Glu Thr Ala Leu Lys Met Ala Arg Gln
            115                 120                 125

Tyr Trp Ile Ala Ser Gly Glu Pro Gly Arg Thr Arg Phe Leu Ser Leu
        130                 135                 140

Arg Asn Gly Tyr His Gly Val His Met Gly Thr Ser Val Gly Gly
145                 150                 155                 160

Asn Gly Val Tyr His Tyr Asn His Gly Gln Leu Leu Ala Gly Cys His
                    165                 170                 175

Leu Leu Asp Thr Pro Trp Leu Tyr Arg Asn Pro Trp Asp Cys Arg Asp
                180                 185                 190

Pro Gln Ala Leu Thr Ala His Cys Ile Arg Gln Leu Glu Glu Gln Ile
            195                 200                 205

Ala Leu Leu Gly Ala Gln Thr Ile Ala Ala Leu Ile Ala Glu Pro Val
        210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                    245                 250                 255

Val Val Thr Gly Phe Gly Arg Ser Gly Cys Met Leu Gly Ser Arg Gly
                260                 265                 270

Trp Gly Val Ala Pro Asp Ile Leu Cys Leu Ala Lys Gly Ile Thr Ala
            275                 280                 285

Gly Tyr Ile Pro Leu Gly Ala Thr Leu Phe Asn Gln Arg Ile Ala Asp
        290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Ala Leu Ala Val Leu
                    325                 330                 335

Asp Ile Val Glu Ala Glu Asp Leu Pro Gly Asn Ala Ala Lys Val Gly
                340                 345                 350

Ala Gln Leu Leu Glu Gln Leu Gln Pro Leu Val Glu Arg Tyr Ala Val
            355                 360                 365

Val Gly Glu Val Arg Gly Lys Gly Leu Met Ile Ala Leu Asp Leu Val
        370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Arg Pro
                    405                 410                 415

Ile Gly Asn Lys Ile Ile Leu Ser Pro Pro Leu Thr Leu Thr Arg Asp
                420                 425                 430

Glu Ala Gly Leu Met Val Ser Ala Leu Glu Ala Ala Phe Ala Arg Cys
            435                 440                 445

Gly
```

<210> SEQ ID NO 16
<211> LENGTH: 449
<212> TYPE: PRT
<213> ORGANISM: unknown
<220> FEATURE:
<223> OTHER INFORMATION: isolated from library

<400> SEQUENCE: 16

```
Met Tyr Glu Lys Tyr Lys Asn Ala Glu Lys Lys Phe Trp His Pro Met
1               5                   10                  15
```

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
            35                  40                  45

Gly Val Gly Gly Leu Ala Asn Val Asn Ile Gly His Asn Arg Ala Ser
50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
            85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
            115                 120                 125

Tyr Trp Ile Ala Ser Gly Glu Pro Gly Arg Thr Arg Phe Leu Ser Leu
130                 135                 140

Arg Asn Gly Tyr His Gly Val His Met Gly Gly Thr Ser Val Gly Gly
145                 150                 155                 160

Asn Gly Val Tyr His Tyr Asn His Gly Gln Leu Leu Ala Gly Cys His
            165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
            195                 200                 205

Ala Leu Leu Gly Ala Gln Thr Ile Ala Ala Leu Ile Ala Glu Pro Val
210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
            245                 250                 255

Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala
            275                 280                 285

Gly Tyr Ile Pro Leu Gly Ala Thr Leu Phe Asn Gln Arg Ile Ala Asp
290                 295                 300

Ala Ile Glu Asn Gly Gln Gly Phe Ser His Met Ile His Gly Tyr
305                 310                 315                 320

Thr Tyr Ser Gly His Pro Thr Ala Cys Ala Ala Leu Ala Val Leu
            325                 330                 335

Asp Ile Val Glu Ala Glu Asp Leu Pro Gly Asn Ala Ala Lys Val Gly
            340                 345                 350

Ala Gln Leu Leu Glu Gln Leu Gln Pro Leu Val Glu Arg Tyr Ala Val
            355                 360                 365

Val Gly Glu Val Arg Gly Lys Gly Leu Met Ile Ala Leu Asp Leu Val
            370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Arg Pro
            405                 410                 415

Ile Gly Asn Lys Ile Ile Leu Ser Pro Pro Leu Thr Leu Thr Arg Asp
            420                 425                 430

Glu Ala Gly Leu Met Val Ser Ala Leu Glu Ala Ala Phe Ala Arg Cys
            435                 440                 445

Gly

<210> SEQ ID NO 17
<211> LENGTH: 449
<212> TYPE: PRT
<213> ORGANISM: unknown
<220> FEATURE:
<223> OTHER INFORMATION: isolated from library

<400> SEQUENCE: 17

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
        35                  40                  45

Gly Val Gly Gly Leu Ile Asn Val Asn Ile Gly His Asn Arg Ala Ser
    50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
    130                 135                 140

Arg Asn Gly Tyr His Gly Val His Met Gly Gly Thr Ser Val Gly Gly
145                 150                 155                 160

Asn Gly Val Tyr His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
    210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala
        275                 280                 285

Gly Tyr Ile Pro Leu Gly Ala Thr Leu Phe Asn Gln Arg Ile Ala Asp
    290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Ala Leu Ala Val Leu
                325                 330                 335

Asp Ile Val Glu Ala Glu Asp Leu Pro Gly Asn Ala Ala Lys Val Gly

```
                        340                 345                 350
Ala Gln Leu Leu Glu Gln Leu Gln Pro Leu Val Glu Arg Tyr Ala Val
                355                 360                 365

Val Gly Glu Val Arg Gly Lys Gly Leu Met Ile Ala Leu Asp Leu Val
        370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Arg Pro
                405                 410                 415

Ile Gly Asn Lys Ile Ile Leu Ser Pro Pro Leu Thr Leu Thr Arg Asp
                420                 425                 430

Glu Ala Gly Leu Met Val Ser Ala Leu Glu Ala Ala Phe Ala Arg Cys
                435                 440                 445

Gly

<210> SEQ ID NO 18
<211> LENGTH: 449
<212> TYPE: PRT
<213> ORGANISM: unknown
<220> FEATURE:
<223> OTHER INFORMATION: isolated from library

<400> SEQUENCE: 18

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
                20                  25                  30

Gly Asp Gly Asn Tyr Ile Thr Asp Ile Asp Gly Gln Arg Met Leu Asp
            35                  40                  45

Gly Val Gly Gly Leu Leu Asn Val Asn Ile Gly His Asn Arg Ala Ser
        50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
                100                 105                 110

Ser Gly Gly Ser Asp Ala Val Glu Thr Ala Leu Lys Met Ala Arg Gln
            115                 120                 125

Tyr Trp Ile Ala Ser Gly Glu Pro Gly Arg Thr Arg Phe Leu Ser Leu
        130                 135                 140

Arg Asn Gly Tyr His Gly Val His Met Gly Gly Thr Ser Val Gly Gly
145                 150                 155                 160

Asn Gly Val Tyr His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
        210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255
```

```
Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala
            275                 280                 285

Gly Tyr Ile Pro Leu Gly Ala Thr Leu Phe Asn Gln Arg Ile Ala Asp
            290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Leu Ala Val Leu
            325                 330                 335

Asp Ile Val Glu Ala Glu Asp Leu Pro Gly Asn Ala Ala Lys Val Gly
            340                 345                 350

Ala Gln Leu Leu Glu Gln Leu Gln Pro Leu Val Glu Arg Tyr Ala Val
            355                 360                 365

Val Gly Glu Val Arg Gly Lys Gly Leu Met Ile Ala Leu Asp Leu Val
            370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Arg Pro
                    405                 410                 415

Ile Gly Asn Lys Ile Ile Leu Ser Pro Pro Leu Thr Leu Thr Arg Asp
                    420                 425                 430

Glu Ala Gly Leu Met Val Ser Ala Leu Glu Ala Ala Phe Ala Arg Cys
            435                 440                 445

Gly

<210> SEQ ID NO 19
<211> LENGTH: 449
<212> TYPE: PRT
<213> ORGANISM: unknown
<220> FEATURE:
<223> OTHER INFORMATION: isolated from library

<400> SEQUENCE: 19

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
                20                  25                  30

Gly Asp Gly Asn Tyr Ile Thr Asp Ile Asp Gly Gln Arg Met Leu Asp
            35                  40                  45

Gly Val Gly Gly Leu Tyr Asn Val Asn Ile Gly His Asn Arg Ala Ser
        50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
    130                 135                 140

Arg Asn Gly Tyr His Gly Val His Met Gly Gly Thr Ser Val Gly Gly
145                 150                 155                 160
```

Asn Gly Val Tyr His Tyr Asn His Gly Gln Leu Leu Ala Gly Cys His
            165                 170                 175

Leu Leu Asp Thr Pro Trp Leu Tyr Arg Asn Pro Trp Asp Cys Arg Asp
        180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Leu Ile Ala Glu Pro Val
    210                 215                 220

Gln Gly Ala Gly Gly Val Ile Val Pro Ala Asp Tyr Trp Pro Arg
225                 230                 235                 240

Leu Arg Glu Val Cys Asp Arg His Gly Ile Leu Leu Ile Ala Asp Glu
                    245                 250                 255

Val Val Thr Gly Phe Gly Arg Ser Gly Cys Met Leu Gly Ser Arg Gly
                260                 265                 270

Trp Gly Val Ala Pro Asp Ile Leu Cys Leu Ala Lys Gly Ile Thr Ala
            275                 280                 285

Gly Tyr Ile Pro Leu Gly Ala Thr Leu Phe Asn Gln Arg Ile Ala Asp
        290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Ala Leu Ala Val Leu
                    325                 330                 335

Asp Ile Val Glu Ala Glu Asp Leu Pro Gly Asn Ala Ala Lys Val Gly
                340                 345                 350

Ala Gln Leu Leu Glu Gln Leu Gln Pro Leu Val Glu Arg Tyr Ala Val
            355                 360                 365

Val Gly Glu Val Arg Gly Lys Gly Leu Met Ile Ala Leu Asp Leu Val
        370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Arg Pro
                    405                 410                 415

Ile Gly Asn Lys Ile Ile Leu Ser Pro Pro Leu Thr Leu Thr Arg Asp
                420                 425                 430

Glu Ala Gly Leu Met Val Ser Ala Leu Glu Ala Ala Phe Ala Arg Cys
            435                 440                 445

Gly

<210> SEQ ID NO 20
<211> LENGTH: 449
<212> TYPE: PRT
<213> ORGANISM: unknown
<220> FEATURE:
<223> OTHER INFORMATION: isolated from library

<400> SEQUENCE: 20

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
        35                  40                  45

Gly Val Gly Gly Leu Ser Asn Val Asn Ile Gly His Asn Arg Ala Ser
    50                  55                  60

Val Lys Ala Ala Ile Ala Ala Gln Leu Asp Glu Leu Ala Tyr Tyr Gln

```
            65                  70                  75                  80
    Thr Phe Asp Gly Ile Ala His Pro Arg Val Phe Asp Leu Ala Glu Arg
                        85                  90                  95

Leu Thr Gly Met Phe Ala Gln Glu Arg Met Ala Arg Val Leu Phe Ser
                    100                 105                 110

Ser Gly Gly Ser Asp Ala Val Glu Thr Ala Leu Lys Met Ala Arg Gln
                115                 120                 125

Tyr Trp Ile Ala Ser Gly Glu Pro Gly Arg Thr Arg Phe Leu Ser Leu
            130                 135                 140

Arg Asn Gly Tyr His Gly Val His Met Gly Gly Thr Ser Val Gly Gly
    145                 150                 155                 160

Asn Gly Val Tyr His Tyr Asn His Gly Gln Leu Leu Ala Gly Cys His
                    165                 170                 175

Leu Leu Asp Thr Pro Trp Leu Tyr Arg Asn Pro Trp Asp Cys Arg Asp
                180                 185                 190

Pro Gln Ala Leu Thr Ala His Cys Ile Arg Gln Leu Glu Glu Gln Ile
            195                 200                 205

Ala Leu Leu Gly Ala Gln Thr Ile Ala Ala Leu Ile Ala Glu Pro Val
    210                 215                 220

Gln Gly Ala Gly Gly Val Ile Val Pro Pro Ala Asp Tyr Trp Pro Arg
    225                 230                 235                 240

Leu Arg Glu Val Cys Asp Arg His Gly Ile Leu Leu Ile Ala Asp Glu
                    245                 250                 255

Val Val Thr Gly Phe Gly Arg Ser Gly Cys Met Leu Gly Ser Arg Gly
                260                 265                 270

Trp Gly Val Ala Pro Asp Ile Leu Cys Leu Ala Lys Gly Ile Thr Ala
            275                 280                 285

Gly Tyr Ile Pro Leu Gly Ala Thr Leu Phe Asn Gln Arg Ile Ala Asp
    290                 295                 300

Ala Ile Glu Asn Gly Gln Gly Phe Ser His Met Ile Met His Gly Tyr
    305                 310                 315                 320

Thr Tyr Ser Gly His Pro Thr Ala Cys Ala Ala Ala Leu Ala Val Leu
                    325                 330                 335

Asp Ile Val Glu Ala Glu Asp Leu Pro Gly Asn Ala Ala Lys Val Gly
                340                 345                 350

Ala Gln Leu Leu Glu Gln Leu Gln Pro Leu Val Glu Arg Tyr Ala Val
            355                 360                 365

Val Gly Glu Val Arg Gly Lys Gly Leu Met Ile Ala Leu Asp Leu Val
    370                 375                 380

Ser Asp Lys Arg Thr Arg Gln Pro Leu Asp Pro Ala Ala Gly Gln Pro
    385                 390                 395                 400

Ser Arg Ile Ala Asp Glu Ala Arg Arg Ala Gly Val Leu Val Arg Pro
                    405                 410                 415

Ile Gly Asn Lys Ile Ile Leu Ser Pro Pro Leu Thr Leu Thr Arg Asp
                420                 425                 430

Glu Ala Gly Leu Met Val Ser Ala Leu Glu Ala Ala Phe Ala Arg Cys
            435                 440                 445

Gly

<210> SEQ ID NO 21
<211> LENGTH: 449
<212> TYPE: PRT
<213> ORGANISM: unknown
<220> FEATURE:
```

<223> OTHER INFORMATION: isolated from library

<400> SEQUENCE: 21

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
        35                  40                  45

Gly Val Gly Gly Leu Cys Asn Val Asn Ile Gly His Asn Arg Ala Ser
    50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
    130                 135                 140

Arg Asn Gly Tyr His Gly Val His Met Gly Gly Thr Ser Val Gly Gly
145                 150                 155                 160

Asn Gly Val Tyr His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
    210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala
        275                 280                 285

Gly Tyr Ile Pro Leu Gly Ala Thr Leu Phe Asn Gln Arg Ile Ala Asp
    290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Ala Leu Ala Val Leu
                325                 330                 335

Asp Ile Val Glu Ala Glu Asp Leu Pro Gly Asn Ala Ala Lys Val Gly
            340                 345                 350

Ala Gln Leu Leu Glu Gln Leu Gln Pro Leu Val Glu Arg Tyr Ala Val
        355                 360                 365

Val Gly Glu Val Arg Gly Lys Gly Leu Met Ile Ala Leu Asp Leu Val
    370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Arg Pro
            405                 410                 415

Ile Gly Asn Lys Ile Ile Leu Ser Pro Pro Leu Thr Leu Thr Arg Asp
        420                 425                 430

Glu Ala Gly Leu Met Val Ser Ala Leu Glu Ala Ala Phe Ala Arg Cys
        435                 440                 445

Gly

<210> SEQ ID NO 22
<211> LENGTH: 449
<212> TYPE: PRT
<213> ORGANISM: unknown
<220> FEATURE:
<223> OTHER INFORMATION: isolated from library

<400> SEQUENCE: 22

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
        35                  40                  45

Gly Val Gly Gly Leu Phe Asn Val Asn Ile Gly His Asn Arg Ala Ser
    50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
    130                 135                 140

Arg Asn Gly Tyr His Gly Val His Met Gly Gly Thr Ser Val Gly Gly
145                 150                 155                 160

Asn Gly Val Tyr His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
    210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala
        275                 280                 285

Gly Tyr Ile Pro Leu Gly Ala Thr Leu Phe Asn Gln Arg Ile Ala Asp
    290                 295                 300

Ala Ile Glu Asn Gly Gln Gly Phe Ser His Met Ile Met His Gly Tyr

```
             305                 310                 315                 320
Thr Tyr Ser Gly His Pro Thr Ala Cys Ala Ala Leu Ala Val Leu
                325                 330                 335
Asp Ile Val Glu Ala Glu Asp Leu Pro Gly Asn Ala Ala Lys Val Gly
                340                 345                 350
Ala Gln Leu Leu Glu Gln Leu Gln Pro Leu Val Glu Arg Tyr Ala Val
                355                 360                 365
Val Gly Glu Val Arg Gly Lys Gly Leu Met Ile Ala Leu Asp Leu Val
            370                 375                 380
Ser Asp Lys Arg Thr Arg Gln Pro Leu Asp Pro Ala Ala Gly Gln Pro
385                 390                 395                 400
Ser Arg Ile Ala Asp Glu Ala Arg Arg Ala Gly Val Leu Val Arg Pro
                405                 410                 415
Ile Gly Asn Lys Ile Ile Leu Ser Pro Pro Leu Thr Leu Thr Arg Asp
                420                 425                 430
Glu Ala Gly Leu Met Val Ser Ala Leu Glu Ala Ala Phe Ala Arg Cys
                435                 440                 445
Gly

<210> SEQ ID NO 23
<211> LENGTH: 449
<212> TYPE: PRT
<213> ORGANISM: unknown
<220> FEATURE:
<223> OTHER INFORMATION: isolated from library

<400> SEQUENCE: 23

Met Tyr Glu Lys Tyr Lys Asn Ala Glu Lys Lys Phe Trp His Pro Met
1               5                   10                  15
Gly Ser Ser Ala Ala Pro His Arg Asp Lys Thr Leu Val Ile Ala Arg
                20                  25                  30
Gly Asp Gly Asn Tyr Ile Thr Asp Ile Asp Gly Gln Arg Met Leu Asp
            35                  40                  45
Gly Val Gly Gly Leu Val Asn Val Asn Ile Gly His Asn Arg Ala Ser
        50                  55                  60
Val Lys Ala Ala Ile Ala Ala Gln Leu Asp Glu Leu Ala Tyr Tyr Gln
65                  70                  75                  80
Thr Phe Asp Gly Ile Ala His Pro Arg Val Phe Asp Leu Ala Glu Arg
                85                  90                  95
Leu Thr Gly Met Phe Ala Gln Glu Arg Met Ala Arg Val Leu Phe Ser
                100                 105                 110
Ser Gly Gly Ser Asp Ala Val Glu Thr Ala Leu Lys Met Ala Arg Gln
            115                 120                 125
Tyr Trp Ile Ala Ser Gly Glu Pro Gly Arg Thr Arg Phe Leu Ser Leu
        130                 135                 140
Arg Asn Gly Tyr His Gly Val His Met Gly Gly Thr Ser Val Gly Gly
145                 150                 155                 160
Asn Gly Val Tyr His Tyr Asn His Gly Gln Leu Leu Ala Gly Cys His
                165                 170                 175
Leu Leu Asp Thr Pro Trp Leu Tyr Arg Asn Pro Trp Cys Arg Asp
                180                 185                 190
Pro Gln Ala Leu Thr Ala His Cys Ile Arg Gln Leu Glu Glu Gln Ile
            195                 200                 205
Ala Leu Leu Gly Ala Gln Thr Ile Ala Ala Leu Ile Ala Glu Pro Val
        210                 215                 220
```

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
            245                 250                 255

Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala
        275                 280                 285

Gly Tyr Ile Pro Leu Gly Ala Thr Leu Phe Asn Gln Arg Ile Ala Asp
        290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Ala Leu Ala Val Leu
            325                 330                 335

Asp Ile Val Glu Ala Glu Asp Leu Pro Gly Asn Ala Ala Lys Val Gly
            340                 345                 350

Ala Gln Leu Leu Glu Gln Leu Gln Pro Leu Val Glu Arg Tyr Ala Val
        355                 360                 365

Val Gly Glu Val Arg Gly Lys Gly Leu Met Ile Ala Leu Asp Leu Val
        370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Arg Pro
            405                 410                 415

Ile Gly Asn Lys Ile Ile Leu Ser Pro Pro Leu Thr Leu Thr Arg Asp
            420                 425                 430

Glu Ala Gly Leu Met Val Ser Ala Leu Glu Ala Ala Phe Ala Arg Cys
        435                 440                 445

Gly

<210> SEQ ID NO 24
<211> LENGTH: 449
<212> TYPE: PRT
<213> ORGANISM: unknown
<220> FEATURE:
<223> OTHER INFORMATION: isolated from library

<400> SEQUENCE: 24

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
        35                  40                  45

Gly Val Gly Gly Leu Trp Asn Val Asn Ile Gly His Asn Arg Ala Ser
    50                  55                  60

Val Lys Ala Ala Ile Ala Ala Gln Leu Asp Glu Leu Ala Tyr Tyr Gln
65                  70                  75                  80

Thr Val Asp Gly Ile Ala His Pro Arg Val Phe Asp Leu Ala Glu Arg
            85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
            130                 135                 140

Arg Asn Gly Tyr His Gly Val His Met Gly Gly Thr Ser Val Gly Gly
145                 150                 155                 160

Asn Gly Val Tyr His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
            195                 200                 205

Ala Leu Leu Gly Ala Gln Thr Ile Ala Ala Leu Ile Ala Glu Pro Val
210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
                260                 265                 270

Trp Gly Val Ala Pro Asp Ile Leu Cys Leu Ala Lys Gly Ile Thr Ala
            275                 280                 285

Gly Tyr Ile Pro Leu Gly Ala Thr Leu Phe Asn Gln Arg Ile Ala Asp
            290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Ala Leu Ala Val Leu
                325                 330                 335

Asp Ile Val Glu Ala Glu Asp Leu Pro Gly Asn Ala Ala Lys Val Gly
            340                 345                 350

Ala Gln Leu Leu Glu Gln Leu Gln Pro Leu Val Glu Arg Tyr Ala Val
            355                 360                 365

Val Gly Glu Val Arg Gly Lys Gly Leu Met Ile Ala Leu Asp Leu Val
370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Ala Gly Val Leu Val Arg Pro
                405                 410                 415

Ile Gly Asn Lys Ile Ile Leu Ser Pro Pro Leu Thr Leu Thr Arg Asp
            420                 425                 430

Glu Ala Gly Leu Met Val Ser Ala Leu Glu Ala Ala Phe Ala Arg Cys
            435                 440                 445

Gly

<210> SEQ ID NO 25
<211> LENGTH: 449
<212> TYPE: PRT
<213> ORGANISM: unknown
<220> FEATURE:
<223> OTHER INFORMATION: isolated from library

<400> SEQUENCE: 25

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp

```
            35                  40                  45
Gly Val Gly Gly Leu Trp Asn Val Asn Ile Gly His Asn Arg Ala Ser
         50                  55                  60
Val Lys Ala Ala Ile Ala Ala Gln Leu Asp Glu Leu Ala Tyr Tyr Gln
 65                  70                  75                  80
Thr Ala Asp Gly Ile Ala His Pro Arg Val Phe Asp Leu Ala Glu Arg
                     85                  90                  95
Leu Thr Gly Met Phe Ala Gln Glu Arg Met Ala Arg Val Leu Phe Ser
                100                 105                 110
Ser Gly Gly Ser Asp Ala Val Glu Thr Ala Leu Lys Met Ala Arg Gln
            115                 120                 125
Tyr Trp Ile Ala Ser Gly Glu Pro Gly Arg Thr Arg Phe Leu Ser Leu
        130                 135                 140
Arg Asn Gly Tyr His Gly Val His Met Gly Thr Ser Val Gly Gly
145                 150                 155                 160
Asn Gly Val Tyr His Tyr Asn His Gly Gln Leu Leu Ala Gly Cys His
                165                 170                 175
Leu Leu Asp Thr Pro Trp Leu Tyr Arg Asn Pro Trp Asp Cys Arg Asp
                180                 185                 190
Pro Gln Ala Leu Thr Ala His Cys Ile Arg Gln Leu Glu Glu Gln Ile
            195                 200                 205
Ala Leu Leu Gly Ala Gln Thr Ile Ala Ala Leu Ile Ala Glu Pro Val
210                 215                 220
Gln Gly Ala Gly Gly Val Ile Val Pro Pro Ala Asp Tyr Trp Pro Arg
225                 230                 235                 240
Leu Arg Glu Val Cys Asp Arg His Gly Ile Leu Leu Ile Ala Asp Glu
                245                 250                 255
Val Val Thr Gly Phe Gly Arg Ser Gly Cys Met Leu Gly Ser Arg Gly
                260                 265                 270
Trp Gly Val Ala Pro Asp Ile Leu Cys Leu Ala Lys Gly Ile Thr Ala
            275                 280                 285
Gly Tyr Ile Pro Leu Gly Ala Thr Leu Phe Asn Gln Arg Ile Ala Asp
        290                 295                 300
Ala Ile Glu Asn Gly Gln Gly Phe Ser His Met Ile Met His Gly Tyr
305                 310                 315                 320
Thr Tyr Ser Gly His Pro Thr Ala Cys Ala Ala Leu Ala Val Leu
                325                 330                 335
Asp Ile Val Glu Ala Glu Asp Leu Pro Gly Asn Ala Ala Lys Val Gly
                340                 345                 350
Ala Gln Leu Leu Glu Gln Leu Gln Pro Leu Val Glu Arg Tyr Ala Val
            355                 360                 365
Val Gly Glu Val Arg Gly Lys Gly Leu Met Ile Ala Leu Asp Leu Val
        370                 375                 380
Ser Asp Lys Arg Thr Arg Gln Pro Leu Asp Pro Ala Ala Gly Gln Pro
385                 390                 395                 400
Ser Arg Ile Ala Asp Glu Ala Arg Arg Ala Gly Val Leu Val Arg Pro
                405                 410                 415
Ile Gly Asn Lys Ile Ile Leu Ser Pro Pro Leu Thr Leu Thr Arg Asp
                420                 425                 430
Glu Ala Gly Leu Met Val Ser Ala Leu Glu Ala Ala Phe Ala Arg Cys
            435                 440                 445
Gly
```

<210> SEQ ID NO 26
<211> LENGTH: 449
<212> TYPE: PRT
<213> ORGANISM: unknown
<220> FEATURE:
<223> OTHER INFORMATION: isolated from library

<400> SEQUENCE: 26

```
Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
        35                  40                  45

Gly Val Gly Gly Leu Trp Asn Val Asn Ile Gly His Asn Arg Ala Ser
    50                  55                  60

Val Lys Ala Ala Ile Ala Ala Gln Leu Asp Glu Leu Ala Tyr Tyr Gln
65                  70                  75                  80

Thr Gly Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
    130                 135                 140

Arg Asn Gly Tyr His Gly Val His Met Gly Gly Thr Ser Val Gly Gly
145                 150                 155                 160

Asn Gly Val Tyr His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
    210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala
        275                 280                 285

Gly Tyr Ile Pro Leu Gly Ala Thr Leu Phe Asn Gln Arg Ile Ala Asp
    290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Ala Leu Ala Val Leu
                325                 330                 335

Asp Ile Val Glu Ala Glu Asp Leu Pro Gly Asn Ala Ala Lys Val Gly
            340                 345                 350

Ala Gln Leu Leu Glu Gln Leu Gln Pro Leu Val Glu Arg Tyr Ala Val
        355                 360                 365
```

Val Gly Glu Val Arg Gly Lys Gly Leu Met Ile Ala Leu Asp Leu Val
    370             375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Arg Pro
                405                 410                 415

Ile Gly Asn Lys Ile Ile Leu Ser Pro Pro Leu Thr Leu Thr Arg Asp
                420                 425                 430

Glu Ala Gly Leu Met Val Ser Ala Leu Glu Ala Ala Phe Ala Arg Cys
                435                 440                 445

Gly

<210> SEQ ID NO 27
<211> LENGTH: 449
<212> TYPE: PRT
<213> ORGANISM: unknown
<220> FEATURE:
<223> OTHER INFORMATION: isolated from library

<400> SEQUENCE: 27

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
                20                  25                  30

Gly Asp Gly Asn Tyr Ile Thr Asp Ile Asp Gly Gln Arg Met Leu Asp
            35                  40                  45

Gly Val Gly Gly Leu Trp Asn Val Asn Ile Gly His Asn Arg Ala Ser
50                  55                  60

Val Lys Ala Ala Ile Ala Ala Gln Leu Asp Glu Leu Ala Tyr Tyr Gln
65                  70                  75                  80

Thr Leu Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
130                 135                 140

Arg Asn Gly Tyr His Gly Val His Met Gly Gly Thr Ser Val Gly Gly
145                 150                 155                 160

Asn Gly Val Tyr His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala

```
                275                 280                 285
Gly Tyr Ile Pro Leu Gly Ala Thr Leu Phe Asn Gln Arg Ile Ala Asp
290                 295                 300
Ala Ile Glu Asn Gly Gln Gly Phe Ser His Met Ile Met His Gly Tyr
305                 310                 315                 320
Thr Tyr Ser Gly His Pro Thr Ala Cys Ala Ala Leu Ala Val Leu
                325                 330                 335
Asp Ile Val Glu Ala Glu Asp Leu Pro Gly Asn Ala Ala Lys Val Gly
                340                 345                 350
Ala Gln Leu Leu Glu Gln Leu Gln Pro Leu Val Glu Arg Tyr Ala Val
                355                 360                 365
Val Gly Glu Val Arg Gly Lys Gly Leu Met Ile Ala Leu Asp Leu Val
    370                 375                 380
Ser Asp Lys Arg Thr Arg Gln Pro Leu Asp Pro Ala Ala Gly Gln Pro
385                 390                 395                 400
Ser Arg Ile Ala Asp Glu Ala Arg Arg Ala Gly Val Leu Val Arg Pro
                405                 410                 415
Ile Gly Asn Lys Ile Ile Leu Ser Pro Pro Leu Thr Leu Thr Arg Asp
                420                 425                 430
Glu Ala Gly Leu Met Val Ser Ala Leu Glu Ala Ala Phe Ala Arg Cys
                435                 440                 445
Gly

<210> SEQ ID NO 28
<211> LENGTH: 449
<212> TYPE: PRT
<213> ORGANISM: unknown
<220> FEATURE:
<223> OTHER INFORMATION: isolated from library

<400> SEQUENCE: 28

Met Tyr Glu Lys Tyr Lys Asn Ala Glu Lys Lys Phe Trp His Pro Met
1               5                   10                  15
Gly Ser Ser Ala Ala Pro His Arg Asp Lys Thr Leu Val Ile Ala Arg
                20                  25                  30
Gly Asp Gly Asn Tyr Ile Thr Asp Ile Asp Gly Gln Arg Met Leu Asp
            35                  40                  45
Gly Val Gly Gly Leu Trp Asn Val Asn Ile Gly His Asn Arg Ala Ser
        50                  55                  60
Val Lys Ala Ala Ile Ala Ala Gln Leu Asp Glu Leu Ala Tyr Tyr Gln
65                  70                  75                  80
Thr Tyr Asp Gly Ile Ala His Pro Arg Val Phe Asp Leu Ala Glu Arg
                85                  90                  95
Leu Thr Gly Met Phe Ala Gln Glu Arg Met Ala Arg Val Leu Phe Ser
                100                 105                 110
Ser Gly Gly Ser Asp Ala Val Glu Thr Ala Leu Lys Met Ala Arg Gln
                115                 120                 125
Tyr Trp Ile Ala Ser Gly Glu Pro Gly Arg Thr Arg Phe Leu Ser Leu
            130                 135                 140
Arg Asn Gly Tyr His Gly Val His Met Gly Gly Thr Ser Val Gly Gly
145                 150                 155                 160
Asn Gly Val Tyr His Tyr Asn His Gly Gln Leu Leu Ala Gly Cys His
                165                 170                 175
Leu Leu Asp Thr Pro Trp Leu Tyr Arg Asn Pro Trp Asp Cys Arg Asp
                180                 185                 190
```

```
Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
                260                 265                 270

Trp Gly Val Ala Pro Asp Ile Leu Cys Leu Ala Lys Gly Ile Thr Ala
                275                 280                 285

Gly Tyr Ile Pro Leu Gly Ala Thr Leu Phe Asn Gln Arg Ile Ala Asp
                290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Ala Leu Ala Val Leu
                325                 330                 335

Asp Ile Val Glu Ala Glu Asp Leu Pro Gly Asn Ala Ala Lys Val Gly
                340                 345                 350

Ala Gln Leu Leu Glu Gln Leu Gln Pro Leu Val Glu Arg Tyr Ala Val
                355                 360                 365

Val Gly Glu Val Arg Gly Lys Gly Leu Met Ile Ala Leu Asp Leu Val
                370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Arg Pro
                405                 410                 415

Ile Gly Asn Lys Ile Ile Leu Ser Pro Pro Leu Thr Leu Thr Arg Asp
                420                 425                 430

Glu Ala Gly Leu Met Val Ser Ala Leu Glu Ala Ala Phe Ala Arg Cys
                435                 440                 445

Gly
```

<210> SEQ ID NO 29
<211> LENGTH: 449
<212> TYPE: PRT
<213> ORGANISM: unknown
<220> FEATURE:
<223> OTHER INFORMATION: isolated from library

<400> SEQUENCE: 29

```
Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
                20                  25                  30

Gly Asp Gly Asn Tyr Ile Thr Asp Ile Asp Gly Gln Arg Met Leu Asp
            35                  40                  45

Gly Val Gly Gly Leu Trp Asn Val Asn Ile Gly His Asn Arg Ala Ser
        50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95
```

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
    130                 135                 140

Arg Tyr Gly Tyr His Gly Val His Met Gly Gly Thr Ser Val Gly Gly
145                 150                 155                 160

Asn Gly Val Tyr His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
    210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala
        275                 280                 285

Gly Tyr Ile Pro Leu Gly Ala Thr Leu Phe Asn Gln Arg Ile Ala Asp
    290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Ala Leu Ala Val Leu
                325                 330                 335

Asp Ile Val Glu Ala Glu Asp Leu Pro Gly Asn Ala Ala Lys Val Gly
            340                 345                 350

Ala Gln Leu Leu Glu Gln Leu Gln Pro Leu Val Glu Arg Tyr Ala Val
        355                 360                 365

Val Gly Glu Val Arg Gly Lys Gly Leu Met Ile Ala Leu Asp Leu Val
    370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Arg Pro
                405                 410                 415

Ile Gly Asn Lys Ile Ile Leu Ser Pro Pro Leu Thr Leu Thr Arg Asp
            420                 425                 430

Glu Ala Gly Leu Met Val Ser Ala Leu Glu Ala Ala Phe Ala Arg Cys
        435                 440                 445

Gly

<210> SEQ ID NO 30
<211> LENGTH: 449
<212> TYPE: PRT
<213> ORGANISM: unknown
<220> FEATURE:
<223> OTHER INFORMATION: isolated from library

<400> SEQUENCE: 30

Met Tyr Glu Lys Tyr Lys Asn Ala Glu Lys Lys Phe Trp His Pro Met

-continued

```
1               5                   10                  15
Gly Ser Ser Ala Ala Pro His Arg Asp Lys Thr Leu Val Ile Ala Arg
                20                  25                  30
Gly Asp Gly Asn Tyr Ile Thr Asp Ile Asp Gly Gln Arg Met Leu Asp
                35                  40                  45
Gly Val Gly Gly Leu Trp Asn Val Asn Ile Gly His Asn Arg Ala Ser
    50                  55                  60
Val Lys Ala Ala Ile Ala Ala Gln Leu Asp Glu Leu Ala Tyr Tyr Gln
65                  70                  75                  80
Thr Phe Asp Gly Ile Ala His Pro Arg Val Phe Asp Leu Ala Glu Arg
                85                  90                  95
Leu Thr Gly Met Phe Ala Gln Glu Arg Met Ala Arg Val Leu Phe Ser
                100                 105                 110
Ser Gly Gly Ser Asp Ala Val Glu Thr Ala Leu Lys Met Ala Arg Gln
                115                 120                 125
Tyr Trp Ile Ala Ser Gly Glu Pro Gly Arg Thr Arg Phe Leu Ser Leu
                130                 135                 140
Arg Asp Gly Tyr His Gly Val His Met Gly Gly Thr Ser Val Gly Gly
145                 150                 155                 160
Asn Gly Val Tyr His Tyr Asn His Gly Gln Leu Leu Ala Gly Cys His
                165                 170                 175
Leu Leu Asp Thr Pro Trp Leu Tyr Arg Asn Pro Trp Asp Cys Arg Asp
                180                 185                 190
Pro Gln Ala Leu Thr Ala His Cys Ile Arg Gln Leu Glu Glu Gln Ile
                195                 200                 205
Ala Leu Leu Gly Ala Gln Thr Ile Ala Ala Leu Ile Ala Glu Pro Val
                210                 215                 220
Gln Gly Ala Gly Gly Val Ile Val Pro Pro Ala Asp Tyr Trp Pro Arg
225                 230                 235                 240
Leu Arg Glu Val Cys Asp Arg His Gly Ile Leu Leu Ile Ala Asp Glu
                245                 250                 255
Val Val Thr Gly Phe Gly Arg Ser Gly Cys Met Leu Gly Ser Arg Gly
                260                 265                 270
Trp Gly Val Ala Pro Asp Ile Leu Cys Leu Ala Lys Gly Ile Thr Ala
                275                 280                 285
Gly Tyr Ile Pro Leu Gly Ala Thr Leu Phe Asn Gln Arg Ile Ala Asp
                290                 295                 300
Ala Ile Glu Asn Gly Gln Gly Phe Ser His Met Ile Met His Gly Tyr
305                 310                 315                 320
Thr Tyr Ser Gly His Pro Thr Ala Cys Ala Ala Ala Leu Ala Val Leu
                325                 330                 335
Asp Ile Val Glu Ala Glu Asp Leu Pro Gly Asn Ala Ala Lys Val Gly
                340                 345                 350
Ala Gln Leu Leu Glu Gln Leu Gln Pro Leu Val Glu Arg Tyr Ala Val
                355                 360                 365
Val Gly Glu Val Arg Gly Lys Gly Leu Met Ile Ala Leu Asp Leu Val
                370                 375                 380
Ser Asp Lys Arg Thr Arg Gln Pro Leu Asp Pro Ala Ala Gly Gln Pro
385                 390                 395                 400
Ser Arg Ile Ala Asp Glu Ala Arg Ala Gly Val Leu Val Arg Pro
                405                 410                 415
Ile Gly Asn Lys Ile Ile Leu Ser Pro Pro Leu Thr Leu Thr Arg Asp
                420                 425                 430
```

Glu Ala Gly Leu Met Val Ser Ala Leu Glu Ala Ala Phe Ala Arg Cys
            435                 440                 445
Gly

<210> SEQ ID NO 31
<211> LENGTH: 449
<212> TYPE: PRT
<213> ORGANISM: unknown
<220> FEATURE:
<223> OTHER INFORMATION: isolated from library

<400> SEQUENCE: 31

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
        35                  40                  45

Gly Val Gly Gly Leu Trp Asn Val Asn Ile Gly His Asn Arg Ala Ser
    50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
    130                 135                 140

Arg Ser Gly Tyr His Gly Val His Met Gly Gly Thr Ser Val Gly Gly
145                 150                 155                 160

Asn Gly Val Tyr His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
    210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala
        275                 280                 285

Gly Tyr Ile Pro Leu Gly Ala Thr Leu Phe Asn Gln Arg Ile Ala Asp
    290                 295                 300

Ala Ile Glu Asn Gly Gln Gly Phe Ser His Met Ile His Gly Tyr
305                 310                 315                 320

Thr Tyr Ser Gly His Pro Thr Ala Cys Ala Ala Leu Ala Val Leu
                325                 330                 335

Asp Ile Val Glu Ala Glu Asp Leu Pro Gly Asn Ala Ala Lys Val Gly
            340                 345                 350

Ala Gln Leu Leu Glu Gln Leu Gln Pro Leu Val Glu Arg Tyr Ala Val
            355                 360                 365

Val Gly Glu Val Arg Gly Lys Gly Leu Met Ile Ala Leu Asp Leu Val
        370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Arg Pro
                405                 410                 415

Ile Gly Asn Lys Ile Ile Leu Ser Pro Pro Leu Thr Leu Thr Arg Asp
            420                 425                 430

Glu Ala Gly Leu Met Val Ser Ala Leu Glu Ala Ala Phe Ala Arg Cys
            435                 440                 445

Gly

<210> SEQ ID NO 32
<211> LENGTH: 449
<212> TYPE: PRT
<213> ORGANISM: unknown
<220> FEATURE:
<223> OTHER INFORMATION: isolated from library

<400> SEQUENCE: 32

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
        35                  40                  45

Gly Val Gly Gly Leu Trp Asn Val Asn Ile Gly His Asn Arg Ala Ser
    50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
130                 135                 140

Arg Asn Gly Phe His Gly Val His Met Gly Gly Thr Ser Val Gly Gly
145                 150                 155                 160

Asn Gly Val Tyr His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
    210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu

```
            245                 250                 255
Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala
            275                 280                 285

Gly Tyr Ile Pro Leu Gly Ala Thr Leu Phe Asn Gln Arg Ile Ala Asp
            290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Leu Ala Val Leu
            325                 330                 335

Asp Ile Val Glu Ala Glu Asp Leu Pro Gly Asn Ala Ala Lys Val Gly
            340                 345                 350

Ala Gln Leu Leu Glu Gln Leu Gln Pro Leu Val Glu Arg Tyr Ala Val
            355                 360                 365

Val Gly Glu Val Arg Gly Lys Gly Leu Met Ile Ala Leu Asp Leu Val
            370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Arg Pro
                    405                 410                 415

Ile Gly Asn Lys Ile Ile Leu Ser Pro Pro Leu Thr Leu Thr Arg Asp
                420                 425                 430

Glu Ala Gly Leu Met Val Ser Ala Leu Glu Ala Ala Phe Ala Arg Cys
                    435                 440                 445

Gly

<210> SEQ ID NO 33
<211> LENGTH: 449
<212> TYPE: PRT
<213> ORGANISM: unknown
<220> FEATURE:
<223> OTHER INFORMATION: isolated from library

<400> SEQUENCE: 33

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
            35                  40                  45

Gly Val Gly Gly Leu Trp Asn Val Asn Ile Gly His Asn Arg Ala Ser
        50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
    130                 135                 140

Arg Asn Gly Ser His Gly Val His Met Gly Gly Thr Ser Val Gly Gly
145                 150                 155                 160
```

-continued

Asn Gly Val Tyr His Tyr Asn His Gly Gln Leu Leu Ala Gly Cys His
            165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
            195                 200                 205

Ala Leu Leu Gly Ala Gln Thr Ile Ala Leu Ile Ala Glu Pro Val
210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
                260                 265                 270

Trp Gly Val Ala Pro Asp Ile Leu Cys Leu Ala Lys Gly Ile Thr Ala
            275                 280                 285

Gly Tyr Ile Pro Leu Gly Ala Thr Leu Phe Asn Gln Arg Ile Ala Asp
            290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Ala Leu Ala Val Leu
                325                 330                 335

Asp Ile Val Glu Ala Glu Asp Leu Pro Gly Asn Ala Ala Lys Val Gly
                340                 345                 350

Ala Gln Leu Leu Glu Gln Leu Gln Pro Leu Val Glu Arg Tyr Ala Val
            355                 360                 365

Val Gly Glu Val Arg Gly Lys Gly Leu Met Ile Ala Leu Asp Leu Val
370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Arg Pro
                405                 410                 415

Ile Gly Asn Lys Ile Ile Leu Ser Pro Pro Leu Thr Leu Thr Arg Asp
                420                 425                 430

Glu Ala Gly Leu Met Val Ser Ala Leu Glu Ala Ala Phe Ala Arg Cys
            435                 440                 445

Gly

<210> SEQ ID NO 34
<211> LENGTH: 449
<212> TYPE: PRT
<213> ORGANISM: unknown
<220> FEATURE:
<223> OTHER INFORMATION: isolated from library

<400> SEQUENCE: 34

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
            35                  40                  45

Gly Val Gly Gly Leu Trp Asn Val Asn Ile Gly His Asn Arg Ala Ser
50                  55                  60

Val Lys Ala Ala Ile Ala Gln Leu Asp Glu Leu Ala Tyr Tyr Gln
 65                  70                  75                  80

Thr Phe Asp Gly Ile Ala His Pro Arg Val Phe Asp Leu Ala Glu Arg
                 85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
    130                 135                 140

Arg Asn Gly Gly His Gly Val His Met Gly Gly Thr Ser Val Gly Gly
145                 150                 155                 160

Asn Gly Val Tyr His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Gly Gln Ile
        195                 200                 205

Ala Leu Leu Gly Ala Gln Thr Ile Ala Ala Leu Ile Ala Glu Pro Val
210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala
        275                 280                 285

Gly Tyr Ile Pro Leu Gly Ala Thr Leu Phe Asn Gln Arg Ile Ala Asp
    290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Ala Leu Ala Val Leu
                325                 330                 335

Asp Ile Val Glu Ala Glu Asp Leu Pro Gly Asn Ala Ala Lys Val Gly
            340                 345                 350

Ala Gln Leu Leu Glu Gln Leu Gln Pro Leu Val Glu Arg Tyr Ala Val
        355                 360                 365

Val Gly Glu Val Arg Gly Lys Gly Leu Met Ile Ala Leu Asp Leu Val
370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Arg Pro
                405                 410                 415

Ile Gly Asn Lys Ile Ile Leu Ser Pro Pro Leu Thr Leu Thr Arg Asp
            420                 425                 430

Glu Ala Gly Leu Met Val Ser Ala Leu Glu Ala Ala Phe Ala Arg Cys
        435                 440                 445

Gly

<210> SEQ ID NO 35
<211> LENGTH: 449
<212> TYPE: PRT
<213> ORGANISM: unknown

```
<220> FEATURE:
<223> OTHER INFORMATION: isolated from library

<400> SEQUENCE: 35

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
        35                  40                  45

Gly Val Gly Gly Leu Trp Asn Val Asn Ile Gly His Asn Arg Ala Ser
    50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
    130                 135                 140

Arg Asn Gly Tyr His Gly Ala His Met Gly Gly Thr Ser Val Gly Gly
145                 150                 155                 160

Asn Gly Val Tyr His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
    210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala
        275                 280                 285

Gly Tyr Ile Pro Leu Gly Ala Thr Leu Phe Asn Gln Arg Ile Ala Asp
    290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Leu Ala Val Leu Leu
                325                 330                 335

Asp Ile Val Glu Ala Glu Asp Leu Pro Gly Asn Ala Ala Lys Val Gly
            340                 345                 350

Ala Gln Leu Leu Glu Gln Leu Gln Pro Leu Val Glu Arg Tyr Ala Val
        355                 360                 365

Val Gly Glu Val Arg Gly Lys Gly Leu Met Ile Ala Leu Asp Leu Val
    370                 375                 380

Ser Asp Lys Arg Thr Arg Gln Pro Leu Asp Pro Ala Ala Gly Gln Pro
385                 390                 395                 400
```

-continued

```
Ser Arg Ile Ala Asp Glu Ala Arg Arg Ala Gly Val Leu Val Arg Pro
                405                 410                 415

Ile Gly Asn Lys Ile Ile Leu Ser Pro Pro Leu Thr Leu Thr Arg Asp
            420                 425                 430

Glu Ala Gly Leu Met Val Ser Ala Leu Glu Ala Ala Phe Ala Arg Cys
        435                 440                 445

Gly

<210> SEQ ID NO 36
<211> LENGTH: 449
<212> TYPE: PRT
<213> ORGANISM: unknown
<220> FEATURE:
<223> OTHER INFORMATION: isolated from library

<400> SEQUENCE: 36

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
        35                  40                  45

Gly Val Gly Gly Leu Trp Asn Val Asn Ile Gly His Asn Arg Ala Ser
    50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
    130                 135                 140

Arg Asn Gly Tyr His Gly Trp His Met Gly Gly Thr Ser Val Gly Gly
145                 150                 155                 160

Asn Gly Val Tyr His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
    210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala
        275                 280                 285

Gly Tyr Ile Pro Leu Gly Ala Thr Leu Phe Asn Gln Arg Ile Ala Asp
    290                 295                 300
```

```
Ala Ile Glu Asn Gly Gln Gly Phe Ser His Met Ile Met His Gly Tyr
305                 310                 315                 320

Thr Tyr Ser Gly His Pro Thr Ala Cys Ala Ala Leu Ala Val Leu
            325                 330                 335

Asp Ile Val Glu Ala Glu Asp Leu Pro Gly Asn Ala Ala Lys Val Gly
            340                 345                 350

Ala Gln Leu Leu Glu Gln Leu Gln Pro Leu Val Glu Arg Tyr Ala Val
            355                 360                 365

Val Gly Glu Val Arg Gly Lys Gly Leu Met Ile Ala Leu Asp Leu Val
            370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Ala Gly Val Leu Val Arg Pro
            405                 410                 415

Ile Gly Asn Lys Ile Ile Leu Ser Pro Pro Leu Thr Leu Thr Arg Asp
            420                 425                 430

Glu Ala Gly Leu Met Val Ser Ala Leu Glu Ala Ala Phe Ala Arg Cys
            435                 440                 445

Gly

<210> SEQ ID NO 37
<211> LENGTH: 449
<212> TYPE: PRT
<213> ORGANISM: unknown
<220> FEATURE:
<223> OTHER INFORMATION: isolated from library

<400> SEQUENCE: 37

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
            35                  40                  45

Gly Val Gly Gly Leu Trp Asn Val Asn Ile Gly His Asn Arg Ala Ser
        50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
130                 135                 140

Arg Asn Gly Tyr His Gly Ile His Met Gly Thr Ser Val Gly Gly
145                 150                 155                 160

Asn Gly Val Tyr His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
```

```
            210                 215                 220
Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
                260                 265                 270

Trp Gly Val Ala Pro Asp Ile Leu Cys Leu Ala Lys Gly Ile Thr Ala
            275                 280                 285

Gly Tyr Ile Pro Leu Gly Ala Thr Leu Phe Asn Gln Arg Ile Ala Asp
        290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Leu Ala Val Leu
                325                 330                 335

Asp Ile Val Glu Ala Glu Asp Leu Pro Gly Asn Ala Ala Lys Val Gly
                340                 345                 350

Ala Gln Leu Leu Glu Gln Leu Gln Pro Leu Val Glu Arg Tyr Ala Val
                355                 360                 365

Val Gly Glu Val Arg Gly Lys Gly Leu Met Ile Ala Leu Asp Leu Val
        370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Ala Gly Val Leu Val Arg Pro
                405                 410                 415

Ile Gly Asn Lys Ile Ile Leu Ser Pro Pro Leu Thr Leu Thr Arg Asp
                420                 425                 430

Glu Ala Gly Leu Met Val Ser Ala Leu Glu Ala Ala Phe Ala Arg Cys
                435                 440                 445

Gly

<210> SEQ ID NO 38
<211> LENGTH: 449
<212> TYPE: PRT
<213> ORGANISM: unknown
<220> FEATURE:
<223> OTHER INFORMATION: isolated from library

<400> SEQUENCE: 38

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
                20                  25                  30

Gly Asp Gly Asn Tyr Ile Thr Asp Ile Asp Gly Gln Arg Met Leu Asp
            35                  40                  45

Gly Val Gly Gly Leu Trp Asn Val Asn Ile Gly His Asn Arg Ala Ser
        50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
                100                 105                 110

Ser Gly Gly Ser Asp Ala Val Glu Thr Ala Leu Lys Met Ala Arg Gln
            115                 120                 125
```

```
Tyr Trp Ile Ala Ser Gly Glu Pro Gly Arg Thr Arg Phe Leu Ser Leu
        130                 135                 140

Arg Asn Gly Tyr His Gly Phe His Met Gly Thr Ser Val Gly Gly
145                 150                 155                 160

Asn Gly Val Tyr His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala
        275                 280                 285

Gly Tyr Ile Pro Leu Gly Ala Thr Leu Phe Asn Gln Arg Ile Ala Asp
290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Ala Leu Ala Val Leu
                325                 330                 335

Asp Ile Val Glu Ala Glu Asp Leu Pro Gly Asn Ala Ala Lys Val Gly
            340                 345                 350

Ala Gln Leu Leu Glu Gln Leu Gln Pro Leu Val Glu Arg Tyr Ala Val
        355                 360                 365

Val Gly Glu Val Arg Gly Lys Gly Leu Met Ile Ala Leu Asp Leu Val
370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Arg Pro
                405                 410                 415

Ile Gly Asn Lys Ile Ile Leu Ser Pro Pro Leu Thr Leu Thr Arg Asp
            420                 425                 430

Glu Ala Gly Leu Met Val Ser Ala Leu Glu Ala Ala Phe Ala Arg Cys
        435                 440                 445

Gly

<210> SEQ ID NO 39
<211> LENGTH: 449
<212> TYPE: PRT
<213> ORGANISM: unknown
<220> FEATURE:
<223> OTHER INFORMATION: isolated from library

<400> SEQUENCE: 39

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30
```

```
Gly Asp Gly Asn Tyr Ile Thr Asp Ile Asp Gly Gln Arg Met Leu Asp
         35                  40                  45

Gly Val Gly Gly Leu Trp Asn Val Asn Ile Gly His Asn Arg Ala Ser
 50                  55                  60

Val Lys Ala Ala Ile Ala Ala Gln Leu Asp Glu Leu Ala Tyr Tyr Gln
 65                  70                  75                  80

Thr Phe Asp Gly Ile Ala His Pro Arg Val Phe Asp Leu Ala Glu Arg
                 85                  90                  95

Leu Thr Gly Met Phe Ala Gln Glu Arg Met Ala Arg Val Leu Phe Ser
             100                 105                 110

Ser Gly Gly Ser Asp Ala Val Glu Thr Ala Leu Lys Met Ala Arg Gln
             115                 120                 125

Tyr Trp Ile Ala Ser Gly Glu Pro Gly Arg Thr Arg Phe Leu Ser Leu
130                 135                 140

Arg Asn Gly Tyr His Gly Tyr His Met Gly Gly Thr Ser Val Gly Gly
145                 150                 155                 160

Asn Gly Val Tyr His Tyr Asn His Gly Gln Leu Leu Ala Gly Cys His
                 165                 170                 175

Leu Leu Asp Thr Pro Trp Leu Tyr Arg Asn Pro Trp Asp Cys Arg Asp
             180                 185                 190

Pro Gln Ala Leu Thr Ala His Cys Ile Arg Gln Leu Glu Glu Gln Ile
             195                 200                 205

Ala Leu Leu Gly Ala Gln Thr Ile Ala Ala Leu Ile Ala Glu Pro Val
210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                 245                 250                 255

Val Val Thr Gly Phe Gly Arg Ser Gly Cys Met Leu Gly Ser Arg Gly
             260                 265                 270

Trp Gly Val Ala Pro Asp Ile Leu Cys Leu Ala Lys Gly Ile Thr Ala
             275                 280                 285

Gly Tyr Ile Pro Leu Gly Ala Thr Leu Phe Asn Gln Arg Ile Ala Asp
290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Leu Ala Val Leu
                 325                 330                 335

Asp Ile Val Glu Ala Glu Asp Leu Pro Gly Asn Ala Ala Lys Val Gly
             340                 345                 350

Ala Gln Leu Leu Glu Gln Leu Gln Pro Leu Val Glu Arg Tyr Ala Val
             355                 360                 365

Val Gly Glu Val Arg Gly Lys Gly Leu Met Ile Ala Leu Asp Leu Val
370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Ala Gly Val Leu Val Arg Pro
                 405                 410                 415

Ile Gly Asn Lys Ile Ile Leu Ser Pro Pro Leu Thr Leu Thr Arg Asp
             420                 425                 430

Glu Ala Gly Leu Met Val Ser Ala Leu Glu Ala Ala Phe Ala Arg Cys
             435                 440                 445

Gly
```

<210> SEQ ID NO 40
<211> LENGTH: 449
<212> TYPE: PRT
<213> ORGANISM: unknown
<220> FEATURE:
<223> OTHER INFORMATION: isolated from library

<400> SEQUENCE: 40

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
        35                  40                  45

Gly Val Gly Gly Leu Trp Asn Val Asn Ile Gly His Asn Arg Ala Ser
    50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
    130                 135                 140

Arg Asn Gly Tyr His Gly Ser His Met Gly Gly Thr Ser Val Gly Gly
145                 150                 155                 160

Asn Gly Val Tyr His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
    210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala
        275                 280                 285

Gly Tyr Ile Pro Leu Gly Ala Thr Leu Phe Asn Gln Arg Ile Ala Asp
    290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Leu Ala Val Leu Leu
                325                 330                 335

Asp Ile Val Glu Ala Glu Asp Leu Pro Gly Asn Ala Ala Lys Val Gly
            340                 345                 350

Ala Gln Leu Leu Glu Gln Leu Gln Pro Leu Val Glu Arg Tyr Ala Val
        355                 360                 365

```
Val Gly Glu Val Arg Gly Lys Gly Leu Met Ile Ala Leu Asp Leu Val
        370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Arg Pro
                405                 410                 415

Ile Gly Asn Lys Ile Ile Leu Ser Pro Pro Leu Thr Leu Thr Arg Asp
                420                 425                 430

Glu Ala Gly Leu Met Val Ser Ala Leu Glu Ala Ala Phe Ala Arg Cys
            435                 440                 445

Gly
```

<210> SEQ ID NO 41
<211> LENGTH: 449
<212> TYPE: PRT
<213> ORGANISM: unknown
<220> FEATURE:
<223> OTHER INFORMATION: isolated from library

<400> SEQUENCE: 41

```
Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
        35                  40                  45

Gly Val Gly Gly Leu Trp Asn Val Asn Ile Gly His Asn Arg Ala Ser
    50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
130                 135                 140

Arg Asn Gly Tyr His Gly Val His Met Gly Gly Thr Ser Val Gly Gly
145                 150                 155                 160

Ala Gly Val Tyr His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
    210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
            260                 265                 270
```

-continued

```
Trp Gly Val Ala Pro Asp Ile Leu Cys Leu Ala Lys Gly Ile Thr Ala
            275                 280                 285

Gly Tyr Ile Pro Leu Gly Ala Thr Leu Phe Asn Gln Arg Ile Ala Asp
        290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Leu Ala Val Leu
                325                 330                 335

Asp Ile Val Glu Ala Glu Asp Leu Pro Gly Asn Ala Ala Lys Val Gly
            340                 345                 350

Ala Gln Leu Leu Glu Gln Leu Gln Pro Leu Val Glu Arg Tyr Ala Val
        355                 360                 365

Val Gly Glu Val Arg Gly Lys Gly Leu Met Ile Ala Leu Asp Leu Val
    370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Arg Pro
                405                 410                 415

Ile Gly Asn Lys Ile Ile Leu Ser Pro Pro Leu Thr Leu Thr Arg Asp
            420                 425                 430

Glu Ala Gly Leu Met Val Ser Ala Leu Glu Ala Ala Phe Ala Arg Cys
        435                 440                 445

Gly
```

<210> SEQ ID NO 42
<211> LENGTH: 449
<212> TYPE: PRT
<213> ORGANISM: unknown
<220> FEATURE:
<223> OTHER INFORMATION: isolated from library

<400> SEQUENCE: 42

```
Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
        35                  40                  45

Gly Val Gly Gly Leu Trp Asn Val Asn Ile Gly His Asn Arg Ala Ser
    50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
    130                 135                 140

Arg Asn Gly Tyr His Gly Val His Met Gly Gly Thr Ser Val Gly Gly
145                 150                 155                 160

Phe Gly Val Tyr His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
```

```
            180                 185                 190
Pro Gln Ala Leu Thr Ala His Cys Ile Arg Gln Leu Glu Glu Gln Ile
        195                 200                 205
Ala Leu Leu Gly Ala Gln Thr Ile Ala Ala Leu Ile Ala Glu Pro Val
    210                 215                 220
Gln Gly Ala Gly Gly Val Ile Val Pro Pro Ala Asp Tyr Trp Pro Arg
225                 230                 235                 240
Leu Arg Glu Val Cys Asp Arg His Gly Ile Leu Leu Ile Ala Asp Glu
                245                 250                 255
Val Val Thr Gly Phe Gly Arg Ser Gly Cys Met Leu Gly Ser Arg Gly
            260                 265                 270
Trp Gly Val Ala Pro Asp Ile Leu Cys Leu Ala Lys Gly Ile Thr Ala
        275                 280                 285
Gly Tyr Ile Pro Leu Gly Ala Thr Leu Phe Asn Gln Arg Ile Ala Asp
    290                 295                 300
Ala Ile Glu Asn Gly Gln Gly Phe Ser His Met Ile Met His Gly Tyr
305                 310                 315                 320
Thr Tyr Ser Gly His Pro Thr Ala Cys Ala Ala Ala Leu Ala Val Leu
                325                 330                 335
Asp Ile Val Glu Ala Glu Asp Leu Pro Gly Asn Ala Ala Lys Val Gly
            340                 345                 350
Ala Gln Leu Leu Glu Gln Leu Gln Pro Leu Val Glu Arg Tyr Ala Val
        355                 360                 365
Val Gly Glu Val Arg Gly Lys Gly Leu Met Ile Ala Leu Asp Leu Val
    370                 375                 380
Ser Asp Lys Arg Thr Arg Gln Pro Leu Asp Pro Ala Ala Gly Gln Pro
385                 390                 395                 400
Ser Arg Ile Ala Asp Glu Ala Arg Ala Gly Val Leu Val Arg Pro
                405                 410                 415
Ile Gly Asn Lys Ile Ile Leu Ser Pro Pro Leu Thr Leu Thr Arg Asp
            420                 425                 430
Glu Ala Gly Leu Met Val Ser Ala Leu Glu Ala Ala Phe Ala Arg Cys
        435                 440                 445
Gly

<210> SEQ ID NO 43
<211> LENGTH: 449
<212> TYPE: PRT
<213> ORGANISM: unknown
<220> FEATURE:
<223> OTHER INFORMATION: isolated from library

<400> SEQUENCE: 43

Met Tyr Glu Lys Tyr Lys Asn Ala Glu Lys Lys Phe Trp His Pro Met
1               5                   10                  15
Gly Ser Ser Ala Ala Pro His Arg Asp Lys Thr Leu Val Ile Ala Arg
            20                  25                  30
Gly Asp Gly Asn Tyr Ile Thr Asp Ile Asp Gly Gln Arg Met Leu Asp
        35                  40                  45
Gly Val Gly Gly Leu Trp Asn Val Asn Ile Gly His Asn Arg Ala Ser
    50                  55                  60
Val Lys Ala Ala Ile Ala Ala Gln Leu Asp Glu Leu Ala Tyr Tyr Gln
65                  70                  75                  80
Thr Phe Asp Gly Ile Ala His Pro Arg Val Phe Asp Leu Ala Glu Arg
                85                  90                  95
```

-continued

```
Leu Thr Gly Met Phe Ala Gln Glu Arg Met Ala Arg Val Leu Phe Ser
            100                 105                 110
Ser Gly Gly Ser Asp Ala Val Glu Thr Ala Leu Lys Met Ala Arg Gln
        115                 120                 125
Tyr Trp Ile Ala Ser Gly Glu Pro Gly Arg Thr Arg Phe Leu Ser Leu
    130                 135                 140
Arg Asn Gly Tyr His Gly Val His Met Gly Gly Thr Ser Val Gly Gly
145                 150                 155                 160
Met Gly Val Tyr His Tyr Asn His Gly Gln Leu Leu Ala Gly Cys His
                165                 170                 175
Leu Leu Asp Thr Pro Trp Leu Tyr Arg Asn Pro Trp Asp Cys Arg Asp
            180                 185                 190
Pro Gln Ala Leu Thr Ala His Cys Ile Arg Gln Leu Glu Glu Gln Ile
        195                 200                 205
Ala Leu Leu Gly Ala Gln Thr Ile Ala Ala Leu Ile Ala Glu Pro Val
    210                 215                 220
Gln Gly Ala Gly Gly Val Ile Val Pro Pro Ala Asp Tyr Trp Pro Arg
225                 230                 235                 240
Leu Arg Glu Val Cys Asp Arg His Gly Ile Leu Leu Ile Ala Asp Glu
                245                 250                 255
Val Val Thr Gly Phe Gly Arg Ser Gly Cys Met Leu Gly Ser Arg Gly
            260                 265                 270
Trp Gly Val Ala Pro Asp Ile Leu Cys Leu Ala Lys Gly Ile Thr Ala
        275                 280                 285
Gly Tyr Ile Pro Leu Gly Ala Thr Leu Phe Asn Gln Arg Ile Ala Asp
    290                 295                 300
Ala Ile Glu Asn Gly Gln Gly Phe Ser His Met Ile Met His Gly Tyr
305                 310                 315                 320
Thr Tyr Ser Gly His Pro Thr Ala Cys Ala Ala Ala Leu Ala Val Leu
                325                 330                 335
Asp Ile Val Glu Ala Glu Asp Leu Pro Gly Asn Ala Ala Lys Val Gly
            340                 345                 350
Ala Gln Leu Leu Glu Gln Leu Gln Pro Leu Val Glu Arg Tyr Ala Val
        355                 360                 365
Val Gly Glu Val Arg Gly Lys Gly Leu Met Ile Ala Leu Asp Leu Val
    370                 375                 380
Ser Asp Lys Arg Thr Arg Gln Pro Leu Asp Pro Ala Ala Gly Gln Pro
385                 390                 395                 400
Ser Arg Ile Ala Asp Glu Ala Arg Arg Ala Gly Val Leu Val Arg Pro
                405                 410                 415
Ile Gly Asn Lys Ile Ile Leu Ser Pro Pro Leu Thr Leu Thr Arg Asp
            420                 425                 430
Glu Ala Gly Leu Met Val Ser Ala Leu Glu Ala Ala Phe Ala Arg Cys
        435                 440                 445
Gly
```

<210> SEQ ID NO 44
<211> LENGTH: 449
<212> TYPE: PRT
<213> ORGANISM: unknown
<220> FEATURE:
<223> OTHER INFORMATION: isolated from library

<400> SEQUENCE: 44

```
Met Tyr Glu Lys Tyr Lys Asn Ala Glu Lys Lys Phe Trp His Pro Met
1               5                   10                  15
Gly Ser Ser Ala Ala Pro His Arg Asp Lys Thr Leu Val Ile Ala Arg
            20                  25                  30
Gly Asp Gly Asn Tyr Ile Thr Asp Ile Asp Gly Gln Arg Met Leu Asp
        35                  40                  45
Gly Val Gly Gly Leu Trp Asn Val Asn Ile Gly His Asn Arg Ala Ser
    50                  55                  60
Val Lys Ala Ala Ile Ala Ala Gln Leu Asp Glu Leu Ala Tyr Tyr Gln
65              70                  75                  80
Thr Phe Asp Gly Ile Ala His Pro Arg Val Phe Asp Leu Ala Glu Arg
                85                  90                  95
Leu Thr Gly Met Phe Ala Gln Glu Arg Met Ala Arg Val Leu Phe Ser
            100                 105                 110
Ser Gly Gly Ser Asp Ala Val Glu Thr Ala Leu Lys Met Ala Arg Gln
        115                 120                 125
Tyr Trp Ile Ala Ser Gly Glu Pro Gly Arg Thr Arg Phe Leu Ser Leu
    130                 135                 140
Arg Asn Gly Tyr His Gly Val His Met Gly Gly Thr Ser Val Gly Gly
145             150                 155                 160
Tyr Gly Val Tyr His Tyr Asn His Gly Gln Leu Leu Ala Gly Cys His
                165                 170                 175
Leu Leu Asp Thr Pro Trp Leu Tyr Arg Asn Pro Trp Asp Cys Arg Asp
            180                 185                 190
Pro Gln Ala Leu Thr Ala His Cys Ile Arg Gln Leu Glu Glu Gln Ile
        195                 200                 205
Ala Leu Leu Gly Ala Gln Thr Ile Ala Ala Leu Ile Ala Glu Pro Val
    210                 215                 220
Gln Gly Ala Gly Gly Val Ile Val Pro Pro Ala Asp Tyr Trp Pro Arg
225             230                 235                 240
Leu Arg Glu Val Cys Asp Arg His Gly Ile Leu Leu Ile Ala Asp Glu
                245                 250                 255
Val Val Thr Gly Phe Gly Arg Ser Gly Cys Met Leu Gly Ser Arg Gly
            260                 265                 270
Trp Gly Val Ala Pro Asp Ile Leu Cys Leu Ala Lys Gly Ile Thr Ala
        275                 280                 285
Gly Tyr Ile Pro Leu Gly Ala Thr Leu Phe Asn Gln Arg Ile Ala Asp
    290                 295                 300
Ala Ile Glu Asn Gly Gln Gly Phe Ser His Met Ile Met His Gly Tyr
305             310                 315                 320
Thr Tyr Ser Gly His Pro Thr Ala Cys Ala Ala Ala Leu Ala Val Leu
                325                 330                 335
Asp Ile Val Glu Ala Glu Asp Leu Pro Gly Asn Ala Ala Lys Val Gly
            340                 345                 350
Ala Gln Leu Leu Glu Gln Leu Gln Pro Leu Val Glu Arg Tyr Ala Val
        355                 360                 365
Val Gly Glu Val Arg Gly Lys Gly Leu Met Ile Ala Leu Asp Leu Val
    370                 375                 380
Ser Asp Lys Arg Thr Arg Gln Pro Leu Asp Pro Ala Ala Gly Gln Pro
385             390                 395                 400
Ser Arg Ile Ala Asp Glu Ala Arg Arg Ala Gly Val Leu Val Arg Pro
                405                 410                 415
Ile Gly Asn Lys Ile Ile Leu Ser Pro Pro Leu Thr Leu Thr Arg Asp
```

```
                    420                 425                 430
Glu Ala Gly Leu Met Val Ser Ala Leu Glu Ala Ala Phe Ala Arg Cys
                435                 440                 445
Gly

<210> SEQ ID NO 45
<211> LENGTH: 449
<212> TYPE: PRT
<213> ORGANISM: unknown
<220> FEATURE:
<223> OTHER INFORMATION: isolated from library

<400> SEQUENCE: 45

Met Tyr Glu Lys Tyr Lys Asn Ala Glu Lys Lys Phe Trp His Pro Met
  1               5                  10                  15

Gly Ser Ser Ala Ala Pro His Arg Asp Lys Thr Leu Val Ile Ala Arg
                 20                  25                  30

Gly Asp Gly Asn Tyr Ile Thr Asp Ile Asp Gly Gln Arg Met Leu Asp
             35                  40                  45

Gly Val Gly Gly Leu Trp Asn Val Asn Ile Gly His Asn Arg Ala Ser
 50                  55                  60

Val Lys Ala Ala Ile Ala Ala Gln Leu Asp Glu Leu Ala Tyr Tyr Gln
 65                  70                  75                  80

Thr Phe Asp Gly Ile Ala His Pro Arg Val Phe Asp Leu Ala Glu Arg
                 85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
    130                 135                 140

Arg Asn Gly Tyr His Gly Val His Met Gly Gly Thr Ser Val Gly Gly
145                 150                 155                 160

Gln Gly Val Tyr His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
    210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala
        275                 280                 285

Gly Tyr Ile Pro Leu Gly Ala Thr Leu Phe Asn Gln Arg Ile Ala Asp
    290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Ala Leu Ala Val Leu
                325                 330                 335
```

```
Asp Ile Val Glu Ala Glu Asp Leu Pro Gly Asn Ala Ala Lys Val Gly
            340                 345                 350

Ala Gln Leu Leu Glu Gln Leu Gln Pro Leu Val Glu Arg Tyr Ala Val
            355                 360                 365

Val Gly Glu Val Arg Gly Lys Gly Leu Met Ile Ala Leu Asp Leu Val
370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Ala Gly Val Leu Val Arg Pro
            405                 410                 415

Ile Gly Asn Lys Ile Ile Leu Ser Pro Pro Leu Thr Leu Thr Arg Asp
            420                 425                 430

Glu Ala Gly Leu Met Val Ser Ala Leu Glu Ala Ala Phe Ala Arg Cys
            435                 440                 445

Gly

<210> SEQ ID NO 46
<211> LENGTH: 449
<212> TYPE: PRT
<213> ORGANISM: unknown
<220> FEATURE:
<223> OTHER INFORMATION: isolated from library

<400> SEQUENCE: 46

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
        35                  40                  45

Gly Val Gly Gly Leu Trp Asn Val Asn Ile Gly His Asn Arg Ala Ser
    50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
130                 135                 140

Arg Asn Gly Tyr His Gly Val His Met Gly Gly Thr Ser Val Gly Gly
145                 150                 155                 160

Ile Gly Val Tyr His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
    210                 215                 220

Gln Gly Ala Gly Gly Val Ile Val Pro Pro Ala Asp Tyr Trp Pro Arg
225                 230                 235                 240
```

-continued

```
Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala
        275                 280                 285

Gly Tyr Ile Pro Leu Gly Ala Thr Leu Phe Asn Gln Arg Ile Ala Asp
    290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Ala Leu Ala Val Leu
                325                 330                 335

Asp Ile Val Glu Ala Glu Asp Leu Pro Gly Asn Ala Ala Lys Val Gly
            340                 345                 350

Ala Gln Leu Leu Glu Gln Leu Gln Pro Leu Val Glu Arg Tyr Ala Val
        355                 360                 365

Val Gly Glu Val Arg Gly Lys Gly Leu Met Ile Ala Leu Asp Leu Val
    370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Ala Gly Val Leu Val Arg Pro
                405                 410                 415

Ile Gly Asn Lys Ile Ile Leu Ser Pro Pro Leu Thr Leu Thr Arg Asp
            420                 425                 430

Glu Ala Gly Leu Met Val Ser Ala Leu Glu Ala Ala Phe Ala Arg Cys
        435                 440                 445

Gly
```

```
<210> SEQ ID NO 47
<211> LENGTH: 449
<212> TYPE: PRT
<213> ORGANISM: unknown
<220> FEATURE:
<223> OTHER INFORMATION: isolated from library

<400> SEQUENCE: 47

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
        35                  40                  45

Gly Val Gly Gly Leu Trp Asn Val Asn Ile Gly His Asn Arg Ala Ser
    50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
    130                 135                 140

Arg Asn Gly Tyr His Gly Val His Met Gly Gly Thr Ser Val Gly Gly
```

```
            145                 150                 155                 160
    Asn Gly Val Leu His Tyr Asn His Gly Gln Leu Leu Ala Gly Cys His
                    165                 170                 175

Leu Leu Asp Thr Pro Trp Leu Tyr Arg Asn Pro Trp Asp Cys Arg Asp
                    180                 185                 190

Pro Gln Ala Leu Thr Ala His Cys Ile Arg Gln Leu Glu Glu Gln Ile
                    195                 200                 205

Ala Leu Leu Gly Ala Gln Thr Ile Ala Ala Leu Ile Ala Glu Pro Val
    210                 215                 220

Gln Gly Ala Gly Gly Val Ile Val Pro Pro Ala Asp Tyr Trp Pro Arg
    225                 230                 235                 240

Leu Arg Glu Val Cys Asp Arg His Gly Ile Leu Leu Ile Ala Asp Glu
                    245                 250                 255

Val Val Thr Gly Phe Gly Arg Ser Gly Cys Met Leu Gly Ser Arg Gly
                    260                 265                 270

Trp Gly Val Ala Pro Asp Ile Leu Cys Leu Ala Lys Gly Ile Thr Ala
                    275                 280                 285

Gly Tyr Ile Pro Leu Gly Ala Thr Leu Phe Asn Gln Arg Ile Ala Asp
                    290                 295                 300

Ala Ile Glu Asn Gly Gln Gly Phe Ser His Met Ile Met His Gly Tyr
    305                 310                 315                 320

Thr Tyr Ser Gly His Pro Thr Ala Cys Ala Ala Leu Ala Val Leu
                    325                 330                 335

Asp Ile Val Glu Ala Glu Asp Leu Pro Gly Asn Ala Ala Lys Val Gly
                    340                 345                 350

Ala Gln Leu Leu Glu Gln Leu Gln Pro Leu Val Glu Arg Tyr Ala Val
                    355                 360                 365

Val Gly Glu Val Arg Gly Lys Gly Leu Met Ile Ala Leu Asp Leu Val
                    370                 375                 380

Ser Asp Lys Arg Thr Arg Gln Pro Leu Asp Pro Ala Ala Gly Gln Pro
    385                 390                 395                 400

Ser Arg Ile Ala Asp Glu Ala Arg Arg Ala Gly Val Leu Val Arg Pro
                    405                 410                 415

Ile Gly Asn Lys Ile Ile Leu Ser Pro Pro Leu Thr Leu Thr Arg Asp
                    420                 425                 430

Glu Ala Gly Leu Met Val Ser Ala Leu Glu Ala Ala Phe Ala Arg Cys
                    435                 440                 445

Gly

<210> SEQ ID NO 48
<211> LENGTH: 449
<212> TYPE: PRT
<213> ORGANISM: unknown
<220> FEATURE:
<223> OTHER INFORMATION: isolated from library

<400> SEQUENCE: 48

Met Tyr Glu Lys Tyr Lys Asn Ala Glu Lys Lys Phe Trp His Pro Met
    1               5                   10                  15

Gly Ser Ser Ala Ala Pro His Arg Asp Lys Thr Leu Val Ile Ala Arg
                    20                  25                  30

Gly Asp Gly Asn Tyr Ile Thr Asp Ile Asp Gly Gln Arg Met Leu Asp
                    35                  40                  45

Gly Val Gly Gly Leu Trp Asn Val Asn Ile Gly His Asn Arg Ala Ser
                    50                  55                  60
```

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
            85                  90                  95

Leu Thr Gly Met Phe Ala Gln Glu Arg Met Ala Arg Val Leu Phe Ser
        100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
        130                 135                 140

Arg Asn Gly Tyr His Gly Val His Met Gly Thr Ser Val Gly Gly
145                 150                 155                 160

Asn Gly Val Met His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
            245                 250                 255

Val Val Thr Gly Phe Gly Arg Ser Gly Cys Met Leu Gly Ser Arg Gly
        260                 265                 270

Trp Gly Val Ala Pro Asp Ile Leu Cys Leu Ala Lys Gly Ile Thr Ala
        275                 280                 285

Gly Tyr Ile Pro Leu Gly Ala Thr Leu Phe Asn Gln Arg Ile Ala Asp
        290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Ala Leu Ala Val Leu
                325                 330                 335

Asp Ile Val Glu Ala Glu Asp Leu Pro Gly Asn Ala Ala Lys Val Gly
            340                 345                 350

Ala Gln Leu Leu Glu Gln Leu Gln Pro Leu Val Glu Arg Tyr Ala Val
        355                 360                 365

Val Gly Glu Val Arg Gly Lys Gly Leu Met Ile Ala Leu Asp Leu Val
370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Ala Gly Val Leu Val Arg Pro
            405                 410                 415

Ile Gly Asn Lys Ile Ile Leu Ser Pro Pro Leu Thr Leu Thr Arg Asp
        420                 425                 430

Glu Ala Gly Leu Met Val Ser Ala Leu Glu Ala Ala Phe Ala Arg Cys
        435                 440                 445

Gly

<210> SEQ ID NO 49
<211> LENGTH: 449
<212> TYPE: PRT

<213> ORGANISM: unknown
<220> FEATURE:
<223> OTHER INFORMATION: isolated from library

<400> SEQUENCE: 49

```
Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
        35                  40                  45

Gly Val Gly Gly Leu Trp Asn Val Asn Ile Gly His Asn Arg Ala Ser
    50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
    130                 135                 140

Arg Asn Gly Tyr His Gly Val His Met Gly Thr Ser Val Gly Gly
145                 150                 155                 160

Asn Gly Val Ala His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
    210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala
        275                 280                 285

Gly Tyr Ile Pro Leu Gly Ala Thr Leu Phe Asn Gln Arg Ile Ala Asp
    290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Leu Ala Val Leu
                325                 330                 335

Asp Ile Val Glu Ala Glu Asp Leu Pro Gly Asn Ala Ala Lys Val Gly
            340                 345                 350

Ala Gln Leu Leu Glu Gln Leu Gln Pro Leu Val Glu Arg Tyr Ala Val
        355                 360                 365

Val Gly Glu Val Arg Gly Lys Gly Leu Met Ile Ala Leu Asp Leu Val
    370                 375                 380

Ser Asp Lys Arg Thr Arg Gln Pro Leu Asp Pro Ala Ala Gly Gln Pro
```

```
                385                 390                 395                 400
        Ser Arg Ile Ala Asp Glu Ala Arg Arg Ala Gly Val Leu Val Arg Pro
                        405                 410                 415

Ile Gly Asn Lys Ile Ile Leu Ser Pro Pro Leu Thr Leu Thr Arg Asp
                        420                 425                 430

Glu Ala Gly Leu Met Val Ser Ala Leu Glu Ala Ala Phe Ala Arg Cys
                        435                 440                 445

Gly

<210> SEQ ID NO 50
<211> LENGTH: 449
<212> TYPE: PRT
<213> ORGANISM: unknown
<220> FEATURE:
<223> OTHER INFORMATION: isolated from library

<400> SEQUENCE: 50

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
                20                  25                  30

Gly Asp Gly Asn Tyr Ile Thr Asp Ile Asp Gly Gln Arg Met Leu Asp
            35                  40                  45

Gly Val Gly Gly Leu Trp Asn Val Asn Ile Gly His Asn Arg Ala Ser
    50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
    130                 135                 140

Arg Asn Gly Tyr His Gly Val His Met Gly Gly Thr Ser Val Gly Gly
145                 150                 155                 160

Asn Gly Val Phe His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
    210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala
        275                 280                 285

Gly Tyr Ile Pro Leu Gly Ala Thr Leu Phe Asn Gln Arg Ile Ala Asp
    290                 295                 300
```

```
Ala Ile Glu Asn Gly Gln Gly Phe Ser His Met Ile Met His Gly Tyr
305                 310                 315                 320

Thr Tyr Ser Gly His Pro Thr Ala Cys Ala Ala Leu Ala Val Leu
            325                 330                 335

Asp Ile Val Glu Ala Glu Asp Leu Pro Gly Asn Ala Ala Lys Val Gly
        340                 345                 350

Ala Gln Leu Leu Glu Gln Leu Gln Pro Leu Val Glu Arg Tyr Ala Val
            355                 360                 365

Val Gly Glu Val Arg Gly Lys Gly Leu Met Ile Ala Leu Asp Leu Val
        370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Arg Pro
            405                 410                 415

Ile Gly Asn Lys Ile Ile Leu Ser Pro Pro Leu Thr Leu Thr Arg Asp
        420                 425                 430

Glu Ala Gly Leu Met Val Ser Ala Leu Glu Ala Ala Phe Ala Arg Cys
            435                 440                 445

Gly

<210> SEQ ID NO 51
<211> LENGTH: 449
<212> TYPE: PRT
<213> ORGANISM: unknown
<220> FEATURE:
<223> OTHER INFORMATION: isolated from library

<400> SEQUENCE: 51

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
        35                  40                  45

Gly Val Gly Gly Leu Trp Asn Val Asn Ile Gly His Asn Arg Ala Ser
    50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
    130                 135                 140

Arg Asn Gly Tyr His Gly Val His Met Gly Gly Thr Ser Val Gly Gly
145                 150                 155                 160

Asn Gly Val Ile His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205
```

```
Ala Leu Leu Gly Ala Gln Thr Ile Ala Ala Leu Ile Ala Glu Pro Val
        210                 215                 220

Gln Gly Ala Gly Val Ile Val Pro Ala Asp Tyr Trp Pro Arg
225                 230                 235                 240

Leu Arg Glu Val Cys Asp Arg His Gly Ile Leu Leu Ile Ala Asp Glu
                    245                 250                 255

Val Val Thr Gly Phe Gly Arg Ser Gly Cys Met Leu Gly Ser Arg Gly
                260                 265                 270

Trp Gly Val Ala Pro Asp Ile Leu Cys Leu Ala Lys Gly Ile Thr Ala
                275                 280                 285

Gly Tyr Ile Pro Leu Gly Ala Thr Leu Phe Asn Gln Arg Ile Ala Asp
        290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Leu Ala Val Leu
                    325                 330                 335

Asp Ile Val Glu Ala Glu Asp Leu Pro Gly Asn Ala Ala Lys Val Gly
                340                 345                 350

Ala Gln Leu Leu Glu Gln Leu Gln Pro Leu Val Glu Arg Tyr Ala Val
        355                 360                 365

Val Gly Glu Val Arg Gly Lys Gly Leu Met Ile Ala Leu Asp Leu Val
370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Arg Pro
                405                 410                 415

Ile Gly Asn Lys Ile Ile Leu Ser Pro Pro Leu Thr Leu Thr Arg Asp
                420                 425                 430

Glu Ala Gly Leu Met Val Ser Ala Leu Glu Ala Ala Phe Ala Arg Cys
        435                 440                 445

Gly
```

<210> SEQ ID NO 52
<211> LENGTH: 449
<212> TYPE: PRT
<213> ORGANISM: unknown
<220> FEATURE:
<223> OTHER INFORMATION: isolated from library

<400> SEQUENCE: 52

```
Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
                20                  25                  30

Gly Asp Gly Asn Tyr Ile Thr Asp Ile Asp Gly Gln Arg Met Leu Asp
            35                  40                  45

Gly Val Gly Gly Leu Trp Asn Val Asn Ile Gly His Asn Arg Ala Ser
        50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
                100                 105                 110

Ser Gly Gly Ser Asp Ala Val Glu Thr Ala Leu Lys Met Ala Arg Gln
```

```
                115                 120                 125
Tyr Trp Ile Ala Ser Gly Glu Pro Gly Arg Thr Arg Phe Leu Ser Leu
            130                 135                 140

Arg Asn Gly Tyr His Gly Val His Met Gly Gly Thr Ser Val Gly Gly
145                 150                 155                 160

Asn Gly Val Tyr His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
            195                 200                 205

Ala Leu Leu Gly Ala Gln Thr Ile Ala Ala Leu Ile Ala Ser Pro Val
            210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala
            275                 280                 285

Gly Tyr Ile Pro Leu Gly Ala Thr Leu Phe Asn Gln Arg Ile Ala Asp
290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Ala Leu Ala Val Leu
                325                 330                 335

Asp Ile Val Glu Ala Glu Asp Leu Pro Gly Asn Ala Ala Lys Val Gly
            340                 345                 350

Ala Gln Leu Leu Glu Gln Leu Gln Pro Leu Val Glu Arg Tyr Ala Val
            355                 360                 365

Val Gly Glu Val Arg Gly Lys Gly Leu Met Ile Ala Leu Asp Leu Val
            370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Arg Pro
                405                 410                 415

Ile Gly Asn Lys Ile Ile Leu Ser Pro Pro Leu Thr Leu Thr Arg Asp
            420                 425                 430

Glu Ala Gly Leu Met Val Ser Ala Leu Glu Ala Ala Phe Ala Arg Cys
            435                 440                 445

Gly

<210> SEQ ID NO 53
<211> LENGTH: 449
<212> TYPE: PRT
<213> ORGANISM: unknown
<220> FEATURE:
<223> OTHER INFORMATION: isolated from library

<400> SEQUENCE: 53

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30
```

-continued

Gly Asp Gly Asn Tyr Ile Thr Asp Ile Asp Gly Gln Arg Met Leu Asp
            35                  40                  45

Gly Val Gly Gly Leu Trp Asn Val Asn Ile Gly His Asn Arg Ala Ser
 50                  55                  60

Val Lys Ala Ala Ile Ala Ala Gln Leu Asp Glu Leu Ala Tyr Tyr Gln
 65                  70                  75                  80

Thr Phe Asp Gly Ile Ala His Pro Arg Val Phe Asp Leu Ala Glu Arg
                 85                  90                  95

Leu Thr Gly Met Phe Ala Gln Glu Arg Met Ala Arg Val Leu Phe Ser
                100                 105                 110

Ser Gly Gly Ser Asp Ala Val Glu Thr Ala Leu Lys Met Ala Arg Gln
                115                 120                 125

Tyr Trp Ile Ala Ser Gly Glu Pro Gly Arg Thr Arg Phe Leu Ser Leu
            130                 135                 140

Arg Asn Gly Tyr His Gly Val His Met Gly Gly Thr Ser Val Gly Gly
145                 150                 155                 160

Asn Gly Val Tyr His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
                180                 185                 190

Pro Gln Ala Leu Thr Ala His Cys Ile Arg Gln Leu Glu Glu Gln Ile
            195                 200                 205

Ala Leu Leu Gly Ala Gln Thr Ile Ala Ala Leu Ile Ala Ala Pro Val
            210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
                260                 265                 270

Trp Gly Val Ala Pro Asp Ile Leu Cys Leu Ala Lys Gly Ile Thr Ala
            275                 280                 285

Gly Tyr Ile Pro Leu Gly Ala Thr Leu Phe Asn Gln Arg Ile Ala Asp
290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Ala Leu Ala Val Leu
                325                 330                 335

Asp Ile Val Glu Ala Glu Asp Leu Pro Gly Asn Ala Ala Lys Val Gly
                340                 345                 350

Ala Gln Leu Leu Glu Gln Leu Gln Pro Leu Val Glu Arg Tyr Ala Val
            355                 360                 365

Val Gly Glu Val Arg Gly Lys Gly Leu Met Ile Ala Leu Asp Leu Val
 370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Arg Pro
                405                 410                 415

Ile Gly Asn Lys Ile Ile Leu Ser Pro Pro Leu Thr Leu Thr Arg Asp
                420                 425                 430

Glu Ala Gly Leu Met Val Ser Ala Leu Glu Ala Ala Phe Ala Arg Cys
            435                 440                 445

-continued

Gly

<210> SEQ ID NO 54
<211> LENGTH: 449
<212> TYPE: PRT
<213> ORGANISM: unknown
<220> FEATURE:
<223> OTHER INFORMATION: isolated from library

<400> SEQUENCE: 54

```
Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
        35                  40                  45

Gly Val Gly Gly Leu Trp Asn Val Asn Ile Gly His Asn Arg Ala Ser
    50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
    130                 135                 140

Arg Asn Gly Tyr His Gly Val His Met Gly Gly Thr Ser Val Gly Gly
145                 150                 155                 160

Asn Gly Val Tyr His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Asp Pro Val
    210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala
        275                 280                 285

Gly Tyr Ile Pro Leu Gly Ala Thr Leu Phe Asn Gln Arg Ile Ala Asp
    290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Leu Ala Val Leu
                325                 330                 335

Asp Ile Val Glu Ala Glu Asp Leu Pro Gly Asn Ala Ala Lys Val Gly
            340                 345                 350

Ala Gln Leu Leu Glu Gln Leu Gln Pro Leu Val Glu Arg Tyr Ala Val
```

```
                355                 360                 365
Val Gly Glu Val Arg Gly Lys Gly Leu Met Ile Ala Leu Asp Leu Val
        370                 375                 380
Ser Asp Lys Arg Thr Arg Gln Pro Leu Asp Pro Ala Ala Gly Gln Pro
385                 390                 395                 400
Ser Arg Ile Ala Asp Glu Ala Arg Arg Ala Gly Val Leu Val Arg Pro
                405                 410                 415
Ile Gly Asn Lys Ile Ile Leu Ser Pro Pro Leu Thr Leu Thr Arg Asp
            420                 425                 430
Glu Ala Gly Leu Met Val Ser Ala Leu Glu Ala Ala Phe Ala Arg Cys
            435                 440                 445
Gly

<210> SEQ ID NO 55
<211> LENGTH: 449
<212> TYPE: PRT
<213> ORGANISM: unknown
<220> FEATURE:
<223> OTHER INFORMATION: isolated from library

<400> SEQUENCE: 55

Met Tyr Glu Lys Tyr Lys Asn Ala Glu Lys Lys Phe Trp His Pro Met
1               5                   10                  15
Gly Ser Ser Ala Ala Pro His Arg Asp Lys Thr Leu Val Ile Ala Arg
            20                  25                  30
Gly Asp Gly Asn Tyr Ile Thr Asp Ile Asp Gly Gln Arg Met Leu Asp
        35                  40                  45
Gly Val Gly Gly Leu Trp Asn Val Asn Ile Gly His Asn Arg Ala Ser
    50                  55                  60
Val Lys Ala Ala Ile Ala Ala Gln Leu Asp Glu Leu Ala Tyr Tyr Gln
65                  70                  75                  80
Thr Phe Asp Gly Ile Ala His Pro Arg Val Phe Asp Leu Ala Glu Arg
                85                  90                  95
Leu Thr Gly Met Phe Ala Gln Glu Arg Met Ala Arg Val Leu Phe Ser
            100                 105                 110
Ser Gly Gly Ser Asp Ala Val Glu Thr Ala Leu Lys Met Ala Arg Gln
        115                 120                 125
Tyr Trp Ile Ala Ser Gly Glu Pro Gly Arg Thr Arg Phe Leu Ser Leu
    130                 135                 140
Arg Asn Gly Tyr His Gly Val His Met Gly Gly Thr Ser Val Gly Gly
145                 150                 155                 160
Asn Gly Val Tyr His Tyr Asn His Gly Gln Leu Leu Ala Gly Cys His
                165                 170                 175
Leu Leu Asp Thr Pro Trp Leu Tyr Arg Asn Pro Trp Asp Cys Arg Asp
            180                 185                 190
Pro Gln Ala Leu Thr Ala His Cys Ile Arg Gln Leu Glu Glu Gln Ile
        195                 200                 205
Ala Leu Leu Gly Ala Gln Thr Ile Ala Ala Leu Ile Ala Glu Pro Val
    210                 215                 220
Gln Gly Tyr Gly Gly Val Ile Val Pro Pro Ala Asp Tyr Trp Pro Arg
225                 230                 235                 240
Leu Arg Glu Val Cys Asp Arg His Gly Ile Leu Leu Ile Ala Asp Glu
                245                 250                 255
Val Val Thr Gly Phe Gly Arg Ser Gly Cys Met Leu Gly Ser Arg Gly
            260                 265                 270
```

```
Trp Gly Val Ala Pro Asp Ile Leu Cys Leu Ala Lys Gly Ile Thr Ala
        275                 280                 285

Gly Tyr Ile Pro Leu Gly Ala Thr Leu Phe Asn Gln Arg Ile Ala Asp
        290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Leu Ala Val Leu
            325                 330                 335

Asp Ile Val Glu Ala Glu Asp Leu Pro Gly Asn Ala Ala Lys Val Gly
                340                 345                 350

Ala Gln Leu Leu Glu Gln Leu Gln Pro Leu Val Glu Arg Tyr Ala Val
            355                 360                 365

Val Gly Glu Val Arg Gly Lys Gly Leu Met Ile Ala Leu Asp Leu Val
        370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Arg Pro
                405                 410                 415

Ile Gly Asn Lys Ile Ile Leu Ser Pro Pro Leu Thr Leu Thr Arg Asp
            420                 425                 430

Glu Ala Gly Leu Met Val Ser Ala Leu Glu Ala Ala Phe Ala Arg Cys
        435                 440                 445

Gly

<210> SEQ ID NO 56
<211> LENGTH: 449
<212> TYPE: PRT
<213> ORGANISM: unknown
<220> FEATURE:
<223> OTHER INFORMATION: isolated from library

<400> SEQUENCE: 56

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
        35                  40                  45

Gly Val Gly Gly Leu Trp Asn Val Asn Ile Gly His Asn Arg Ala Ser
    50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
    130                 135                 140

Arg Asn Gly Tyr His Gly Val His Met Gly Gly Thr Ser Val Gly Gly
145                 150                 155                 160

Asn Gly Val Tyr His Tyr Asn His Gly Gln Leu Leu Ala Gly Cys His
                165                 170                 175
```

```
Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
    210                 215                 220

Gln Gly Val Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala
        275                 280                 285

Gly Tyr Ile Pro Leu Gly Ala Thr Leu Phe Asn Gln Arg Ile Ala Asp
    290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Ala Leu Ala Val Leu
                325                 330                 335

Asp Ile Val Glu Ala Glu Asp Leu Pro Gly Asn Ala Ala Lys Val Gly
            340                 345                 350

Ala Gln Leu Leu Glu Gln Leu Gln Pro Leu Val Glu Arg Tyr Ala Val
        355                 360                 365

Val Gly Glu Val Arg Gly Lys Gly Leu Met Ile Ala Leu Asp Leu Val
    370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Arg Pro
                405                 410                 415

Ile Gly Asn Lys Ile Ile Leu Ser Pro Pro Leu Thr Leu Thr Arg Asp
            420                 425                 430

Glu Ala Gly Leu Met Val Ser Ala Leu Glu Ala Ala Phe Ala Arg Cys
        435                 440                 445

Gly

<210> SEQ ID NO 57
<211> LENGTH: 449
<212> TYPE: PRT
<213> ORGANISM: unknown
<220> FEATURE:
<223> OTHER INFORMATION: isolated from library

<400> SEQUENCE: 57

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
        35                  40                  45

Gly Val Gly Gly Leu Trp Asn Val Asn Ile Gly His Asn Arg Ala Ser
    50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
```

|     |     |     |     | 85  |     |     |     |     | 90  |     |     |     |     | 95  |     |
| --- | --- | --- | --- | --- | --- | --- | --- | --- | --- | --- | --- | --- | --- | --- | --- |

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
            115                 120                 125

Tyr Trp Ile Ala Ser Gly Pro Gly Arg Thr Arg Phe Leu Ser Leu
    130                 135                 140

Arg Asn Gly Tyr His Gly Val His Met Gly Gly Thr Ser Val Gly Gly
145                 150                 155                 160

Asn Gly Val Tyr His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
    210                 215                 220

Gln Gly Ile Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala
    275                 280                 285

Gly Tyr Ile Pro Leu Gly Ala Thr Leu Phe Asn Gln Arg Ile Ala Asp
    290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Ala Leu Ala Val Leu
                325                 330                 335

Asp Ile Val Glu Ala Glu Asp Leu Pro Gly Asn Ala Ala Lys Val Gly
            340                 345                 350

Ala Gln Leu Leu Glu Gln Leu Gln Pro Leu Val Glu Arg Tyr Ala Val
    355                 360                 365

Val Gly Glu Val Arg Gly Lys Gly Leu Met Ile Ala Leu Asp Leu Val
    370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Arg Pro
                405                 410                 415

Ile Gly Asn Lys Ile Ile Leu Ser Pro Pro Leu Thr Leu Thr Arg Asp
            420                 425                 430

Glu Ala Gly Leu Met Val Ser Ala Leu Glu Ala Ala Phe Ala Arg Cys
            435                 440                 445

Gly

<210> SEQ ID NO 58
<211> LENGTH: 449
<212> TYPE: PRT
<213> ORGANISM: unknown
<220> FEATURE:
<223> OTHER INFORMATION: isolated from library

<400> SEQUENCE: 58

-continued

```
Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
                20                  25                  30

Gly Asp Gly Asn Tyr Ile Thr Asp Ile Asp Gly Gln Arg Met Leu Asp
            35                  40                  45

Gly Val Gly Gly Leu Trp Asn Val Asn Ile Gly His Asn Arg Ala Ser
        50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
130                 135                 140

Arg Asn Gly Tyr His Gly Val His Met Gly Gly Thr Ser Val Gly Gly
145                 150                 155                 160

Asn Gly Val Tyr His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
210                 215                 220

Gln Gly Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala
        275                 280                 285

Gly Tyr Ile Pro Leu Gly Ala Thr Leu Phe Asn Gln Arg Ile Ala Asp
290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Leu Ala Val Leu
                325                 330                 335

Asp Ile Val Glu Ala Glu Asp Leu Pro Gly Asn Ala Ala Lys Val Gly
            340                 345                 350

Ala Gln Leu Leu Glu Gln Leu Gln Pro Leu Val Glu Arg Tyr Ala Val
        355                 360                 365

Val Gly Glu Val Arg Gly Lys Gly Leu Met Ile Ala Leu Asp Leu Val
370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Arg Pro
                405                 410                 415
```

```
Ile Gly Asn Lys Ile Ile Leu Ser Pro Pro Leu Thr Leu Thr Arg Asp
            420                 425                 430

Glu Ala Gly Leu Met Val Ser Ala Leu Glu Ala Phe Ala Arg Cys
            435                 440                 445

Gly

<210> SEQ ID NO 59
<211> LENGTH: 449
<212> TYPE: PRT
<213> ORGANISM: unknown
<220> FEATURE:
<223> OTHER INFORMATION: isolated from library

<400> SEQUENCE: 59

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
        35                  40                  45

Gly Val Gly Gly Leu Trp Asn Val Asn Ile Gly His Asn Arg Ala Ser
50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
130                 135                 140

Arg Asn Gly Tyr His Gly Val His Met Gly Gly Thr Ser Val Gly Gly
145                 150                 155                 160

Asn Gly Val Tyr His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
210                 215                 220

Gln Gly Phe Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala
        275                 280                 285

Gly Tyr Ile Pro Leu Gly Ala Thr Leu Phe Asn Gln Arg Ile Ala Asp
290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Ala Leu Ala Val Leu
```

```
                    325                 330                 335
Asp Ile Val Glu Ala Glu Asp Leu Pro Gly Asn Ala Ala Lys Val Gly
                340                 345                 350

Ala Gln Leu Leu Glu Gln Leu Gln Pro Leu Val Glu Arg Tyr Ala Val
            355                 360                 365

Val Gly Glu Val Arg Gly Lys Gly Leu Met Ile Ala Leu Asp Leu Val
        370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Ala Gly Val Leu Val Arg Pro
                405                 410                 415

Ile Gly Asn Lys Ile Ile Leu Ser Pro Pro Leu Thr Leu Thr Arg Asp
                420                 425                 430

Glu Ala Gly Leu Met Val Ser Ala Leu Glu Ala Ala Phe Ala Arg Cys
            435                 440                 445

Gly

<210> SEQ ID NO 60
<211> LENGTH: 449
<212> TYPE: PRT
<213> ORGANISM: unknown
<220> FEATURE:
<223> OTHER INFORMATION: isolated from library

<400> SEQUENCE: 60

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
        35                  40                  45

Gly Val Gly Gly Leu Trp Asn Val Asn Ile Gly His Asn Arg Ala Ser
    50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
    130                 135                 140

Arg Asn Gly Tyr His Gly Val His Met Gly Thr Ser Val Gly Gly
145                 150                 155                 160

Asn Gly Val Tyr His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
    210                 215                 220

Gln Gly Met Gly Gly Val Ile Val Pro Pro Ala Asp Tyr Trp Pro Arg
225                 230                 235                 240
```

```
Leu Arg Glu Val Cys Asp Arg His Gly Ile Leu Leu Ile Ala Asp Glu
            245                 250                 255

Val Val Thr Gly Phe Gly Arg Ser Gly Cys Met Leu Gly Ser Arg Gly
        260                 265                 270

Trp Gly Val Ala Pro Asp Ile Leu Cys Leu Ala Lys Gly Ile Thr Ala
        275                 280                 285

Gly Tyr Ile Pro Leu Gly Ala Thr Leu Phe Asn Gln Arg Ile Ala Asp
        290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Ala Leu Ala Val Leu
            325                 330                 335

Asp Ile Val Glu Ala Glu Asp Leu Pro Gly Asn Ala Ala Lys Val Gly
            340                 345                 350

Ala Gln Leu Leu Glu Gln Leu Gln Pro Leu Val Glu Arg Tyr Ala Val
            355                 360                 365

Val Gly Glu Val Arg Gly Lys Gly Leu Met Ile Ala Leu Asp Leu Val
        370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Arg Pro
            405                 410                 415

Ile Gly Asn Lys Ile Ile Leu Ser Pro Pro Leu Thr Leu Thr Arg Asp
            420                 425                 430

Glu Ala Gly Leu Met Val Ser Ala Leu Glu Ala Ala Phe Ala Arg Cys
            435                 440                 445

Gly

<210> SEQ ID NO 61
<211> LENGTH: 449
<212> TYPE: PRT
<213> ORGANISM: unknown
<220> FEATURE:
<223> OTHER INFORMATION: isolated from library

<400> SEQUENCE: 61

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
        35                  40                  45

Gly Val Gly Gly Leu Trp Asn Val Asn Ile Gly His Asn Arg Ala Ser
    50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
            85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
    130                 135                 140
```

```
Arg Asn Gly Tyr His Gly Val His Met Gly Thr Ser Val Gly Gly
145                 150                 155                 160

Asn Gly Val Tyr His Tyr Asn His Gly Gln Leu Leu Ala Gly Cys His
            165                 170                 175

Leu Leu Asp Thr Pro Trp Leu Tyr Arg Asn Pro Trp Asp Cys Arg Asp
        180                 185                 190

Pro Gln Ala Leu Thr Ala His Cys Ile Arg Gln Leu Glu Glu Gln Ile
    195                 200                 205

Ala Leu Leu Gly Ala Gln Thr Ile Ala Ala Leu Ile Ala Glu Pro Val
210                 215                 220

Gln Gly Ala Ala Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
            245                 250                 255

Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala
    275                 280                 285

Gly Tyr Ile Pro Leu Gly Ala Thr Leu Phe Asn Gln Arg Ile Ala Asp
290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Ala Leu Ala Val Leu
            325                 330                 335

Asp Ile Val Glu Ala Glu Asp Leu Pro Gly Asn Ala Ala Lys Val Gly
        340                 345                 350

Ala Gln Leu Leu Glu Gln Leu Gln Pro Leu Val Glu Arg Tyr Ala Val
    355                 360                 365

Val Gly Glu Val Arg Gly Lys Gly Leu Met Ile Ala Leu Asp Leu Val
370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Arg Pro
            405                 410                 415

Ile Gly Asn Lys Ile Ile Leu Ser Pro Pro Leu Thr Leu Thr Arg Asp
            420                 425                 430

Glu Ala Gly Leu Met Val Ser Ala Leu Glu Ala Ala Phe Ala Arg Cys
        435                 440                 445

Gly

<210> SEQ ID NO 62
<211> LENGTH: 449
<212> TYPE: PRT
<213> ORGANISM: unknown
<220> FEATURE:
<223> OTHER INFORMATION: isolated from library

<400> SEQUENCE: 62

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
        35                  40                  45

Gly Val Gly Gly Leu Trp Asn Val Asn Ile Gly His Asn Arg Ala Ser
```

```
                50                  55                  60
Val Lys Ala Ala Ile Ala Ala Gln Leu Asp Glu Leu Ala Tyr Tyr Gln
 65                  70                  75                  80

Thr Phe Asp Gly Ile Ala His Pro Arg Val Phe Asp Leu Ala Glu Arg
                 85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
            115                 120                 125

Tyr Trp Ile Ala Ser Gly Glu Pro Gly Arg Thr Arg Phe Leu Ser Leu
130                 135                 140

Arg Asn Gly Tyr His Gly Val His Met Gly Gly Thr Ser Val Gly Gly
145                 150                 155                 160

Asn Gly Val Tyr His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
            195                 200                 205

Ala Leu Leu Gly Ala Gln Thr Ile Ala Ala Leu Ile Ala Glu Pro Val
210                 215                 220

Gln Gly Ala Ile Gly Val Ile Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala
            275                 280                 285

Gly Tyr Ile Pro Leu Gly Ala Thr Leu Phe Asn Gln Arg Ile Ala Asp
290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Leu Ala Val Leu
                325                 330                 335

Asp Ile Val Glu Ala Glu Asp Leu Pro Gly Asn Ala Ala Lys Val Gly
            340                 345                 350

Ala Gln Leu Leu Glu Gln Leu Gln Pro Leu Val Glu Arg Tyr Ala Val
            355                 360                 365

Val Gly Glu Val Arg Gly Lys Gly Leu Met Ile Ala Leu Asp Leu Val
370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Arg Pro
                405                 410                 415

Ile Gly Asn Lys Ile Ile Leu Ser Pro Pro Leu Thr Leu Thr Arg Asp
            420                 425                 430

Glu Ala Gly Leu Met Val Ser Ala Leu Glu Ala Ala Phe Ala Arg Cys
            435                 440                 445

Gly

<210> SEQ ID NO 63
<211> LENGTH: 449
```

```
<212> TYPE: PRT
<213> ORGANISM: unknown
<220> FEATURE:
<223> OTHER INFORMATION: isolated from library

<400> SEQUENCE: 63
```

| | | | | | | | | | | | | | | |
|---|---|---|---|---|---|---|---|---|---|---|---|---|---|---|
| Met | Tyr | Glu | Lys | Tyr | Lys | Asn | Ala | Glu | Lys | Lys | Phe | Trp | His | Pro | Met |
| 1 | | | | 5 | | | | | 10 | | | | | 15 | |
| Gly | Ser | Ser | Ala | Ala | Pro | His | Arg | Asp | Lys | Thr | Leu | Val | Ile | Ala | Arg |
| | | | 20 | | | | | 25 | | | | | 30 | | |
| Gly | Asp | Gly | Asn | Tyr | Ile | Thr | Asp | Ile | Asp | Gly | Gln | Arg | Met | Leu | Asp |
| | | 35 | | | | | 40 | | | | | 45 | | | |
| Gly | Val | Gly | Gly | Leu | Trp | Asn | Val | Asn | Ile | Gly | His | Asn | Arg | Ala | Ser |
| | 50 | | | | | 55 | | | | | 60 | | | | |
| Val | Lys | Ala | Ala | Ile | Ala | Ala | Gln | Leu | Asp | Glu | Leu | Ala | Tyr | Tyr | Gln |
| 65 | | | | | 70 | | | | | 75 | | | | | 80 |
| Thr | Phe | Asp | Gly | Ile | Ala | His | Pro | Arg | Val | Phe | Asp | Leu | Ala | Glu | Arg |
| | | | | 85 | | | | | 90 | | | | | 95 | |
| Leu | Thr | Gly | Met | Phe | Ala | Gln | Glu | Arg | Met | Ala | Arg | Val | Leu | Phe | Ser |
| | | | 100 | | | | | 105 | | | | | 110 | | |
| Ser | Gly | Gly | Ser | Asp | Ala | Val | Glu | Thr | Ala | Leu | Lys | Met | Ala | Arg | Gln |
| | | 115 | | | | | 120 | | | | | 125 | | | |
| Tyr | Trp | Ile | Ala | Ser | Gly | Glu | Pro | Gly | Arg | Thr | Arg | Phe | Leu | Ser | Leu |
| | 130 | | | | | 135 | | | | | 140 | | | | |
| Arg | Asn | Gly | Tyr | His | Gly | Val | His | Met | Gly | Gly | Thr | Ser | Val | Gly | Gly |
| 145 | | | | | 150 | | | | | 155 | | | | | 160 |
| Asn | Gly | Val | Tyr | His | Tyr | Asn | His | Gly | Gln | Leu | Leu | Ala | Gly | Cys | His |
| | | | | 165 | | | | | 170 | | | | | 175 | |
| Leu | Leu | Asp | Thr | Pro | Trp | Leu | Tyr | Arg | Asn | Pro | Trp | Asp | Cys | Arg | Asp |
| | | | 180 | | | | | 185 | | | | | 190 | | |
| Pro | Gln | Ala | Leu | Thr | Ala | His | Cys | Ile | Arg | Gln | Leu | Glu | Glu | Gln | Ile |
| | | 195 | | | | | 200 | | | | | 205 | | | |
| Ala | Leu | Leu | Gly | Ala | Gln | Thr | Ile | Ala | Ala | Leu | Ile | Ala | Glu | Pro | Val |
| | 210 | | | | | 215 | | | | | 220 | | | | |
| Gln | Gly | Ala | Gly | Gly | Ala | Ile | Val | Pro | Pro | Ala | Asp | Tyr | Trp | Pro | Arg |
| 225 | | | | | 230 | | | | | 235 | | | | | 240 |
| Leu | Arg | Glu | Val | Cys | Asp | Arg | His | Gly | Ile | Leu | Leu | Ile | Ala | Asp | Glu |
| | | | | 245 | | | | | 250 | | | | | 255 | |
| Val | Val | Thr | Gly | Phe | Gly | Arg | Ser | Gly | Cys | Met | Leu | Gly | Ser | Arg | Gly |
| | | | 260 | | | | | 265 | | | | | 270 | | |
| Trp | Gly | Val | Ala | Pro | Asp | Ile | Leu | Cys | Leu | Ala | Lys | Gly | Ile | Thr | Ala |
| | | 275 | | | | | 280 | | | | | 285 | | | |
| Gly | Tyr | Ile | Pro | Leu | Gly | Ala | Thr | Leu | Phe | Asn | Gln | Arg | Ile | Ala | Asp |
| | 290 | | | | | 295 | | | | | 300 | | | | |
| Ala | Ile | Glu | Asn | Gly | Gln | Gly | Phe | Ser | His | Met | Ile | Met | His | Gly | Tyr |
| 305 | | | | | 310 | | | | | 315 | | | | | 320 |
| Thr | Tyr | Ser | Gly | His | Pro | Thr | Ala | Cys | Ala | Ala | Leu | Ala | Val | Leu | Leu |
| | | | | 325 | | | | | 330 | | | | | 335 | |
| Asp | Ile | Val | Glu | Ala | Glu | Asp | Leu | Pro | Gly | Asn | Ala | Ala | Lys | Val | Gly |
| | | | 340 | | | | | 345 | | | | | 350 | | |
| Ala | Gln | Leu | Leu | Glu | Gln | Leu | Gln | Pro | Leu | Val | Glu | Arg | Tyr | Ala | Val |
| | | 355 | | | | | 360 | | | | | 365 | | | |
| Val | Gly | Glu | Val | Arg | Gly | Lys | Gly | Leu | Met | Ile | Ala | Leu | Asp | Leu | Val |
| | 370 | | | | | 375 | | | | | 380 | | | | |

```
Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Arg Pro
                405                 410                 415

Ile Gly Asn Lys Ile Ile Leu Ser Pro Pro Leu Thr Leu Thr Arg Asp
            420                 425                 430

Glu Ala Gly Leu Met Val Ser Ala Leu Glu Ala Ala Phe Ala Arg Cys
        435                 440                 445

Gly

<210> SEQ ID NO 64
<211> LENGTH: 449
<212> TYPE: PRT
<213> ORGANISM: unknown
<220> FEATURE:
<223> OTHER INFORMATION: isolated from library

<400> SEQUENCE: 64

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
        35                  40                  45

Gly Val Gly Gly Leu Trp Asn Val Asn Ile Gly His Asn Arg Ala Ser
    50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
    130                 135                 140

Arg Asn Gly Tyr His Gly Val His Met Gly Gly Thr Ser Val Gly Gly
145                 150                 155                 160

Asn Gly Val Tyr His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
    210                 215                 220

Gln Gly Ala Gly Gly Ile Val Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala
        275                 280                 285

Gly Tyr Ile Pro Leu Gly Ala Thr Leu Phe Asn Gln Arg Ile Ala Asp
```

```
                290                 295                 300
Ala Ile Glu Asn Gly Gln Gly Phe Ser His Met Ile Met His Gly Tyr
305                 310                 315                 320

Thr Tyr Ser Gly His Pro Thr Ala Cys Ala Ala Leu Ala Val Leu
            325                 330                 335

Asp Ile Val Glu Ala Glu Asp Leu Pro Gly Asn Ala Ala Lys Val Gly
                340                 345                 350

Ala Gln Leu Leu Glu Gln Leu Gln Pro Leu Val Glu Arg Tyr Ala Val
            355                 360                 365

Val Gly Glu Val Arg Gly Lys Gly Leu Met Ile Ala Leu Asp Leu Val
        370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Arg Pro
                405                 410                 415

Ile Gly Asn Lys Ile Ile Leu Ser Pro Pro Leu Thr Leu Thr Arg Asp
            420                 425                 430

Glu Ala Gly Leu Met Val Ser Ala Leu Glu Ala Ala Phe Ala Arg Cys
        435                 440                 445

Gly

<210> SEQ ID NO 65
<211> LENGTH: 449
<212> TYPE: PRT
<213> ORGANISM: unknown
<220> FEATURE:
<223> OTHER INFORMATION: isolated from library

<400> SEQUENCE: 65

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
        35                  40                  45

Gly Val Gly Gly Leu Trp Asn Val Asn Ile Gly His Asn Arg Ala Ser
    50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
    130                 135                 140

Arg Asn Gly Tyr His Gly Val His Met Gly Gly Thr Ser Val Gly Gly
145                 150                 155                 160

Asn Gly Val Tyr His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205
```

Ala Leu Leu Gly Ala Gln Thr Ile Ala Ala Leu Ile Ala Glu Pro Val
    210                 215                 220

Gln Gly Ala Gly Gly Ile Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala
        275                 280                 285

Gly Tyr Ile Pro Leu Gly Ala Thr Leu Phe Asn Gln Arg Ile Ala Asp
    290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Leu Ala Val Leu
                325                 330                 335

Asp Ile Val Glu Ala Glu Asp Leu Pro Gly Asn Ala Ala Lys Val Gly
                340                 345                 350

Ala Gln Leu Leu Glu Gln Leu Gln Pro Leu Val Glu Arg Tyr Ala Val
        355                 360                 365

Val Gly Glu Val Arg Gly Lys Gly Leu Met Ile Ala Leu Asp Leu Val
    370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Arg Pro
                405                 410                 415

Ile Gly Asn Lys Ile Ile Leu Ser Pro Pro Leu Thr Leu Thr Arg Asp
            420                 425                 430

Glu Ala Gly Leu Met Val Ser Ala Leu Glu Ala Ala Phe Ala Arg Cys
        435                 440                 445

Gly

<210> SEQ ID NO 66
<211> LENGTH: 449
<212> TYPE: PRT
<213> ORGANISM: unknown
<220> FEATURE:
<223> OTHER INFORMATION: isolated from library

<400> SEQUENCE: 66

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
        35                  40                  45

Gly Val Gly Gly Leu Trp Asn Val Asn Ile Gly His Asn Arg Ala Ser
    50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
         115                 120                 125

Tyr Trp Ile Ala Ser Gly Glu Pro Gly Arg Thr Arg Phe Leu Ser Leu
     130                 135                 140

Arg Asn Gly Tyr His Gly Val His Met Gly Gly Thr Ser Val Gly Gly
145                 150                 155                 160

Asn Gly Val Tyr His Tyr Asn His Gly Gln Leu Leu Ala Gly Cys His
                 165                 170                 175

Leu Leu Asp Thr Pro Trp Leu Tyr Arg Asn Pro Trp Asp Cys Arg Asp
             180                 185                 190

Pro Gln Ala Leu Thr Ala His Cys Ile Arg Gln Leu Glu Glu Gln Ile
         195                 200                 205

Ala Leu Leu Gly Ala Gln Thr Ile Ala Ala Leu Ile Ala Glu Pro Val
210                 215                 220

Gln Gly Ala Gly Gly Leu Ile Val Pro Pro Ala Asp Tyr Trp Pro Arg
225                 230                 235                 240

Leu Arg Glu Val Cys Asp Arg His Gly Ile Leu Leu Ile Ala Asp Glu
                 245                 250                 255

Val Val Thr Gly Phe Gly Arg Ser Gly Cys Met Leu Gly Ser Arg Gly
             260                 265                 270

Trp Gly Val Ala Pro Asp Ile Leu Cys Leu Ala Lys Gly Ile Thr Ala
         275                 280                 285

Gly Tyr Ile Pro Leu Gly Ala Thr Leu Phe Asn Gln Arg Ile Ala Asp
     290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Ala Leu Ala Val Leu
                 325                 330                 335

Asp Ile Val Glu Ala Glu Asp Leu Pro Gly Asn Ala Ala Lys Val Gly
             340                 345                 350

Ala Gln Leu Leu Glu Gln Leu Gln Pro Leu Val Glu Arg Tyr Ala Val
         355                 360                 365

Val Gly Glu Val Arg Gly Lys Gly Leu Met Ile Ala Leu Asp Leu Val
370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Arg Pro
                 405                 410                 415

Ile Gly Asn Lys Ile Ile Leu Ser Pro Pro Leu Thr Leu Thr Arg Asp
             420                 425                 430

Glu Ala Gly Leu Met Val Ser Ala Leu Glu Ala Ala Phe Ala Arg Cys
         435                 440                 445

Gly

<210> SEQ ID NO 67
<211> LENGTH: 449
<212> TYPE: PRT
<213> ORGANISM: unknown
<220> FEATURE:
<223> OTHER INFORMATION: isolated from library

<400> SEQUENCE: 67

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg

-continued

```
                20                  25                  30
Gly Asp Gly Asn Tyr Ile Thr Asp Ile Asp Gly Gln Arg Met Leu Asp
            35                  40                  45
Gly Val Gly Gly Leu Trp Asn Val Asn Ile Gly His Asn Arg Ala Ser
50                      55                  60
Val Lys Ala Ala Ile Ala Gln Leu Asp Glu Leu Ala Tyr Tyr Gln
65                  70                  75                  80
Thr Phe Asp Gly Ile Ala His Pro Arg Val Phe Asp Leu Ala Glu Arg
                85                  90                  95
Leu Thr Gly Met Phe Ala Gln Glu Arg Met Ala Arg Val Leu Phe Ser
                100                 105                 110
Ser Gly Gly Ser Asp Ala Val Glu Thr Ala Leu Lys Met Ala Arg Gln
            115                 120                 125
Tyr Trp Ile Ala Ser Gly Glu Pro Gly Arg Thr Arg Phe Leu Ser Leu
                130                 135                 140
Arg Asn Gly Tyr His Gly Val His Met Gly Gly Thr Ser Val Gly Gly
145                 150                 155                 160
Asn Gly Val Tyr His Tyr Asn His Gly Gln Leu Leu Ala Gly Cys His
                165                 170                 175
Leu Leu Asp Thr Pro Trp Leu Tyr Arg Asn Pro Trp Asp Cys Arg Asp
                180                 185                 190
Pro Gln Ala Leu Thr Ala His Cys Ile Arg Gln Leu Glu Glu Gln Ile
            195                 200                 205
Ala Leu Leu Gly Ala Gln Thr Ile Ala Ala Leu Ile Ala Glu Pro Val
        210                 215                 220
Gln Gly Ala Gly Gly Val Ile Val Pro Pro Ala Asp Tyr Trp Pro Arg
225                 230                 235                 240
Leu Arg Glu Val Cys Asp Arg His Gly Ile Leu Leu Ile Ala Asp Glu
                245                 250                 255
Ala Val Thr Gly Phe Gly Arg Ser Gly Cys Met Leu Gly Ser Arg Gly
                260                 265                 270
Trp Gly Val Ala Pro Asp Ile Leu Cys Leu Ala Lys Gly Ile Thr Ala
        275                 280                 285
Gly Tyr Ile Pro Leu Gly Ala Thr Leu Phe Asn Gln Arg Ile Ala Asp
        290                 295                 300
Ala Ile Glu Asn Gly Gln Gly Phe Ser His Met Ile Met His Gly Tyr
305                 310                 315                 320
Thr Tyr Ser Gly His Pro Thr Ala Cys Ala Ala Ala Leu Ala Val Leu
                325                 330                 335
Asp Ile Val Glu Ala Glu Asp Leu Pro Gly Asn Ala Ala Lys Val Gly
            340                 345                 350
Ala Gln Leu Leu Glu Gln Leu Gln Pro Leu Val Glu Arg Tyr Ala Val
                355                 360                 365
Val Gly Glu Val Arg Gly Lys Gly Leu Met Ile Ala Leu Asp Leu Val
        370                 375                 380
Ser Asp Lys Arg Thr Arg Gln Pro Leu Asp Pro Ala Ala Gly Gln Pro
385                 390                 395                 400
Ser Arg Ile Ala Asp Glu Ala Arg Ala Gly Val Leu Val Arg Pro
                405                 410                 415
Ile Gly Asn Lys Ile Ile Leu Ser Pro Pro Leu Thr Leu Thr Arg Asp
            420                 425                 430
Glu Ala Gly Leu Met Val Ser Ala Leu Glu Ala Ala Phe Ala Arg Cys
            435                 440                 445
```

Gly

<210> SEQ ID NO 68
<211> LENGTH: 449
<212> TYPE: PRT
<213> ORGANISM: unknown
<220> FEATURE:
<223> OTHER INFORMATION: isolated from library

<400> SEQUENCE: 68

```
Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
        35                  40                  45

Gly Val Gly Gly Leu Trp Asn Val Asn Ile Gly His Asn Arg Ala Ser
    50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
    130                 135                 140

Arg Asn Gly Tyr His Gly Val His Met Gly Gly Thr Ser Val Gly Gly
145                 150                 155                 160

Asn Gly Val Tyr His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
    210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Ile Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala
        275                 280                 285

Gly Tyr Ile Pro Leu Gly Ala Thr Leu Phe Asn Gln Arg Ile Ala Asp
    290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Ala Leu Ala Val Leu
                325                 330                 335

Asp Ile Val Glu Ala Glu Asp Leu Pro Gly Asn Ala Ala Lys Val Gly
            340                 345                 350
```

```
Ala Gln Leu Leu Glu Gln Leu Gln Pro Leu Val Glu Arg Tyr Ala Val
            355                 360                 365

Val Gly Glu Val Arg Gly Lys Gly Leu Met Ile Ala Leu Asp Leu Val
    370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Ala Gly Val Leu Val Arg Pro
                405                 410                 415

Ile Gly Asn Lys Ile Ile Leu Ser Pro Pro Leu Thr Leu Thr Arg Asp
                420                 425                 430

Glu Ala Gly Leu Met Val Ser Ala Leu Glu Ala Ala Phe Ala Arg Cys
            435                 440                 445

Gly

<210> SEQ ID NO 69
<211> LENGTH: 449
<212> TYPE: PRT
<213> ORGANISM: unknown
<220> FEATURE:
<223> OTHER INFORMATION: isolated from library

<400> SEQUENCE: 69

Met Tyr Glu Lys Tyr Lys Asn Ala Glu Lys Lys Phe Trp His Pro Met
1               5                  10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
        35                  40                  45

Gly Val Gly Gly Leu Trp Asn Val Asn Ile Gly His Asn Arg Ala Ser
    50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
    130                 135                 140

Arg Asn Gly Tyr His Gly Val His Met Gly Gly Thr Ser Val Gly Gly
145                 150                 155                 160

Asn Gly Val Tyr His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
    210                 215                 220

Gln Gly Ala Gly Gly Val Ile Val Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Ala Thr Gly Phe Gly Arg Ser Gly Cys Met Leu Gly Ser Arg Gly
```

```
                    260                 265                 270
Trp Gly Val Ala Pro Asp Ile Leu Cys Leu Ala Lys Gly Ile Thr Ala
            275                 280                 285
Gly Tyr Ile Pro Leu Gly Ala Thr Leu Phe Asn Gln Arg Ile Ala Asp
            290                 295                 300
Ala Ile Glu Asn Gly Gln Gly Phe Ser His Met Ile Met His Gly Tyr
305                 310                 315                 320
Thr Tyr Ser Gly His Pro Thr Ala Cys Ala Ala Leu Ala Val Leu
            325                 330                 335
Asp Ile Val Glu Ala Glu Asp Leu Pro Gly Asn Ala Ala Lys Val Gly
            340                 345                 350
Ala Gln Leu Leu Glu Gln Leu Gln Pro Leu Val Glu Arg Tyr Ala Val
            355                 360                 365
Val Gly Glu Val Arg Gly Lys Gly Leu Met Ile Ala Leu Asp Leu Val
            370                 375                 380
Ser Asp Lys Arg Thr Arg Gln Pro Leu Asp Pro Ala Ala Gly Gln Pro
385                 390                 395                 400
Ser Arg Ile Ala Asp Glu Ala Arg Ala Gly Val Leu Val Arg Pro
            405                 410                 415
Ile Gly Asn Lys Ile Ile Leu Ser Pro Pro Leu Thr Leu Thr Arg Asp
            420                 425                 430
Glu Ala Gly Leu Met Val Ser Ala Leu Glu Ala Phe Ala Arg Cys
            435                 440                 445
Gly

<210> SEQ ID NO 70
<211> LENGTH: 449
<212> TYPE: PRT
<213> ORGANISM: unknown
<220> FEATURE:
<223> OTHER INFORMATION: isolated from library

<400> SEQUENCE: 70

Met Tyr Glu Lys Tyr Lys Asn Ala Glu Lys Lys Phe Trp His Pro Met
1               5                   10                  15
Gly Ser Ser Ala Ala Pro His Arg Asp Lys Thr Leu Val Ile Ala Arg
            20                  25                  30
Gly Asp Gly Asn Tyr Ile Thr Asp Ile Asp Gly Gln Arg Met Leu Asp
        35                  40                  45
Gly Val Gly Gly Leu Trp Asn Val Asn Ile Gly His Asn Arg Ala Ser
    50                  55                  60
Val Lys Ala Ala Ile Ala Ala Gln Leu Asp Glu Leu Ala Tyr Tyr Gln
65                  70                  75                  80
Thr Phe Asp Gly Ile Ala His Pro Arg Val Phe Asp Leu Ala Glu Arg
                85                  90                  95
Leu Thr Gly Met Phe Ala Gln Glu Arg Met Ala Arg Val Leu Phe Ser
            100                 105                 110
Ser Gly Gly Ser Asp Ala Val Glu Thr Ala Leu Lys Met Ala Arg Gln
        115                 120                 125
Tyr Trp Ile Ala Ser Gly Glu Pro Gly Arg Thr Arg Phe Leu Ser Leu
    130                 135                 140
Arg Asn Gly Tyr His Gly Val His Met Gly Gly Thr Ser Val Gly Gly
145                 150                 155                 160
Asn Gly Val Tyr His Tyr Asn His Gly Gln Leu Leu Ala Gly Cys His
                165                 170                 175
```

```
Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
    210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala
        275                 280                 285

Gly Tyr Ile Pro Leu Gly Ala Thr Leu Phe Asn Gln Arg Ile Ala Asp
    290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Leu Ala Val Leu
                325                 330                 335

Asp Ile Val Glu Ala Glu Asp Leu Pro Gly Asn Ala Ala Lys Val Gly
            340                 345                 350

Ala Gln Leu Leu Glu Gln Leu Gln Pro Leu Val Glu Arg Tyr Ala Val
        355                 360                 365

Val Gly Glu Val Arg Gly Lys Gly Leu Leu Ile Ala Leu Asp Leu Val
    370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Ala Gly Val Leu Val Arg Pro
                405                 410                 415

Ile Gly Asn Lys Ile Ile Leu Ser Pro Pro Leu Thr Leu Thr Arg Asp
            420                 425                 430

Glu Ala Gly Leu Met Val Ser Ala Leu Glu Ala Ala Phe Ala Arg Cys
        435                 440                 445

Gly

<210> SEQ ID NO 71
<211> LENGTH: 449
<212> TYPE: PRT
<213> ORGANISM: unknown
<220> FEATURE:
<223> OTHER INFORMATION: isolated from library

<400> SEQUENCE: 71

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
        35                  40                  45

Gly Val Gly Gly Leu Trp Asn Val Asn Ile Gly His Asn Arg Ala Ser
    50                  55                  60

Val Lys Ala Ala Ile Ala Ala Gln Leu Asp Glu Leu Ala Tyr Tyr Gln
65                  70                  75                  80
```

Thr Phe Asp Gly Ile Ala His Pro Arg Val Phe Asp Leu Ala Glu Arg
            85                  90                  95

Leu Thr Gly Met Phe Ala Gln Glu Arg Met Ala Arg Val Leu Phe Ser
        100                 105                 110

Ser Gly Gly Ser Asp Ala Val Glu Thr Ala Leu Lys Met Ala Arg Gln
        115                 120                 125

Tyr Trp Ile Ala Ser Gly Pro Gly Arg Thr Arg Phe Leu Ser Leu
        130                 135             140

Arg Asn Gly Tyr His Gly Val His Met Gly Thr Ser Val Gly Gly
145                 150                 155                 160

Asn Gly Val Tyr His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
            195                 200                 205

Ala Leu Leu Gly Ala Gln Thr Ile Ala Ala Leu Ile Ala Glu Pro Val
        210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala
        275                 280                 285

Gly Tyr Ile Pro Leu Gly Ala Thr Leu Phe Asn Gln Arg Ile Ala Asp
        290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Ala Leu Ala Val Leu
                325                 330                 335

Asp Ile Val Glu Ala Glu Asp Leu Pro Gly Asn Ala Ala Lys Val Gly
            340                 345                 350

Ala Gln Leu Leu Glu Gln Leu Gln Pro Leu Val Glu Arg Tyr Ala Val
        355                 360                 365

Val Gly Glu Val Arg Gly Lys Gly Leu Val Ile Ala Leu Asp Leu Val
370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Ala Gly Val Leu Val Arg Pro
                405                 410                 415

Ile Gly Asn Lys Ile Ile Leu Ser Pro Pro Leu Thr Leu Thr Arg Asp
            420                 425                 430

Glu Ala Gly Leu Met Val Ser Ala Leu Glu Ala Ala Phe Ala Arg Cys
        435                 440                 445

Gly

<210> SEQ ID NO 72
<211> LENGTH: 449
<212> TYPE: PRT
<213> ORGANISM: unknown
<220> FEATURE:
<223> OTHER INFORMATION: isolated from library

```
<400> SEQUENCE: 72

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
        35                  40                  45

Gly Val Gly Gly Leu Trp Asn Val Asn Ile Gly His Asn Arg Ala Ser
    50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
    130                 135                 140

Arg Asn Gly Tyr His Gly Val His Met Gly Gly Thr Ser Val Gly Gly
145                 150                 155                 160

Asn Gly Val Tyr His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
    210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala
        275                 280                 285

Gly Tyr Ile Pro Leu Gly Ala Thr Leu Phe Asn Gln Arg Ile Ala Asp
    290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Ala Leu Ala Val Leu
                325                 330                 335

Asp Ile Val Glu Ala Glu Asp Leu Pro Gly Asn Ala Ala Lys Val Gly
            340                 345                 350

Ala Gln Leu Leu Glu Gln Leu Gln Pro Leu Val Glu Arg Tyr Ala Val
        355                 360                 365

Val Gly Glu Val Arg Gly Lys Gly Leu Ile Ile Ala Leu Asp Leu Val
    370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Ala Gly Val Leu Val Arg Pro
                405                 410                 415
```

```
Ile Gly Asn Lys Ile Ile Leu Ser Pro Pro Leu Thr Leu Thr Arg Asp
                420                 425                 430

Glu Ala Gly Leu Met Val Ser Ala Leu Glu Ala Ala Phe Ala Arg Cys
            435                 440                 445

Gly

<210> SEQ ID NO 73
<211> LENGTH: 449
<212> TYPE: PRT
<213> ORGANISM: unknown
<220> FEATURE:
<223> OTHER INFORMATION: isolated from library

<400> SEQUENCE: 73

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
                20                  25                  30

Gly Asp Gly Asn Tyr Ile Thr Asp Ile Asp Gly Gln Arg Met Leu Asp
            35                  40                  45

Gly Val Gly Gly Leu Trp Asn Val Asn Ile Gly His Asn Arg Ala Ser
50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
130                 135                 140

Arg Asn Gly Tyr His Gly Val His Met Gly Gly Thr Ser Val Gly Gly
145                 150                 155                 160

Asn Gly Val Tyr His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala
        275                 280                 285

Gly Tyr Ile Pro Leu Gly Ala Thr Leu Phe Asn Gln Arg Ile Ala Asp
290                 295                 300

Ala Ile Glu Asn Gly Gln Gly Phe Ser His Met Ile Met His Gly Tyr
305                 310                 315                 320
```

Thr Tyr Ser Gly His Pro Thr Ala Cys Ala Ala Leu Ala Val Leu
                    325                 330                 335

Asp Ile Val Glu Ala Glu Asp Leu Pro Gly Asn Ala Ala Lys Val Gly
                340                 345                 350

Ala Gln Leu Leu Glu Gln Leu Gln Pro Leu Val Glu Arg Tyr Ala Val
            355                 360                 365

Val Gly Glu Val Arg Gly Lys Gly Leu Phe Ile Ala Leu Asp Leu Val
        370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Arg Pro
                405                 410                 415

Ile Gly Asn Lys Ile Ile Leu Ser Pro Pro Leu Thr Leu Thr Arg Asp
                420                 425                 430

Glu Ala Gly Leu Met Val Ser Ala Leu Glu Ala Ala Phe Ala Arg Cys
                435                 440                 445

Gly

<210> SEQ ID NO 74
<211> LENGTH: 449
<212> TYPE: PRT
<213> ORGANISM: unknown
<220> FEATURE:
<223> OTHER INFORMATION: isolated from library

<400> SEQUENCE: 74

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
        35                  40                  45

Gly Val Gly Gly Leu Trp Asn Val Asn Ile Gly His Asn Arg Ala Ser
    50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
    130                 135                 140

Arg Asn Gly Tyr His Gly Val His Met Gly Gly Thr Ser Val Gly Gly
145                 150                 155                 160

Asn Gly Val Tyr His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
    210                 215                 220

Gln Gly Ala Gly Gly Val Ile Val Pro Pro Ala Asp Tyr Trp Pro Arg

```
                225                 230                 235                 240
Leu Arg Glu Val Cys Asp Arg His Gly Ile Leu Leu Ile Ala Asp Glu
                    245                 250                 255

Val Val Thr Gly Phe Gly Arg Ser Gly Cys Met Leu Gly Ser Arg Gly
                    260                 265                 270

Trp Gly Val Ala Pro Asp Ile Leu Cys Leu Ala Lys Gly Ile Thr Ala
                    275                 280                 285

Gly Tyr Ile Pro Leu Gly Ala Thr Leu Phe Asn Gln Arg Ile Ala Asp
                    290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Leu Ala Val Leu
                    325                 330                 335

Asp Ile Val Glu Ala Glu Asp Leu Pro Gly Asn Ala Ala Lys Val Gly
                    340                 345                 350

Ala Gln Leu Leu Glu Gln Leu Gln Pro Leu Val Glu Arg Tyr Ala Val
                    355                 360                 365

Val Gly Glu Val Arg Gly Lys Gly Leu Tyr Ile Ala Leu Asp Leu Val
                    370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Arg Pro
                    405                 410                 415

Ile Gly Asn Lys Ile Ile Leu Ser Pro Pro Leu Thr Leu Thr Arg Asp
                    420                 425                 430

Glu Ala Gly Leu Met Val Ser Ala Leu Glu Ala Ala Phe Ala Arg Cys
                    435                 440                 445

Gly

<210> SEQ ID NO 75
<211> LENGTH: 449
<212> TYPE: PRT
<213> ORGANISM: unknown
<220> FEATURE:
<223> OTHER INFORMATION: isolated from library

<400> SEQUENCE: 75

Met Tyr Glu Lys Tyr Lys Asn Ala Glu Lys Lys Phe Trp His Pro Met
1                   5                   10                  15

Gly Ser Ser Ala Ala Pro His Arg Asp Lys Thr Leu Val Ile Ala Arg
                    20                  25                  30

Gly Asp Gly Asn Tyr Ile Thr Asp Ile Asp Gly Gln Arg Met Leu Asp
                    35                  40                  45

Gly Val Gly Gly Leu Trp Asn Val Asn Ile Gly His Asn Arg Ala Ser
                    50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                    85                  90                  95

Leu Thr Gly Met Phe Ala Gln Glu Arg Met Ala Arg Val Leu Phe Ser
                    100                 105                 110

Ser Gly Gly Ser Asp Ala Val Glu Thr Ala Leu Lys Met Ala Arg Gln
                    115                 120                 125

Tyr Trp Ile Ala Ser Gly Glu Pro Gly Arg Thr Arg Phe Leu Ser Leu
                    130                 135                 140
```

Arg Asn Gly Tyr His Gly Val His Met Gly Gly Thr Ser Val Gly Gly
145                 150                 155                 160

Asn Gly Val Tyr His Tyr Asn His Gly Gln Leu Leu Ala Gly Cys His
            165                 170                 175

Leu Leu Asp Thr Pro Trp Leu Tyr Arg Asn Pro Trp Asp Cys Arg Asp
        180                 185                 190

Pro Gln Ala Leu Thr Ala His Cys Ile Arg Gln Leu Glu Glu Gln Ile
    195                 200                 205

Ala Leu Leu Gly Ala Gln Thr Ile Ala Ala Leu Ile Ala Glu Pro Val
210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
            245                 250                 255

Val Val Thr Gly Phe Gly Arg Ser Gly Cys Met Leu Gly Ser Arg Gly
                260                 265                 270

Trp Gly Val Ala Pro Asp Ile Leu Cys Leu Ala Lys Gly Ile Thr Ala
        275                 280                 285

Gly Tyr Ile Pro Leu Gly Ala Thr Leu Phe Asn Gln Arg Ile Ala Asp
290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Ala Leu Ala Val Leu
            325                 330                 335

Asp Ile Val Glu Ala Glu Asp Leu Pro Gly Asn Ala Ala Lys Val Gly
                340                 345                 350

Ala Gln Leu Leu Glu Gln Leu Gln Pro Leu Val Glu Arg Tyr Ala Val
        355                 360                 365

Val Gly Glu Val Arg Gly Lys Gly Leu Thr Ile Ala Leu Asp Leu Val
370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Arg Pro
            405                 410                 415

Ile Gly Asn Lys Ile Ile Leu Ser Pro Pro Leu Thr Leu Thr Arg Asp
                420                 425                 430

Glu Ala Gly Leu Met Val Ser Ala Leu Glu Ala Ala Phe Ala Arg Cys
        435                 440                 445

Gly

<210> SEQ ID NO 76
<211> LENGTH: 449
<212> TYPE: PRT
<213> ORGANISM: unknown
<220> FEATURE:
<223> OTHER INFORMATION: isolated from library

<400> SEQUENCE: 76

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
        35                  40                  45

Gly Val Gly Gly Leu Trp Asn Val Asn Ile Gly His Asn Arg Ala Ser
50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
130                 135                 140

Arg Asn Gly Tyr His Gly Val His Met Gly Gly Thr Ser Val Gly Gly
145                 150                 155                 160

Asn Gly Val Tyr His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala
        275                 280                 285

Gly Tyr Ile Pro Leu Gly Ala Thr Leu Phe Asn Gln Arg Ile Ala Asp
290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Ala Leu Ala Val Leu
                325                 330                 335

Asp Ile Val Glu Ala Glu Asp Leu Pro Gly Asn Ala Ala Lys Val Gly
            340                 345                 350

Ala Gln Leu Leu Glu Gln Leu Gln Pro Leu Val Glu Arg Tyr Ala Val
        355                 360                 365

Val Gly Glu Val Arg Gly Lys Gly Leu Ala Ile Ala Leu Asp Leu Val
370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Ala Gly Val Leu Val Arg Pro
                405                 410                 415

Ile Gly Asn Lys Ile Ile Leu Ser Pro Pro Leu Thr Leu Thr Arg Asp
            420                 425                 430

Glu Ala Gly Leu Met Val Ser Ala Leu Glu Ala Ala Phe Ala Arg Cys
        435                 440                 445

Gly

<210> SEQ ID NO 77

<211> LENGTH: 449
<212> TYPE: PRT
<213> ORGANISM: unknown
<220> FEATURE:
<223> OTHER INFORMATION: isolated from library

<400> SEQUENCE: 77

```
Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
        35                  40                  45

Gly Val Gly Gly Leu Trp Asn Val Asn Ile Gly His Asn Arg Ala Ser
    50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
    130                 135                 140

Arg Asn Gly Tyr His Gly Val His Met Gly Gly Thr Ser Val Gly Gly
145                 150                 155                 160

Asn Gly Val Tyr His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
    210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala
        275                 280                 285

Gly Tyr Ile Pro Leu Gly Ala Thr Leu Phe Asn Gln Arg Ile Ala Asp
    290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Ala Leu Ala Val Leu
                325                 330                 335

Asp Ile Val Glu Ala Glu Asp Leu Pro Gly Asn Ala Ala Lys Val Gly
            340                 345                 350

Ala Gln Leu Leu Glu Gln Leu Gln Pro Leu Val Glu Arg Tyr Ala Val
        355                 360                 365

Val Gly Glu Val Arg Gly Lys Gly Leu Cys Ile Ala Leu Asp Leu Val
    370                 375                 380
```

```
Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Arg Pro
                405                 410                 415

Ile Gly Asn Lys Ile Ile Leu Ser Pro Pro Leu Thr Leu Thr Arg Asp
            420                 425                 430

Glu Ala Gly Leu Met Val Ser Ala Leu Glu Ala Ala Phe Ala Arg Cys
            435                 440                 445

Gly

<210> SEQ ID NO 78
<211> LENGTH: 449
<212> TYPE: PRT
<213> ORGANISM: unknown
<220> FEATURE:
<223> OTHER INFORMATION: isolated from library

<400> SEQUENCE: 78

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
        35                  40                  45

Gly Val Gly Gly Leu Trp Asn Val Asn Ile Gly His Asn Arg Ala Ser
    50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
    130                 135                 140

Arg Asn Gly Tyr His Gly Val His Met Gly Gly Thr Ser Val Gly Gly
145                 150                 155                 160

Asn Gly Val Tyr His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
    210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala
        275                 280                 285
```

```
Gly Tyr Ile Pro Leu Gly Ala Thr Leu Phe Asn Gln Arg Ile Ala Asp
        290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Leu Ala Val Leu
                325                 330                 335

Asp Ile Val Glu Ala Glu Asp Leu Pro Gly Asn Ala Ala Lys Val Gly
            340                 345                 350

Ala Gln Leu Leu Glu Gln Leu Pro Leu Val Glu Arg Tyr Ala Val
            355                 360                 365

Val Gly Glu Val Arg Gly Lys Gly Leu Met Ile Ala Leu Asp Leu Val
370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Ala Pro
                405                 410                 415

Ile Gly Asn Lys Ile Ile Leu Ser Pro Pro Leu Thr Leu Thr Arg Asp
                420                 425                 430

Glu Ala Gly Leu Met Val Ser Ala Leu Glu Ala Ala Phe Ala Arg Cys
            435                 440                 445

Gly

<210> SEQ ID NO 79
<211> LENGTH: 449
<212> TYPE: PRT
<213> ORGANISM: unknown
<220> FEATURE:
<223> OTHER INFORMATION: isolated from library

<400> SEQUENCE: 79

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
        35                  40                  45

Gly Val Gly Gly Leu Trp Asn Val Asn Ile Gly His Asn Arg Ala Ser
    50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
    130                 135                 140

Arg Asn Gly Tyr His Gly Val His Met Gly Gly Thr Ser Val Gly Gly
145                 150                 155                 160

Asn Gly Val Tyr His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
```

```
                195                 200                 205
Ala Leu Leu Gly Ala Gln Thr Ile Ala Ala Leu Ile Ala Glu Pro Val
    210                 215                 220
Gln Gly Ala Gly Gly Val Ile Val Pro Pro Ala Asp Tyr Trp Pro Arg
225                 230                 235                 240
Leu Arg Glu Val Cys Asp Arg His Gly Ile Leu Leu Ile Ala Asp Glu
                245                 250                 255
Val Val Thr Gly Phe Gly Arg Ser Gly Cys Met Leu Gly Ser Arg Gly
                260                 265                 270
Trp Gly Val Ala Pro Asp Ile Leu Cys Leu Ala Lys Gly Ile Thr Ala
            275                 280                 285
Gly Tyr Ile Pro Leu Gly Ala Thr Leu Phe Asn Gln Arg Ile Ala Asp
            290                 295                 300
Ala Ile Glu Asn Gly Gln Gly Phe Ser His Met Ile Met His Gly Tyr
305                 310                 315                 320
Thr Tyr Ser Gly His Pro Thr Ala Cys Ala Ala Ala Leu Ala Val Leu
                325                 330                 335
Asp Ile Val Glu Ala Glu Asp Leu Pro Gly Asn Ala Ala Lys Val Gly
                340                 345                 350
Ala Gln Leu Leu Glu Gln Leu Gln Pro Leu Val Glu Arg Tyr Ala Val
            355                 360                 365
Val Gly Glu Val Arg Gly Lys Gly Leu Met Ile Ala Leu Asp Leu Val
            370                 375                 380
Ser Asp Lys Arg Thr Arg Gln Pro Leu Asp Pro Ala Ala Gly Gln Pro
385                 390                 395                 400
Ser Arg Ile Ala Asp Glu Ala Arg Ala Gly Val Leu Val Val Pro
                405                 410                 415
Ile Gly Asn Lys Ile Ile Leu Ser Pro Pro Leu Thr Leu Thr Arg Asp
            420                 425                 430
Glu Ala Gly Leu Met Val Ser Ala Leu Glu Ala Ala Phe Ala Arg Cys
            435                 440                 445
Gly

<210> SEQ ID NO 80
<211> LENGTH: 449
<212> TYPE: PRT
<213> ORGANISM: unknown
<220> FEATURE:
<223> OTHER INFORMATION: isolated from library

<400> SEQUENCE: 80

Met Tyr Glu Lys Tyr Lys Asn Ala Glu Lys Lys Phe Trp His Pro Met
1               5                   10                  15
Gly Ser Ser Ala Ala Pro His Arg Asp Lys Thr Leu Val Ile Ala Arg
                20                  25                  30
Gly Asp Gly Asn Tyr Ile Thr Asp Ile Asp Gly Gln Arg Met Leu Asp
            35                  40                  45
Gly Val Gly Gly Leu Trp Asn Val Asn Ile Gly His Asn Arg Ala Ser
        50                  55                  60
Val Lys Ala Ala Ile Ala Ala Gln Leu Asp Glu Leu Ala Tyr Tyr Gln
65                  70                  75                  80
Thr Phe Asp Gly Ile Ala His Pro Arg Val Phe Asp Leu Ala Glu Arg
                85                  90                  95
Leu Thr Gly Met Phe Ala Gln Glu Arg Met Ala Arg Val Leu Phe Ser
                100                 105                 110
```

Ser Gly Gly Ser Asp Ala Val Glu Thr Ala Leu Lys Met Ala Arg Gln
            115                 120                 125

Tyr Trp Ile Ala Ser Gly Glu Pro Gly Arg Thr Arg Phe Leu Ser Leu
    130                 135                 140

Arg Asn Gly Tyr His Gly Val His Met Gly Gly Thr Ser Val Gly Gly
145                 150                 155                 160

Asn Gly Val Tyr His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
    210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala
        275                 280                 285

Gly Tyr Ile Pro Leu Gly Ala Thr Leu Phe Asn Gln Arg Ile Ala Asp
    290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Ala Leu Ala Val Leu
                325                 330                 335

Asp Ile Val Glu Ala Glu Asp Leu Pro Gly Asn Ala Ala Lys Val Gly
            340                 345                 350

Ala Gln Leu Leu Glu Gln Leu Gln Pro Leu Val Glu Arg Tyr Ala Val
        355                 360                 365

Val Gly Glu Val Arg Gly Lys Gly Leu Met Ile Ala Leu Asp Leu Val
    370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Ala Gly Val Leu Val Leu Pro
                405                 410                 415

Ile Gly Asn Lys Ile Ile Leu Ser Pro Pro Leu Thr Leu Thr Arg Asp
            420                 425                 430

Glu Ala Gly Leu Met Val Ser Ala Leu Glu Ala Ala Phe Ala Arg Cys
        435                 440                 445

Gly

<210> SEQ ID NO 81
<211> LENGTH: 449
<212> TYPE: PRT
<213> ORGANISM: unknown
<220> FEATURE:
<223> OTHER INFORMATION: isolated from library

<400> SEQUENCE: 81

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
              20                  25                  30

Gly Asp Gly Asn Tyr Ile Thr Asp Ile Asp Gly Gln Arg Met Leu Asp
              35                  40                  45

Gly Val Gly Gly Leu Trp Asn Val Asn Ile Gly His Asn Arg Ala Ser
 50                  55                  60

Val Lys Ala Ala Ile Ala Ala Gln Leu Asp Glu Leu Ala Tyr Tyr Gln
 65                  70                  75                  80

Thr Phe Asp Gly Ile Ala His Pro Arg Val Phe Asp Leu Ala Glu Arg
              85                  90                  95

Leu Thr Gly Met Phe Ala Gln Glu Arg Met Ala Arg Val Leu Phe Ser
              100                 105                 110

Ser Gly Gly Ser Asp Ala Val Glu Thr Ala Leu Lys Met Ala Arg Gln
              115                 120                 125

Tyr Trp Ile Ala Ser Gly Glu Pro Gly Arg Thr Arg Phe Leu Ser Leu
              130                 135                 140

Arg Asn Gly Tyr His Gly Val His Met Gly Gly Thr Ser Val Gly Gly
145                 150                 155                 160

Asn Gly Val Tyr His Tyr Asn His Gly Gln Leu Leu Ala Gly Cys His
              165                 170                 175

Leu Leu Asp Thr Pro Trp Leu Tyr Arg Asn Pro Trp Asp Cys Arg Asp
              180                 185                 190

Pro Gln Ala Leu Thr Ala His Cys Ile Arg Gln Leu Glu Glu Gln Ile
              195                 200                 205

Ala Leu Leu Gly Ala Gln Thr Ile Ala Ala Leu Ile Ala Glu Pro Val
              210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
              245                 250                 255

Val Val Thr Gly Phe Gly Arg Ser Gly Cys Met Leu Gly Ser Arg Gly
              260                 265                 270

Trp Gly Val Ala Pro Asp Ile Leu Cys Leu Ala Lys Gly Ile Thr Ala
              275                 280                 285

Gly Tyr Ile Pro Leu Gly Ala Thr Leu Phe Asn Gln Arg Ile Ala Asp
              290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Leu Ala Val Leu
              325                 330                 335

Asp Ile Val Glu Ala Glu Asp Leu Pro Gly Asn Ala Ala Lys Val Gly
              340                 345                 350

Ala Gln Leu Leu Glu Gln Leu Gln Pro Leu Val Glu Arg Tyr Ala Val
              355                 360                 365

Val Gly Glu Val Arg Gly Lys Gly Leu Met Ile Ala Leu Asp Leu Val
              370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Gly Pro
              405                 410                 415

Ile Gly Asn Lys Ile Ile Leu Ser Pro Pro Leu Thr Leu Thr Arg Asp
              420                 425                 430

Glu Ala Gly Leu Met Val Ser Ala Leu Glu Ala Ala Phe Ala Arg Cys

-continued

```
              435                 440                 445
Gly

<210> SEQ ID NO 82
<211> LENGTH: 449
<212> TYPE: PRT
<213> ORGANISM: unknown
<220> FEATURE:
<223> OTHER INFORMATION: isolated from library

<400> SEQUENCE: 82

Met Tyr Glu Lys Tyr Lys Asn Ala Glu Lys Lys Phe Trp His Pro Met
1               5                  10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
        35                  40                  45

Gly Val Gly Gly Leu Trp Asn Val Asn Ile Gly His Asn Arg Ala Ser
    50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
    130                 135                 140

Arg Asn Gly Tyr His Gly Val His Met Gly Gly Thr Ser Val Gly Gly
145                 150                 155                 160

Asn Gly Val Tyr His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
    210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala
        275                 280                 285

Gly Tyr Ile Pro Leu Gly Ala Thr Leu Phe Asn Gln Arg Ile Ala Asp
    290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Ala Leu Ala Val Leu
                325                 330                 335

Asp Ile Val Glu Ala Glu Asp Leu Pro Gly Asn Ala Ala Lys Val Gly
            340                 345                 350
```

-continued

Ala Gln Leu Leu Glu Gln Leu Gln Pro Leu Val Glu Arg Tyr Ala Val
            355                 360                 365

Val Gly Glu Val Arg Gly Lys Gly Leu Met Ile Ala Leu Asp Leu Val
    370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Tyr Pro
                405                 410                 415

Ile Gly Asn Lys Ile Ile Leu Ser Pro Pro Leu Thr Leu Thr Arg Asp
                420                 425                 430

Glu Ala Gly Leu Met Val Ser Ala Leu Glu Ala Ala Phe Ala Arg Cys
            435                 440                 445

Gly

<210> SEQ ID NO 83
<211> LENGTH: 449
<212> TYPE: PRT
<213> ORGANISM: unknown
<220> FEATURE:
<223> OTHER INFORMATION: isolated from library

<400> SEQUENCE: 83

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
        35                  40                  45

Gly Val Gly Gly Leu Trp Asn Val Asn Ile Gly His Asn Arg Ala Ser
    50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
    130                 135                 140

Arg Asn Gly Tyr His Gly Val His Met Gly Thr Ser Val Gly Gly
145                 150                 155                 160

Asn Gly Val Tyr His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
    210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

-continued

```
Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala
        275                 280                 285

Gly Tyr Ile Pro Leu Gly Ala Thr Leu Phe Asn Gln Arg Ile Ala Asp
    290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Leu Ala Val Leu
            325                 330                 335

Asp Ile Val Glu Ala Glu Asp Leu Pro Gly Asn Ala Ala Lys Val Gly
            340                 345                 350

Ala Gln Leu Leu Glu Gln Leu Gln Pro Leu Val Glu Arg Tyr Ala Val
        355                 360                 365

Val Gly Glu Val Arg Gly Lys Gly Leu Met Ile Ala Leu Asp Leu Val
    370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Thr Pro
            405                 410                 415

Ile Gly Asn Lys Ile Ile Leu Ser Pro Pro Leu Thr Leu Thr Arg Asp
            420                 425                 430

Glu Ala Gly Leu Met Val Ser Ala Leu Glu Ala Ala Phe Ala Arg Cys
        435                 440                 445

Gly

<210> SEQ ID NO 84
<211> LENGTH: 449
<212> TYPE: PRT
<213> ORGANISM: unknown
<220> FEATURE:
<223> OTHER INFORMATION: isolated from library

<400> SEQUENCE: 84

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
        35                  40                  45

Gly Val Gly Gly Leu Trp Asn Val Asn Ile Gly His Asn Arg Ala Ser
    50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
    130                 135                 140

Arg Asn Gly Tyr His Gly Val His Met Gly Gly Thr Ser Val Gly Gly
145                 150                 155                 160

Asn Gly Val Tyr His Tyr Asn His Gly Gln Leu Leu Ala Gly Cys His
```

```
                      165                 170                 175
Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
            195                 200                 205

Ala Leu Leu Gly Ala Gln Thr Ile Ala Ala Leu Ile Ala Glu Pro Val
            210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
                260                 265                 270

Trp Gly Val Ala Pro Asp Ile Leu Cys Leu Ala Lys Gly Ile Thr Ala
                275                 280                 285

Gly Tyr Ile Pro Leu Gly Ala Thr Leu Phe Asn Gln Arg Ile Ala Asp
                290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Leu Ala Val Leu
                325                 330                 335

Asp Ile Val Glu Ala Glu Asp Leu Pro Gly Asn Ala Ala Lys Val Gly
                340                 345                 350

Ala Gln Leu Leu Glu Gln Leu Gln Pro Leu Val Glu Arg Tyr Ala Val
                355                 360                 365

Val Gly Glu Val Arg Gly Lys Gly Leu Met Ile Ala Leu Asp Leu Val
                370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Cys Pro
                405                 410                 415

Ile Gly Asn Lys Ile Ile Leu Ser Pro Pro Leu Thr Leu Thr Arg Asp
                420                 425                 430

Glu Ala Gly Leu Met Val Ser Ala Leu Glu Ala Ala Phe Ala Arg Cys
                435                 440                 445

Gly

<210> SEQ ID NO 85
<211> LENGTH: 449
<212> TYPE: PRT
<213> ORGANISM: unknown
<220> FEATURE:
<223> OTHER INFORMATION: isolated from library

<400> SEQUENCE: 85

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
            35                  40                  45

Gly Val Gly Gly Leu Trp Asn Val Asn Ile Gly His Asn Arg Ala Ser
            50                  55                  60

Val Lys Ala Ala Ile Ala Ala Gln Leu Asp Glu Leu Ala Tyr Tyr Gln
65                  70                  75                  80
```

-continued

```
Thr Phe Asp Gly Ile Ala His Pro Arg Val Phe Asp Leu Ala Glu Arg
             85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
            115                 120                 125

Tyr Trp Ile Ala Ser Gly Glu Pro Gly Arg Thr Arg Phe Leu Ser Leu
            130                 135             140

Arg Asn Gly Tyr His Gly Val His Met Gly Gly Thr Ser Val Gly Gly
145             150                 155                 160

Asn Gly Val Tyr His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
            195                 200                 205

Ala Leu Leu Gly Ala Gln Thr Ile Ala Ala Leu Ile Ala Glu Pro Val
210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
                260                 265                 270

Trp Gly Val Ala Pro Asp Ile Leu Cys Leu Ala Lys Gly Ile Thr Ala
            275                 280                 285

Gly Tyr Ile Pro Leu Gly Ala Thr Leu Phe Asn Gln Arg Ile Ala Asp
            290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Ala Leu Ala Val Leu
                325                 330                 335

Asp Ile Val Glu Ala Asp Leu Pro Gly Asn Ala Ala Lys Val Gly
                340                 345                 350

Ala Gln Leu Leu Glu Gln Leu Gln Pro Leu Val Glu Arg Tyr Ala Val
            355                 360                 365

Val Gly Glu Val Arg Gly Lys Gly Leu Met Ile Ala Leu Asp Leu Val
370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Ala Gly Val Leu Val Arg Pro
                405                 410                 415

Thr Gly Asn Lys Ile Ile Leu Ser Pro Pro Leu Thr Leu Thr Arg Asp
                420                 425                 430

Glu Ala Gly Leu Met Val Ser Ala Leu Glu Ala Ala Phe Ala Arg Cys
            435                 440                 445

Gly
```

<210> SEQ ID NO 86
<211> LENGTH: 449
<212> TYPE: PRT
<213> ORGANISM: unknown
<220> FEATURE:
<223> OTHER INFORMATION: isolated from library

<400> SEQUENCE: 86

```
Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
        35                  40                  45

Gly Val Gly Gly Leu Trp Asn Val Asn Ile Gly His Asn Arg Ala Ser
    50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
    130                 135                 140

Arg Asn Gly Tyr His Gly Val His Met Gly Gly Thr Ser Val Gly Gly
145                 150                 155                 160

Asn Gly Val Tyr His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
    210                 215                 220

Gln Gly Ala Gly Gly Val Ile Val Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala
        275                 280                 285

Gly Tyr Ile Pro Leu Gly Ala Thr Leu Phe Asn Gln Arg Ile Ala Asp
    290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Ala Leu Ala Val Leu
                325                 330                 335

Asp Ile Val Glu Ala Asp Leu Pro Gly Asn Ala Ala Lys Val Gly
            340                 345                 350

Ala Gln Leu Leu Glu Gln Leu Gln Pro Leu Val Glu Arg Tyr Ala Val
        355                 360                 365

Val Gly Glu Val Arg Gly Lys Gly Leu Met Ile Ala Leu Asp Leu Val
    370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Arg Pro
```

-continued

```
                    405                 410                 415
Cys Gly Asn Lys Ile Ile Leu Ser Pro Pro Leu Thr Leu Thr Arg Asp
            420                 425                 430
Glu Ala Gly Leu Met Val Ser Ala Leu Glu Ala Ala Phe Ala Arg Cys
        435                 440                 445
Gly

<210> SEQ ID NO 87
<211> LENGTH: 449
<212> TYPE: PRT
<213> ORGANISM: unknown
<220> FEATURE:
<223> OTHER INFORMATION: isolated from library

<400> SEQUENCE: 87

Met Tyr Glu Lys Tyr Lys Asn Ala Glu Lys Lys Phe Trp His Pro Met
1               5                   10                  15
Gly Ser Ser Ala Ala Pro His Arg Asp Lys Thr Leu Val Ile Ala Arg
            20                  25                  30
Gly Asp Gly Asn Tyr Ile Thr Asp Ile Asp Gly Gln Arg Met Leu Asp
        35                  40                  45
Gly Val Gly Gly Leu Trp Asn Val Asn Ile Gly His Asn Arg Ala Ser
    50                  55                  60
Val Lys Ala Ala Ile Ala Ala Gln Leu Asp Glu Leu Ala Tyr Tyr Gln
65                  70                  75                  80
Thr Phe Asp Gly Ile Ala His Pro Arg Val Phe Asp Leu Ala Glu Arg
                85                  90                  95
Leu Thr Gly Met Phe Ala Gln Glu Arg Met Ala Arg Val Leu Phe Ser
            100                 105                 110
Ser Gly Gly Ser Asp Ala Val Glu Thr Ala Leu Lys Met Ala Arg Gln
        115                 120                 125
Tyr Trp Ile Ala Ser Gly Glu Pro Gly Arg Thr Arg Phe Leu Ser Leu
    130                 135                 140
Arg Asn Gly Tyr His Gly Val His Met Gly Gly Thr Ser Val Gly Gly
145                 150                 155                 160
Asn Gly Val Tyr His Tyr Asn His Gly Gln Leu Leu Ala Gly Cys His
                165                 170                 175
Leu Leu Asp Thr Pro Trp Leu Tyr Arg Asn Pro Trp Asp Cys Arg Asp
            180                 185                 190
Pro Gln Ala Leu Thr Ala His Cys Ile Arg Gln Leu Glu Glu Gln Ile
        195                 200                 205
Ala Leu Leu Gly Ala Gln Thr Ile Ala Ala Leu Ile Ala Glu Pro Val
    210                 215                 220
Gln Gly Ala Gly Gly Val Ile Val Pro Pro Ala Asp Tyr Trp Pro Arg
225                 230                 235                 240
Leu Arg Glu Val Cys Asp Arg His Gly Ile Leu Leu Ile Ala Asp Glu
                245                 250                 255
Val Val Thr Gly Phe Gly Arg Ser Gly Cys Met Leu Gly Ser Arg Gly
            260                 265                 270
Trp Gly Val Ala Pro Asp Ile Leu Cys Leu Ala Lys Gly Ile Thr Ala
        275                 280                 285
Gly Tyr Ile Pro Leu Gly Ala Thr Leu Phe Asn Gln Arg Ile Ala Asp
    290                 295                 300
Ala Ile Glu Asn Gly Gln Gly Phe Ser His Met Ile Met His Gly Tyr
305                 310                 315                 320
```

```
Thr Tyr Ser Gly His Pro Thr Ala Cys Ala Ala Leu Ala Val Leu
            325                 330                 335

Asp Ile Val Glu Ala Glu Asp Leu Pro Gly Asn Ala Ala Lys Val Gly
            340                 345                 350

Ala Gln Leu Leu Glu Gln Leu Gln Pro Leu Val Glu Arg Tyr Ala Val
            355                 360                 365

Val Gly Glu Val Arg Gly Lys Gly Leu Met Ile Ala Leu Asp Leu Val
370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Arg Pro
            405                 410                 415

Phe Gly Asn Lys Ile Ile Leu Ser Pro Pro Leu Thr Leu Thr Arg Asp
            420                 425                 430

Glu Ala Gly Leu Met Val Ser Ala Leu Glu Ala Ala Phe Ala Arg Cys
            435                 440                 445

Gly

<210> SEQ ID NO 88
<211> LENGTH: 449
<212> TYPE: PRT
<213> ORGANISM: unknown
<220> FEATURE:
<223> OTHER INFORMATION: isolated from library

<400> SEQUENCE: 88

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
            35                  40                  45

Gly Val Gly Gly Leu Trp Asn Val Asn Ile Gly His Asn Arg Ala Ser
50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
            85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
            115                 120                 125

Tyr Trp Ile Ala Ser Gly Glu Pro Gly Arg Thr Arg Phe Leu Ser Leu
            130                 135                 140

Arg Asn Gly Tyr His Gly Val His Met Gly Gly Thr Ser Val Gly Gly
145                 150                 155                 160

Asn Gly Val Tyr His Tyr Asn His Gly Gln Leu Leu Ala Gly Cys His
            165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
            195                 200                 205

Ala Leu Leu Gly Ala Gln Thr Ile Ala Ala Leu Ile Ala Glu Pro Val
            210                 215                 220
```

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
            245                 250                 255

Val Val Thr Gly Phe Gly Arg Ser Gly Cys Met Leu Gly Ser Arg Gly
        260                 265                 270

Trp Gly Val Ala Pro Asp Ile Leu Cys Leu Ala Lys Gly Ile Thr Ala
    275                 280                 285

Gly Tyr Ile Pro Leu Gly Ala Thr Leu Phe Asn Gln Arg Ile Ala Asp
    290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Leu Ala Val Leu
            325                 330                 335

Asp Ile Val Glu Ala Glu Asp Leu Pro Gly Asn Ala Ala Lys Val Gly
            340                 345                 350

Ala Gln Leu Leu Glu Gln Leu Gln Pro Leu Val Glu Arg Tyr Ala Val
            355                 360                 365

Val Gly Glu Val Arg Gly Lys Gly Leu Met Ile Ala Leu Asp Leu Val
        370                 375                 380

Ser Asp Lys Arg Thr Arg Gln Pro Leu Asp Pro Ala Ala Gly Gln Pro
385                 390                 395                 400

Ser Arg Ile Ala Asp Glu Arg Arg Ala Gly Val Leu Val Arg Pro
            405                 410                 415

Val Gly Asn Lys Ile Ile Leu Ser Pro Pro Leu Thr Leu Thr Arg Asp
        420                 425                 430

Glu Ala Gly Leu Met Val Ser Ala Leu Glu Ala Ala Phe Ala Arg Cys
        435                 440                 445

Gly

<210> SEQ ID NO 89
<211> LENGTH: 449
<212> TYPE: PRT
<213> ORGANISM: unknown
<220> FEATURE:
<223> OTHER INFORMATION: isolated from library

<400> SEQUENCE: 89

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
        35                  40                  45

Gly Val Gly Gly Leu Trp Asn Val Asn Ile Gly His Asn Arg Ala Ser
    50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
            85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu

```
                    130                 135                 140
Arg Asn Gly Tyr His Gly Val His Met Gly Gly Thr Ser Val Gly Gly
145                 150                 155                 160

Asn Gly Val Tyr His Tyr Asn His Gly Gln Leu Leu Ala Gly Cys His
                    165                 170                 175

Leu Leu Asp Thr Pro Trp Leu Tyr Arg Asn Pro Trp Asp Cys Arg Asp
                180                 185                 190

Pro Gln Ala Leu Thr Ala His Cys Ile Arg Gln Leu Glu Glu Gln Ile
            195                 200                 205

Ala Leu Leu Gly Ala Gln Thr Ile Ala Ala Leu Ile Ala Glu Pro Val
210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
                260                 265                 270

Trp Gly Val Ala Pro Asp Ile Leu Cys Leu Ala Lys Gly Ile Thr Ala
                275                 280                 285

Gly Tyr Ile Pro Leu Gly Ala Thr Leu Phe Asn Gln Arg Ile Ala Asp
        290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Ala Leu Ala Val Leu
                325                 330                 335

Asp Ile Val Glu Ala Glu Asp Leu Pro Gly Asn Ala Ala Lys Val Gly
                340                 345                 350

Ala Gln Leu Leu Glu Gln Leu Gln Pro Leu Val Glu Arg Tyr Ala Val
                355                 360                 365

Val Gly Glu Val Arg Gly Lys Gly Leu Met Ile Ala Leu Asp Leu Val
                370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Arg Pro
                405                 410                 415

Tyr Gly Asn Lys Ile Ile Leu Ser Pro Pro Leu Thr Leu Thr Arg Asp
                420                 425                 430

Glu Ala Gly Leu Met Val Ser Ala Leu Glu Ala Ala Phe Ala Arg Cys
                435                 440                 445

Gly

<210> SEQ ID NO 90
<211> LENGTH: 449
<212> TYPE: PRT
<213> ORGANISM: unknown
<220> FEATURE:
<223> OTHER INFORMATION: isolated from library

<400> SEQUENCE: 90

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
                20                  25                  30

Gly Asp Gly Asn Tyr Ile Thr Asp Ile Asp Gly Gln Arg Met Leu Asp
            35                  40                  45
```

Gly Val Gly Gly Leu Trp Asn Val Asn Ile Gly His Asn Arg Ala Ser
50              55                  60

Val Lys Ala Ala Ile Ala Gln Leu Asp Glu Leu Ala Tyr Tyr Gln
65              70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
            115                 120                 125

Tyr Trp Ile Ala Ser Gly Glu Pro Gly Arg Thr Arg Phe Leu Ser Leu
            130                 135                 140

Arg Asn Gly Tyr His Gly Val His Met Gly Gly Thr Ser Val Gly Gly
145                 150                 155                 160

Asn Gly Val Tyr His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
            195                 200                 205

Ala Leu Leu Gly Ala Gln Thr Ile Ala Ala Leu Ile Ala Glu Pro Val
210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
                260                 265                 270

Trp Gly Val Ala Pro Asp Ile Leu Cys Leu Ala Lys Gly Ile Thr Ala
            275                 280                 285

Gly Tyr Ile Pro Leu Gly Ala Thr Leu Phe Asn Gln Arg Ile Ala Asp
            290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Ala Leu Ala Val Leu
                325                 330                 335

Asp Ile Val Glu Ala Glu Asp Leu Pro Gly Asn Ala Ala Lys Val Gly
                340                 345                 350

Ala Gln Leu Leu Glu Gln Leu Gln Pro Leu Val Glu Arg Tyr Ala Val
            355                 360                 365

Val Gly Glu Val Arg Gly Lys Gly Leu Met Ile Ala Leu Asp Leu Val
370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Arg Pro
            405                 410                 415

Ala Gly Asn Lys Ile Ile Leu Ser Pro Pro Leu Thr Leu Thr Arg Asp
            420                 425                 430

Glu Ala Gly Leu Met Val Ser Ala Leu Glu Ala Ala Phe Ala Arg Cys
            435                 440                 445

Gly

```
<210> SEQ ID NO 91
<211> LENGTH: 449
<212> TYPE: PRT
<213> ORGANISM: unknown
<220> FEATURE:
<223> OTHER INFORMATION: isolated from library

<400> SEQUENCE: 91

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
        35                  40                  45

Gly Val Gly Gly Leu Trp Asn Val Asn Ile Gly His Asn Arg Ala Ser
    50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
    130                 135                 140

Arg Asn Gly Tyr His Gly Val His Met Gly Gly Thr Ser Val Gly Gly
145                 150                 155                 160

Asn Gly Val Tyr His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
    210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala
        275                 280                 285

Gly Tyr Ile Pro Leu Gly Ala Thr Leu Phe Asn Gln Arg Ile Ala Asp
    290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Ala Leu Ala Val Leu
                325                 330                 335

Asp Ile Val Glu Ala Glu Asp Leu Pro Gly Asn Ala Ala Lys Val Gly
            340                 345                 350

Ala Gln Leu Leu Glu Gln Leu Gln Pro Leu Val Glu Arg Tyr Ala Val
        355                 360                 365

Val Gly Glu Val Arg Gly Lys Gly Leu Met Ile Ala Leu Asp Leu Val
```

```
                370                 375                 380
Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Arg Pro
                405                 410                 415

Ile Gly Asn Lys Ile Val Leu Ser Pro Pro Leu Thr Leu Thr Arg Asp
                420                 425                 430

Glu Ala Gly Leu Met Val Ser Ala Leu Glu Ala Ala Phe Ala Arg Cys
                435                 440                 445

Gly

<210> SEQ ID NO 92
<211> LENGTH: 449
<212> TYPE: PRT
<213> ORGANISM: unknown
<220> FEATURE:
<223> OTHER INFORMATION: isolated from library

<400> SEQUENCE: 92

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
                20                  25                  30

Gly Asp Gly Asn Tyr Ile Thr Asp Ile Asp Gly Gln Arg Met Leu Asp
            35                  40                  45

Gly Val Gly Gly Leu Trp Asn Val Asn Ile Gly His Asn Arg Ala Ser
        50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
130                 135                 140

Arg Asn Gly Tyr His Gly Val His Met Gly Gly Thr Ser Val Gly Gly
145                 150                 155                 160

Asn Gly Val Tyr His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala
        275                 280                 285
```

```
Gly Tyr Ile Pro Leu Gly Ala Thr Leu Phe Asn Gln Arg Ile Ala Asp
            290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Leu Ala Val Leu
            325                 330                 335

Asp Ile Val Glu Ala Glu Asp Leu Pro Gly Asn Ala Ala Lys Val Gly
            340                 345                 350

Ala Gln Leu Leu Glu Gln Leu Gln Pro Leu Val Glu Arg Tyr Ala Val
            355                 360                 365

Val Gly Glu Val Arg Gly Lys Gly Leu Met Ile Ala Leu Asp Leu Val
            370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Arg Pro
            405                 410                 415

Ile Gly Asn Lys Ile Ser Leu Ser Pro Pro Leu Thr Leu Thr Arg Asp
            420                 425                 430

Glu Ala Gly Leu Met Val Ser Ala Leu Glu Ala Ala Phe Ala Arg Cys
            435                 440                 445

Gly

<210> SEQ ID NO 93
<211> LENGTH: 449
<212> TYPE: PRT
<213> ORGANISM: unknown
<220> FEATURE:
<223> OTHER INFORMATION: isolated from library

<400> SEQUENCE: 93

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
        35                  40                  45

Gly Val Gly Gly Leu Trp Asn Val Asn Ile Gly His Asn Arg Ala Ser
    50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
    130                 135                 140

Arg Asn Gly Tyr His Gly Val His Met Gly Gly Thr Ser Val Gly Gly
145                 150                 155                 160

Asn Gly Val Tyr His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190
```

Pro Gln Ala Leu Thr Ala His Cys Ile Arg Gln Leu Glu Gln Ile
        195                 200                 205

Ala Leu Leu Gly Ala Gln Thr Ile Ala Ala Leu Ile Ala Glu Pro Val
    210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Ile Ala Asp Glu
                245                 250                 255

Val Val Thr Gly Phe Gly Arg Ser Gly Cys Met Leu Gly Ser Arg Gly
                260                 265                 270

Trp Gly Val Ala Pro Asp Ile Leu Cys Leu Ala Lys Gly Ile Thr Ala
        275                 280                 285

Gly Tyr Ile Pro Leu Gly Ala Thr Leu Phe Asn Gln Arg Ile Ala Asp
        290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Ala Leu Ala Val Leu
                325                 330                 335

Asp Ile Val Glu Ala Glu Asp Leu Pro Gly Asn Ala Ala Lys Val Gly
                340                 345                 350

Ala Gln Leu Leu Glu Gln Leu Gln Pro Leu Val Glu Arg Tyr Ala Val
        355                 360                 365

Val Gly Glu Val Arg Gly Lys Gly Leu Met Ile Ala Leu Asp Leu Val
        370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Ala Gly Val Leu Val Arg Pro
                405                 410                 415

Ile Gly Asn Lys Ile Ala Leu Ser Pro Pro Leu Thr Leu Thr Arg Asp
                420                 425                 430

Glu Ala Gly Leu Met Val Ser Ala Leu Glu Ala Ala Phe Ala Arg Cys
        435                 440                 445

Gly

<210> SEQ ID NO 94
<211> LENGTH: 449
<212> TYPE: PRT
<213> ORGANISM: unknown
<220> FEATURE:
<223> OTHER INFORMATION: isolated from library

<400> SEQUENCE: 94

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
        35                  40                  45

Gly Val Gly Gly Leu Trp Asn Val Asn Ile Gly His Asn Arg Ala Ser
    50                  55                  60

Val Lys Ala Ala Ile Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser

```
            100                 105                 110
Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
    130                 135                 140

Arg Asn Gly Tyr His Gly Val His Met Gly Thr Ser Val Gly Gly
145                 150                 155                 160

Asn Gly Val Tyr His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
    210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala
        275                 280                 285

Gly Tyr Ile Pro Leu Gly Ala Thr Leu Phe Asn Gln Arg Ile Ala Asp
    290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Leu Ala Val Leu
                325                 330                 335

Asp Ile Val Glu Ala Glu Asp Leu Pro Gly Asn Ala Ala Lys Val Gly
            340                 345                 350

Ala Gln Leu Leu Glu Gln Leu Gln Pro Leu Val Glu Arg Tyr Ala Val
        355                 360                 365

Val Gly Glu Val Arg Gly Lys Gly Leu Met Ile Ala Leu Asp Leu Val
    370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Arg Pro
                405                 410                 415

Ile Gly Asn Lys Ile Leu Leu Ser Pro Pro Leu Thr Leu Thr Arg Asp
            420                 425                 430

Glu Ala Gly Leu Met Val Ser Ala Leu Glu Ala Ala Phe Ala Arg Cys
        435                 440                 445

Gly

<210> SEQ ID NO 95
<211> LENGTH: 449
<212> TYPE: PRT
<213> ORGANISM: unknown
<220> FEATURE:
<223> OTHER INFORMATION: isolated from library

<400> SEQUENCE: 95

Met Tyr Glu Lys Tyr Lys Asn Ala Glu Lys Lys Phe Trp His Pro Met
1               5                   10                  15
```

```
Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
        35                  40                  45

Gly Val Gly Gly Leu Trp Asn Val Asn Ile Gly His Asn Arg Ala Ser
    50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
    130                 135                 140

Arg Asn Gly Tyr His Gly Val His Met Gly Gly Thr Ser Val Gly Gly
145                 150                 155                 160

Asn Gly Val Tyr His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
    210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala
        275                 280                 285

Gly Tyr Ile Pro Leu Gly Ala Thr Leu Phe Asn Gln Arg Ile Ala Asp
    290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Leu Ala Val Leu Leu
                325                 330                 335

Asp Ile Val Glu Ala Glu Asp Leu Pro Gly Asn Ala Ala Lys Val Gly
            340                 345                 350

Ala Gln Leu Leu Glu Gln Leu Gln Pro Leu Val Glu Arg Tyr Ala Val
        355                 360                 365

Val Gly Glu Val Arg Gly Lys Gly Leu Met Ile Ala Leu Asp Leu Val
    370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Arg Pro
                405                 410                 415

Ile Gly Asn Lys Ile Cys Leu Ser Pro Pro Leu Thr Leu Thr Arg Asp
            420                 425                 430
```

-continued

Glu Ala Gly Leu Met Val Ser Ala Leu Glu Ala Ala Phe Ala Arg Cys
            435                 440                 445

Gly

<210> SEQ ID NO 96
<211> LENGTH: 449
<212> TYPE: PRT
<213> ORGANISM: unknown
<220> FEATURE:
<223> OTHER INFORMATION: isolated from library

<400> SEQUENCE: 96

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
        35                  40                  45

Gly Val Gly Gly Leu Trp Asn Val Asn Ile Gly His Asn Arg Ala Ser
    50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
    130                 135                 140

Arg Asn Gly Tyr His Gly Val His Met Gly Gly Thr Ser Val Gly Gly
145                 150                 155                 160

Asn Gly Val Tyr His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
    210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala
        275                 280                 285

Gly Tyr Ile Pro Leu Gly Ala Thr Leu Phe Asn Gln Arg Ile Ala Asp
    290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Ala Leu Ala Val Leu
                325                 330                 335

Asp Ile Val Glu Ala Glu Asp Leu Pro Gly Asn Ala Ala Lys Val Gly

```
                    340                 345                 350
Ala Gln Leu Leu Glu Gln Leu Gln Pro Leu Val Glu Arg Tyr Ala Val
                355                 360                 365
Val Gly Glu Val Arg Gly Lys Gly Leu Met Ile Ala Leu Asp Leu Val
                370                 375                 380
Ser Asp Lys Arg Thr Arg Gln Pro Leu Asp Pro Ala Ala Gly Gln Pro
385                 390                 395                 400
Ser Arg Ile Ala Asp Glu Ala Arg Arg Ala Gly Val Leu Val Arg Pro
                405                 410                 415
Val Gly Asn Lys Ile Ser Leu Ser Pro Pro Leu Thr Leu Thr Arg Asp
                420                 425                 430
Glu Ala Gly Leu Met Val Ser Ala Leu Glu Ala Ala Phe Ala Arg Cys
                435                 440                 445
Gly

<210> SEQ ID NO 97
<211> LENGTH: 449
<212> TYPE: PRT
<213> ORGANISM: unknown
<220> FEATURE:
<223> OTHER INFORMATION: isolated from library

<400> SEQUENCE: 97

Met Tyr Glu Lys Tyr Lys Asn Ala Glu Lys Lys Phe Trp His Pro Met
1               5                   10                  15
Gly Ser Ser Ala Ala Pro His Arg Asp Lys Thr Leu Val Ile Ala Arg
                20                  25                  30
Gly Asp Gly Asn Tyr Ile Thr Asp Ile Asp Gly Gln Arg Met Leu Asp
            35                  40                  45
Gly Val Gly Gly Leu Trp Asn Val Asn Ile Gly His Asn Arg Ala Ser
        50                  55                  60
Val Lys Ala Ala Ile Ala Ala Gln Leu Asp Glu Leu Ala Tyr Tyr Gln
65                  70                  75                  80
Thr Phe Asp Gly Ile Ala His Pro Arg Val Phe Asp Leu Ala Glu Arg
                85                  90                  95
Leu Thr Gly Met Phe Ala Gln Glu Arg Met Ala Arg Val Leu Phe Ser
                100                 105                 110
Ser Gly Gly Ser Asp Ala Val Glu Thr Ala Leu Lys Met Ala Arg Gln
                115                 120                 125
Tyr Trp Ile Ala Ser Gly Glu Pro Gly Arg Thr Arg Phe Leu Ser Leu
            130                 135                 140
Arg Asn Gly Tyr His Gly Val His Met Gly Gly Thr Ser Val Gly Gly
145                 150                 155                 160
Asn Gly Val Tyr His Tyr Asn His Gly Gln Leu Leu Ala Gly Cys His
                165                 170                 175
Leu Leu Asp Thr Pro Trp Leu Tyr Arg Asn Pro Trp Asp Cys Arg Asp
                180                 185                 190
Pro Gln Ala Leu Thr Ala His Cys Ile Arg Gln Leu Glu Glu Gln Ile
            195                 200                 205
Ala Leu Leu Gly Ala Gln Thr Ile Ala Ala Leu Ile Ala Glu Pro Val
        210                 215                 220
Gln Gly Ala Gly Gly Val Ile Val Pro Pro Ala Asp Tyr Trp Pro Arg
225                 230                 235                 240
Leu Arg Glu Val Cys Asp Arg His Gly Ile Leu Leu Ile Ala Asp Glu
                245                 250                 255
```

Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala
            275                 280                 285

Gly Tyr Ile Pro Leu Gly Ala Thr Leu Phe Asn Gln Arg Ile Ala Asp
            290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Leu Ala Val Leu
            325                 330                 335

Asp Ile Val Glu Ala Glu Asp Leu Pro Gly Asn Ala Ala Lys Val Gly
            340                 345                 350

Ala Gln Leu Leu Glu Gln Leu Gln Pro Leu Val Glu Arg Tyr Ala Val
            355                 360                 365

Val Gly Glu Val Arg Gly Lys Gly Leu Met Ile Ala Leu Asp Leu Val
            370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Arg Pro
            405                 410                 415

Val Gly Asn Lys Ile Cys Leu Ser Pro Pro Leu Thr Leu Thr Arg Asp
            420                 425                 430

Glu Ala Gly Leu Met Val Ser Ala Leu Glu Ala Ala Phe Ala Arg Cys
            435                 440                 445

Gly

<210> SEQ ID NO 98
<211> LENGTH: 449
<212> TYPE: PRT
<213> ORGANISM: unknown
<220> FEATURE:
<223> OTHER INFORMATION: isolated from library

<400> SEQUENCE: 98

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
            35                  40                  45

Gly Val Gly Gly Leu Trp Asn Val Asn Ile Gly His Asn Arg Ala Ser
        50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
            115                 120                 125

Tyr Trp Ile Ala Ser Gly Glu Pro Gly Arg Thr Arg Phe Leu Ser Leu
        130                 135                 140

Arg Asn Gly Tyr His Gly Val His Met Gly Gly Thr Ser Val Gly Gly
145                 150                 155                 160

Asn Gly Val Tyr His Tyr Asn His Gly Gln Leu Leu Ala Gly Cys His
            165                 170                 175

Leu Leu Asp Thr Pro Trp Leu Tyr Arg Asn Pro Trp Asp Cys Arg Asp
        180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala
        275                 280                 285

Gly Tyr Ile Pro Leu Gly Ala Thr Leu Phe Asn Gln Arg Ile Ala Asp
        290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Ala Leu Ala Val Leu
                325                 330                 335

Asp Ile Val Glu Ala Glu Asp Leu Pro Gly Asn Ala Ala Lys Val Gly
            340                 345                 350

Ala Gln Leu Leu Glu Gln Leu Gln Pro Leu Val Glu Arg Tyr Ala Val
        355                 360                 365

Val Gly Glu Val Arg Gly Lys Gly Leu Met Ile Ala Leu Asp Leu Val
        370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Arg Pro
                405                 410                 415

Ala Gly Asn Lys Ile Ser Leu Ser Pro Pro Leu Thr Leu Thr Arg Asp
            420                 425                 430

Glu Ala Gly Leu Met Val Ser Ala Leu Glu Ala Ala Phe Ala Arg Cys
        435                 440                 445

Gly

<210> SEQ ID NO 99
<211> LENGTH: 449
<212> TYPE: PRT
<213> ORGANISM: unknown
<220> FEATURE:
<223> OTHER INFORMATION: isolated from library

<400> SEQUENCE: 99

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
        35                  40                  45

Gly Val Gly Gly Leu Trp Asn Val Asn Ile Gly His Asn Arg Ala Ser
    50                  55                  60

Val Lys Ala Ala Ile Ala Ala Gln Leu Asp Glu Leu Ala Tyr Tyr Gln

```
             65                  70                  75                  80
        Thr Phe Asp Gly Ile Ala His Pro Arg Val Phe Asp Leu Ala Glu Arg
                         85                  90                  95

Leu Thr Gly Met Phe Ala Gln Glu Arg Met Ala Arg Val Leu Phe Ser
                        100                 105                 110

Ser Gly Gly Ser Asp Ala Val Glu Thr Ala Leu Lys Met Ala Arg Gln
                        115                 120                 125

Tyr Trp Ile Ala Ser Gly Glu Pro Gly Arg Thr Arg Phe Leu Ser Leu
                        130                 135                 140

Arg Asn Gly Tyr His Gly Val His Met Gly Gly Thr Ser Val Gly Gly
        145                 150                 155                 160

Asn Gly Val Tyr His Tyr Asn His Gly Gln Leu Leu Ala Gly Cys His
                        165                 170                 175

Leu Leu Asp Thr Pro Trp Leu Tyr Arg Asn Pro Trp Asp Cys Arg Asp
                        180                 185                 190

Pro Gln Ala Leu Thr Ala His Cys Ile Arg Gln Leu Glu Glu Gln Ile
                        195                 200                 205

Ala Leu Leu Gly Ala Gln Thr Ile Ala Ala Leu Ile Ala Glu Pro Val
                        210                 215                 220

Gln Gly Ala Gly Gly Val Ile Val Pro Pro Ala Asp Tyr Trp Pro Arg
        225                 230                 235                 240

Leu Arg Glu Val Cys Asp Arg His Gly Ile Leu Leu Ile Ala Asp Glu
                        245                 250                 255

Val Val Thr Gly Phe Gly Arg Ser Gly Cys Met Leu Gly Ser Arg Gly
                        260                 265                 270

Trp Gly Val Ala Pro Asp Ile Leu Cys Leu Ala Lys Gly Ile Thr Ala
                        275                 280                 285

Gly Tyr Ile Pro Leu Gly Ala Thr Leu Phe Asn Gln Arg Ile Ala Asp
                        290                 295                 300

Ala Ile Glu Asn Gly Gln Gly Phe Ser His Met Ile Met His Gly Tyr
        305                 310                 315                 320

Thr Tyr Ser Gly His Pro Thr Ala Cys Ala Ala Ala Leu Ala Val Leu
                        325                 330                 335

Asp Ile Val Glu Ala Glu Asp Leu Pro Gly Asn Ala Ala Lys Val Gly
                        340                 345                 350

Ala Gln Leu Leu Glu Gln Leu Gln Pro Leu Val Glu Arg Tyr Ala Val
                        355                 360                 365

Val Gly Glu Val Arg Gly Lys Gly Leu Met Ile Ala Leu Asp Leu Val
        370                 375                 380

Ser Asp Lys Arg Thr Arg Gln Pro Leu Asp Pro Ala Ala Gly Gln Pro
        385                 390                 395                 400

Ser Arg Ile Ala Asp Glu Ala Arg Arg Ala Gly Val Leu Val Arg Pro
                        405                 410                 415

Phe Gly Asn Lys Ile Val Leu Ser Pro Pro Leu Thr Leu Thr Arg Asp
                        420                 425                 430

Glu Ala Gly Leu Met Val Ser Ala Leu Glu Ala Ala Phe Ala Arg Cys
                        435                 440                 445

Gly

<210> SEQ ID NO 100
<211> LENGTH: 449
<212> TYPE: PRT
<213> ORGANISM: unknown
<220> FEATURE:
```

<223> OTHER INFORMATION: isolated from library

<400> SEQUENCE: 100

```
Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
        35                  40                  45

Gly Val Gly Gly Leu Trp Asn Val Asn Ile Gly His Asn Arg Ala Ser
    50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
    130                 135                 140

Arg Asn Gly Tyr His Gly Val His Met Gly Gly Thr Ser Val Gly Gly
145                 150                 155                 160

Asn Gly Val Tyr His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
    210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala
        275                 280                 285

Gly Tyr Ile Pro Leu Gly Ala Thr Leu Phe Asn Gln Arg Ile Ala Asp
    290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Ala Leu Ala Val Leu
                325                 330                 335

Asp Ile Val Glu Ala Glu Asp Leu Pro Gly Asn Ala Ala Lys Val Gly
            340                 345                 350

Ala Gln Leu Leu Glu Gln Leu Gln Pro Leu Val Glu Arg Tyr Ala Val
        355                 360                 365

Val Gly Glu Val Arg Gly Lys Gly Leu Met Ile Ala Leu Asp Leu Val
    370                 375                 380

Ser Asp Lys Arg Thr Arg Gln Pro Leu Asp Pro Ala Ala Gly Gln Pro
385                 390                 395                 400
```

Ser Arg Ile Ala Asp Glu Arg Arg Ala Gly Val Leu Val Arg Pro
            405                 410                 415

Ala Gly Asn Lys Ile Cys Leu Ser Pro Pro Leu Thr Leu Thr Arg Asp
        420                 425                 430

Glu Ala Gly Leu Met Val Ser Ala Leu Glu Ala Ala Phe Ala Arg Cys
        435                 440                 445

Gly

<210> SEQ ID NO 101
<211> LENGTH: 449
<212> TYPE: PRT
<213> ORGANISM: unknown
<220> FEATURE:
<223> OTHER INFORMATION: isolated from library

<400> SEQUENCE: 101

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
        35                  40                  45

Gly Val Gly Gly Leu Trp Asn Val Asn Ile Gly His Asn Arg Ala Ser
50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
130                 135                 140

Arg Asn Gly Tyr His Gly Val His Met Gly Gly Thr Ser Val Gly Gly
145                 150                 155                 160

Met Gly Val Leu His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala
        275                 280                 285

Gly Tyr Ile Pro Leu Gly Ala Thr Leu Phe Asn Gln Arg Ile Ala Asp
290                 295                 300

Ala Ile Glu Asn Gly Gln Gly Phe Ser His Met Ile Met His Gly Tyr

```
            305                 310                 315                 320
        Thr Tyr Ser Gly His Pro Thr Ala Cys Ala Ala Leu Ala Val Leu
                    325                 330                 335

Asp Ile Val Glu Ala Glu Asp Leu Pro Gly Asn Ala Ala Lys Val Gly
                    340                 345                 350

Ala Gln Leu Leu Glu Gln Leu Gln Pro Leu Val Glu Arg Tyr Ala Val
                    355                 360                 365

Val Gly Glu Val Arg Gly Lys Gly Leu Met Ile Ala Leu Asp Leu Val
                    370                 375                 380

Ser Asp Lys Arg Thr Arg Gln Pro Leu Asp Pro Ala Ala Gly Gln Pro
        385                 390                 395                 400

Ser Arg Ile Ala Asp Glu Ala Arg Arg Ala Gly Val Leu Val Arg Pro
                        405                 410                 415

Ile Gly Asn Lys Ile Ile Leu Ser Pro Pro Leu Thr Leu Thr Arg Asp
                        420                 425                 430

Glu Ala Gly Leu Met Val Ser Ala Leu Glu Ala Ala Phe Ala Arg Cys
                        435                 440                 445

Gly

<210> SEQ ID NO 102
<211> LENGTH: 449
<212> TYPE: PRT
<213> ORGANISM: unknown
<220> FEATURE:
<223> OTHER INFORMATION: isolated from library

<400> SEQUENCE: 102

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
                20                  25                  30

Gly Asp Gly Asn Tyr Ile Thr Asp Ile Asp Gly Gln Arg Met Leu Asp
            35                  40                  45

Gly Val Gly Gly Leu Trp Asn Val Asn Ile Gly His Asn Arg Ala Ser
        50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
                100                 105                 110

Ser Gly Gly Ser Asp Ala Val Glu Thr Ala Leu Lys Met Ala Arg Gln
            115                 120                 125

Tyr Trp Ile Ala Ser Gly Glu Pro Gly Arg Thr Arg Phe Leu Ser Leu
        130                 135                 140

Arg Asn Gly Tyr His Gly Val His Met Gly Gly Thr Ser Val Gly Gly
145                 150                 155                 160

Ile Gly Val Leu His Tyr Asn His Gly Gln Leu Leu Ala Gly Cys His
                165                 170                 175

Leu Leu Asp Thr Pro Trp Leu Tyr Arg Asn Pro Trp Cys Arg Asp
                180                 185                 190

Pro Gln Ala Leu Thr Ala His Cys Ile Arg Gln Leu Glu Glu Gln Ile
            195                 200                 205

Ala Leu Leu Gly Ala Gln Thr Ile Ala Ala Leu Ile Ala Glu Pro Val
        210                 215                 220
```

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
            245                 250                 255

Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala
            275                 280                 285

Gly Tyr Ile Pro Leu Gly Ala Thr Leu Phe Asn Gln Arg Ile Ala Asp
            290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Ala Leu Ala Val Leu
                325                 330                 335

Asp Ile Val Glu Ala Glu Asp Leu Pro Gly Asn Ala Ala Lys Val Gly
            340                 345                 350

Ala Gln Leu Leu Glu Gln Leu Gln Pro Leu Val Glu Arg Tyr Ala Val
            355                 360                 365

Val Gly Glu Val Arg Gly Lys Gly Leu Met Ile Ala Leu Asp Leu Val
            370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Arg Pro
            405                 410                 415

Ile Gly Asn Lys Ile Ile Leu Ser Pro Pro Leu Thr Leu Thr Arg Asp
            420                 425                 430

Glu Ala Gly Leu Met Val Ser Ala Leu Glu Ala Ala Phe Ala Arg Cys
            435                 440                 445

Gly

<210> SEQ ID NO 103
<211> LENGTH: 449
<212> TYPE: PRT
<213> ORGANISM: unknown
<220> FEATURE:
<223> OTHER INFORMATION: isolated from library

<400> SEQUENCE: 103

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
        35                  40                  45

Gly Val Gly Gly Leu Trp Asn Val Asn Ile Gly His Asn Arg Ala Ser
    50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
            130                 135                 140

Arg Asn Gly Tyr His Gly Val His Met Gly Gly Thr Ser Val Gly Gly
145                 150                 155                 160

Gln Gly Val Leu His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
                180                 185                 190

Pro Gln Ala Leu Thr Ala His Cys Ile Arg Gln Leu Glu Glu Gln Ile
                195                 200                 205

Ala Leu Leu Gly Ala Gln Thr Ile Ala Ala Leu Ile Ala Glu Pro Val
210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
                260                 265                 270

Trp Gly Val Ala Pro Asp Ile Leu Cys Leu Ala Lys Gly Ile Thr Ala
            275                 280                 285

Gly Tyr Ile Pro Leu Gly Ala Thr Leu Phe Asn Gln Arg Ile Ala Asp
290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Ala Leu Ala Val Leu
                325                 330                 335

Asp Ile Val Glu Ala Glu Asp Leu Pro Gly Asn Ala Ala Lys Val Gly
                340                 345                 350

Ala Gln Leu Leu Glu Gln Leu Gln Pro Leu Val Glu Arg Tyr Ala Val
            355                 360                 365

Val Gly Glu Val Arg Gly Lys Gly Leu Met Ile Ala Leu Asp Leu Val
370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Ala Gly Val Leu Val Arg Pro
                405                 410                 415

Ile Gly Asn Lys Ile Ile Leu Ser Pro Pro Leu Thr Leu Thr Arg Asp
                420                 425                 430

Glu Ala Gly Leu Met Val Ser Ala Leu Glu Ala Ala Phe Ala Arg Cys
            435                 440                 445

Gly

<210> SEQ ID NO 104
<211> LENGTH: 449
<212> TYPE: PRT
<213> ORGANISM: unknown
<220> FEATURE:
<223> OTHER INFORMATION: isolated from library

<400> SEQUENCE: 104

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp

```
                35                  40                  45
Gly Val Gly Gly Leu Trp Asn Val Asn Ile Gly His Asn Arg Ala Ser
 50                  55                  60

Val Lys Ala Ala Ile Ala Ala Gln Leu Asp Glu Leu Ala Tyr Tyr Gln
 65                  70                  75                  80

Thr Phe Asp Gly Ile Ala His Pro Arg Val Phe Asp Leu Ala Glu Arg
                 85                  90                  95

Leu Thr Gly Met Phe Ala Gln Glu Arg Met Ala Arg Val Leu Phe Ser
                100                 105                 110

Ser Gly Gly Ser Asp Ala Val Glu Thr Ala Leu Lys Met Ala Arg Gln
                115                 120                 125

Tyr Trp Ile Ala Ser Gly Glu Pro Gly Arg Thr Arg Phe Leu Ser Leu
                130                 135                 140

Arg Asn Gly Tyr His Gly Val His Met Gly Gly Thr Ser Val Gly Gly
145                 150                 155                 160

Ile Gly Val Met His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
                180                 185                 190

Pro Gln Ala Leu Thr Ala His Cys Ile Arg Gln Leu Glu Glu Gln Ile
                195                 200                 205

Ala Leu Leu Gly Ala Gln Thr Ile Ala Ala Leu Ile Ala Glu Pro Val
210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
                260                 265                 270

Trp Gly Val Ala Pro Asp Ile Leu Cys Leu Ala Lys Gly Ile Thr Ala
                275                 280                 285

Gly Tyr Ile Pro Leu Gly Ala Thr Leu Phe Asn Gln Arg Ile Ala Asp
                290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Leu Ala Val Leu
                325                 330                 335

Asp Ile Val Glu Ala Glu Asp Leu Pro Gly Asn Ala Ala Lys Val Gly
                340                 345                 350

Ala Gln Leu Leu Glu Gln Leu Gln Pro Leu Val Glu Arg Tyr Ala Val
                355                 360                 365

Val Gly Glu Val Arg Gly Lys Gly Leu Met Ile Ala Leu Asp Leu Val
                370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Arg Pro
                405                 410                 415

Ile Gly Asn Lys Ile Ile Leu Ser Pro Pro Leu Thr Leu Thr Arg Asp
                420                 425                 430

Glu Ala Gly Leu Met Val Ser Ala Leu Glu Ala Ala Phe Ala Arg Cys
                435                 440                 445

Gly
```

```
<210> SEQ ID NO 105
<211> LENGTH: 449
<212> TYPE: PRT
<213> ORGANISM: unknown
<220> FEATURE:
<223> OTHER INFORMATION: isolated from library

<400> SEQUENCE: 105
```

| | | | | | | | | | | | | | | | |
|---|---|---|---|---|---|---|---|---|---|---|---|---|---|---|---|
| Met | Tyr | Glu | Lys | Tyr | Lys | Asn | Ala | Glu | Lys | Lys | Phe | Trp | His | Pro | Met |
| 1 | | | | 5 | | | | | 10 | | | | | 15 | |
| Gly | Ser | Ser | Ala | Ala | Pro | His | Arg | Asp | Lys | Thr | Leu | Val | Ile | Ala | Arg |
| | | | | 20 | | | | | 25 | | | | | 30 | |
| Gly | Asp | Gly | Asn | Tyr | Ile | Thr | Asp | Ile | Asp | Gly | Gln | Arg | Met | Leu | Asp |
| | | | 35 | | | | | 40 | | | | | 45 | | |
| Gly | Val | Gly | Gly | Leu | Trp | Asn | Val | Asn | Ile | Gly | His | Asn | Arg | Ala | Ser |
| | 50 | | | | | 55 | | | | | 60 | | | | |
| Val | Lys | Ala | Ala | Ile | Ala | Ala | Gln | Leu | Asp | Glu | Leu | Ala | Tyr | Tyr | Gln |
| 65 | | | | | 70 | | | | | 75 | | | | | 80 |
| Thr | Phe | Asp | Gly | Ile | Ala | His | Pro | Arg | Val | Phe | Asp | Leu | Ala | Glu | Arg |
| | | | | 85 | | | | | 90 | | | | | 95 | |
| Leu | Thr | Gly | Met | Phe | Ala | Gln | Glu | Arg | Met | Ala | Arg | Val | Leu | Phe | Ser |
| | | | 100 | | | | | 105 | | | | | 110 | | |
| Ser | Gly | Gly | Ser | Asp | Ala | Val | Glu | Thr | Ala | Leu | Lys | Met | Ala | Arg | Gln |
| | | | 115 | | | | | 120 | | | | | 125 | | |
| Tyr | Trp | Ile | Ala | Ser | Gly | Glu | Pro | Gly | Arg | Thr | Arg | Phe | Leu | Ser | Leu |
| | 130 | | | | | 135 | | | | | 140 | | | | |
| Arg | Asn | Gly | Tyr | His | Gly | Val | His | Met | Gly | Thr | Ser | Val | Gly | Gly |
| 145 | | | | | 150 | | | | | 155 | | | | | 160 |
| Met | Gly | Val | Met | His | Tyr | Asn | His | Gly | Gln | Leu | Leu | Ala | Gly | Cys | His |
| | | | | 165 | | | | | 170 | | | | | 175 | |
| Leu | Leu | Asp | Thr | Pro | Trp | Leu | Tyr | Arg | Asn | Pro | Trp | Asp | Cys | Arg | Asp |
| | | | 180 | | | | | 185 | | | | | 190 | | |
| Pro | Gln | Ala | Leu | Thr | Ala | His | Cys | Ile | Arg | Gln | Leu | Glu | Glu | Gln | Ile |
| | | | 195 | | | | | 200 | | | | | 205 | | |
| Ala | Leu | Leu | Gly | Ala | Gln | Thr | Ile | Ala | Ala | Leu | Ile | Ala | Glu | Pro | Val |
| | 210 | | | | | 215 | | | | | 220 | | | | |
| Gln | Gly | Ala | Gly | Gly | Val | Ile | Val | Pro | Pro | Ala | Asp | Tyr | Trp | Pro | Arg |
| 225 | | | | | 230 | | | | | 235 | | | | | 240 |
| Leu | Arg | Glu | Val | Cys | Asp | Arg | His | Gly | Ile | Leu | Leu | Ile | Ala | Asp | Glu |
| | | | | 245 | | | | | 250 | | | | | 255 | |
| Val | Val | Thr | Gly | Phe | Gly | Arg | Ser | Gly | Cys | Met | Leu | Gly | Ser | Arg | Gly |
| | | | 260 | | | | | 265 | | | | | 270 | | |
| Trp | Gly | Val | Ala | Pro | Asp | Ile | Leu | Cys | Leu | Ala | Lys | Gly | Ile | Thr | Ala |
| | | 275 | | | | | 280 | | | | | 285 | | | |
| Gly | Tyr | Ile | Pro | Leu | Gly | Ala | Thr | Leu | Phe | Asn | Gln | Arg | Ile | Ala | Asp |
| | 290 | | | | | 295 | | | | | 300 | | | | |
| Ala | Ile | Glu | Asn | Gly | Gln | Gly | Phe | Ser | His | Met | Ile | Met | His | Gly | Tyr |
| 305 | | | | | 310 | | | | | 315 | | | | | 320 |
| Thr | Tyr | Ser | Gly | His | Pro | Thr | Ala | Cys | Ala | Ala | Leu | Ala | Val | Leu |
| | | | | 325 | | | | | 330 | | | | | 335 | |
| Asp | Ile | Val | Glu | Ala | Glu | Asp | Leu | Pro | Gly | Asn | Ala | Ala | Lys | Val | Gly |
| | | | 340 | | | | | 345 | | | | | 350 | | |
| Ala | Gln | Leu | Leu | Glu | Gln | Leu | Gln | Pro | Leu | Val | Glu | Arg | Tyr | Ala | Val |
| | | 355 | | | | | 360 | | | | | 365 | | | |

```
Val Gly Glu Val Arg Gly Lys Gly Leu Met Ile Ala Leu Asp Leu Val
    370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Arg Pro
                    405                 410                 415

Ile Gly Asn Lys Ile Ile Leu Ser Pro Pro Leu Thr Leu Thr Arg Asp
                420                 425                 430

Glu Ala Gly Leu Met Val Ser Ala Leu Glu Ala Ala Phe Ala Arg Cys
                435                 440                 445

Gly

<210> SEQ ID NO 106
<211> LENGTH: 449
<212> TYPE: PRT
<213> ORGANISM: unknown
<220> FEATURE:
<223> OTHER INFORMATION: isolated from library

<400> SEQUENCE: 106

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
                20                  25                  30

Gly Asp Gly Asn Tyr Ile Thr Asp Ile Asp Gly Gln Arg Met Leu Asp
            35                  40                  45

Gly Val Gly Gly Leu Trp Asn Val Asn Ile Gly His Asn Arg Ala Ser
    50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
130                 135                 140

Arg Asn Gly Tyr His Gly Val His Met Gly Gly Thr Ser Val Gly Gly
145                 150                 155                 160

Gln Gly Val Met His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala
```

```
                   275                 280                 285
Gly Tyr Ile Pro Leu Gly Ala Thr Leu Phe Asn Gln Arg Ile Ala Asp
    290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Leu Ala Val Leu
                325                 330                 335

Asp Ile Val Glu Ala Glu Asp Leu Pro Gly Asn Ala Ala Lys Val Gly
            340                 345                 350

Ala Gln Leu Leu Glu Gln Leu Gln Pro Leu Val Glu Arg Tyr Ala Val
                355                 360                 365

Val Gly Glu Val Arg Gly Lys Gly Leu Met Ile Ala Leu Asp Leu Val
    370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Arg Pro
                405                 410                 415

Ile Gly Asn Lys Ile Ile Leu Ser Pro Pro Leu Thr Leu Thr Arg Asp
            420                 425                 430

Glu Ala Gly Leu Met Val Ser Ala Leu Glu Ala Ala Phe Ala Arg Cys
                435                 440                 445

Gly

<210> SEQ ID NO 107
<211> LENGTH: 449
<212> TYPE: PRT
<213> ORGANISM: unknown
<220> FEATURE:
<223> OTHER INFORMATION: isolated from library

<400> SEQUENCE: 107

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
        35                  40                  45

Gly Val Gly Gly Leu Trp Asn Val Asn Ile Gly His Asn Arg Ala Ser
    50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
    130                 135                 140

Arg Asn Gly Tyr His Gly Val His Met Gly Gly Thr Ser Val Gly Gly
145                 150                 155                 160

Ile Gly Val Phe His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190
```

Pro Gln Ala Leu Thr Ala His Cys Ile Arg Gln Leu Glu Glu Gln Ile
    195                 200                 205

Ala Leu Leu Gly Ala Gln Thr Ile Ala Ala Leu Ile Ala Glu Pro Val
    210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
                260                 265                 270

Trp Gly Val Ala Pro Asp Ile Leu Cys Leu Ala Lys Gly Ile Thr Ala
                275                 280                 285

Gly Tyr Ile Pro Leu Gly Ala Thr Leu Phe Asn Gln Arg Ile Ala Asp
            290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Ala Leu Ala Val Leu
                325                 330                 335

Asp Ile Val Glu Ala Glu Asp Leu Pro Gly Asn Ala Ala Lys Val Gly
                340                 345                 350

Ala Gln Leu Leu Glu Gln Leu Gln Pro Leu Val Glu Arg Tyr Ala Val
            355                 360                 365

Val Gly Glu Val Arg Gly Lys Gly Leu Met Ile Ala Leu Asp Leu Val
370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Arg Pro
                405                 410                 415

Ile Gly Asn Lys Ile Ile Leu Ser Pro Pro Leu Thr Leu Thr Arg Asp
            420                 425                 430

Glu Ala Gly Leu Met Val Ser Ala Leu Glu Ala Ala Phe Ala Arg Cys
            435                 440                 445

Gly

<210> SEQ ID NO 108
<211> LENGTH: 449
<212> TYPE: PRT
<213> ORGANISM: unknown
<220> FEATURE:
<223> OTHER INFORMATION: isolated from library

<400> SEQUENCE: 108

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
        35                  40                  45

Gly Val Gly Gly Leu Trp Asn Val Asn Ile Gly His Asn Arg Ala Ser
    50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
    130                 135                 140

Arg Tyr Gly Tyr His Gly Val His Met Gly Gly Thr Ser Val Gly Gly
145                 150                 155                 160

Gln Gly Val Tyr His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
    210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala
        275                 280                 285

Gly Tyr Ile Pro Leu Gly Ala Thr Leu Phe Asn Gln Arg Ile Ala Asp
    290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Ala Leu Ala Val Leu
                325                 330                 335

Asp Ile Val Glu Ala Glu Asp Leu Pro Gly Asn Ala Ala Lys Val Gly
            340                 345                 350

Ala Gln Leu Leu Glu Gln Leu Gln Pro Leu Val Glu Arg Tyr Ala Val
        355                 360                 365

Val Gly Glu Val Arg Gly Lys Gly Leu Met Ile Ala Leu Asp Leu Val
    370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Arg Pro
                405                 410                 415

Ile Gly Asn Lys Ile Ile Leu Ser Pro Pro Leu Thr Leu Thr Arg Asp
            420                 425                 430

Glu Ala Gly Leu Met Val Ser Ala Leu Glu Ala Ala Phe Ala Arg Cys
        435                 440                 445

Gly

<210> SEQ ID NO 109
<211> LENGTH: 449
<212> TYPE: PRT
<213> ORGANISM: unknown
<220> FEATURE:
<223> OTHER INFORMATION: isolated from library

<400> SEQUENCE: 109

Met Tyr Glu Lys Tyr Lys Asn Ala Glu Lys Lys Phe Trp His Pro Met

-continued

```
1               5                   10                  15
Gly Ser Ser Ala Ala Pro His Arg Asp Lys Thr Leu Val Ile Ala Arg
            20                  25                  30
Gly Asp Gly Asn Tyr Ile Thr Asp Ile Asp Gly Gln Arg Met Leu Asp
            35                  40                  45
Gly Val Gly Gly Ser Trp Asn Val Asn Ile Gly His Asn Arg Ala Ser
50                  55                  60
Val Lys Ala Ala Ile Ala Ala Gln Leu Asp Glu Leu Ala Tyr Tyr Gln
65                  70                  75                  80
Thr Phe Asp Gly Ile Ala His Pro Arg Val Phe Asp Leu Ala Glu Arg
                85                  90                  95
Leu Thr Gly Met Phe Ala Gln Glu Arg Met Ala Arg Val Leu Phe Ser
                100                 105                 110
Ser Gly Gly Ser Asp Ala Val Glu Thr Ala Leu Lys Met Ala Arg Gln
                115                 120                 125
Tyr Trp Ile Ala Ser Gly Glu Pro Gly Arg Thr Arg Phe Leu Ser Leu
130                 135                 140
Arg Asn Gly Tyr His Gly Val His Met Gly Gly Thr Ser Val Gly Gly
145                 150                 155                 160
Ile Gly Val Leu His Tyr Asn His Gly Gln Leu Leu Ala Gly Cys His
                165                 170                 175
Leu Leu Asp Thr Pro Trp Leu Tyr Arg Asn Pro Trp Asp Cys Arg Asp
                180                 185                 190
Pro Gln Ala Leu Thr Ala His Cys Ile Arg Gln Leu Glu Glu Gln Ile
                195                 200                 205
Ala Leu Leu Gly Ala Gln Thr Ile Ala Ala Leu Ile Ala Glu Pro Val
210                 215                 220
Gln Gly Ala Gly Gly Val Ile Val Pro Pro Ala Asp Tyr Trp Pro Arg
225                 230                 235                 240
Leu Arg Glu Val Cys Asp Arg His Gly Ile Leu Leu Ile Ala Asp Glu
                245                 250                 255
Val Val Thr Gly Phe Gly Arg Ser Gly Cys Met Leu Gly Ser Arg Gly
                260                 265                 270
Trp Gly Val Ala Pro Asp Ile Leu Cys Leu Ala Lys Gly Ile Thr Ala
                275                 280                 285
Gly Tyr Ile Pro Leu Gly Ala Thr Leu Phe Asn Gln Arg Ile Ala Asp
                290                 295                 300
Ala Ile Glu Asn Gly Gln Gly Phe Ser His Met Ile Met His Gly Tyr
305                 310                 315                 320
Thr Tyr Ser Gly His Pro Thr Ala Cys Ala Ala Ala Leu Ala Val Leu
                325                 330                 335
Asp Ile Val Glu Ala Glu Asp Leu Pro Gly Asn Ala Ala Lys Val Gly
                340                 345                 350
Ala Gln Leu Leu Glu Gln Leu Gln Pro Leu Val Glu Arg Tyr Ala Val
                355                 360                 365
Val Gly Glu Val Arg Gly Lys Gly Leu Met Ile Ala Leu Asp Leu Val
370                 375                 380
Ser Asp Lys Arg Thr Arg Gln Pro Leu Asp Pro Ala Ala Gly Gln Pro
385                 390                 395                 400
Ser Arg Ile Ala Asp Glu Ala Arg Ala Gly Val Leu Val Arg Pro
                405                 410                 415
Ile Gly Asn Lys Ile Ile Leu Ser Pro Pro Leu Thr Leu Thr Arg Asp
                420                 425                 430
```

Glu Ala Gly Leu Met Val Ser Ala Leu Glu Ala Ala Phe Ala Arg Cys
            435                 440                 445
Gly

<210> SEQ ID NO 110
<211> LENGTH: 449
<212> TYPE: PRT
<213> ORGANISM: unknown
<220> FEATURE:
<223> OTHER INFORMATION: isolated from library

<400> SEQUENCE: 110

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
        35                  40                  45

Gly Val Gly Gly Leu Trp Asn Val Asn Ile Gly His Asn Arg Ala Ser
    50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
    130                 135                 140

Arg Asn Gly Tyr His Gly Val His Met Gly Gly Thr Ser Val Gly Gly
145                 150                 155                 160

Ile Gly Val Leu His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
    210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Gly
        275                 280                 285

Gly Tyr Ile Pro Leu Gly Ala Thr Leu Phe Asn Gln Arg Ile Ala Asp
    290                 295                 300

Ala Ile Glu Asn Gly Gln Gly Phe Ser His Met Ile His Gly Tyr
305                 310                 315                 320

Thr Tyr Ser Gly His Pro Thr Cys Ala Ala Leu Ala Val Leu
                325                 330                 335

-continued

```
Asp Ile Val Glu Ala Glu Asp Leu Pro Gly Asn Ala Ala Lys Val Gly
                340                 345                 350

Ala Gln Leu Leu Glu Gln Leu Gln Pro Leu Val Glu Arg Tyr Ala Val
            355                 360                 365

Val Gly Glu Val Arg Gly Lys Gly Leu Met Ile Ala Leu Asp Leu Val
        370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Arg Pro
                405                 410                 415

Ile Gly Asn Lys Ile Ile Leu Ser Pro Pro Leu Thr Leu Thr Arg Asp
            420                 425                 430

Glu Ala Gly Leu Met Val Ser Ala Leu Glu Ala Ala Phe Ala Arg Cys
        435                 440                 445

Gly

<210> SEQ ID NO 111
<211> LENGTH: 449
<212> TYPE: PRT
<213> ORGANISM: unknown
<220> FEATURE:
<223> OTHER INFORMATION: isolated from library

<400> SEQUENCE: 111

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
        35                  40                  45

Gly Val Gly Gly Leu Trp Asn Val Asn Ile Gly His Asn Arg Ala Ser
    50                  55                  60

Val Lys Asn Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
    130                 135                 140

Arg Asn Gly Tyr His Gly Val His Met Gly Gly Thr Ser Val Gly Gly
145                 150                 155                 160

Ile Gly Val Leu His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
    210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
```

```
            245                 250                 255
Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala
            275                 280                 285

Gly Tyr Ile Pro Leu Gly Ala Thr Leu Phe Asn Gln Arg Ile Ala Asp
            290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Leu Ala Val Leu
            325                 330                 335

Asp Ile Val Glu Ala Glu Asp Leu Pro Gly Asn Ala Ala Lys Val Gly
            340                 345                 350

Ala Gln Leu Leu Glu Gln Leu Gln Pro Leu Val Glu Arg Tyr Ala Val
            355                 360                 365

Val Gly Glu Val Arg Gly Lys Gly Leu Met Ile Ala Leu Asp Leu Val
            370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Arg Pro
            405                 410                 415

Ile Gly Asn Lys Ile Ile Leu Ser Pro Pro Leu Thr Leu Thr Arg Asp
            420                 425                 430

Glu Ala Gly Leu Met Val Ser Ala Leu Glu Ala Ala Phe Ala Arg Cys
            435                 440                 445

Gly

<210> SEQ ID NO 112
<211> LENGTH: 449
<212> TYPE: PRT
<213> ORGANISM: unknown
<220> FEATURE:
<223> OTHER INFORMATION: isolated from library

<400> SEQUENCE: 112

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Arg Arg Met Leu Asp
        35                  40                  45

Gly Val Gly Gly Leu Trp Asn Val Asn Ile Gly His Asn Arg Ala Ser
    50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
    130                 135                 140

Arg Asn Gly Tyr His Gly Val His Met Gly Gly Thr Ser Val Gly Gly
145                 150                 155                 160
```

Ile Gly Val Leu His Tyr Asn His Gly Gln Leu Leu Ala Gly Cys His
            165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
            195                 200                 205

Ala Leu Leu Gly Ala Gln Thr Ile Ala Leu Ile Ala Glu Pro Val
            210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
            245                 250                 255

Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala
            275                 280                 285

Gly Tyr Ile Pro Leu Gly Ala Thr Leu Phe Asn Gln Arg Ile Ala Asp
            290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Ala Leu Ala Val Leu
            325                 330                 335

Asp Ile Val Glu Ala Glu Asp Leu Pro Gly Asn Ala Ala Lys Val Gly
            340                 345                 350

Ala Gln Leu Leu Glu Gln Leu Gln Pro Leu Val Glu Arg Tyr Ala Val
            355                 360                 365

Val Gly Glu Val Arg Gly Lys Gly Leu Met Ile Ala Leu Asp Leu Val
            370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Arg Pro
            405                 410                 415

Ile Gly Asn Lys Ile Ile Leu Ser Pro Pro Leu Thr Leu Thr Arg Asp
            420                 425                 430

Glu Ala Gly Leu Met Val Ser Ala Leu Glu Ala Ala Phe Ala Arg Cys
            435                 440                 445

Gly

<210> SEQ ID NO 113
<211> LENGTH: 449
<212> TYPE: PRT
<213> ORGANISM: unknown
<220> FEATURE:
<223> OTHER INFORMATION: isolated from library

<400> SEQUENCE: 113

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
            35                  40                  45

Gly Val Gly Gly Leu Trp Asn Val Asn Ile Gly His Asn Arg Ala Ser
        50                  55                  60

Val Lys Ala Pro Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
    130                 135                 140

Arg Asn Gly Tyr His Gly Val His Met Gly Gly Thr Ser Val Gly Gly
145                 150                 155                 160

Ile Gly Val Leu His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala
        275                 280                 285

Gly Tyr Ile Pro Leu Gly Ala Thr Leu Phe Asn Gln Arg Ile Ala Asp
    290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Ala Leu Ala Val Leu
                325                 330                 335

Asp Ile Val Glu Ala Glu Asp Leu Pro Gly Asn Ala Ala Lys Val Gly
            340                 345                 350

Ala Gln Leu Leu Glu Gln Leu Gln Pro Leu Val Glu Arg Tyr Ala Val
        355                 360                 365

Val Gly Glu Val Arg Gly Lys Gly Leu Met Ile Ala Leu Asp Leu Val
370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Arg Pro
                405                 410                 415

Ile Gly Asn Lys Ile Ile Leu Ser Pro Pro Leu Thr Leu Thr Arg Asp
            420                 425                 430

Glu Ala Gly Leu Met Val Ser Ala Leu Glu Ala Ala Phe Ala Arg Cys
        435                 440                 445

Gly

<210> SEQ ID NO 114
<211> LENGTH: 449
<212> TYPE: PRT
<213> ORGANISM: unknown

<220> FEATURE:
<223> OTHER INFORMATION: isolated from library

<400> SEQUENCE: 114

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
        35                  40                  45

Gly Val Gly Gly Leu Trp Asn Val Asn Ile Gly His Asn Arg Ala Ser
    50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
    130                 135                 140

Arg Asn Gly Tyr His Gly Val His Met Gly Gly Thr Ser Val Gly Gly
145                 150                 155                 160

Ile Gly Val Leu His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
    210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala
        275                 280                 285

Gly Tyr Ile Pro Leu Gly Ala Thr Leu Phe Asn Gln Arg Ile Ala Asp
    290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Leu Ala Val Leu
                325                 330                 335

Asp Ile Val Glu Ala Glu Asp Leu Pro Gly Asn Ala Gly Lys Val Gly
            340                 345                 350

Ala Gln Leu Leu Glu Gln Leu Gln Pro Leu Val Glu Arg Tyr Ala Val
        355                 360                 365

Val Gly Glu Val Arg Gly Lys Gly Leu Met Ile Ala Leu Asp Leu Val
    370                 375                 380

Ser Asp Lys Arg Thr Arg Gln Pro Leu Asp Pro Ala Ala Gly Gln Pro
385                 390                 395                 400

```
Ser Arg Ile Ala Asp Glu Ala Arg Arg Ala Gly Val Leu Val Arg Pro
                405                 410                 415

Ile Gly Asn Lys Ile Ile Leu Ser Pro Pro Leu Thr Leu Thr Arg Asp
            420                 425                 430

Glu Ala Gly Leu Met Val Ser Ala Leu Glu Ala Phe Ala Arg Cys
        435                 440                 445

Gly

<210> SEQ ID NO 115
<211> LENGTH: 449
<212> TYPE: PRT
<213> ORGANISM: unknown
<220> FEATURE:
<223> OTHER INFORMATION: isolated from library

<400> SEQUENCE: 115

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
        35                  40                  45

Gly Val Gly Gly Leu Trp Asn Val Asn Ile Gly His Asn Arg Ala Ser
    50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
    130                 135                 140

Arg Asn Gly Tyr His Gly Val His Met Gly Gly Thr Ser Val Gly Gly
145                 150                 155                 160

Ile Gly Val Leu His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
    210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala
        275                 280                 285

Gly Tyr Ile Pro Leu Gly Ala Thr Leu Phe Asn Gln Arg Ile Ala Asp
    290                 295                 300
```

```
Ala Ile Glu Asn Gly Gln Gly Phe Ser His Met Ile Met His Gly Tyr
305                 310                 315                 320

Thr Tyr Ser Gly His Pro Thr Ala Cys Ala Ala Leu Ala Val Leu
            325                 330                 335

Asp Ile Val Glu Ala Glu Asp Leu Pro Gly Asn Ala Ala Lys Val Gly
            340                 345                 350

Ala Gln Leu Leu Glu Gln Leu Gln Pro Leu Val Glu Arg Tyr Ala Val
            355                 360                 365

Val Gly Glu Val Arg Gly Lys Gly Leu Met Ile Ala Leu Asp Leu Val
            370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Ala Gly Val Leu Val Arg Pro
            405                 410                 415

Ile Gly Asn Lys Ile Ile Leu Ser Pro Pro Leu Thr Leu Asn Arg Asp
            420                 425                 430

Glu Ala Gly Leu Met Val Ser Ala Leu Glu Ala Ala Phe Ala Arg Cys
            435                 440                 445

Gly
```

<210> SEQ ID NO 116
<211> LENGTH: 449
<212> TYPE: PRT
<213> ORGANISM: unknown
<220> FEATURE:
<223> OTHER INFORMATION: isolated from library

<400> SEQUENCE: 116

```
Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
            35                  40                  45

Gly Val Gly Gly Leu Trp Asn Val Asn Ile Gly His Asn Arg Ala Ser
        50                  55                  60

Val Lys Ala Ala Ile Ala Ala Gln Leu Asp Glu Leu Ala Tyr Tyr Gln
65              70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
130                 135                 140

Arg Asn Gly Tyr His Gly Val His Met Gly Thr Ser Val Gly Gly
145                 150                 155                 160

Ile Gly Val Leu His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
```

-continued

```
            210                 215                 220
Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
            245                 250                 255

Val Val Thr Gly Phe Gly Arg Ser Gly Cys Met Leu Gly Ser Arg Gly
                260                 265                 270

Trp Gly Val Ala Pro Asp Ile Leu Cys Leu Ala Lys Gly Ile Thr Ala
            275                 280                 285

Gly Tyr Ile Pro Leu Gly Ala Thr Leu Phe Asn Gln Arg Ile Ala Asp
                290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Leu Ala Val Leu
                325                 330                 335

Asp Ile Val Glu Ala Glu Asp Leu Pro Gly Asn Ala Ala Lys Val Gly
                340                 345                 350

Ala Gln Leu Leu Glu Gln Leu Gln Pro Leu Val Glu Arg Tyr Ala Val
            355                 360                 365

Val Gly Glu Val Arg Gly Lys Gly Leu Met Ile Ala Leu Asp Leu Val
            370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Ala Gly Val Leu Val Arg Pro
                405                 410                 415

Ile Gly Asn His Ile Ile Leu Ser Pro Pro Leu Thr Leu Thr Arg Asp
                420                 425                 430

Glu Ala Gly Leu Met Val Ser Ala Leu Glu Ala Ala Phe Ala Arg Cys
            435                 440                 445

Gly

<210> SEQ ID NO 117
<211> LENGTH: 449
<212> TYPE: PRT
<213> ORGANISM: unknown
<220> FEATURE:
<223> OTHER INFORMATION: isolated from library

<400> SEQUENCE: 117

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
        35                  40                  45

Gly Val Gly Gly Leu Trp Asn Val Asn Ile Gly His Asn Arg Ala Ser
    50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125
```

Tyr Trp Ile Ala Ser Gly Glu Pro Gly Arg Thr Arg Phe Leu Ser Leu
            130                 135                 140

Arg Asn Gly Tyr His Gly Val His Met Gly Thr Ser Val Gly Gly
145                 150                 155                 160

Ile Gly Val Leu His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
                260                 265                 270

Trp Gly Val Ala Pro Asp Ile Leu Cys Leu Ala Lys Gly Ile Thr Ala
            275                 280                 285

Gly Tyr Ile Pro Leu Gly Ala Thr Leu Phe Asn Glu Arg Ile Ala Asp
290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Ala Leu Ala Val Leu
                325                 330                 335

Asp Ile Val Glu Ala Glu Asp Leu Pro Gly Asn Ala Ala Lys Val Gly
            340                 345                 350

Ala Gln Leu Leu Glu Gln Leu Gln Pro Leu Val Glu Arg Tyr Ala Val
        355                 360                 365

Val Gly Glu Val Arg Gly Lys Gly Leu Met Ile Ala Leu Asp Leu Val
370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Arg Pro
                405                 410                 415

Ile Gly Asn Lys Ile Ile Leu Ser Pro Pro Leu Thr Leu Thr Arg Asp
            420                 425                 430

Glu Ala Gly Leu Met Val Ser Ala Leu Glu Ala Ala Phe Ala Arg Cys
        435                 440                 445

Gly

<210> SEQ ID NO 118
<211> LENGTH: 449
<212> TYPE: PRT
<213> ORGANISM: unknown
<220> FEATURE:
<223> OTHER INFORMATION: isolated from library

<400> SEQUENCE: 118

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

-continued

```
Gly Asp Gly Asn Tyr Ile Thr Asp Ile Asp Gly Gln Arg Met Leu Asp
         35                  40                  45

Gly Val Gly Gly Leu Trp Asn Val Asn Ile Gly His Asn Arg Ala Ser
 50                  55                  60

Val Lys Ala Ala Ile Ala Ala Gln Met Asp Glu Leu Ala Tyr Tyr Gln
 65                  70                  75                  80

Thr Phe Asp Gly Ile Ala His Pro Arg Val Phe Asp Leu Ala Glu Arg
                 85                  90                  95

Leu Thr Gly Met Phe Ala Gln Glu Arg Met Ala Arg Val Leu Phe Ser
                100                 105                 110

Ser Gly Gly Ser Asp Ala Val Glu Thr Ala Leu Lys Met Ala Arg Gln
                115                 120                 125

Tyr Trp Ile Ala Ser Gly Glu Pro Gly Arg Thr Arg Phe Leu Ser Leu
130                 135                 140

Arg Asn Gly Tyr His Gly Val His Met Gly Gly Thr Ser Val Gly Gly
145                 150                 155                 160

Ile Gly Val Leu His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
                180                 185                 190

Pro Gln Ala Leu Thr Ala His Cys Ile Arg Gln Leu Glu Glu Gln Ile
                195                 200                 205

Ala Leu Leu Gly Ala Gln Thr Ile Ala Ala Leu Ile Ala Glu Pro Val
210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
                260                 265                 270

Trp Gly Val Ala Pro Asp Ile Leu Cys Leu Ala Lys Gly Ile Thr Ala
                275                 280                 285

Gly Tyr Ile Pro Leu Gly Ala Thr Leu Phe Asn Gln Arg Ile Ala Asp
290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Ala Leu Ala Val Leu
                325                 330                 335

Asp Ile Val Glu Ala Glu Asp Leu Pro Gly Asn Ala Ala Lys Val Gly
                340                 345                 350

Ala Gln Leu Leu Glu Gln Leu Gln Pro Leu Val Glu Arg Tyr Ala Val
                355                 360                 365

Val Gly Glu Val Arg Gly Lys Gly Leu Met Ile Ala Leu Asp Leu Val
                370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Ala Gly Val Leu Val Arg Pro
                405                 410                 415

Ile Gly Asn Lys Ile Ile Leu Ser Pro Pro Leu Thr Leu Thr Arg Asp
                420                 425                 430

Glu Ala Gly Leu Met Val Ser Ala Leu Glu Ala Ala Phe Ala Arg Cys
                435                 440                 445

Gly
```

```
<210> SEQ ID NO 119
<211> LENGTH: 449
<212> TYPE: PRT
<213> ORGANISM: unknown
<220> FEATURE:
<223> OTHER INFORMATION: isolated from library

<400> SEQUENCE: 119
```

| | | | | | | | | | | | | | | | |
|---|---|---|---|---|---|---|---|---|---|---|---|---|---|---|---|
| Met | Tyr | Glu | Lys | Tyr | Lys | Asn | Ala | Glu | Lys | Lys | Phe | Trp | His | Pro | Met |
| 1 | | | | 5 | | | | | 10 | | | | | 15 | |
| Gly | Ser | Ser | Ala | Ala | Pro | His | Arg | Asp | Lys | Thr | Leu | Val | Ile | Ala | Arg |
| | | | 20 | | | | | 25 | | | | | 30 | | |
| Tyr | Asp | Gly | Asn | Tyr | Ile | Thr | Asp | Ile | Asp | Gly | Gln | Arg | Met | Leu | Asp |
| | | 35 | | | | | 40 | | | | | 45 | | | |
| Gly | Val | Gly | Gly | Leu | Trp | Asn | Val | Asn | Ile | Gly | His | Asn | Arg | Ala | Ser |
| | 50 | | | | | 55 | | | | | 60 | | | | |
| Val | Lys | Ala | Ala | Ile | Ala | Ala | Gln | Leu | Asp | Glu | Leu | Ala | Tyr | Tyr | Gln |
| 65 | | | | | 70 | | | | | 75 | | | | | 80 |
| Thr | Phe | Asp | Gly | Ile | Ala | His | Pro | Arg | Val | Phe | Asp | Leu | Ala | Glu | Arg |
| | | | | 85 | | | | | 90 | | | | | 95 | |
| Leu | Thr | Gly | Met | Phe | Ala | Gln | Glu | Arg | Met | Ala | Arg | Val | Leu | Phe | Ser |
| | | | 100 | | | | | 105 | | | | | 110 | | |
| Ser | Gly | Gly | Ser | Asp | Ala | Val | Glu | Thr | Ala | Leu | Lys | Met | Ala | Arg | Gln |
| | | | 115 | | | | | 120 | | | | | 125 | | |
| Tyr | Trp | Ile | Ala | Ser | Gly | Glu | Pro | Gly | Arg | Thr | Arg | Phe | Leu | Ser | Leu |
| | | 130 | | | | | 135 | | | | | 140 | | | |
| Arg | Asn | Gly | Tyr | His | Gly | Val | His | Met | Gly | Gly | Thr | Ser | Val | Gly | Gly |
| 145 | | | | | 150 | | | | | 155 | | | | | 160 |
| Ile | Gly | Val | Leu | His | Tyr | Asn | His | Gly | Gln | Leu | Leu | Ala | Gly | Cys | His |
| | | | | 165 | | | | | 170 | | | | | 175 | |
| Leu | Leu | Asp | Thr | Pro | Trp | Leu | Tyr | Arg | Asn | Pro | Trp | Asp | Cys | Arg | Asp |
| | | | 180 | | | | | 185 | | | | | 190 | | |
| Pro | Gln | Ala | Leu | Thr | Ala | His | Cys | Ile | Arg | Gln | Leu | Glu | Glu | Gln | Ile |
| | | | 195 | | | | | 200 | | | | | 205 | | |
| Ala | Leu | Leu | Gly | Ala | Gln | Thr | Ile | Ala | Ala | Leu | Ile | Ala | Glu | Pro | Val |
| | 210 | | | | | 215 | | | | | 220 | | | | |
| Gln | Gly | Ala | Gly | Val | Ile | Val | Pro | Ala | Asp | Tyr | Trp | Pro | Arg |
| 225 | | | | | 230 | | | | | 235 | | | | 240 |
| Leu | Arg | Glu | Val | Cys | Asp | Arg | His | Gly | Ile | Leu | Leu | Ile | Ala | Asp | Glu |
| | | | | 245 | | | | | 250 | | | | | 255 | |
| Val | Val | Thr | Gly | Phe | Gly | Arg | Ser | Gly | Cys | Met | Leu | Gly | Ser | Arg | Gly |
| | | | 260 | | | | | 265 | | | | | 270 | | |
| Trp | Gly | Val | Ala | Pro | Asp | Ile | Leu | Cys | Leu | Ala | Lys | Gly | Ile | Thr | Ala |
| | | | 275 | | | | | 280 | | | | | 285 | | |
| Gly | Tyr | Ile | Pro | Leu | Gly | Ala | Thr | Leu | Phe | Asn | Gln | Arg | Ile | Ala | Asp |
| | | 290 | | | | | 295 | | | | | 300 | | | |
| Ala | Ile | Glu | Asn | Gly | Gln | Gly | Phe | Ser | His | Met | Ile | Met | His | Gly | Tyr |
| 305 | | | | | 310 | | | | | 315 | | | | | 320 |
| Thr | Tyr | Ser | Gly | His | Pro | Thr | Cys | Ala | Ala | Ala | Leu | Ala | Val | Leu |
| | | | | 325 | | | | | 330 | | | | | 335 |
| Asp | Ile | Val | Glu | Ala | Glu | Asp | Leu | Pro | Gly | Asn | Ala | Ala | Lys | Val | Gly |
| | | | 340 | | | | | 345 | | | | | 350 | | |
| Ala | Gln | Leu | Leu | Glu | Gln | Leu | Gln | Pro | Leu | Val | Glu | Arg | Tyr | Ala | Val |
| | | | 355 | | | | | 360 | | | | | 365 | | |

```
Val Gly Glu Val Arg Gly Lys Gly Leu Met Ile Ala Leu Asp Leu Val
            370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Arg Pro
                405                 410                 415

Ile Gly Asn Lys Ile Ile Leu Ser Pro Pro Leu Thr Leu Thr Arg Asp
            420                 425                 430

Glu Ala Gly Leu Met Val Ser Ala Leu Glu Ala Ala Phe Ala Arg Cys
            435                 440                 445

Gly

<210> SEQ ID NO 120
<211> LENGTH: 449
<212> TYPE: PRT
<213> ORGANISM: unknown
<220> FEATURE:
<223> OTHER INFORMATION: isolated from library

<400> SEQUENCE: 120

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
        35                  40                  45

Gly Val Gly Gly Leu Trp Asn Val Asn Ile Gly His Asn Arg Ala Ser
    50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
    130                 135                 140

Arg Asn Gly Tyr His Gly Val His Met Gly Gly Thr Ser Val Gly Gly
145                 150                 155                 160

Ile Gly Val Leu His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
    210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
            260                 265                 270
```

```
Trp Gly Val Ala Pro Asp Ile Leu Cys Leu Ala Lys Gly Ile Thr Ala
            275                 280                 285
Gly Tyr Ile Pro Leu Gly Ala Thr Leu Phe Asn Gln Arg Ile Ala Asp
290                 295                 300
Ala Ile Glu Asn Gly Gln Gly Phe Ser His Met Ile Met His Gly Tyr
305                 310                 315                 320
Thr Tyr Ser Gly His Pro Thr Ala Cys Ala Ala Leu Ala Val Leu
            325                 330                 335
Asp Ile Val Glu Ala Glu Asp Leu Pro Gly Asn Ala Ala Lys Val Gly
            340                 345                 350
Ala Gln Leu Leu Glu Gln Leu Gln Pro Leu Val Glu Arg Tyr Ala Val
            355                 360                 365
Val Gly Glu Val Arg Gly Lys Gly Leu Met Ile Ala Leu Asp Leu Val
            370                 375                 380
Ser Asp Lys Arg Thr Arg Gln Pro Leu Asp Pro Ala Ala Gly Gln Pro
385                 390                 395                 400
Ser Arg Ile Ala Asp Glu Ala Arg Arg Ala Gly Val Leu Val Arg Pro
            405                 410                 415
Ile Gly Asn Ser Ile Ile Leu Ser Pro Pro Leu Thr Leu Thr Arg Asp
            420                 425                 430
Glu Ala Gly Leu Met Val Ser Ala Leu Glu Ala Ala Phe Ala Arg Cys
            435                 440                 445
Gly

<210> SEQ ID NO 121
<211> LENGTH: 449
<212> TYPE: PRT
<213> ORGANISM: unknown
<220> FEATURE:
<223> OTHER INFORMATION: isolated from library

<400> SEQUENCE: 121

Met Tyr Glu Lys Tyr Lys Asn Ala Glu Lys Lys Phe Trp His Pro Met
1               5                   10                  15
Gly Ser Ser Ala Ala Pro His Arg Asp Lys Thr Leu Val Ile Ala Arg
            20                  25                  30
Gly Asp Gly Asn Tyr Ile Thr Asp Ile Asp Gly Asn Arg Met Leu Asp
            35                  40                  45
Gly Val Gly Gly Leu Trp Asn Val Asn Ile Gly His Asn Arg Ala Ser
        50                  55                  60
Val Lys Ala Ala Ile Ala Ala Gln Leu Asp Glu Leu Ala Tyr Tyr Gln
65                  70                  75                  80
Thr Phe Asp Gly Ile Ala His Pro Arg Val Phe Asp Leu Ala Glu Arg
                85                  90                  95
Leu Thr Gly Met Phe Ala Gln Glu Arg Met Ala Arg Val Leu Phe Ser
            100                 105                 110
Ser Gly Gly Ser Asp Ala Val Glu Thr Ala Leu Lys Met Ala Arg Gln
        115                 120                 125
Tyr Trp Ile Ala Ser Gly Glu Pro Gly Arg Thr Arg Phe Leu Ser Leu
130                 135                 140
Arg Asn Gly Tyr His Gly Val His Met Gly Gly Thr Ser Val Gly Gly
145                 150                 155                 160
Ile Gly Val Leu His Tyr Asn His Gly Gln Leu Leu Ala Gly Cys His
                165                 170                 175
Leu Leu Asp Thr Pro Trp Leu Tyr Arg Asn Pro Trp Asp Cys Arg Asp
```

```
                180                 185                 190
Pro Gln Ala Leu Thr Ala His Cys Ile Arg Gln Leu Glu Glu Gln Ile
            195                 200                 205
Ala Leu Leu Gly Ala Gln Thr Ile Ala Ala Leu Ile Ala Glu Pro Val
        210                 215                 220
Gln Gly Ala Gly Gly Val Ile Val Pro Pro Ala Asp Tyr Trp Pro Arg
225                 230                 235                 240
Leu Arg Glu Val Cys Asp Arg His Gly Ile Leu Leu Ile Ala Asp Glu
                245                 250                 255
Val Val Thr Gly Phe Gly Arg Ser Gly Cys Met Leu Gly Ser Arg Gly
            260                 265                 270
Trp Gly Val Ala Pro Asp Ile Leu Cys Leu Ala Lys Gly Ile Thr Ala
        275                 280                 285
Gly Tyr Ile Pro Leu Gly Ala Thr Leu Phe Asn Gln Arg Ile Ala Asp
    290                 295                 300
Ala Ile Glu Asn Gly Gln Gly Phe Ser His Met Ile Met His Gly Tyr
305                 310                 315                 320
Thr Tyr Ser Gly His Pro Thr Ala Cys Ala Ala Ala Leu Ala Val Leu
                325                 330                 335
Asp Ile Val Glu Ala Glu Asp Leu Pro Gly Asn Ala Ala Lys Val Gly
            340                 345                 350
Ala Gln Leu Leu Glu Gln Leu Gln Pro Leu Val Glu Arg Tyr Ala Val
        355                 360                 365
Val Gly Glu Val Arg Gly Lys Gly Leu Met Ile Ala Leu Asp Leu Val
    370                 375                 380
Ser Asp Lys Arg Thr Arg Gln Pro Leu Asp Pro Ala Ala Gly Gln Pro
385                 390                 395                 400
Ser Arg Ile Ala Asp Glu Ala Arg Arg Ala Gly Val Leu Val Arg Pro
                405                 410                 415
Ile Gly Asn Lys Ile Ile Leu Ser Pro Pro Leu Thr Leu Thr Arg Asp
            420                 425                 430
Glu Ala Gly Leu Met Val Ser Ala Leu Glu Ala Ala Phe Ala Arg Cys
        435                 440                 445
Gly

<210> SEQ ID NO 122
<211> LENGTH: 449
<212> TYPE: PRT
<213> ORGANISM: unknown
<220> FEATURE:
<223> OTHER INFORMATION: isolated from library

<400> SEQUENCE: 122

Met Tyr Glu Lys Tyr Lys Asn Ala Glu Lys Lys Phe Trp His Pro Met
1               5                   10                  15
Gly Ser Ser Ala Ala Pro His Arg Asp Lys Thr Leu Val Ile Ala Arg
            20                  25                  30
Gly Asp Gly Asn Tyr Ile Thr Asp Ile Asp Gly Gln Arg Met Leu Asp
        35                  40                  45
Gly Val Gly Gly Leu Trp Asn Val Asn Ile Gly His Asn Arg Ala Ser
    50                  55                  60
Val Lys Ala Ala Ile Ala Ala Gln Leu Asp Glu Leu Ala Tyr Tyr Gln
65                  70                  75                  80
Thr Phe Asp Gly Ile Ala His Pro Arg Val Phe Asp Leu Ala Glu Arg
                85                  90                  95
```

Leu Thr Gly Met Phe Ala Gln Glu Arg Met Ala Arg Val Leu Phe Ser
                100                 105                 110

Ser Gly Gly Ser Asp Ala Val Glu Thr Ala Leu Lys Met Ala Arg Gln
            115                 120                 125

Tyr Trp Ile Ala Ser Gly Glu Pro Gly Arg Thr Arg Phe Leu Ser Leu
        130                 135                 140

Arg Asn Gly Tyr His Gly Val His Met Gly Gly Thr Ser Val Gly Gly
145                 150                 155                 160

Ile Gly Val Leu His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
        210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala
        275                 280                 285

Gly Tyr Ile Pro Leu Gly Ala Thr Leu Phe Asn Gln Arg Ile Ala Asp
        290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Ala Leu Ala Val Leu
                325                 330                 335

Asp Ile Val Glu Ala Glu Asp Leu Pro Gly Asn Ala Ala Lys Val Gly
            340                 345                 350

Ala Gln Leu Leu Glu Gln Leu Gln Pro Leu Val Glu Arg Tyr Ala Val
        355                 360                 365

Val Gly Glu Val Arg Gly Lys Gly Leu Met Ile Ala Leu Asp Leu Val
370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Arg Pro
                405                 410                 415

Ile Gly Asn Asn Ile Ile Leu Ser Pro Pro Leu Thr Leu Thr Arg Asp
            420                 425                 430

Glu Ala Gly Leu Met Val Ser Ala Leu Glu Ala Ala Phe Ala Arg Cys
        435                 440                 445

Gly

<210> SEQ ID NO 123
<211> LENGTH: 449
<212> TYPE: PRT
<213> ORGANISM: unknown
<220> FEATURE:
<223> OTHER INFORMATION: isolated from library

<400> SEQUENCE: 123

-continued

```
Met Tyr Glu Lys Tyr Lys Asn Ala Glu Lys Lys Phe Trp His Pro Met
 1               5                  10                  15
Gly Ser Ser Ala Ala Pro His Arg Asp Lys Thr Leu Val Ile Ala Arg
                20                  25                  30
Gly Asp Gly Asn Tyr Ile Thr Asp Ile Asp Gly Gln Lys Met Leu Asp
                35                  40                  45
Gly Val Gly Gly Leu Trp Asn Val Asn Ile Gly His Asn Arg Ala Ser
 50                  55                  60
Val Lys Ala Ala Ile Ala Ala Gln Leu Asp Glu Leu Ala Tyr Tyr Gln
 65                  70                  75                  80
Thr Phe Asp Gly Ile Ala His Pro Arg Val Phe Asp Leu Ala Glu Arg
                85                  90                  95
Leu Thr Gly Met Phe Ala Gln Glu Arg Met Ala Arg Val Leu Phe Ser
                100                 105                 110
Ser Gly Gly Ser Asp Ala Val Glu Thr Ala Leu Lys Met Ala Arg Gln
            115                 120                 125
Tyr Trp Ile Ala Ser Gly Glu Pro Gly Arg Thr Arg Phe Leu Ser Leu
                130                 135                 140
Arg Asn Gly Tyr His Gly Val His Met Gly Gly Thr Ser Val Gly Gly
145                 150                 155                 160
Ile Gly Val Leu His Tyr Asn His Gly Gln Leu Leu Ala Gly Cys His
                165                 170                 175
Leu Leu Asp Thr Pro Trp Leu Tyr Arg Asn Pro Trp Asp Cys Arg Asp
            180                 185                 190
Pro Gln Ala Leu Thr Ala His Cys Ile Arg Gln Leu Glu Glu Gln Ile
            195                 200                 205
Ala Leu Leu Gly Ala Gln Thr Ile Ala Ala Leu Ile Ala Glu Pro Val
            210                 215                 220
Gln Gly Ala Gly Gly Val Ile Val Pro Pro Ala Asp Tyr Trp Pro Arg
225                 230                 235                 240
Leu Arg Glu Val Cys Asp Arg His Gly Ile Leu Leu Ile Ala Asp Glu
                245                 250                 255
Val Val Thr Gly Phe Gly Arg Ser Gly Cys Met Leu Gly Ser Arg Gly
                260                 265                 270
Trp Gly Val Ala Pro Asp Ile Leu Cys Leu Ala Lys Gly Ile Thr Ala
            275                 280                 285
Gly Tyr Ile Pro Leu Gly Ala Thr Leu Phe Asn Gln Arg Ile Ala Asp
            290                 295                 300
Ala Ile Glu Asn Gly Gln Gly Phe Ser His Met Ile Met His Gly Tyr
305                 310                 315                 320
Thr Tyr Ser Gly His Pro Thr Ala Cys Ala Ala Ala Leu Ala Val Leu
                325                 330                 335
Asp Ile Val Glu Ala Glu Asp Leu Pro Gly Asn Ala Ala Lys Val Gly
                340                 345                 350
Ala Gln Leu Leu Glu Gln Leu Gln Pro Leu Val Glu Arg Tyr Ala Val
            355                 360                 365
Val Gly Glu Val Arg Gly Lys Gly Leu Met Ile Ala Leu Asp Leu Val
 370                 375                 380
Ser Asp Lys Arg Thr Arg Gln Pro Leu Asp Pro Ala Ala Gly Gln Pro
385                 390                 395                 400
Ser Arg Ile Ala Asp Glu Ala Arg Arg Ala Gly Val Leu Val Arg Pro
                405                 410                 415
Ile Gly Asn Lys Ile Ile Leu Ser Pro Pro Leu Thr Leu Thr Arg Asp
```

```
                420             425             430
Glu Ala Gly Leu Met Val Ser Ala Leu Glu Ala Phe Ala Arg Cys
            435             440             445
Gly

<210> SEQ ID NO 124
<211> LENGTH: 449
<212> TYPE: PRT
<213> ORGANISM: unknown
<220> FEATURE:
<223> OTHER INFORMATION: isolated from library

<400> SEQUENCE: 124

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
        35                  40                  45

Gly Val Gly Gly Leu Trp Asn Val Asn Ile Gly His Asn Arg Ala Ser
    50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
    130                 135                 140

Arg Asn Gly Tyr His Gly Val His Met Gly Gly Thr Ser Val Gly Gly
145                 150                 155                 160

Ile Gly Val Leu His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
    210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala
        275                 280                 285

Gly Tyr Ile Pro Leu Gly Ala Thr Leu Phe Asn Gln Arg Ile Ala Asp
    290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Ala Leu Ala Val Leu
                325                 330                 335
```

-continued

```
Asp Ile Val Glu Ala Glu Asp Leu Pro Gly Asn Ala Ala Lys Val Gly
            340                 345                 350

Ala Gln Leu Leu Glu Gln Leu Gln Pro Leu Val Glu Arg Tyr Ala Val
        355                 360                 365

Val Gly Glu Val Arg Gly Lys Gly Leu Met Ile Ala Leu Asp Leu Val
370                 375                 380

Ser Asp Lys Arg Thr Arg Lys Pro Leu Asp Pro Ala Ala Gly Gln Pro
385                 390                 395                 400

Ser Arg Ile Ala Asp Glu Ala Arg Ala Gly Val Leu Val Arg Pro
            405                 410                 415

Ile Gly Asn Lys Ile Ile Leu Ser Pro Pro Leu Thr Leu Thr Arg Asp
            420                 425                 430

Glu Ala Gly Leu Met Val Ser Ala Leu Glu Ala Ala Phe Ala Arg Cys
        435                 440                 445

Gly

<210> SEQ ID NO 125
<211> LENGTH: 450
<212> TYPE: PRT
<213> ORGANISM: unknown
<220> FEATURE:
<223> OTHER INFORMATION: isolated from library

<400> SEQUENCE: 125

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
        35                  40                  45

Gly Val Gly Gly Leu Trp Asn Val Asn Ile Gly His Asn Arg Ala Ser
    50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
130                 135                 140

Arg Asn Gly Tyr His Gly Val His Met Gly Gly Thr Ser Val Gly Gly
145                 150                 155                 160

Ile Gly Val Leu His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
    210                 215                 220

Gln Gly Ala Gly Gly Val Ile Val Pro Pro Ala Asp Tyr Trp Pro Arg
225                 230                 235                 240
```

```
Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala
        275                 280                 285

Gly Tyr Ile Pro Leu Gly Ala Thr Leu Phe Asn Gln Arg Ile Ala Asp
    290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Ala Leu Ala Val Leu
                325                 330                 335

Asp Ile Val Glu Ala Glu Asp Leu Pro Gly Asn Ala Ala Lys Val Gly
            340                 345                 350

Ala Gln Leu Leu Glu Gln Leu Gln Pro Leu Val Glu Arg His Ala Val
        355                 360                 365

Val Gly Glu Val Arg Gly Lys Gly Leu Met Ile Ala Leu Asp Leu Val
    370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Ala Gly Val Leu Val Arg Pro
                405                 410                 415

Ile Gly Asn Lys Ile Ile Leu Ser Pro Pro Leu Thr Leu Thr Arg Asp
            420                 425                 430

Glu Ala Gly Leu Met Val Ser Ala Leu Glu Ala Ala Phe Ala Arg Cys
        435                 440                 445

Gly Gly
    450

<210> SEQ ID NO 126
<211> LENGTH: 449
<212> TYPE: PRT
<213> ORGANISM: unknown
<220> FEATURE:
<223> OTHER INFORMATION: isolated from library

<400> SEQUENCE: 126

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
        35                  40                  45

Gly Val Gly Gly Leu Trp Asn Val Asn Ile Gly His Asn Arg Ala Ser
    50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
    130                 135                 140
```

```
Arg Asn Gly Tyr His Gly Val His Met Gly Thr Ser Val Gly Gly
145                 150                 155                 160

Ile Gly Val Leu His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
    210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
                260                 265                 270

Trp Gly Val Ala Pro Asp Ile Leu Cys Leu Ala Lys Gly Ile Thr Ala
            275                 280                 285

Gly Tyr Ile Pro Leu Gly Ala Thr Leu Phe Asn Gln Arg Ile Ala Asp
        290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Leu Ala Val Leu
                325                 330                 335

Asp Ile Val Glu Ala Glu Asp Leu Pro Gly Asn Ala Ala Lys Val Gly
            340                 345                 350

Ala Phe Leu Leu Glu Gln Leu Gln Pro Leu Val Glu Arg Tyr Ala Val
        355                 360                 365

Val Gly Glu Val Arg Gly Lys Gly Leu Met Ile Ala Leu Asp Leu Val
    370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Arg Pro
                405                 410                 415

Ile Gly Asn Lys Ile Ile Leu Ser Pro Pro Leu Thr Leu Thr Arg Asp
                420                 425                 430

Glu Ala Gly Leu Met Val Ser Ala Leu Glu Ala Ala Phe Ala Arg Cys
            435                 440                 445

Gly

<210> SEQ ID NO 127
<211> LENGTH: 449
<212> TYPE: PRT
<213> ORGANISM: unknown
<220> FEATURE:
<223> OTHER INFORMATION: isolated from library

<400> SEQUENCE: 127

Met Tyr Glu Lys Tyr Lys Asn Ala Glu Lys Lys Phe Trp His Pro Met
1                   5                   10                  15

Gly Ser Ser Ala Ala Pro His Arg Asp Lys Thr Leu Val Ile Ala Arg
                20                  25                  30

Gly Asp Gly Asn Tyr Ile Thr Asp Ile Asp Gly Gln Arg Met Leu Asp
            35                  40                  45

Gly Val Gly Gly Leu Trp Asn Val Asn Ile Gly His Asn Arg Ala Ser
```

```
            50                  55                  60
Val Lys Ala Ala Ile Ala Ala Gln Leu Asp Glu Leu Ala Tyr Tyr Gln
 65                  70                  75                  80

Thr Phe Asp Gly Ile Ala His Pro Arg Val Phe Asp Leu Ala Glu Arg
                 85                  90                  95

Leu Thr Gly Met Phe Ala Gln Glu Arg Met Ala Arg Val Leu Phe Ser
                100                 105                 110

Ser Gly Gly Ser Asp Ala Val Glu Thr Ala Leu Lys Met Ala Arg Gln
            115                 120                 125

Tyr Trp Ile Ala Ser Gly Glu Pro Gly Arg Thr Arg Phe Leu Ser Leu
        130                 135                 140

Arg Asn Gly Tyr His Gly Val His Met Gly Gly Thr Ser Val Gly Gly
145                 150                 155                 160

Ile Gly Val Leu His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
                180                 185                 190

Pro Gln Ala Leu Thr Ala His Cys Ile Arg Gln Leu Glu Glu Gln Ile
            195                 200                 205

Ala Leu Leu Gly Ala Gln Thr Ile Ala Ala Leu Ile Ala Glu Pro Val
        210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
                260                 265                 270

Trp Gly Val Ala Pro Asp Ile Leu Cys Leu Ala Lys Gly Ile Thr Ala
            275                 280                 285

Gly Tyr Ile Pro Leu Gly Ala Thr Leu Phe Asn Gln Arg Ile Ala Asp
        290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Ala Leu Ala Val Leu
                325                 330                 335

Asp Ile Val Glu Ala Glu Asp Leu Pro Gly Asn Ala Ala Lys Val Gly
            340                 345                 350

Ala Gln Leu Leu Glu Gln Leu Gln Pro Leu Val Glu Arg Tyr Ala Val
        355                 360                 365

Val Gly Glu Val Arg Gly Lys Gly Leu Met Ile Ala Leu Asp Leu Val
370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Arg Pro
                405                 410                 415

Ile Gly Asn Lys Ile Ile Leu Ser Pro Pro Leu Thr Leu Thr Arg Asp
                420                 425                 430

Asp Ala Gly Leu Met Val Ser Ala Leu Glu Ala Ala Phe Ala Arg Cys
            435                 440                 445

Gly

<210> SEQ ID NO 128
<211> LENGTH: 449
```

-continued

```
<212> TYPE: PRT
<213> ORGANISM: unknown
<220> FEATURE:
<223> OTHER INFORMATION: isolated from library

<400> SEQUENCE: 128

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
        35                  40                  45

Gly Val Gly Gly Leu Trp Asn Val Asn Ile Gly His Asn Arg Ala Ser
    50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
    130                 135                 140

Arg Asn Gly Tyr His Gly Val His Met Gly Gly Thr Ser Val Gly Gly
145                 150                 155                 160

Ile Gly Val Leu His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
    210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala
        275                 280                 285

Gly Tyr Ile Pro Leu Gly Ala Thr Leu Phe Asn Gln Arg Ile Ala Asp
    290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Leu Ala Val Leu Leu
                325                 330                 335

Asp Ile Val Glu Ala Glu Asp Leu Pro Gly Asn Ala Ala Lys Val Gly
            340                 345                 350

Arg Gln Leu Leu Glu Gln Leu Gln Pro Leu Val Glu Arg Tyr Ala Val
        355                 360                 365

Val Gly Glu Val Arg Gly Lys Gly Leu Met Ile Ala Leu Asp Leu Val
    370                 375                 380
```

```
Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Arg Pro
                405                 410                 415

Ile Gly Asn Lys Ile Ile Leu Ser Pro Pro Leu Thr Leu Thr Arg Asp
            420                 425                 430

Glu Ala Gly Leu Met Val Ser Ala Leu Glu Ala Ala Phe Ala Arg Cys
        435                 440                 445

Gly

<210> SEQ ID NO 129
<211> LENGTH: 449
<212> TYPE: PRT
<213> ORGANISM: unknown
<220> FEATURE:
<223> OTHER INFORMATION: isolated from library

<400> SEQUENCE: 129

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
        35                  40                  45

Gly Val Gly Gly Leu Trp Asn Val Asn Ile Gly His Asn Arg Ala Ser
    50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
    130                 135                 140

Arg Asn Gly Tyr His Gly Val His Met Gly Gly Thr Ser Val Gly Gly
145                 150                 155                 160

Ile Gly Val Leu His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
    210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala
        275                 280                 285

Gly Tyr Ile Pro Leu Gly Ala Thr Leu Phe Asn Gln Arg Ile Ala Asp
```

```
                290                 295                 300
Ala Ile Glu Asn Gly Gln Gly Phe Ser His Met Ile Met His Gly Tyr
305                 310                 315                 320

Thr Tyr Ser Gly His Pro Thr Ala Cys Ala Ala Leu Ala Val Leu
            325                 330                 335

Asp Ile Val Glu Ala Glu Asp Leu Pro Gly Asn Ala Ala Lys Val Gly
                340                 345                 350

Ala Gln Leu Leu Glu Gln Leu Gln Pro Leu Val Glu Arg Phe Ala Val
            355                 360                 365

Val Gly Glu Val Arg Gly Lys Gly Leu Met Ile Ala Leu Asp Leu Val
    370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Arg Pro
                405                 410                 415

Ile Gly Asn Lys Ile Ile Leu Ser Pro Pro Leu Thr Leu Thr Arg Asp
            420                 425                 430

Glu Ala Gly Leu Met Val Ser Ala Leu Glu Ala Ala Phe Ala Arg Cys
        435                 440                 445

Gly

<210> SEQ ID NO 130
<211> LENGTH: 449
<212> TYPE: PRT
<213> ORGANISM: unknown
<220> FEATURE:
<223> OTHER INFORMATION: isolated from library

<400> SEQUENCE: 130

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly His Arg Met Leu Asp
        35                  40                  45

Gly Val Gly Gly Leu Trp Asn Val Asn Ile Gly His Asn Arg Ala Ser
    50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
    130                 135                 140

Arg Asn Gly Tyr His Gly Val His Met Gly Gly Thr Ser Val Gly Gly
145                 150                 155                 160

Ile Gly Val Leu His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205
```

```
Ala Leu Leu Gly Ala Gln Thr Ile Ala Ala Leu Ile Ala Glu Pro Val
    210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
                260                 265                 270

Trp Gly Val Ala Pro Asp Ile Leu Cys Leu Ala Lys Gly Ile Thr Ala
            275                 280                 285

Gly Tyr Ile Pro Leu Gly Ala Thr Leu Phe Asn Gln Arg Ile Ala Asp
    290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Ala Leu Ala Val Leu
                325                 330                 335

Asp Ile Val Glu Ala Glu Asp Leu Pro Gly Asn Ala Ala Lys Val Gly
                340                 345                 350

Ala Gln Leu Leu Glu Gln Leu Gln Pro Leu Val Glu Arg Tyr Ala Val
            355                 360                 365

Val Gly Glu Val Arg Gly Lys Gly Leu Met Ile Ala Leu Asp Leu Val
    370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Arg Pro
                405                 410                 415

Ile Gly Asn Lys Ile Ile Leu Ser Pro Pro Leu Thr Leu Thr Arg Asp
                420                 425                 430

Glu Ala Gly Leu Met Val Ser Ala Leu Glu Ala Ala Phe Ala Arg Cys
            435                 440                 445

Gly
```

<210> SEQ ID NO 131
<211> LENGTH: 449
<212> TYPE: PRT
<213> ORGANISM: unknown
<220> FEATURE:
<223> OTHER INFORMATION: isolated from library

<400> SEQUENCE: 131

```
Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Leu Ile Ala Arg
            20                  25                  30

Gly Asp Gly Asn Tyr Ile Thr Asp Ile Asp Gly Gln Arg Met Leu Asp
        35                  40                  45

Gly Val Gly Gly Leu Trp Asn Val Asn Ile Gly His Asn Arg Ala Ser
    50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
            100                 105                 110
```

Ser Gly Gly Ser Asp Ala Val Glu Thr Ala Leu Lys Met Ala Arg Gln
            115                 120                 125

Tyr Trp Ile Ala Ser Gly Glu Pro Gly Arg Thr Arg Phe Leu Ser Leu
        130                 135                 140

Arg Asn Gly Tyr His Gly Val His Met Gly Gly Thr Ser Val Gly Gly
145                 150                 155                 160

Ile Gly Val Leu His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
    210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala
        275                 280                 285

Gly Tyr Ile Pro Leu Gly Ala Thr Leu Phe Asn Gln Arg Ile Ala Asp
    290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Ala Leu Ala Val Leu
                325                 330                 335

Asp Ile Val Glu Ala Glu Asp Leu Pro Gly Asn Ala Ala Lys Val Gly
            340                 345                 350

Ala Gln Leu Leu Glu Gln Leu Gln Pro Leu Val Glu Arg Tyr Ala Val
        355                 360                 365

Val Gly Glu Val Arg Gly Lys Gly Leu Met Ile Ala Leu Asp Leu Val
    370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Arg Pro
                405                 410                 415

Ile Gly Asn Lys Ile Ile Leu Ser Pro Pro Leu Thr Leu Thr Arg Asp
            420                 425                 430

Glu Ala Gly Leu Met Val Ser Ala Leu Glu Ala Ala Phe Ala Arg Cys
        435                 440                 445

Gly

<210> SEQ ID NO 132
<211> LENGTH: 449
<212> TYPE: PRT
<213> ORGANISM: unknown
<220> FEATURE:
<223> OTHER INFORMATION: isolated from library

<400> SEQUENCE: 132

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg

```
            20                  25                  30
Gly Asp Gly Asn Tyr Ile Thr Asp Ile Asp Gly Gln Arg Met Leu Asp
            35                  40                  45
Gly Val Gly Gly Leu Trp Asn Val Asn Ile Gly His Asn Arg Ala Ser
50                  55                  60
Val Lys Ala Ala Ile Ala Gln Leu Asp Glu Leu Ala Tyr Tyr Gln
65                  70                  75                  80
Thr Phe Asp Gly Ile Ala Thr Pro Arg Val Phe Asp Leu Ala Glu Arg
                    85                  90                  95
Leu Thr Gly Met Phe Ala Gln Glu Arg Met Ala Arg Val Leu Phe Ser
                100                 105                 110
Ser Gly Gly Ser Asp Ala Val Glu Thr Ala Leu Lys Met Ala Arg Gln
            115                 120                 125
Tyr Trp Ile Ala Ser Gly Glu Pro Gly Arg Thr Arg Phe Leu Ser Leu
            130                 135                 140
Arg Asn Gly Tyr His Gly Val His Met Gly Gly Thr Ser Val Gly Gly
145                 150                 155                 160
Ile Gly Val Leu His Tyr Asn His Gly Gln Leu Leu Ala Gly Cys His
                165                 170                 175
Leu Leu Asp Thr Pro Trp Leu Tyr Arg Asn Pro Trp Asp Cys Arg Asp
                180                 185                 190
Pro Gln Ala Leu Thr Ala His Cys Ile Arg Gln Leu Glu Glu Gln Ile
            195                 200                 205
Ala Leu Leu Gly Ala Gln Thr Ile Ala Ala Leu Ile Ala Glu Pro Val
            210                 215                 220
Gln Gly Ala Gly Gly Val Ile Val Pro Pro Ala Asp Tyr Trp Pro Arg
225                 230                 235                 240
Leu Arg Glu Val Cys Asp Arg His Gly Ile Leu Leu Ile Ala Asp Glu
                245                 250                 255
Val Val Thr Gly Phe Gly Arg Ser Gly Cys Met Leu Gly Ser Arg Gly
                260                 265                 270
Trp Gly Val Ala Pro Asp Ile Leu Cys Leu Ala Lys Gly Ile Thr Ala
            275                 280                 285
Gly Tyr Ile Pro Leu Gly Ala Thr Leu Phe Asn Gln Arg Ile Ala Asp
            290                 295                 300
Ala Ile Glu Asn Gly Gln Gly Phe Ser His Met Ile His Gly Tyr
305                 310                 315                 320
Thr Tyr Ser Gly His Pro Thr Ala Cys Ala Ala Ala Leu Ala Val Leu
                325                 330                 335
Asp Ile Val Glu Ala Glu Asp Leu Pro Gly Asn Ala Ala Lys Val Gly
            340                 345                 350
Ala Gln Leu Leu Glu Gln Leu Gln Pro Leu Val Glu Arg Tyr Ala Val
            355                 360                 365
Val Gly Glu Val Arg Gly Lys Gly Leu Met Ile Ala Leu Asp Leu Val
            370                 375                 380
Ser Asp Lys Arg Thr Arg Gln Pro Leu Asp Pro Ala Ala Gly Gln Pro
385                 390                 395                 400
Ser Arg Ile Ala Asp Glu Ala Arg Ala Gly Val Leu Val Arg Pro
                405                 410                 415
Ile Gly Asn Lys Ile Ile Leu Ser Pro Pro Leu Thr Leu Thr Arg Asp
            420                 425                 430
Glu Ala Gly Leu Met Val Ser Ala Leu Glu Ala Ala Phe Ala Arg Cys
            435                 440                 445
```

Gly

<210> SEQ ID NO 133
<211> LENGTH: 449
<212> TYPE: PRT
<213> ORGANISM: unknown
<220> FEATURE:
<223> OTHER INFORMATION: isolated from library

<400> SEQUENCE: 133

```
Met Tyr Glu Lys Tyr Lys Asn Ala Arg Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
        35                  40                  45

Gly Val Gly Gly Leu Trp Asn Val Asn Ile Gly His Asn Arg Ala Ser
50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
130                 135                 140

Arg Asn Gly Tyr His Gly Val His Met Gly Gly Thr Ser Val Gly Gly
145                 150                 155                 160

Ile Gly Val Leu His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala
        275                 280                 285

Gly Tyr Ile Pro Leu Gly Ala Thr Leu Phe Asn Gln Arg Ile Ala Asp
290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Ala Leu Ala Val Leu
                325                 330                 335

Asp Ile Val Glu Ala Glu Asp Leu Pro Gly Asn Ala Ala Lys Val Gly
            340                 345                 350
```

```
Ala Gln Leu Leu Glu Gln Leu Gln Pro Leu Val Glu Arg Tyr Ala Val
        355                 360                 365

Val Gly Glu Val Arg Gly Lys Gly Leu Met Ile Ala Leu Asp Leu Val
    370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Ala Gly Val Leu Val Arg Pro
                405                 410                 415

Ile Gly Asn Lys Ile Ile Leu Ser Pro Pro Leu Thr Leu Thr Arg Asp
                420                 425                 430

Glu Ala Gly Leu Met Val Ser Ala Leu Glu Ala Ala Phe Ala Arg Cys
                435                 440                 445

Gly

<210> SEQ ID NO 134
<211> LENGTH: 449
<212> TYPE: PRT
<213> ORGANISM: unknown
<220> FEATURE:
<223> OTHER INFORMATION: isolated from library

<400> SEQUENCE: 134

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
                20                  25                  30

Gly Asp Gly Asn Tyr Ile Thr Asp Ile Asp Gly Gln Arg Met Leu Asp
            35                  40                  45

Gly Val Gly Gly Leu Trp Asn Val Asn Ile Gly His Asn Arg Ala Ser
        50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
                100                 105                 110

Ser Gly Gly Ser Asp Ala Val Glu Thr Ala Leu Lys Met Ala Arg Gln
            115                 120                 125

Tyr Trp Ile Ala Ser Gly Glu Pro Gly Arg Thr Arg Phe Leu Ser Leu
130                 135                 140

Arg Asn Ser Tyr His Gly Val His Met Gly Gly Thr Ser Val Gly Gly
145                 150                 155                 160

Ile Gly Val Leu His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
                180                 185                 190

Pro Gln Ala Leu Thr Ala His Cys Ile Arg Gln Leu Glu Glu Gln Ile
            195                 200                 205

Ala Leu Leu Gly Ala Gln Thr Ile Ala Ala Leu Ile Ala Glu Pro Val
        210                 215                 220

Gln Gly Ala Gly Gly Val Ile Val Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
```

```
                    260                 265                 270
Trp Gly Val Ala Pro Asp Ile Leu Cys Leu Ala Lys Gly Ile Thr Ala
                275                 280                 285

Gly Tyr Ile Pro Leu Gly Ala Thr Leu Phe Asn Gln Arg Ile Ala Asp
            290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Leu Ala Val Leu
                325                 330                 335

Asp Ile Val Glu Ala Glu Asp Leu Pro Gly Asn Ala Ala Lys Val Gly
                340                 345                 350

Ala Gln Leu Leu Glu Gln Leu Gln Pro Leu Val Glu Arg Tyr Ala Val
                355                 360                 365

Val Gly Glu Val Arg Gly Lys Gly Leu Met Ile Ala Leu Asp Leu Val
                370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Ala Gly Val Leu Val Arg Pro
                405                 410                 415

Ile Gly Asn Lys Ile Ile Leu Ser Pro Pro Leu Thr Leu Thr Arg Asp
                420                 425                 430

Glu Ala Gly Leu Met Val Ser Ala Leu Glu Ala Phe Ala Arg Cys
                435                 440                 445

Gly

<210> SEQ ID NO 135
<211> LENGTH: 449
<212> TYPE: PRT
<213> ORGANISM: unknown
<220> FEATURE:
<223> OTHER INFORMATION: isolated from library

<400> SEQUENCE: 135

Met Tyr Glu Lys Tyr Lys Leu Ala Glu Lys Lys Phe Trp His Pro Met
1               5                   10                  15

Gly Ser Ser Ala Ala Pro His Arg Asp Lys Thr Leu Val Ile Ala Arg
                20                  25                  30

Gly Asp Gly Asn Tyr Ile Thr Asp Ile Asp Gly Gln Arg Met Leu Asp
            35                  40                  45

Gly Val Gly Gly Leu Trp Asn Val Asn Ile Gly His Asn Arg Ala Ser
        50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
                100                 105                 110

Ser Gly Gly Ser Asp Ala Val Glu Thr Ala Leu Lys Met Ala Arg Gln
            115                 120                 125

Tyr Trp Ile Ala Ser Gly Glu Pro Gly Arg Thr Arg Phe Leu Ser Leu
        130                 135                 140

Arg Asn Gly Tyr His Gly Val His Met Gly Gly Thr Ser Val Gly Gly
145                 150                 155                 160

Ile Gly Val Leu His Tyr Asn His Gly Gln Leu Leu Ala Gly Cys His
                165                 170                 175
```

```
Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
    210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Ile Ala Asp Glu
                245                 250                 255

Val Val Thr Gly Phe Gly Arg Ser Gly Cys Met Leu Gly Ser Arg Gly
                260                 265                 270

Trp Gly Val Ala Pro Asp Ile Leu Cys Leu Ala Lys Gly Ile Thr Ala
            275                 280                 285

Gly Tyr Ile Pro Leu Gly Ala Thr Leu Phe Asn Gln Arg Ile Ala Asp
        290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Ala Leu Ala Val Leu
                325                 330                 335

Asp Ile Val Glu Ala Glu Asp Leu Pro Gly Asn Ala Ala Lys Val Gly
            340                 345                 350

Ala Gln Leu Leu Glu Gln Leu Gln Pro Leu Val Glu Arg Tyr Ala Val
        355                 360                 365

Val Gly Glu Val Arg Gly Lys Gly Leu Met Ile Ala Leu Asp Leu Val
    370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Ala Gly Val Leu Val Arg Pro
                405                 410                 415

Ile Gly Asn Lys Ile Ile Leu Ser Pro Pro Leu Thr Leu Thr Arg Asp
            420                 425                 430

Glu Ala Gly Leu Met Val Ser Ala Leu Glu Ala Ala Phe Ala Arg Cys
        435                 440                 445

Gly

<210> SEQ ID NO 136
<211> LENGTH: 449
<212> TYPE: PRT
<213> ORGANISM: unknown
<220> FEATURE:
<223> OTHER INFORMATION: isolated from library

<400> SEQUENCE: 136

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
        35                  40                  45

Gly Val Gly Gly Leu Trp Asn Val Asn Ile Gly His Asn Arg Ala Ser
    50                  55                  60

Val Lys Ala Ala Ile Ala Ala Gln Leu Asp Glu Leu Ala Tyr Tyr Gln
65                  70                  75                  80
```

-continued

Thr Phe Asp Gly Ile Ala His Pro Arg Val Phe Asp Leu Ala Glu Arg
                 85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Pro Gly Arg Thr Lys Phe Leu Ser Leu
        130                 135                 140

Arg Asn Gly Tyr His Gly Val His Met Gly Thr Ser Val Gly Gly
145                 150                 155                 160

Ile Gly Val Leu His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
        210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Ile Ala Asp Glu
                245                 250                 255

Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala
        275                 280                 285

Gly Tyr Ile Pro Leu Gly Ala Thr Leu Phe Asn Gln Arg Ile Ala Asp
        290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Ala Leu Ala Val Leu
                325                 330                 335

Asp Ile Val Glu Ala Glu Asp Leu Pro Gly Asn Ala Ala Lys Val Gly
            340                 345                 350

Ala Gln Leu Leu Glu Gln Leu Gln Pro Leu Val Glu Arg Tyr Ala Val
        355                 360                 365

Val Gly Glu Val Arg Gly Lys Gly Leu Met Ile Ala Leu Asp Leu Val
370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Ala Gly Val Leu Val Arg Pro
                405                 410                 415

Ile Gly Asn Lys Ile Ile Leu Ser Pro Pro Leu Thr Leu Thr Arg Asp
            420                 425                 430

Glu Ala Gly Leu Met Val Ser Ala Leu Glu Ala Ala Phe Ala Arg Cys
        435                 440                 445

Gly

<210> SEQ ID NO 137
<211> LENGTH: 449
<212> TYPE: PRT
<213> ORGANISM: unknown
<220> FEATURE:
<223> OTHER INFORMATION: isolated from library

```
<400> SEQUENCE: 137

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
        35                  40                  45

Gly Val Gly Gly Leu Trp Asn Val Asn Ile Gly His Asn Arg Ala Ser
    50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
    130                 135                 140

Arg Asn Gly Tyr His Gly Val His Met Gly Gly Thr Ser Val Gly Gly
145                 150                 155                 160

Ile Gly Val Leu Arg Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
    210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala
        275                 280                 285

Gly Tyr Ile Pro Leu Gly Ala Thr Leu Phe Asn Gln Arg Ile Ala Asp
    290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Leu Ala Val Leu
                325                 330                 335

Asp Ile Val Glu Ala Glu Asp Leu Pro Gly Asn Ala Ala Lys Val Gly
            340                 345                 350

Ala Gln Leu Leu Glu Gln Leu Gln Pro Leu Val Glu Arg Tyr Ala Val
        355                 360                 365

Val Gly Glu Val Arg Gly Lys Gly Leu Met Ile Ala Leu Asp Leu Val
    370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Arg Pro
                405                 410                 415
```

```
Ile Gly Asn Lys Ile Ile Leu Ser Pro Pro Leu Thr Leu Thr Arg Asp
            420                 425                 430

Glu Ala Gly Leu Met Val Ser Ala Leu Glu Ala Ala Phe Ala Arg Cys
            435                 440                 445

Gly

<210> SEQ ID NO 138
<211> LENGTH: 449
<212> TYPE: PRT
<213> ORGANISM: unknown
<220> FEATURE:
<223> OTHER INFORMATION: isolated from library

<400> SEQUENCE: 138

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
        35                  40                  45

Gly Val Gly Gly Leu Trp Asn Val Asn Ile Gly His Asn Arg Ala Ser
    50                  55                  60

Val Lys Ala Ala Ile Ala Ala Gln Leu Asp Glu Leu Ala Tyr Tyr Gln
65                  70                  75                  80

Thr Phe Asp Gly Ile Ala Asn Pro Arg Val Phe Asp Leu Ala Glu Arg
                85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
130                 135                 140

Arg Asn Gly Tyr His Gly Val His Met Gly Gly Thr Ser Val Gly Gly
145                 150                 155                 160

Ile Gly Val Leu His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
    210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala
        275                 280                 285

Gly Tyr Ile Pro Leu Gly Ala Thr Leu Phe Asn Gln Arg Ile Ala Asp
    290                 295                 300

Ala Ile Glu Asn Gly Gln Gly Phe Ser His Met Ile Met His Gly Tyr
305                 310                 315                 320
```

```
Thr Tyr Ser Gly His Pro Thr Ala Cys Ala Ala Leu Ala Val Leu
                325                 330                 335

Asp Ile Val Glu Ala Glu Asp Leu Pro Gly Asn Ala Ala Lys Val Gly
            340                 345                 350

Ala Gln Leu Leu Glu Gln Leu Gln Pro Leu Val Glu Arg Tyr Ala Val
            355                 360                 365

Val Gly Glu Val Arg Gly Lys Gly Leu Met Ile Ala Leu Asp Leu Val
    370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Arg Pro
                405                 410                 415

Ile Gly Asn Lys Ile Ile Leu Ser Pro Pro Leu Thr Leu Thr Arg Asp
            420                 425                 430

Glu Ala Gly Leu Met Val Ser Ala Leu Glu Ala Ala Phe Ala Arg Cys
                435                 440                 445

Gly

<210> SEQ ID NO 139
<211> LENGTH: 449
<212> TYPE: PRT
<213> ORGANISM: unknown
<220> FEATURE:
<223> OTHER INFORMATION: isolated from library

<400> SEQUENCE: 139

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Ile Ile Ala Arg
            20                  25                  30

Gly Asp Gly Asn Tyr Ile Thr Asp Ile Asp Gly Gln Arg Met Leu Asp
        35                  40                  45

Gly Val Gly Gly Leu Trp Asn Val Asn Ile Gly His Asn Arg Ala Ser
    50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
    130                 135                 140

Arg Asn Gly Tyr His Gly Val His Met Gly Gly Thr Ser Val Gly Gly
145                 150                 155                 160

Ile Gly Val Leu His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
    210                 215                 220

Gln Gly Ala Gly Gly Val Ile Val Pro Pro Ala Asp Tyr Trp Pro Arg
```

```
            225                 230                 235                 240
Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
                260                 265                 270

Trp Gly Val Ala Pro Asp Ile Leu Cys Leu Ala Lys Gly Ile Thr Ala
                275                 280                 285

Gly Tyr Ile Pro Leu Gly Ala Thr Leu Phe Asn Gln Arg Ile Ala Asp
                290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Leu Ala Val Leu
                325                 330                 335

Asp Ile Val Glu Ala Glu Asp Leu Pro Gly Asn Ala Ala Lys Val Gly
                340                 345                 350

Ala Gln Leu Leu Glu Gln Leu Gln Pro Leu Val Glu Arg Tyr Ala Val
                355                 360                 365

Val Gly Glu Val Arg Gly Lys Gly Leu Met Ile Ala Leu Asp Leu Val
                370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Arg Pro
                405                 410                 415

Ile Gly Asn Lys Ile Ile Leu Ser Pro Pro Leu Thr Leu Thr Arg Asp
                420                 425                 430

Glu Ala Gly Leu Met Val Ser Ala Leu Glu Ala Ala Phe Ala Arg Cys
                435                 440                 445

Gly

<210> SEQ ID NO 140
<211> LENGTH: 449
<212> TYPE: PRT
<213> ORGANISM: unknown
<220> FEATURE:
<223> OTHER INFORMATION: isolated from library

<400> SEQUENCE: 140

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
                20                  25                  30

Gly Asp Gly Asn Tyr Ile Thr Asp Ile Asp Gly Gln Arg Met Leu Asp
                35                  40                  45

Gly Val Gly Gly Leu Trp Asn Val Asn Ile Gly His Asn Arg Ala Ser
                50                  55                  60

Val Lys Ala Ala Ile Ala Gly Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
                100                 105                 110

Ser Gly Gly Ser Asp Ala Val Glu Thr Ala Leu Lys Met Ala Arg Gln
                115                 120                 125

Tyr Trp Ile Ala Ser Gly Glu Pro Gly Arg Thr Arg Phe Leu Ser Leu
                130                 135                 140
```

```
Arg Asn Gly Tyr His Gly Val His Met Gly Gly Thr Ser Val Gly Gly
145                 150                 155                 160

Ile Gly Val Leu His Tyr Asn His Gly Gln Leu Leu Ala Gly Cys His
            165                 170                 175

Leu Leu Asp Thr Pro Trp Leu Tyr Arg Asn Pro Trp Asp Cys Arg Asp
        180                 185                 190

Pro Gln Ala Leu Thr Ala His Cys Ile Arg Gln Leu Glu Glu Gln Ile
            195                 200                 205

Ala Leu Leu Gly Ala Gln Thr Ile Ala Ala Leu Ile Ala Glu Pro Val
        210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala
        275                 280                 285

Gly Tyr Ile Pro Leu Gly Ala Thr Leu Phe Asn Gln Arg Ile Ala Asp
290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Ala Leu Ala Val Leu
            325                 330                 335

Asp Ile Val Glu Ala Glu Asp Leu Pro Gly Asn Ala Ala Lys Val Gly
        340                 345                 350

Ala Gln Leu Leu Glu Gln Leu Gln Pro Leu Val Glu Arg Tyr Ala Val
            355                 360                 365

Val Gly Glu Val Arg Gly Lys Gly Leu Met Ile Ala Leu Asp Leu Val
        370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Arg Pro
                405                 410                 415

Ile Gly Asn Lys Ile Ile Leu Ser Pro Pro Leu Thr Leu Thr Arg Asp
            420                 425                 430

Glu Ala Gly Leu Met Val Ser Ala Leu Glu Ala Ala Phe Ala Arg Cys
        435                 440                 445

Gly

<210> SEQ ID NO 141
<211> LENGTH: 449
<212> TYPE: PRT
<213> ORGANISM: unknown
<220> FEATURE:
<223> OTHER INFORMATION: isolated from library

<400> SEQUENCE: 141

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
        35                  40                  45
```

Gly Val Gly Gly Leu Trp Asn Val Asn Ile Gly His Asn Arg Ala Ser
 50                  55                  60

Val Lys Ala Ala Ile Ala Ala Gln Leu Asp Glu Leu Ala Tyr Tyr Gln
 65                  70                  75                  80

Thr Phe Asp Gly Ile Ala His Pro Arg Val Phe Asp Leu Ala Glu Arg
                 85                  90                  95

Leu Thr Gly Met Phe Ala Gln Glu Arg Met Ala Arg Val Leu Phe Ser
            100                 105                 110

Ser Ser Gly Ser Asp Ala Val Glu Thr Ala Leu Lys Met Ala Arg Gln
            115                 120                 125

Tyr Trp Ile Ala Ser Gly Glu Pro Gly Arg Thr Arg Phe Leu Ser Leu
        130                 135                 140

Arg Asn Gly Tyr His Gly Val His Met Gly Gly Thr Ser Val Gly Gly
145                 150                 155                 160

Ile Gly Val Leu His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala
        275                 280                 285

Gly Tyr Ile Pro Leu Gly Ala Thr Leu Phe Asn Gln Arg Ile Ala Asp
        290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Ala Leu Ala Val Leu
                325                 330                 335

Asp Ile Val Glu Ala Glu Asp Leu Pro Gly Asn Ala Ala Lys Val Gly
            340                 345                 350

Ala Gln Leu Leu Glu Gln Leu Gln Pro Leu Val Glu Arg Tyr Ala Val
        355                 360                 365

Val Gly Glu Val Arg Gly Lys Gly Leu Met Ile Ala Leu Asp Leu Val
370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Arg Pro
                405                 410                 415

Ile Gly Asn Lys Ile Ile Leu Ser Pro Pro Leu Thr Leu Thr Arg Asp
            420                 425                 430

Glu Ala Gly Leu Met Val Ser Ala Leu Glu Ala Ala Phe Ala Arg Cys
        435                 440                 445

Gly

<210> SEQ ID NO 142

```
<211> LENGTH: 449
<212> TYPE: PRT
<213> ORGANISM: unknown
<220> FEATURE:
<223> OTHER INFORMATION: isolated from library

<400> SEQUENCE: 142

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
        35                  40                  45

Gly Val Gly Gly Leu Trp Asn Val Asn Ile Gly His Asn Arg Ala Ser
    50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Ile Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
    130                 135                 140

Arg Asn Gly Tyr His Gly Val His Met Gly Gly Thr Ser Val Gly Gly
145                 150                 155                 160

Ile Gly Val Leu His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
    210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala
        275                 280                 285

Gly Tyr Ile Pro Leu Gly Ala Thr Leu Phe Asn Gln Arg Ile Ala Asp
    290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Ala Leu Ala Val Leu
                325                 330                 335

Asp Ile Val Glu Ala Glu Asp Leu Pro Gly Asn Ala Ala Lys Val Gly
            340                 345                 350

Ala Gln Leu Leu Glu Gln Leu Gln Pro Leu Val Glu Arg Tyr Ala Val
        355                 360                 365

Val Gly Glu Val Arg Gly Lys Gly Leu Met Ile Ala Leu Asp Leu Val
    370                 375                 380
```

```
Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Arg Pro
                405                 410                 415

Ile Gly Asn Lys Ile Ile Leu Ser Pro Pro Leu Thr Leu Thr Arg Asp
            420                 425                 430

Glu Ala Gly Leu Met Val Ser Ala Leu Glu Ala Ala Phe Ala Arg Cys
            435                 440                 445

Gly

<210> SEQ ID NO 143
<211> LENGTH: 449
<212> TYPE: PRT
<213> ORGANISM: unknown
<220> FEATURE:
<223> OTHER INFORMATION: isolated from library

<400> SEQUENCE: 143

Met Tyr Glu Lys Tyr Lys Asn Ala Glu Lys Lys Phe Trp His Pro Met
1               5                   10                  15

Gly Ser Ser Ala Ala Pro His Arg Asp Lys Thr Leu Val Ile Ala Arg
            20                  25                  30

Gly Asp Gly Asn Tyr Ile Thr Asp Ile Asp Gly Gln Arg Met Leu Asp
        35                  40                  45

Gly Val Gly Gly Leu Trp Asn Val Asn Ile Gly His Asn Arg Ala Ser
    50                  55                  60

Val Lys Ala Ala Ile Ala Ala Gln Leu Asp Glu Leu Ala Tyr Tyr Gln
65                  70                  75                  80

Thr Phe Asp Gly Ile Ala His Pro Arg Val Phe Asp Leu Ala Glu Arg
                85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
    130                 135                 140

Arg Asn Gly Tyr His Gly Val His Met Gly Gly Thr Ser Val Gly Gly
145                 150                 155                 160

Ile Gly Val Leu His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
    210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala
        275                 280                 285
```

```
Gly Tyr Ile Pro Leu Gly Ala Thr Leu Phe Asn Gln Arg Ile Ala Asp
        290                 295                 300
Ala Ile Glu Asn Gly Gln Gly Phe Ser His Met Ile Met His Gly Tyr
305                 310                 315                 320
Thr Tyr Ser Gly His Pro Thr Ala Cys Ala Ala Leu Ala Val Leu
                325                 330                 335
Asp Ile Val Glu Ala Glu Asp Leu Pro Gly Asn Ala Ala Lys Val Gly
            340                 345                 350
Ala Gln Leu Leu Glu Gln Leu Gln Pro Leu Val Glu Arg Tyr Ala Val
        355                 360                 365
Val Gly Glu Val Arg Gly Lys Gly Leu Met Ile Ala Leu Asp Leu Val
370                 375                 380
Ser Asp Lys Arg Thr Arg Glu Pro Leu Asp Pro Ala Ala Gly Gln Pro
385                 390                 395                 400
Ser Arg Ile Ala Asp Glu Ala Arg Arg Ala Gly Val Leu Val Arg Pro
                405                 410                 415
Ile Gly Asn Lys Ile Ile Leu Ser Pro Pro Leu Thr Leu Thr Arg Asp
            420                 425                 430
Glu Ala Gly Leu Met Val Ser Ala Leu Glu Ala Ala Phe Ala Arg Cys
        435                 440                 445
Gly

<210> SEQ ID NO 144
<211> LENGTH: 449
<212> TYPE: PRT
<213> ORGANISM: unknown
<220> FEATURE:
<223> OTHER INFORMATION: isolated from library

<400> SEQUENCE: 144

Met Tyr Glu Lys Tyr Lys Asn Ala Glu Lys Lys Phe Trp His Pro Trp
1               5                   10                  15
Gly Ser Ser Ala Ala Pro His Arg Asp Lys Thr Leu Val Ile Ala Arg
            20                  25                  30
Gly Asp Gly Asn Tyr Ile Thr Asp Ile Asp Gly Gln Arg Met Leu Asp
        35                  40                  45
Gly Val Gly Gly Leu Trp Asn Val Asn Ile Gly His Asn Arg Ala Ser
    50                  55                  60
Val Lys Ala Ala Ile Ala Ala Gln Leu Asp Glu Leu Ala Tyr Tyr Gln
65                  70                  75                  80
Thr Phe Asp Gly Ile Ala His Pro Arg Val Phe Asp Leu Ala Glu Arg
                85                  90                  95
Leu Thr Gly Met Phe Ala Gln Glu Arg Met Ala Arg Val Leu Phe Ser
            100                 105                 110
Ser Gly Gly Ser Asp Ala Val Glu Thr Ala Leu Lys Met Ala Arg Gln
        115                 120                 125
Tyr Trp Ile Ala Ser Gly Glu Pro Gly Arg Thr Arg Phe Leu Ser Leu
    130                 135                 140
Arg Asn Gly Tyr His Gly Val His Met Gly Gly Thr Ser Val Gly Gly
145                 150                 155                 160
Ile Gly Val Leu His Tyr Asn His Gly Gln Leu Leu Ala Gly Cys His
                165                 170                 175
Leu Leu Asp Thr Pro Trp Leu Tyr Arg Asn Pro Trp Asp Cys Arg Asp
            180                 185                 190
Pro Gln Ala Leu Thr Ala His Cys Ile Arg Gln Leu Glu Glu Gln Ile
```

```
                195                 200                 205
Ala Leu Leu Gly Ala Gln Thr Ile Ala Leu Ile Ala Glu Pro Val
            210                 215                 220
Gln Gly Ala Gly Gly Ala Ile Val Pro Pro Ala Asp Tyr Trp Pro Arg
225                 230                 235                 240
Leu Arg Glu Val Cys Asp Arg His Gly Ile Leu Leu Ile Ala Asp Glu
                245                 250                 255
Val Val Thr Gly Phe Gly Arg Ser Gly Cys Met Leu Gly Ser Arg Gly
                260                 265                 270
Trp Gly Val Ala Pro Asp Ile Leu Cys Leu Ala Lys Gly Ile Thr Ala
            275                 280                 285
Gly Tyr Ile Pro Leu Gly Ala Thr Leu Phe Asn Gln Arg Ile Ala Asp
            290                 295                 300
Ala Ile Glu Asn Gly Gln Gly Phe Ser His Met Ile Met His Gly Tyr
305                 310                 315                 320
Thr Tyr Ser Gly His Pro Thr Ala Cys Ala Ala Leu Ala Val Leu
                325                 330                 335
Asp Ile Val Glu Ala Glu Asp Leu Pro Gly Asn Ala Ala Lys Val Gly
                340                 345                 350
Ala Gln Leu Leu Glu Gln Leu Gln Pro Leu Val Glu Arg Tyr Ala Val
            355                 360                 365
Val Gly Glu Val Arg Gly Lys Gly Leu Met Ile Ala Leu Asp Leu Val
            370                 375                 380
Ser Asp Lys Arg Thr Arg Gln Pro Leu Asp Pro Ala Ala Gly Gln Pro
385                 390                 395                 400
Ser Arg Ile Ala Asp Glu Ala Arg Arg Ala Gly Val Leu Val Arg Pro
                405                 410                 415
Ile Gly Asn Lys Ile Ile Leu Ser Pro Pro Leu Thr Leu Thr Arg Asp
            420                 425                 430
Glu Ala Gly Leu Met Val Ser Ala Leu Glu Ala Ala Phe Ala Arg Cys
            435                 440                 445
Gly

<210> SEQ ID NO 145
<211> LENGTH: 449
<212> TYPE: PRT
<213> ORGANISM: unknown
<220> FEATURE:
<223> OTHER INFORMATION: isolated from library

<400> SEQUENCE: 145

Met Tyr Glu Lys Tyr Lys Asn Ala Glu Lys Lys Phe Trp His Pro Phe
1               5                   10                  15
Gly Ser Ser Ala Ala Pro His Arg Asp Lys Thr Leu Val Ile Ala Arg
                20                  25                  30
Gly Asp Gly Asn Tyr Ile Thr Asp Ile Asp Gly Gln Arg Met Leu Asp
            35                  40                  45
Gly Val Gly Gly Leu Trp Asn Val Asn Ile Gly His Asn Arg Ala Ser
        50                  55                  60
Val Lys Ala Ala Ile Ala Ala Gln Leu Asp Glu Leu Ala Tyr Tyr Gln
65                  70                  75                  80
Thr Phe Asp Gly Ile Ala His Pro Arg Val Phe Asp Leu Ala Glu Arg
                85                  90                  95
Leu Thr Gly Met Phe Ala Gln Glu Arg Met Ala Arg Val Leu Phe Ser
                100                 105                 110
```

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
        130                 135                 140

Arg Asn Gly Tyr His Gly Val His Met Gly Gly Thr Ser Val Gly Gly
145                 150                 155                 160

Met Gly Val Ile His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
    210                 215                 220

Gln Gly Ala Gly Gly Ala Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala
        275                 280                 285

Gly Tyr Ile Pro Leu Gly Ala Thr Leu Phe Asn Gln Arg Ile Ala Asp
    290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Ala Leu Ala Val Leu
                325                 330                 335

Asp Ile Val Glu Ala Glu Asp Leu Pro Gly Asn Ala Ala Lys Val Gly
            340                 345                 350

Ala Gln Leu Leu Glu Gln Leu Gln Pro Leu Val Glu Arg Tyr Ala Val
        355                 360                 365

Val Gly Glu Val Arg Gly Lys Gly Leu Met Ile Ala Leu Asp Leu Val
    370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Ala Gly Val Leu Val Arg Pro
                405                 410                 415

Ile Gly Asn Lys Ile Ile Leu Ser Pro Pro Leu Thr Leu Thr Arg Asp
            420                 425                 430

Glu Ala Gly Leu Met Val Ser Ala Leu Glu Ala Ala Phe Ala Arg Cys
        435                 440                 445

Gly

<210> SEQ ID NO 146
<211> LENGTH: 449
<212> TYPE: PRT
<213> ORGANISM: unknown
<220> FEATURE:
<223> OTHER INFORMATION: isolated from library

<400> SEQUENCE: 146

Met Tyr Glu Lys Tyr Lys Asn Ala Glu Lys Lys Phe Trp His Pro Trp
1               5                   10                  15

```
Gly Ser Ser Ala Ala Pro His Arg Asp Lys Thr Leu Val Ile Ala Arg
             20                  25                  30

Gly Asp Gly Asn Tyr Ile Thr Asp Ile Asp Gly Gln Arg Met Leu Asp
         35                  40                  45

Gly Val Gly Gly Leu Ala Asn Val Asn Ile Gly His Asn Arg Ala Ser
     50                  55                  60

Val Lys Ala Ala Ile Ala Ala Gln Leu Asp Glu Leu Ala Tyr Tyr Gln
 65                  70                  75                  80

Thr Phe Asp Gly Ile Ala His Pro Arg Val Phe Asp Leu Ala Glu Arg
                 85                  90                  95

Leu Thr Gly Met Phe Ala Gln Glu Arg Met Ala Arg Val Leu Phe Ser
            100                 105                 110

Ser Gly Gly Ser Asp Ala Val Glu Thr Ala Leu Lys Met Ala Arg Gln
        115                 120                 125

Tyr Trp Ile Ala Ser Gly Glu Pro Gly Arg Thr Arg Phe Leu Ser Leu
    130                 135                 140

Arg Asn Gly Tyr His Gly Val His Met Gly Gly Thr Ser Val Gly Gly
145                 150                 155                 160

Gln Gly Val Leu His Tyr Asn His Gly Gln Leu Leu Ala Gly Cys His
                165                 170                 175

Leu Leu Asp Thr Pro Trp Leu Tyr Arg Asn Pro Trp Asp Cys Arg Asp
            180                 185                 190

Pro Gln Ala Leu Thr Ala His Cys Ile Arg Gln Leu Glu Glu Gln Ile
        195                 200                 205

Ala Leu Leu Gly Ala Gln Thr Ile Ala Ala Leu Ile Ala Glu Pro Val
210                 215                 220

Gln Gly Ala Gly Gly Val Ile Val Pro Pro Ala Asp Tyr Trp Pro Arg
225                 230                 235                 240

Leu Arg Glu Val Cys Asp Arg His Gly Ile Leu Leu Ile Ala Asp Glu
                245                 250                 255

Val Val Thr Gly Phe Gly Arg Ser Gly Cys Met Leu Gly Ser Arg Gly
            260                 265                 270

Trp Gly Val Ala Pro Asp Ile Leu Cys Leu Ala Lys Gly Ile Thr Ala
    275                 280                 285

Gly Tyr Ile Pro Leu Gly Ala Thr Leu Phe Asn Gln Arg Ile Ala Asp
290                 295                 300

Ala Ile Glu Asn Gly Gln Gly Phe Ser His Met Ile Met His Gly Tyr
305                 310                 315                 320

Thr Tyr Ser Gly His Pro Thr Ala Cys Ala Ala Leu Ala Val Leu
                325                 330                 335

Asp Ile Val Glu Ala Glu Asp Leu Pro Gly Asn Ala Ala Lys Val Gly
            340                 345                 350

Ala Gln Leu Leu Glu Gln Leu Gln Pro Leu Val Glu Arg Tyr Ala Val
        355                 360                 365

Val Gly Glu Val Arg Gly Lys Gly Leu Met Ile Ala Leu Asp Leu Val
    370                 375                 380

Ser Asp Lys Arg Thr Arg Gln Pro Leu Asp Pro Ala Ala Gly Gln Pro
385                 390                 395                 400

Ser Arg Ile Ala Asp Glu Ala Arg Arg Ala Gly Val Leu Val Arg Pro
                405                 410                 415

Ile Gly Asn Lys Ile Ile Leu Ser Pro Pro Leu Thr Leu Thr Arg Asp
            420                 425                 430

Glu Ala Gly Leu Met Val Ser Ala Leu Glu Ala Ala Phe Ala Arg Cys
```

Gly

<210> SEQ ID NO 147
<211> LENGTH: 476
<212> TYPE: PRT
<213> ORGANISM: Arthrobacter citreus

<400> SEQUENCE: 147

Met Gly Leu Thr Val Gln Lys Ile Asn Trp Glu Gln Val Lys Glu Trp
1               5                   10                  15

Asp Arg Lys Tyr Leu Met Arg Thr Phe Ser Thr Gln Asn Glu Tyr Gln
            20                  25                  30

Pro Val Pro Ile Glu Ser Thr Glu Gly Asp Tyr Leu Ile Met Pro Gly
        35                  40                  45

Gly Thr Arg Leu Leu Asp Phe Phe Asn Gln Leu Tyr Cys Val Asn Leu
    50                  55                  60

Gly Gln Lys Asn Gln Lys Val Asn Ala Ala Ile Lys Glu Ala Leu Asp
65                  70                  75                  80

Arg Tyr Gly Phe Val Trp Asp Thr Tyr Ala Thr Asp Tyr Lys Ala Lys
                85                  90                  95

Ala Ala Lys Ile Ile Ile Glu Asp Ile Leu Gly Asp Glu Asp Trp Pro
            100                 105                 110

Gly Lys Val Arg Phe Val Ser Thr Gly Ser Glu Ala Val Glu Thr Ala
        115                 120                 125

Leu Asn Ile Ala Arg Leu Tyr Thr Asn Arg Pro Leu Val Val Thr Arg
    130                 135                 140

Glu His Asp Tyr His Gly Trp Thr Gly Ala Ala Thr Val Thr Arg
145                 150                 155                 160

Leu Arg Ser Phe Arg Ser Gly Leu Val Gly Glu Asn Ser Glu Ser Phe
                165                 170                 175

Ser Ala Gln Ile Pro Gly Ser Ser Tyr Asn Ser Ala Val Leu Met Ala
            180                 185                 190

Pro Ser Ser Asn Met Phe Gln Asp Ser Asn Gly Asn Cys Leu Lys Asp
        195                 200                 205

Glu Asn Gly Glu Leu Leu Ser Val Lys Tyr Thr Arg Arg Met Ile Glu
    210                 215                 220

Asn Tyr Gly Pro Glu Gln Val Ala Ala Val Ile Thr Glu Val Ser Gln
225                 230                 235                 240

Gly Val Gly Ser Thr Met Pro Pro Tyr Glu Tyr Ile Pro Gln Leu Arg
                245                 250                 255

Lys Met Thr Lys Glu Leu Gly Val Leu Trp Ile Ala Asp Glu Val Leu
            260                 265                 270

Thr Gly Phe Gly Arg Thr Gly Lys Trp Phe Gly Tyr Gln His Tyr Gly
        275                 280                 285

Val Gln Pro Asp Ile Ile Thr Met Gly Lys Gly Leu Ser Ser Ser Ser
    290                 295                 300

Leu Pro Ala Gly Ala Val Val Ser Lys Glu Ile Ala Ala Phe Met
305                 310                 315                 320

Asp Lys His Arg Trp Glu Ser Val Ser Thr Tyr Ala Gly His Pro Val
                325                 330                 335

Ala Met Ala Ala Val Cys Ala Asn Leu Glu Val Met Met Glu Glu Asn
            340                 345                 350

Leu Val Glu Gln Ala Lys Asn Ser Gly Glu Tyr Ile Arg Ser Lys Leu

```
            355                 360                 365
Glu Leu Leu Gln Glu Lys His Lys Ser Ile Gly Asn Phe Asp Gly Tyr
370                 375                 380

Gly Leu Leu Trp Ile Val Asp Ile Val Asn Ala Lys Thr Lys Thr Pro
385                 390                 395                 400

Tyr Val Lys Leu Asp Arg Asn Phe Arg His Gly Met Asn Pro Asn Gln
                405                 410                 415

Ile Pro Thr Gln Ile Ile Met Glu Lys Ala Leu Glu Lys Gly Val Leu
            420                 425                 430

Ile Gly Gly Ala Met Pro Asn Thr Met Arg Ile Gly Ala Ser Leu Asn
        435                 440                 445

Val Ser Arg Gly Asp Ile Asp Lys Ala Met Asp Ala Leu Asp Tyr Ala
    450                 455                 460

Leu Asp Tyr Leu Glu Ser Gly Glu Trp Gln Gln Ser
465                 470                 475

<210> SEQ ID NO 148
<211> LENGTH: 476
<212> TYPE: PRT
<213> ORGANISM: Arthrobacter citreus

<400> SEQUENCE: 148

Met Gly Leu Thr Val Gln Lys Ile Asn Trp Glu Gln Val Lys Glu Trp
1               5                   10                  15

Asp Arg Lys Tyr Leu Met Arg Thr Phe Ser Thr Gln Asn Glu Tyr Gln
            20                  25                  30

Pro Val Pro Ile Glu Ser Thr Glu Gly Asp Tyr Leu Ile Met Pro Asp
        35                  40                  45

Gly Thr Arg Leu Leu Asp Phe Phe Asn Gln Leu Tyr Cys Val Asn Leu
    50                  55                  60

Gly Gln Lys Asn Gln Lys Val Asn Ala Ala Ile Lys Glu Ala Leu Asp
65                  70                  75                  80

Arg Tyr Gly Phe Val Trp Asp Thr Tyr Ala Thr Asp Tyr Lys Ala Lys
                85                  90                  95

Ala Ala Lys Ile Ile Ile Glu Asp Ile Leu Gly Asp Glu Asp Trp Pro
            100                 105                 110

Gly Lys Val Arg Phe Val Ser Thr Gly Ser Glu Ala Val Glu Thr Ala
        115                 120                 125

Leu Asn Ile Ala Arg Leu Tyr Thr Asn Arg Pro Leu Val Val Thr Arg
    130                 135                 140

Glu His Asp Tyr His Gly Trp Thr Gly Gly Ala Ala Thr Val Thr Arg
145                 150                 155                 160

Leu Arg Ser Tyr Arg Ser Gly Leu Val Gly Glu Asn Ser Glu Ser Phe
                165                 170                 175

Ser Ala Gln Ile Pro Gly Ser Ser Tyr Asn Ser Ala Val Leu Met Ala
            180                 185                 190

Pro Ser Pro Asn Met Phe Gln Asp Ser Asn Gly Asn Cys Leu Lys Asp
        195                 200                 205

Glu Asn Gly Glu Leu Leu Ser Val Lys Tyr Thr Arg Arg Met Ile Glu
    210                 215                 220

Asn Tyr Gly Pro Glu Gln Val Ala Ala Val Ile Thr Glu Val Ser Gln
225                 230                 235                 240

Gly Ala Gly Ser Ala Met Pro Pro Tyr Glu Tyr Ile Pro Gln Leu Arg
                245                 250                 255
```

-continued

```
Lys Met Thr Lys Glu Leu Gly Val Leu Trp Ile Asn Asp Glu Val Leu
            260                 265                 270

Thr Gly Phe Gly Arg Thr Gly Lys Trp Phe Gly Tyr Gln His Tyr Gly
            275                 280                 285

Val Gln Pro Asp Ile Ile Thr Met Gly Lys Gly Leu Ser Ser Ser Ser
    290                 295                 300

Leu Pro Ala Gly Ala Val Val Ser Lys Glu Ile Ala Ala Phe Met
305                 310                 315                 320

Asp Lys His Arg Trp Glu Ser Val Ser Thr Tyr Ala Gly His Pro Val
            325                 330                 335

Ala Met Ala Ala Val Cys Ala Asn Leu Glu Val Met Met Glu Glu Asn
            340                 345                 350

Leu Val Glu Gln Ala Lys Asn Ser Gly Glu Tyr Ile Arg Ser Lys Leu
            355                 360                 365

Glu Leu Leu Gln Glu Lys His Lys Ser Ile Gly Asn Phe Asp Gly Tyr
            370                 375                 380

Gly Leu Leu Trp Ile Val Asp Ile Val Asn Ala Lys Thr Lys Thr Pro
385                 390                 395                 400

Tyr Val Lys Leu Asp Arg Asn Phe Thr His Gly Met Asn Pro Asn Gln
            405                 410                 415

Ile Pro Thr Gln Ile Ile Met Lys Lys Ala Leu Glu Lys Gly Val Leu
            420                 425                 430

Ile Gly Gly Val Met Pro Asn Thr Met Arg Ile Gly Ala Ser Leu Asn
            435                 440                 445

Val Ser Arg Gly Asp Ile Asp Lys Ala Met Asp Ala Leu Asp Tyr Ala
    450                 455                 460

Leu Asp Tyr Leu Glu Ser Gly Glu Trp Gln Gln Ser
465                 470                 475

<210> SEQ ID NO 149
<211> LENGTH: 476
<212> TYPE: PRT
<213> ORGANISM: Arthrobacter citreus

<400> SEQUENCE: 149

Met Gly Leu Thr Val Gln Lys Ile Asn Trp Glu Gln Val Lys Glu Trp
1               5                   10                  15

Asp Arg Lys Tyr Leu Met Arg Thr Phe Ser Thr Gln Asn Glu Tyr Gln
            20                  25                  30

Pro Val Pro Ile Glu Ser Thr Glu Gly Asp Tyr Leu Ile Met Pro Asp
        35                  40                  45

Gly Thr Arg Leu Leu Asp Phe Phe Asn Gln Leu Tyr Cys Val Asn Leu
    50                  55                  60

Gly Gln Lys Asn Gln Lys Val Asn Ala Ala Ile Lys Glu Ala Leu Asp
65                  70                  75                  80

Arg Tyr Gly Phe Val Trp Asp Thr Tyr Ala Thr Asp Tyr Lys Ala Lys
                85                  90                  95

Ala Ala Lys Ile Ile Ile Glu Asp Ile Leu Gly Asp Glu Asp Trp Pro
            100                 105                 110

Gly Lys Val Arg Phe Val Ser Thr Gly Ser Glu Ala Val Glu Thr Ala
        115                 120                 125

Leu Asn Ile Ala Arg Leu Tyr Thr Asn Arg Pro Leu Val Val Thr Arg
    130                 135                 140

Glu His Asp Tyr His Gly Trp Thr Gly Gly Ala Ala Thr Val Thr Arg
145                 150                 155                 160
```

Leu Arg Ser Tyr Arg Ser Gly Leu Val Gly Glu Asn Ser Glu Ser Phe
            165                 170                 175

Ser Ala Gln Ile Pro Gly Ser Ser Tyr Asn Ser Ala Val Leu Met Ala
            180                 185                 190

Pro Ser Pro Asn Met Phe Gln Asp Ser Asn Gly Asn Cys Leu Lys Asp
            195                 200                 205

Glu Asn Gly Glu Leu Leu Ser Val Lys Tyr Thr Arg Arg Met Ile Glu
        210                 215                 220

Asn Tyr Gly Pro Glu Gln Val Ala Ala Val Ile Thr Glu Val Ser Gln
225                 230                 235                 240

Gly Ala Gly Ser Ala Met Pro Pro Tyr Glu Tyr Ile Pro Gln Leu Arg
                245                 250                 255

Lys Met Thr Lys Glu Leu Gly Val Leu Trp Ile Asn Asp Glu Val Leu
            260                 265                 270

Thr Gly Phe Gly Arg Thr Gly Lys Trp Phe Gly Tyr Gln His Tyr Gly
        275                 280                 285

Val Gln Pro Asp Ile Ile Thr Met Gly Lys Gly Leu Ser Ser Ser Ser
        290                 295                 300

Leu Pro Ala Gly Ala Val Val Ser Lys Glu Ile Ala Ala Phe Met
305                 310                 315                 320

Asp Lys His Arg Trp Glu Ser Gly Ser Thr Tyr Ala Gly His Pro Val
                325                 330                 335

Ala Met Ala Ala Val Cys Ala Asn Leu Glu Val Met Met Glu Glu Asn
            340                 345                 350

Leu Val Glu Gln Ala Lys Asn Ser Gly Glu Tyr Ile Arg Ser Lys Leu
        355                 360                 365

Glu Leu Leu Gln Glu Lys His Lys Ser Ile Gly Asn Phe Asp Gly Tyr
    370                 375                 380

Gly Leu Leu Trp Ile Val Asp Ile Val Asn Ala Lys Thr Lys Thr Pro
385                 390                 395                 400

Tyr Val Lys Leu Asp Arg Asn Phe Thr His Gly Met Asn Pro Asn Gln
                405                 410                 415

Ile Pro Thr Gln Ile Ile Met Lys Lys Ala Leu Glu Lys Gly Val Leu
            420                 425                 430

Ile Gly Gly Val Met Pro Asn Thr Met Arg Ile Gly Ala Ser Leu Asn
        435                 440                 445

Val Ser Arg Gly Asp Ile Asp Lys Ala Met Asp Ala Leu Asp Tyr Ala
    450                 455                 460

Leu Asp Tyr Leu Glu Ser Gly Glu Trp Gln Gln Ser
465                 470                 475

<210> SEQ ID NO 150
<211> LENGTH: 476
<212> TYPE: PRT
<213> ORGANISM: Arthrobacter citreus

<400> SEQUENCE: 150

Met Gly Leu Thr Val Gln Lys Ile Asn Trp Glu Gln Val Lys Glu Trp
1               5                   10                  15

Asp Arg Lys Tyr Leu Met Arg Thr Leu Ser Thr Gln Asn Glu Tyr Gln
            20                  25                  30

Pro Val Pro Ile Glu Ser Thr Glu Gly Asp Tyr Leu Ile Met Pro Asp
        35                  40                  45

Gly Thr Arg Leu Leu Asp Phe Phe Asn Gln Leu Tyr Cys Val Asn Leu

```
                 50                   55                   60
Gly Gln Lys Asn Gln Lys Val Asn Ala Ala Ile Lys Glu Ala Leu Asp
 65                   70                   75                   80

Arg Tyr Gly Phe Val Trp Asp Thr Tyr Ala Thr Asp Tyr Lys Ala Lys
                     85                   90                   95

Ala Ala Lys Ile Ile Ile Glu Asp Ile Leu Gly Asp Glu Asp Trp Pro
                100                  105                  110

Gly Lys Val Arg Phe Val Ser Thr Gly Ser Glu Ala Val Glu Thr Ala
                115                  120                  125

Leu Asn Ile Ala Arg Leu Tyr Thr Asn Arg Pro Leu Val Val Thr Arg
            130                  135                  140

Glu His Asp Tyr His Gly Trp Thr Gly Ala Ala Thr Val Thr Arg
145                  150                  155                  160

Leu Arg Ser Met Arg Ser Gly Leu Val Gly Glu Asn Ser Glu Ser Phe
                165                  170                  175

Ser Ala Gln Ile Pro Gly Ser Ser Tyr Asn Ser Ala Val Leu Met Ala
            180                  185                  190

Pro Ser Pro Asn Met Phe Gln Asp Ser Asn Gly Asn Cys Leu Lys Asp
            195                  200                  205

Glu Asn Gly Glu Leu Leu Ser Val Lys Tyr Thr Arg Arg Met Ile Glu
        210                  215                  220

Asn Tyr Gly Pro Glu Gln Val Ala Ala Val Ile Thr Glu Val Ser Gln
225                  230                  235                  240

Gly Ala Gly Ser Ala Met Pro Pro Tyr Glu Tyr Ile Pro Gln Leu Arg
                245                  250                  255

Lys Met Thr Lys Glu Leu Gly Val Leu Trp Ile Asn Asp Glu Val Leu
                260                  265                  270

Thr Gly Phe Gly Arg Thr Gly Lys Trp Phe Gly Tyr Gln His Tyr Gly
            275                  280                  285

Val Gln Pro Asp Ile Ile Thr Met Gly Lys Gly Leu Ser Ser Ser Ser
        290                  295                  300

Leu Pro Ala Gly Ala Val Val Ser Lys Glu Ile Ala Ala Phe Met
305                  310                  315                  320

Asp Lys His Arg Trp Glu Ser Val Ser Thr Tyr Ala Gly His Pro Val
                325                  330                  335

Ala Met Ala Ala Val Cys Ala Asn Leu Glu Val Met Met Glu Glu Asn
            340                  345                  350

Leu Val Glu Gln Ala Lys Asn Ser Gly Glu Tyr Ile Arg Ser Lys Leu
            355                  360                  365

Glu Leu Leu Gln Glu Lys His Lys Ser Ile Gly Asn Phe Asp Gly Tyr
        370                  375                  380

Gly Leu Leu Trp Ile Val Asp Ile Val Asn Ala Lys Thr Lys Thr Pro
385                  390                  395                  400

Tyr Val Lys Leu Asp Arg Asn Phe Thr His Gly Met Asn Pro Asn Gln
                405                  410                  415

Ile Pro Thr Gln Ile Ile Met Lys Lys Ala Leu Glu Lys Gly Val Leu
            420                  425                  430

Ile Gly Gly Val Met Pro Asn Thr Met Arg Ile Gly Ala Ser Leu Asn
        435                  440                  445

Val Ser Arg Gly Asp Ile Asp Lys Ala Met Asp Ala Leu Asp Tyr Ala
450                  455                  460
```

```
Leu Asp Tyr Leu Glu Ser Gly Glu Trp Gln Gln Ser
465                 470                 475
```